(12) United States Patent
Hayashi et al.

(10) Patent No.: US 12,258,376 B2
(45) Date of Patent: Mar. 25, 2025

(54) FUSION PROTEIN OF DCTN1 PROTEIN WITH RET PROTEIN

(71) Applicant: TAIHO PHARMACEUTICAL CO., LTD., Tokyo (JP)

(72) Inventors: Kohei Hayashi, Tsukuba (JP); Keiji Ishida, Tsukuba (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 616 days.

(21) Appl. No.: 16/640,955

(22) PCT Filed: Aug. 20, 2018

(86) PCT No.: PCT/JP2018/030688
§ 371 (c)(1),
(2) Date: Feb. 21, 2020

(87) PCT Pub. No.: WO2019/039439
PCT Pub. Date: Feb. 28, 2019

(65) Prior Publication Data
US 2020/0190154 A1    Jun. 18, 2020

(30) Foreign Application Priority Data

Aug. 21, 2017  (JP) .................... 2017-158796

(51) Int. Cl.
| | | |
|---|---|---|
| C07K 14/47 | (2006.01) | |
| C07K 16/32 | (2006.01) | |
| C12N 15/63 | (2006.01) | |
| C12Q 1/6806 | (2018.01) | |
| C12Q 1/6813 | (2018.01) | |
| C12Q 1/6876 | (2018.01) | |

(52) U.S. Cl.
CPC .............. *C07K 14/47* (2013.01); *C07K 16/32* (2013.01); *C12N 15/63* (2013.01); *C12Q 1/6806* (2013.01); *C12Q 1/6813* (2013.01); *C12Q 1/6876* (2013.01)

(58) Field of Classification Search
None
See application file for complete search history.

(56) References Cited

U.S. PATENT DOCUMENTS

| | | |
|---|---|---|
| 5,665,721 A | 9/1997 | Bhagwat et al. |
| 2006/0211678 A1 | 9/2006 | Ahmed et al. |
| 2007/0135387 A1 | 6/2007 | Michaelides et al. |
| 2013/0116280 A1* | 5/2013 | Ju ........................ A61P 35/00 435/6.13 |
| 2014/0108453 A1 | 4/2014 | Venkataraman et al. |
| 2014/0121239 A1 | 5/2014 | Aftab |
| 2016/0115168 A1 | 4/2016 | Iguchi et al. |
| 2017/0217970 A1 | 8/2017 | Kawai et al. |
| 2018/0009817 A1 | 1/2018 | Miyazaki et al. |
| 2018/0009818 A1 | 1/2018 | Miyazaki et al. |

FOREIGN PATENT DOCUMENTS

| | | |
|---|---|---|
| JP | 2007-521334 A | 8/2007 |
| JP | 2008-508358 A | 3/2008 |
| JP | 2009-518434 A | 5/2009 |
| JP | 2015505555 A | 2/2015 |
| WO | 96/40686 A1 | 12/1996 |
| WO | 2004056830 A1 | 7/2004 |
| WO | 2005047289 A1 | 5/2005 |
| WO | 2005062795 A2 | 7/2005 |
| WO | 2006017443 A2 | 2/2006 |
| WO | 2007067781 A2 | 6/2007 |
| WO | 2011018894 A1 | 2/2011 |
| WO | 2013059740 A1 | 4/2013 |
| WO | 2013114113 A1 | 8/2013 |
| WO | 2014130975 A1 | 8/2014 |
| WO | 2014184069 A1 | 11/2014 |
| WO | 2015022926 A1 | 2/2015 |
| WO | 2015078417 A1 | 6/2015 |
| WO | 2017038838 A1 | 3/2017 |
| WO | 2017043550 A1 | 3/2017 |
| WO | 2017146116 A1 | 8/2017 |

OTHER PUBLICATIONS

Farrer M.J. et al., DCTN1 mutations in Perry syndrome, Nature genetics, 2009, V. 41, N. 2, p. 163-165.
So M.T. et al., RET mutational spectrum in Hirschsprung disease: evaluation of 601 Chinese patients, PloS one, 2011, V. 6, N. 12, p. e28986.
Colman P.M., Effects of amino acid sequence changes on antibody-antigen interactions, Research in Immunology, 1994, V. 145, N. 1, p. 33-36.
Safdari Y. et al., Antibody humanization methods-a review and update, Biotechnology and Genetic Engineering Reviews, 2013, V. 29, N. 2, p. 175-186.
Shen J. et al., Single variable domain-IgG fusion: a novel recombinant approach to Fc domain-containing bispecific antibodies, Journal of Biological Chemistry, 2006, V. 281, N. 16, p. 10706-10714.
Torres M. et al., The immunoglobulin constant region contributes to affinity and specificity, Trends in immunology, 2008, V. 29, N. 2, p. 91-97.
Teplyakov A. et al., Antibody modeling assessment II. Structures and models, Proteins: Structure, Function, and Bioinformatics, 2014, V. 82, N. 8, p. 1563-1582.

(Continued)

Primary Examiner — Julie Ha
Assistant Examiner — Tara L Martinez
(74) Attorney, Agent, or Firm — Oblon, McClelland, Maier & Neustadt, L.L.P.

(57) ABSTRACT

Provided are a novel polypeptide wherein a portion of DCTN1 protein is fused to a portion of RET protein; a polynucleotide encoding the polypeptide; a method for detecting the polynucleotide or the polypeptide; a method of screening for a compound that inhibits expression of the polynucleotide or expression and/or activity of the polypeptide; and a pharmaceutical composition containing a compound that inhibits RET as an active ingredient.

1 Claim, 5 Drawing Sheets
Specification includes a Sequence Listing.

(56) References Cited

OTHER PUBLICATIONS

Chen X. et al., Fusion protein linkers: property, design and functionality, Advanced drug delivery reviews, 2013, V. 65, N. 10, p. 1357-1369.
Maeda Y. et al., Engineering of functional chimeric protein G-Vargula Luciferase, Analytical biochemistry, 1997, V. 249, N. 2, p. 147-152.
Pakula A.A. et al., Genetic analysis of protein stability and function, Annual Review of genetics, 1989, V. 23 , N. 1, p. 289-310.
Muller S. et al., Spliceosomal peptide P140 for immunotherapy of systemic lupus erythematosus: results of an early phase II clinical trial, Arthritis & Rheumatism: Official Journal of the American College of Rheumatology, 2008, V. 58, N. 12, p. 3873-3883.
Official Action dated May 17, 2022 for the corresponding RU patent application No. 2020111214, 30 pages, with a translation.
Mulligan, "RET revisited: expanding the oncogenic portfolio", Nature Reviews, 14(3): pp. 173-186, (2014).
Ibanez, "Structure and Physiology of the RET Receptor Tyrosine Kinase", Cold Spring Harbor Perspectives in Biology, 5(2) a009134: pp. 1-10, (2013).
Kohno et al., "KIF5B-RET fusions in lung adenocarcinoma", Nature Medicine, 18(3) : pp. 375-377, (2012).
Santoro et al., "RET/PTC activation in papillary thyroid carcinoma: European Journal of Endocrinology Prize Lecture", European Journal of Endocrinology, 155: pp. 645-653, (2006).
Yeganeh et al., "RET Proto Oncogene Mutation Detection and Medullary Thyroid Carcinoma Prevention", Asian Pacific Journal of Cancer Prevention, 16(6): pp. 2107-2117, (2015).
Gattelli et al.,"Ret inhibition decreases growth and metastatic potential of estrogen receptor positive breast cancer cells", EMBO Molecular Medicine, 5: pp. 1335-1350, (2013).
Ito et al., "Expression of glial cell line-derived neurotrophic factor family members and their receptors in pancreatic cancers", Surgery, 138(4): pp. 788-794, (2005).
Dawson et al., "Altered Expression of RET Proto-oncogene Product in Prostatic Intraepithelial Neoplasia and Prostate Cancer", Journal of the National Cancer Institute, 90(7): pp. 519-523, (1998).
Cai et al., "KIF5B-RET Fusions in Chinese Patients With Non-Small Cell Lung Cancer", Cancer, 119: pp. 1486-1494, (2013).
Elisei et al., "Prognostic Significance of Somatic RET Oncogene Mutations in Sporadic Medullary Thyroid Cancer: A 10-Year Follow-Up Study", The Journal of Clinical Endocrinology & Metabolism, 93(3): pp. 682-687, (2008).
Zeng et al., "The Relationship between Over-expression of Glial Cell-derived Neurotrophic Factor and Its RET Receptor with Progression and Prognosis of Human Pancreatic Cancer", The Journal of International Medical Research, 36: pp. 656-664, (2008).
Carlomagno et al., "The Kinase Inhibitor PP1 Blocks Tumorigenesis Induced by RET Oncogenes1" Cancer Research, 62(4): pp. 1077-1082, (2002).
Waltenberger et al., "A Dual Inhibitor of Platelet-Derived Growth Factor b-Receptor and Src Kinase Activity Potently Interferes With Motogenic and Mitogenic Responses to PDGF in Vascular Smooth Muscle Cells A Novel Candidate for Prevention of Vascular Remodeling", Circulation Research, 85(1): pp. 12-22, (1999).
Tatton et al., "The Src-selective Kinase Inhibitor PP1 Also Inhibits Kit and Ber-Abl Tyrosine Kinases*", The Journal of Biological Chemistry, 278(7): pp. 4847-4853, (2003).
Warmuth et al., "Dual-specific Src and Abl kinase inhibitors, PP1 and CGP76030, inhibit growth and survival of cells expressing imatinib mesylate-resistant Bcr-Abl kinases", Blood, 101(2): pp. 664-672, (2003).
Lowe et al., "Osteopetrosis in Src-deficient mice is due to an autonomous defect of osteoclasts", Proceedings of the National Academy of Sciences of the United States of America, 90(10): pp. 4485-4489, (1993).
Molina et al., "Profound block in thymocyte development in mice lacking p56", Nature, 357(6374): pp. 161-164, (1992).

McClellan et al., "Discovery of potent and selective thienopyrimidine inhibitors of Aurora kinases". Bioorganic & Medicinal Chemistry Letters 21, 2011, pp. 5620-5624.
Bavetsias et al., "Aurora Kinase Inhibitors: Current Status and Outlook", Frontiers in Oncology, 2015, vol. 5.
Keefe et al., "Tumor control versus adverse events with targeted anticancer therapies" Nature Reviews Clinical Oncology, 2012, vol. 9, No. 2, pp. 98-109.
International Search Report cited in PCT/JP2017/006672 dated Apr. 25, 2017, 2 pages.
Wang et al., Fusion of dynactin 1 to anaplastic lymphoma kinase in inflammatory myofibroblastic tumor, Human Pathology, 2012, vol. 43, pp. 2047-2052.
F. Hidenori et al., "4784 / 13—TAS0286/HM05, A Novel Highly Selective RET Inhibitor, Prominently Inhibits Various RET Defective Tumor Growth", AACR Annual Meeting 2018 Online Proceedings and Itinerary Planner Home, Abstract, Apr. 17, 2018, 1 page.
F. Hidenori et al., "TAS0286/HMO5, A Novel Highly Selective RET Inhibitor, Prominently Inhibits Various RET Defective Tumor Growth", 4784 Abstract, Mar. 14, 2018, 1 page.
Extended European Search Report dated Jan. 12, 2018, cited in the related European application No. 17756554.6, 6 pages.
Vaughan et al., "Cytoplasmic Dynein Binds Dynactin through a Direct Interaction between the Intermediate Chains and p150 Glued" The Journal of Cell Biology, 1995, Vo. 131, No. 6, pp. 1507-1516.
Yoh et al., Vandetanib in patients with previously treated RET-rearranged advanced non-small-cell lung cancer (LURET): an open-label, multicentre phase 2 trial, Lancet Respiratory Medicine, 2017, vol. 5, pp. 42-50.
Chen et al., "Increasing Incidence of Differentiated Thyroid Cancer in the United States, 1988-2005", Cancer, 2009, vol. 115, No. 16, pp. 3801-3807.
Soares et al., "BRAF mutations and RET/PTC rearrangements are alternative events in the etiopathogenesis of PTC" Oncogene, 2003, vol. 22, No. 29, pp. 4578-4580.
"Integrated Genomic Characterization of Papillary Thyroid Carcinoma", Cell, 2014, vol. 159, No. 3, pp. 676-690.
Drilon et al., "Response to Cabozantinib in Patients with RET Fusion-Positive Lung Adenocarcinomas", Cancer Discovery, 2013, vol. 3, No. 6, pp. 630-635.
"Comprehensive molecular profiling of lung adenocarcinoma", Nature, 2014, vol. 511, No. 7511, pp. 543-550.
Dyson G, "Chemistry of Synthetic Medical Substances", M.: Mir, 1964, pp. 12-19.
Belikov, Pharmaceutical Chemistry in Two Parts, "Pharmaceutical Chemistry", 1993, pp. 43-47.
Patani et al., "Bioisosterism: A Rational Approach in Drug Design", Chemical Reviews, 1996, vol. 96, No. 8, pp. 3147-3176.
Office Action for the related RU patent application No. 2018112252.
Office Action for the related TW patent application No. 105128898.
Fujita et al. (AACR Annual Meeting 2018 Online Proceedings and Itinerary Planner Home, Abstract 4784- TAS0286/H M05, a novel highly selective RET inhibitor, prominently inhibits various RET defective tumor growth, <http://www.abstractsonline.com/pp8/> downloaded Jul. 10, 2018).
Fujita et al. (AACR Annual Meeting 2018 Abstract 4784, Poster #13- TAS0286/H M05, a novel highly selective RET Inhibitor, prominently inhibits various RET defective tumor growth, Apr. 17, 2018).
International Search Report cited in PCT/JP2016/076354 dated Nov. 1, 2016, 4 pages.
Mashkovsky, "MD Medicines", 1993, Part 1-S, 1, 8.
"Small Medical Encyclopedia", vol. 5, Moscow, "Medicine", 1996, pp. 90-96, partial translation.
L.A. Durnov, G.V. Goldobenko, "Pediatric Oncology", Medicine, 2002, p. 139.
D.A. Kharkevich Pharmacology, 10th ed. M.: GEOTAR-Media, 2010, p. 73-74.
Zhulenko V.N., Gorshkov G.I. Pharmacology. M. KolosS, 2008, p. 34-35.
Official Action for the related RU patent application 2018133000, dated Feb. 20, 2021, 24 pages.

(56) References Cited

OTHER PUBLICATIONS

Grupp et al., "Chimeric antigen receptor-modified T cells for acute lymphoid leukemia", New England Journal of Medicine, 2013, vol. 368, No. 16, pp. 1509-1518.
Pakula et al., "Genetic analysis of protein stability and function", Annual review of genetics, 1989, vol. 23, No. 1, pp. 289-310.
Official Action dated Dec. 2, 2022 for RU Pat. Appln. No. 2020111214, 23 pgs.
Russian Office Action issued Jul. 17, 2024, in Russian Patent Application No. 2022110059/04(021147), (with English translation), 42 pages.
Bastin, R. et al., "Salt Selection and Optimisation Procedures for Pharmaceutical New Chemical Entities," Organic Process Research & Development, vol. 4, 2000, pp. 427-435.
Kümmerer, K., "Pharmaceuticals in the Environment," Annual Review of Environment and Resources, vol. 35, Aug. 18, 2010, 22 pages.

\* cited by examiner

① Human Thyroid Cancer Tissue
② Normal Human Thyroid Tissue

① NIH/3T3 Cells
② NIH/3T3 Cells Expressing DCTN1-RET Fusion Gene

```
                        SEQUENCE LISTING

<160> NUMBER OF SEQ ID NOS: 77

<210> SEQ ID NO 1
<211> LENGTH: 4908
<212> TYPE: DNA
<213> ORGANISM: Artificial Sequence
<220> FEATURE:
<223> OTHER INFORMATION: coding sequence of fusion peptide

<400> SEQUENCE: 1
atggcacaga gcaagaggca cgtgtacagc cggacgccca gcggcagcag gatgagtgcg        60
gaggcaagcg cccggcctct gcgggtgggc tcccgtgtag aggtgattgg aaaaggccac       120
cgaggcactg tggcctatgt tggagccaca ctgtttgcca ctggcaaatg ggtaggcgtg       180
attctggatg aagcaaaggg caaaaatgat ggaactgttc aaggcaggaa gtacttcact       240
tgtgatgaag gcatggcat cttgtgcgc cagtcccaga tccaggtatt tgaagatgga       300
gcagatacta cttccccaga gacacctgat tcttctgctt caaaagtcct caaaagagag       360
ggaactgata caactgcaaa gactagcaaa ctgcggggac tgaagcctaa gaaggcaccg       420
acagcccgaa agaccacaac tcggcgaccc aagcccacgc gccagccag tactggggtg       480 gctggggcca gtagctccct gggcccctct ggctcagcgt cagcaggtga gctgagcagc       540
```

```
agtgagccca gcaccccggc tcagactccg ctggcagcac ccatcatccc cacgccggtc    600
ctcacctctc ctggagcagt ccccccgctt ccttccccat ccaaggagga ggagggacta    660
agggctcagg tgcgggacct ggaggagaaa ctagagaccc tgagactgaa acgggcagaa    720
gacaaagcaa agctaaaaga gctggagaaa cacaaaatcc agctggagca ggtgcaggaa    780
tggaagagca aaatgcagga gcagcaggcc gacctgcagc ggcgcctcaa ggaggcgaga    840
aaggaagcca aggaggcgct ggaggcaaag gaacgctata tggaggagat ggctgatact    900
gctgatgcca ttgagatggc cactttggac aaggagatgg ctgaagagcg gctgagtcc     960 ctgcagcagg aggtggaggc actgaaggag cgggtggacg agctcactac tgacttagag    1020
atcctcaagg ctgagattga agagaagggc tcagatggcg ctgcatccag ttatcagctc    1080
aagcagcttg aggagcagaa tgcccgcctg aaggatgccc tggtgaggat gcggatctt     1140 tcttcctcag agaagcagga gcatgtgaag ctccagaagc tcatggaaaa gaagaaccaa    1200
gagctggaag ttgtgaggca acagcgggag cgtctgcagg aggagctaag ccaggcagag    1260
agcaccattg atgagctcaa ggagcaggtg gatgctgctc tgggtgctga ggagatggtg    1320
gagatgctga cagatcggaa cctgaatctg aagagaaag tgcgcgagtt gagggagact    1380
gtgggagact tggaagcgat gaatgagatg aacgatgagc tgcaggagaa tgcacgtgag    1440
acagaactgg agctgcggga gcagctggac atggcaggcg cgcgggttcg tgaggcccag    1500
aagcgtgtgg aggcagccca ggagacggtt gcagactacc agcagaccat caagaagtac    1560
cgccagctga ccgcccatct acaggatgtg aatcgggaac tgacaaacca gcaggaagca    1620
tctgtggaga ggcaacagca gccacctcca gagacctttg acttcaaaat caagtttgct    1680
gagactaagg cccatgccaa ggcaattgag atggaattga ggcagatgga ggtggcccag    1740
gccaatcgac acatgtccct gctgacagcc ttcatgcctg acagcttcct tcggccaggt    1800
ggggaccatg actgcgttct ggtgctgttg ctcatgcctc gtctcatttg caaggcagag    1860
ctgatccgga agcaggccca ggagaagttt gaactaagtg agaactgttc agagcggcct    1920
gggctgcgag gagctgctgg ggagcaactc agctttgctg ctggactggt gtactcgctg    1980
agcctgctgc aggccacgct acaccgctat gagcatgccc tctctcagtg cagtgtggat    2040
gtgtataaga aagtgggcag cctgtaccct gagatgagtg cccatgagcg ctccttggat    2100
ttcctcattg aactgctgca caaggatcag ctggatgaga ctgtcaatgt ggagcctctc    2160
accaaggcca tcaagtacta tcagcatctg tacagcatcc accttgccga acagcctgag    2220
gactgtacta tgcagctggc tgaccacatt aagttcacgc agagtgctct ggactgcatg    2280
agtgtggagg taggacggct gcgtgccttc ttgcagggtg ggcaggaggc tacagatatt    2340
gccctcctgc tccgggatct ggaaacttca tgcagtgaca tccgccagtt ctgcaagaag    2400
atccgaaggc gaatgccagg gacagatgct cctgggatcc cagctgcact ggcctttgga    2460
ccacaggtat ctgacacgct cctagactgc aggaaacact tgacgtgggt cgtggctgtg    2520
ctgcaggagg tggcagctgc tgctgcccag ctcattgccc cactggcaga gaatgagggg    2580
ctacttgtgg ctgctctgga ggaactggct ttcaaagcaa gcgagcagat ctatgggacc    2640
ccctccagca gccccctatga gtgtctgcgc cagtcatgca catcctcat cagtaccatg    2700 aacaagctgg ccacagccat gcaggagggg gagtatgatg cagagcggcc ccccagcaag    2760
cctccaccgg ttgaactgcg ggctgctgcc cttcgtgcag agatcacaga tgctgaaggc    2820
ctgggtttga agctcgaaga tcgagagaca gttattaagg agttgaagaa gtcactcaag    2880
```

```
attaagggag aggagctaag tgaggccaat gtgcggctga gcctcctgga gaagaagttg    2940
gacagtgctg ccaaggatgc agatgagcgc atcgagaaag tccagactcg gctgaggag    3000 acccaggcac tgctgcgaaa gaaggagaaa gagtttgagg agacaatgga tgcactccag    3060
gctgacatcg accagctgga ggcagagaag gcagaactaa agcagcgtct gaacagccag    3120
tccaaacgca cgattgaggg actccggggc cctcctcctt caggcattgc tactctggtc    3180
tctggcattg ctggtgaaga acagcagcga ggagccatcc ctgggcaggc tccagggtct    3240
gtgccaggcc cagggctggt gaaggactca ccactgctgc ttcagcagat ctctgccatg    3300
aggctgcaca tctcccagct ccagcatgag aacagcatcc tcaagggagc ccagatgaag    3360
gcatccttgg catccctgcc ccctctgcat gttgcaaagc tatcccatga gggccctggc    3420
agtgagttac cagctggagc gctgtatcgt aagaccagcc agctgctgga cacattgaat    3480
caattgagca cacacacgca cgtagtagac atcactcgca ccagccctgc tgccaagagc    3540
ccgtcggccc aacttatgga gcaagtggct cagcttaagt ccctgagtga caccgtcgag    3600
aagctcaagg atgaggtcct caaggagaca gtatctcagc ccctggagc cacagtaccc     3660 actgactttg ccaccttccc ttcatcagcc ttcctcaggg aggatccaaa gtgggaattc    3720
cctcggaaga acttggttct tggaaaaact ctaggagaag gcgaatttgg aaaagtggtc    3780
aaggcaacgg ccttccatct gaaaggcaga gcagggtaca ccacggtggc cgtgaagatg    3840
ctgaaagaga acgcctcccc gagtgagctt cgagacctgc tgtcagagtt caacgtcctg    3900
aagcaggtca accacccaca tgtcatcaaa ttgtatgggg cctgcagcca ggatggcccg    3960
ctcctcctca tcgtggagta cgccaaatac ggctccctgc ggggcttcct ccgcgagagc    4020
cgcaaagtgg ggcctggcta cctgggcagt ggaggcagcc gcaactccag ctccctggac    4080
cacccggatg agcgggccct caccatgggc gacctcatct catttgcctg gcagatctca    4140
caggggatgc agtatctggc cgagatgaag ctcgttcatc gggacttggc agccagaaac    4200
atcctggtag ctgaggggcg gaagatgaag atttcggatt tcggcttgtc ccgagatgtt    4260
tatgaagagg attcctacgt gaagaggagc cagggtcgga ttccagttaa atggatggca    4320
attgaatccc tttttgatca tatctacacc acgcaaagtg atgtatggtc ttttggtgtc    4380
ctgctgtggg agatcgtgac cctaggggga aaccccctatc ctgggattcc tcctgagcgg    4440
ctcttcaacc ttctgaagac cggccaccgg atggagagc cagacaactg cagcgaggag    4500
atgtaccgcc tgatgctgca atgctggaag caggagccgg acaaaaggcc ggtgtttgcg    4560
gacatcagca aagacctgga gaagatgatg gttaagagga gagactactt ggaccttgcg    4620
gcgtccactc catctgactc cctgatttat gacgacggcc tctcagagga ggagacaccg    4680
ctggtggact gtaataatgc cccctccct cgagccctcc cttccacatg gattgaaaac    4740
aaactctatg gcatgtcaga cccgaactgg cctggagaga gtcctgtacc actcacgaga    4800
gctgatggca ctaacactgg gtttccaaga tatccaaatg atagtgtata tgctaactgg    4860
atgctttcac cctcagcggc aaaattaatg gacacgtttg atagttaa                4908

<210> SEQ ID NO 2
<211> LENGTH: 1635
<212> TYPE: PRT
<213> ORGANISM: Artificial Sequence
<220> FEATURE:
<223> OTHER INFORMATION: fusion peptide

<400> SEQUENCE: 2

Met Ala Gln Ser Lys Arg His Val Tyr Ser Arg Thr Pro Ser Gly Ser
```

```
1               5                   10                  15
Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
            35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Thr Ala Lys Thr
            115                 120                 125

Ser Lys Leu Arg Gly Leu Lys Pro Lys Ala Pro Thr Ala Arg Lys
    130                 135                 140

Thr Thr Thr Arg Arg Pro Lys Pro Thr Arg Pro Ala Ser Thr Gly Val
145                 150                 155                 160

Ala Gly Ala Ser Ser Leu Gly Pro Ser Gly Ser Ala Ser Ala Gly
                165                 170                 175

Glu Leu Ser Ser Ser Glu Pro Ser Thr Pro Ala Gln Thr Pro Leu Ala
            180                 185                 190

Ala Pro Ile Ile Pro Thr Pro Val Leu Thr Ser Pro Gly Ala Val Pro
            195                 200                 205

Pro Leu Pro Ser Pro Ser Lys Glu Glu Gly Leu Arg Ala Gln Val
    210                 215                 220

Arg Asp Leu Glu Glu Lys Leu Glu Thr Leu Arg Leu Lys Arg Ala Glu
225                 230                 235                 240

Asp Lys Ala Lys Leu Lys Glu Leu Glu Lys His Lys Ile Gln Leu Glu
            245                 250                 255

Gln Val Gln Glu Trp Lys Ser Lys Met Gln Glu Gln Ala Asp Leu
    260                 265                 270

Gln Arg Arg Leu Lys Glu Ala Arg Lys Glu Ala Lys Glu Ala Leu Glu
    275                 280                 285

Ala Lys Glu Arg Tyr Met Glu Glu Met Ala Asp Thr Ala Asp Ala Ile
    290                 295                 300

Glu Met Ala Thr Leu Asp Lys Glu Met Ala Glu Glu Arg Ala Glu Ser
305                 310                 315                 320

Leu Gln Gln Glu Val Glu Ala Leu Lys Glu Arg Val Asp Glu Leu Thr
            325                 330                 335

Thr Asp Leu Glu Ile Leu Lys Ala Glu Ile Glu Glu Lys Gly Ser Asp
            340                 345                 350

Gly Ala Ala Ser Ser Tyr Gln Leu Lys Gln Leu Glu Glu Gln Asn Ala
            355                 360                 365

Arg Leu Lys Asp Ala Leu Val Arg Met Arg Asp Leu Ser Ser Ser Glu
    370                 375                 380

Lys Gln Glu His Val Lys Leu Gln Lys Leu Met Glu Lys Lys Asn Gln
385                 390                 395                 400

Glu Leu Glu Val Val Arg Gln Arg Glu Arg Leu Gln Glu Glu Leu
            405                 410                 415

Ser Gln Ala Glu Ser Thr Ile Asp Glu Leu Lys Glu Gln Val Asp Ala
            420                 425                 430
```

```
Ala Leu Gly Ala Glu Glu Met Val Glu Met Leu Thr Asp Arg Asn Leu
            435                 440                 445

Asn Leu Glu Glu Lys Val Arg Glu Leu Arg Glu Thr Val Gly Asp Leu
450                 455                 460

Glu Ala Met Asn Glu Met Asn Asp Glu Leu Gln Glu Asn Ala Arg Glu
465                 470                 475                 480

Thr Glu Leu Glu Leu Arg Glu Gln Leu Asp Met Ala Gly Ala Arg Val
                485                 490                 495

Arg Glu Ala Gln Lys Arg Val Glu Ala Ala Gln Glu Thr Val Ala Asp
                500                 505                 510

Tyr Gln Gln Thr Ile Lys Lys Tyr Arg Gln Leu Thr Ala His Leu Gln
                515                 520                 525

Asp Val Asn Arg Glu Leu Thr Asn Gln Gln Glu Ala Ser Val Glu Arg
530                 535                 540

Gln Gln Gln Pro Pro Glu Thr Phe Asp Phe Lys Ile Lys Phe Ala
545                 550                 555                 560

Glu Thr Lys Ala His Ala Lys Ala Ile Glu Met Glu Leu Arg Gln Met
                565                 570                 575

Glu Val Ala Gln Ala Asn Arg His Met Ser Leu Leu Thr Ala Phe Met
                580                 585                 590

Pro Asp Ser Phe Leu Arg Pro Gly Gly Asp His Asp Cys Val Leu Val
            595                 600                 605

Leu Leu Leu Met Pro Arg Leu Ile Cys Lys Ala Glu Leu Ile Arg Lys
610                 615                 620

Gln Ala Gln Glu Lys Phe Glu Leu Ser Glu Asn Cys Ser Glu Arg Pro
625                 630                 635                 640

Gly Leu Arg Gly Ala Ala Gly Glu Gln Leu Ser Phe Ala Ala Gly Leu
                645                 650                 655

Val Tyr Ser Leu Ser Leu Leu Gln Ala Thr Leu His Arg Tyr Glu His
                660                 665                 670

Ala Leu Ser Gln Cys Ser Val Asp Val Tyr Lys Lys Val Gly Ser Leu
                675                 680                 685

Tyr Pro Glu Met Ser Ala His Glu Arg Ser Leu Asp Phe Leu Ile Glu
            690                 695                 700

Leu Leu His Lys Asp Gln Leu Asp Glu Thr Val Asn Val Glu Pro Leu
705                 710                 715                 720

Thr Lys Ala Ile Lys Tyr Tyr Gln His Leu Tyr Ser Ile His Leu Ala
                725                 730                 735

Glu Gln Pro Glu Asp Cys Thr Met Gln Leu Ala Asp His Ile Lys Phe
            740                 745                 750

Thr Gln Ser Ala Leu Asp Cys Met Ser Val Glu Val Gly Arg Leu Arg
        755                 760                 765

Ala Phe Leu Gln Gly Gly Gln Glu Ala Thr Asp Ile Ala Leu Leu Leu
    770                 775                 780

Arg Asp Leu Glu Thr Ser Cys Ser Asp Ile Arg Gln Phe Cys Lys Lys
785                 790                 795                 800

Ile Arg Arg Arg Met Pro Gly Thr Asp Ala Pro Gly Ile Pro Ala Ala
                805                 810                 815

Leu Ala Phe Gly Pro Gln Val Ser Asp Thr Leu Leu Asp Cys Arg Lys
            820                 825                 830

His Leu Thr Trp Val Val Ala Val Leu Gln Glu Val Ala Ala Ala Ala
        835                 840                 845
```

```
Ala Gln Leu Ile Ala Pro Leu Ala Glu Asn Glu Gly Leu Leu Val Ala
            850             855             860

Ala Leu Glu Glu Leu Ala Phe Lys Ala Ser Glu Gln Ile Tyr Gly Thr
865             870             875             880

Pro Ser Ser Ser Pro Tyr Glu Cys Leu Arg Gln Ser Cys Asn Ile Leu
                885             890             895

Ile Ser Thr Met Asn Lys Leu Ala Thr Ala Met Gln Glu Gly Glu Tyr
            900             905             910

Asp Ala Glu Arg Pro Pro Ser Lys Pro Pro Val Glu Leu Arg Ala
            915             920             925

Ala Ala Leu Arg Ala Glu Ile Thr Asp Ala Glu Gly Leu Gly Leu Lys
    930             935             940

Leu Glu Asp Arg Glu Thr Val Ile Lys Glu Leu Lys Lys Ser Leu Lys
945             950             955             960

Ile Lys Gly Glu Glu Leu Ser Glu Ala Asn Val Arg Leu Ser Leu Leu
            965             970             975

Glu Lys Lys Leu Asp Ser Ala Ala Lys Asp Ala Asp Glu Arg Ile Glu
        980             985             990

Lys Val Gln Thr Arg Leu Glu Glu Thr Gln Ala Leu Leu Arg Lys Lys
        995             1000            1005

Glu Lys Glu Phe Glu Glu Thr Met Asp Ala Leu Gln Ala Asp Ile
    1010            1015            1020

Asp Gln Leu Glu Ala Glu Lys Ala Glu Leu Lys Gln Arg Leu Asn
    1025            1030            1035

Ser Gln Ser Lys Arg Thr Ile Glu Gly Leu Arg Gly Pro Pro Pro
    1040            1045            1050

Ser Gly Ile Ala Thr Leu Val Ser Gly Ile Ala Gly Glu Glu Gln
    1055            1060            1065

Gln Arg Gly Ala Ile Pro Gly Gln Ala Pro Gly Ser Val Pro Gly
    1070            1075            1080

Pro Gly Leu Val Lys Asp Ser Pro Leu Leu Leu Gln Gln Ile Ser
    1085            1090            1095

Ala Met Arg Leu His Ile Ser Gln Leu Gln His Glu Asn Ser Ile
    1100            1105            1110

Leu Lys Gly Ala Gln Met Lys Ala Ser Leu Ala Ser Leu Pro Pro
    1115            1120            1125

Leu His Val Ala Lys Leu Ser His Glu Gly Pro Gly Ser Glu Leu
    1130            1135            1140

Pro Ala Gly Ala Leu Tyr Arg Lys Thr Ser Gln Leu Leu Glu Thr
    1145            1150            1155

Leu Asn Gln Leu Ser Thr His Thr His Val Val Asp Ile Thr Arg
    1160            1165            1170

Thr Ser Pro Ala Ala Lys Ser Pro Ser Ala Gln Leu Met Glu Gln
    1175            1180            1185

Val Ala Gln Leu Lys Ser Leu Ser Asp Thr Val Glu Lys Leu Lys
    1190            1195            1200

Asp Glu Val Leu Lys Glu Thr Val Ser Gln Arg Pro Gly Ala Thr
    1205            1210            1215

Val Pro Thr Asp Phe Ala Thr Phe Pro Ser Ser Ala Phe Leu Arg
    1220            1225            1230

Glu Asp Pro Lys Trp Glu Phe Pro Arg Lys Asn Leu Val Leu Gly
    1235            1240            1245

Lys Thr Leu Gly Glu Gly Glu Phe Gly Lys Val Val Lys Ala Thr
```

```
            1250                1255                1260
Ala Phe His Leu Lys Gly Arg Ala Gly Tyr Thr Thr Val Ala Val
    1265                1270                1275

Lys Met Leu Lys Glu Asn Ala Ser Pro Ser Glu Leu Arg Asp Leu
    1280                1285                1290

Leu Ser Glu Phe Asn Val Leu Lys Gln Val Asn His Pro His Val
    1295                1300                1305

Ile Lys Leu Tyr Gly Ala Cys Ser Gln Asp Gly Pro Leu Leu Leu
    1310                1315                1320

Ile Val Glu Tyr Ala Lys Tyr Gly Ser Leu Arg Gly Phe Leu Arg
    1325                1330                1335

Glu Ser Arg Lys Val Gly Pro Gly Tyr Leu Gly Ser Gly Gly Ser
    1340                1345                1350

Arg Asn Ser Ser Ser Leu Asp His Pro Asp Glu Arg Ala Leu Thr
    1355                1360                1365

Met Gly Asp Leu Ile Ser Phe Ala Trp Gln Ile Ser Gln Gly Met
    1370                1375                1380

Gln Tyr Leu Ala Glu Met Lys Leu Val His Arg Asp Leu Ala Ala
    1385                1390                1395

Arg Asn Ile Leu Val Ala Glu Gly Arg Lys Met Lys Ile Ser Asp
    1400                1405                1410

Phe Gly Leu Ser Arg Asp Val Tyr Glu Glu Asp Ser Tyr Val Lys
    1415                1420                1425

Arg Ser Gln Gly Arg Ile Pro Val Lys Trp Met Ala Ile Glu Ser
    1430                1435                1440

Leu Phe Asp His Ile Tyr Thr Thr Gln Ser Asp Val Trp Ser Phe
    1445                1450                1455

Gly Val Leu Leu Trp Glu Ile Val Thr Leu Gly Gly Asn Pro Tyr
    1460                1465                1470

Pro Gly Ile Pro Pro Glu Arg Leu Phe Asn Leu Leu Lys Thr Gly
    1475                1480                1485

His Arg Met Glu Arg Pro Asp Asn Cys Ser Glu Glu Met Tyr Arg
    1490                1495                1500

Leu Met Leu Gln Cys Trp Lys Gln Glu Pro Asp Lys Arg Pro Val
    1505                1510                1515

Phe Ala Asp Ile Ser Lys Asp Leu Glu Lys Met Met Val Lys Arg
    1520                1525                1530

Arg Asp Tyr Leu Asp Leu Ala Ala Ser Thr Pro Ser Asp Ser Leu
    1535                1540                1545

Ile Tyr Asp Asp Gly Leu Ser Glu Glu Glu Thr Pro Leu Val Asp
    1550                1555                1560

Cys Asn Asn Ala Pro Leu Pro Arg Ala Leu Pro Ser Thr Trp Ile
    1565                1570                1575

Glu Asn Lys Leu Tyr Gly Met Ser Asp Pro Asn Trp Pro Gly Glu
    1580                1585                1590

Ser Pro Val Pro Leu Thr Arg Ala Asp Gly Thr Asn Thr Gly Phe
    1595                1600                1605

Pro Arg Tyr Pro Asn Asp Ser Val Tyr Ala Asn Trp Met Leu Ser
    1610                1615                1620

Pro Ser Ala Ala Lys Leu Met Asp Thr Phe Asp Ser
    1625                1630                1635

<210> SEQ ID NO 3
```

<211> LENGTH: 4782
<212> TYPE: DNA
<213> ORGANISM: Artificial Sequence
<220> FEATURE:
<223> OTHER INFORMATION: coding sequence of fusion peptide

<400> SEQUENCE: 3

| | |
|---|---|
| atggcacaga gcaagaggca cgtgtacagc cggacgccca gcggcagcag gatgagtgcg | 60 |
| gaggcaagcg cccggcctct gcgggtgggc tcccgtgtag aggtgattgg aaaaggccac | 120 |
| cgaggcactg tggcctatgt tggagccaca ctgtttgcca ctggcaaatg gtaggcgtg | 180 |
| attctggatg aagcaaaggg caaaaatgat ggaactgttc aaggcaggaa gtacttcact | 240 |
| tgtgatgaag ggcatggcat ctttgtgcgc cagtcccaga tccaggtatt tgaagatgga | 300 |
| gcagatacta cttccccaga gacacctgat tcttctgctt caaaagtcct caaaagagag | 360 |
| ggaactgata caactgcaaa gactagcaaa ctgcggggac tgaagcctaa gaaggcaccg | 420 |
| acagcccgaa agaccacaac tcggcgaccc aagcccacgc gcccagccag tactggggtg | 480 |
| gctggggcca gtagctccct gggcccctct ggctcagcgt cagcaggtga gctgagcagc | 540 |
| agtgagccca gcaccccggc tcagactccg ctggcagcac ccatcatccc cacgccggtc | 600 |
| ctcacctctc ctggagcagt cccccgctt ccttccccat ccaaggagga ggaggacta | 660 |
| agggctcagg tgcgggacct ggaggagaaa ctagagaccc tgagactgaa cggcagaa | 720 |
| gacaaagcaa agctaaaaga gctggagaaa cacaaaatcc agctggagca ggtgcaggaa | 780 |
| tggaagagca aaatgcagga gcagcaggcc gacctgcagc ggcgcctcaa ggaggcgaga | 840 |
| aaggaagcca aggaggcgct ggaggcaaag gaacgctata tggaggagat ggctgatact | 900 |
| gctgatgcca ttgagatggc cactttggac aaggagatgg ctgaagagcg gctgagtcc | 960 |
| ctgcagcagg aggtggaggc actgaaggag cgggtggacg agctcactac tgacttagag | 1020 |
| atcctcaagg ctgagattga agagaagggc tcagatggcg ctgcatccag ttatcagctc | 1080 |
| aagcagcttg aggagcagaa tgcccgcctg aaggatgccc tggtgaggat gcgggatctt | 1140 |
| tcttcctcag agaagcagga gcatgtgaag ctccagaagc tcatggaaaa gaagaaccaa | 1200 |
| gagctggaag ttgtgaggca cagcggag cgtctgcagg aggagctaag ccaggcagag | 1260 |
| agcaccattg atgagctcaa ggagcaggtg gatgctgctc tgggtgctga ggagatggtg | 1320 |
| gagatgctga cagatcggaa cctgaatctg aagagaaag tgcgcgagtt gagggagact | 1380 |
| gtgggagact tggaagcgat gaatgagatg aacgatgagc tgcaggagaa tgcacgtgag | 1440 |
| acagaactgg agctgcggga gcagctggac atggcaggcg cgcgggttcg tgaggcccag | 1500 |
| aagcgtgtgg aggcagccca ggagacggtt gcagactacc agcagaccat caagaagtac | 1560 |
| cgccagctga ccgcccatct acaggatgtg aatcgggaac tgacaaacca gcaggaagca | 1620 |
| tctgtggaga ggcaacagca gccacctcca gagacctttg acttcaaaat caagtttgct | 1680 |
| gagactaagg cccatgccaa ggcaattgag atggaattga gcagatgga ggtggcccag | 1740 |
| gccaatcgac acatgtccct gctgacagcc ttcatgcctg acagcttcct tcggccaggt | 1800 |
| ggggaccatg actgcgttct ggtgctgttg ctcatgcctc gtctcatttg caaggcagag | 1860 |
| ctgatccgga gcaggcccca ggagaagttt gaactaagtg agaactgttc agagcggcct | 1920 |
| gggctgcgag gagctgctgg ggagcaactc agctttgctg ctggactggt gtactcgctg | 1980 |
| agcctgctgc aggccacgct acaccgctat gagcatgccc tctctcagtg cagtgtggat | 2040 |
| gtgtataaga agtgggcag cctgtaccct gagatgagtg cccatgagcg ctccttggat | 2100 |
| ttcctcattg aactgctgca aaggatcag ctggatgaga ctgtcaatgt ggagcctctc | 2160 |

```
accaaggcca tcaagtacta tcagcatctg tacagcatcc accttgccga acagcctgag    2220
gactgtacta tgcagctggc tgaccacatt aagttcacgc agagtgctct ggactgcatg    2280
agtgtggagg taggacggct gcgtgccttc ttgcagggtg ggcaggaggc tacagatatt    2340
gccctcctgc tccgggatct ggaaacttca tgcagtgaca tccgccagtt ctgcaagaag    2400
atccgaaggc gaatgccagg gacagatgct cctgggatcc cagctgcact ggcctttgga    2460
ccacaggtat ctgacacgct cctagactgc aggaaacact tgacgtgggt cgtggctgtg    2520
ctgcaggagg tggcagctgc tgctgcccag ctcattgccc cactggcaga gaatgagggg    2580
ctacttgtgg ctgctctgga ggaactggct ttcaaagcaa gcgagcagat ctatgggacc    2640
ccctccagca gccctatga gtgtctgcgc cagtcatgca acatcctcat cagtaccatg    2700
aacaagctgg ccacagccat gcaggagggg gagtatgatg cagagcggcc ccccagcaag    2760
cctccaccgg ttgaactgcg ggctgctgcc cttcgtgcag agatcacaga tgctgaaggc    2820
ctgggtttga agctcgaaga tcgagagaca gttattaagg agttgaagaa gtcactcaag    2880
attaagggag aggagctaag tgaggccaat gtgcggctga gcctcctgga agaagttg     2940 gacagtgctg ccaaggatgc agatgagcgc atcgagaaag tccagactcg gctggaggag    3000
acccaggcac tgctgcgaaa gaaggagaaa gagtttgagg agacaatgga tgcactccag    3060
gctgacatcg accagctgga ggcagagaag gcagaactaa agcagcgtct gaacagccag    3120
tccaaacgca cgattgaggg actccggggc cctcctcctt caggcattgc tactctggtc    3180
tctggcattg ctggtgaaga acagcagcga ggagccatcc ctgggcaggc tccagggtct    3240
gtgccaggcc cagggctggt gaaggactca ccactgctgc ttcagcagat ctctgccatg    3300
aggctgcaca tctcccagct ccagcatgag aacagcatcc tcaagggagc ccagatgaag    3360
gcatccttgg catccctgcc cctctgcat gttgcaaagc tatcccatga gggccctggc    3420
agtgagttac cagctggagc gctgtatcgt aagaccagcc agctgctgga gacattgaat    3480
caattgagca cacacacgca cgtagtagac atcactcgca ccagccctgc tgccaagagc    3540
ccgtcggccc aacttatgga gcaagtggct cagcttaagt ccctgagtga caccgtcgag    3600
aagctcaagg atgaggtcct caaggagaca gtatctcagc gccctggagc cacagtaccc    3660
actgactttg ccaccttccc ttcatcagcc ttcctcaggg aggatccaaa gtgggaattc    3720
cctcggaaga acttggttct tggaaaaact ctaggagaag gcgaatttgg aaaagtggtc    3780
aaggcaacgg ccttccatct gaaaggcaga gcagggtaca ccacggtggc cgtgaagatg    3840
ctgaaagaga acgcctcccc gagtgagctt cgagacctgc tgtcagagtt caacgtcctg    3900
aagcaggtca accacccaca tgtcatcaaa ttgtatgggg cctgcagcca ggatggcccg    3960
ctcctcctca tcgtggagta cgccaaatac ggctccctgc ggggcttcct ccgcgagagc    4020
cgcaaagtgg ggcctggcta cctgggcagt ggaggcagcc gcaactccag ctccctggac    4080
cacccggatg agcgggccct caccatgggc gacctcatct catttgcctg gcagatctca    4140
caggggatgc agtatctggc cgagatgaag ctcgttcatc gggacttggc agccagaaac    4200
atcctggtag ctgaggggcg gaagatgaag atttcggatt tcggcttgtc ccgagatgtt    4260
tatgaagagg attcctacgt gaagaggagc cagggtcgga ttccagttaa atggatggca    4320
attgaatccc ttttgatca tatctacacc acgcaaagtg atgtatggtc ttttggtgtc    4380
ctgctgtggg agatcgtgac cctagggggn aaccccctatc ctgggattcc tcctgagcgg    4440
ctcttcaacc ttctgaagac cggccaccgg atggagaggc cagacaactg cagcgaggag    4500
```

-continued

```
atgtaccgcc tgatgctgca atgctggaag caggagccgg acaaaaggcc ggtgtttgcg    4560
gacatcagca agacctgga gaagatgatg gttaagagga gagactactt ggaccttgcg    4620
gcgtccactc catctgactc cctgatttat gacgacggcc tctcagagga ggagacaccg    4680
ctggtggact gtaataatgc cccctccct cgagccctcc cttccacatg gattgaaaac    4740
aaactctatg gtagaatttc ccatgcattt actagattct ag                      4782
```

<210> SEQ ID NO 4
<211> LENGTH: 1593
<212> TYPE: PRT
<213> ORGANISM: Artificial Sequence
<220> FEATURE:
<223> OTHER INFORMATION: fusion peptide

<400> SEQUENCE: 4

```
Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Thr Ala Lys Thr
        115                 120                 125

Ser Lys Leu Arg Gly Leu Lys Pro Lys Ala Pro Thr Ala Arg Lys
    130                 135                 140

Thr Thr Thr Arg Arg Pro Lys Pro Thr Arg Pro Ala Ser Thr Gly Val
145                 150                 155                 160

Ala Gly Ala Ser Ser Ser Leu Gly Pro Ser Gly Ser Ala Ser Ala Gly
                165                 170                 175

Glu Leu Ser Ser Ser Glu Pro Ser Thr Pro Ala Gln Thr Pro Leu Ala
            180                 185                 190

Ala Pro Ile Ile Pro Thr Pro Val Leu Thr Ser Pro Gly Ala Val Pro
        195                 200                 205

Pro Leu Pro Ser Pro Ser Lys Glu Glu Glu Gly Leu Arg Ala Gln Val
    210                 215                 220

Arg Asp Leu Glu Glu Lys Leu Glu Thr Leu Arg Leu Lys Arg Ala Glu
225                 230                 235                 240

Asp Lys Ala Lys Leu Lys Glu Leu Glu Lys His Lys Ile Gln Leu Glu
                245                 250                 255

Gln Val Gln Glu Trp Lys Ser Lys Met Gln Glu Gln Ala Asp Leu
            260                 265                 270

Gln Arg Arg Leu Lys Glu Ala Arg Lys Glu Ala Lys Glu Ala Leu Glu
        275                 280                 285

Ala Lys Glu Arg Tyr Met Glu Glu Met Ala Asp Thr Ala Asp Ala Ile
    290                 295                 300

Glu Met Ala Thr Leu Asp Lys Glu Met Ala Glu Glu Arg Ala Glu Ser
305                 310                 315                 320
```

```
Leu Gln Gln Glu Val Glu Ala Leu Lys Glu Arg Val Asp Glu Leu Thr
                325                 330                 335

Thr Asp Leu Glu Ile Leu Lys Ala Glu Ile Glu Lys Gly Ser Asp
            340                 345                 350

Gly Ala Ala Ser Ser Tyr Gln Leu Lys Gln Leu Glu Glu Gln Asn Ala
                355                 360                 365

Arg Leu Lys Asp Ala Leu Val Arg Met Arg Asp Leu Ser Ser Ser Glu
    370                 375                 380

Lys Gln Glu His Val Lys Leu Gln Lys Leu Met Glu Lys Lys Asn Gln
385                 390                 395                 400

Glu Leu Glu Val Val Arg Gln Gln Arg Glu Arg Leu Gln Glu Glu Leu
                405                 410                 415

Ser Gln Ala Glu Ser Thr Ile Asp Glu Leu Lys Glu Gln Val Asp Ala
                420                 425                 430

Ala Leu Gly Ala Glu Glu Met Val Glu Met Leu Thr Asp Arg Asn Leu
            435                 440                 445

Asn Leu Glu Glu Lys Val Arg Glu Leu Arg Glu Thr Val Gly Asp Leu
    450                 455                 460

Glu Ala Met Asn Glu Met Asn Asp Glu Leu Gln Glu Asn Ala Arg Glu
465                 470                 475                 480

Thr Glu Leu Glu Leu Arg Glu Gln Leu Asp Met Ala Gly Ala Arg Val
                485                 490                 495

Arg Glu Ala Gln Lys Arg Val Glu Ala Ala Gln Glu Thr Val Ala Asp
                500                 505                 510

Tyr Gln Gln Thr Ile Lys Lys Tyr Arg Gln Leu Thr Ala His Leu Gln
                515                 520                 525

Asp Val Asn Arg Glu Leu Thr Asn Gln Gln Glu Ala Ser Val Glu Arg
    530                 535                 540

Gln Gln Gln Pro Pro Glu Thr Phe Asp Phe Lys Ile Lys Phe Ala
545                 550                 555                 560

Glu Thr Lys Ala His Ala Lys Ala Ile Glu Met Glu Leu Arg Gln Met
                565                 570                 575

Glu Val Ala Gln Ala Asn Arg His Met Ser Leu Leu Thr Ala Phe Met
                580                 585                 590

Pro Asp Ser Phe Leu Arg Pro Gly Gly Asp His Asp Cys Val Leu Val
                595                 600                 605

Leu Leu Leu Met Pro Arg Leu Ile Cys Lys Ala Glu Leu Ile Arg Lys
    610                 615                 620

Gln Ala Gln Glu Lys Phe Glu Leu Ser Glu Asn Cys Ser Glu Arg Pro
625                 630                 635                 640

Gly Leu Arg Gly Ala Ala Gly Glu Gln Leu Ser Phe Ala Ala Gly Leu
                645                 650                 655

Val Tyr Ser Leu Ser Leu Leu Gln Ala Thr Leu His Arg Tyr Glu His
                660                 665                 670

Ala Leu Ser Gln Cys Ser Val Asp Val Tyr Lys Lys Val Gly Ser Leu
    675                 680                 685

Tyr Pro Glu Met Ser Ala His Glu Arg Ser Leu Asp Phe Leu Ile Glu
    690                 695                 700

Leu Leu His Lys Asp Gln Leu Asp Glu Thr Val Asn Val Glu Pro Leu
705                 710                 715                 720

Thr Lys Ala Ile Lys Tyr Tyr Gln His Leu Tyr Ser Ile His Leu Ala
                725                 730                 735
```

-continued

```
Glu Gln Pro Glu Asp Cys Thr Met Gln Leu Ala Asp His Ile Lys Phe
            740                 745                 750

Thr Gln Ser Ala Leu Asp Cys Met Ser Val Glu Val Gly Arg Leu Arg
            755                 760                 765

Ala Phe Leu Gln Gly Gly Gln Glu Ala Thr Asp Ile Ala Leu Leu Leu
            770                 775                 780

Arg Asp Leu Glu Thr Ser Cys Ser Asp Ile Arg Gln Phe Cys Lys Lys
785                 790                 795                 800

Ile Arg Arg Arg Met Pro Gly Thr Asp Ala Pro Gly Ile Pro Ala Ala
                805                 810                 815

Leu Ala Phe Gly Pro Gln Val Ser Asp Thr Leu Leu Asp Cys Arg Lys
            820                 825                 830

His Leu Thr Trp Val Val Ala Val Leu Gln Glu Val Ala Ala Ala Ala
            835                 840                 845

Ala Gln Leu Ile Ala Pro Leu Ala Glu Asn Glu Gly Leu Leu Val Ala
            850                 855                 860

Ala Leu Glu Glu Leu Ala Phe Lys Ala Ser Glu Gln Ile Tyr Gly Thr
865                 870                 875                 880

Pro Ser Ser Ser Pro Tyr Glu Cys Leu Arg Gln Ser Cys Asn Ile Leu
                885                 890                 895

Ile Ser Thr Met Asn Lys Leu Ala Thr Ala Met Gln Glu Gly Glu Tyr
            900                 905                 910

Asp Ala Glu Arg Pro Pro Ser Lys Pro Pro Val Glu Leu Arg Ala
            915                 920                 925

Ala Ala Leu Arg Ala Glu Ile Thr Asp Ala Gly Leu Gly Leu Lys
            930                 935                 940

Leu Glu Asp Arg Glu Thr Val Ile Lys Glu Leu Lys Lys Ser Leu Lys
945                 950                 955                 960

Ile Lys Gly Glu Glu Leu Ser Glu Ala Asn Val Arg Leu Ser Leu Leu
                965                 970                 975

Glu Lys Lys Leu Asp Ser Ala Ala Lys Asp Ala Asp Glu Arg Ile Glu
            980                 985                 990

Lys Val Gln Thr Arg Leu Glu Glu  Thr Gln Ala Leu Leu  Arg Lys Lys
            995                 1000                1005

Glu Lys  Glu Phe Glu Glu Thr  Met Asp Ala Leu Gln  Ala Asp Ile
    1010                1015                1020

Asp Gln  Leu Glu Ala Glu Lys  Ala Glu Leu Lys Gln  Arg Leu Asn
    1025                1030                1035

Ser Gln  Ser Lys Arg Thr Ile  Glu Gly Leu Arg Gly  Pro Pro Pro
    1040                1045                1050

Ser Gly  Ile Ala Thr Leu Val  Ser Gly Ile Ala Gly  Glu Glu Gln
    1055                1060                1065

Gln Arg  Gly Ala Ile Pro Gly  Gln Ala Pro Gly Ser  Val Pro Gly
    1070                1075                1080

Pro Gly  Leu Val Lys Asp Ser  Pro Leu Leu Leu Gln  Gln Ile Ser
    1085                1090                1095

Ala Met  Arg Leu His Ile Ser  Gln Leu Gln His Glu  Asn Ser Ile
    1100                1105                1110

Leu Lys  Gly Ala Gln Met Lys  Ala Ser Leu Ala Ser  Leu Pro Pro
    1115                1120                1125

Leu His  Val Ala Lys Leu Ser  His Glu Gly Pro Gly  Ser Glu Leu
    1130                1135                1140

Pro Ala  Gly Ala Leu Tyr Arg  Lys Thr Ser Gln Leu  Leu Glu Thr
```

```
            1145                1150                1155
Leu Asn Gln Leu Ser Thr His Thr His Val Val Asp Ile Thr Arg
    1160                1165                1170
Thr Ser Pro Ala Ala Lys Ser Pro Ser Ala Gln Leu Met Glu Gln
    1175                1180                1185
Val Ala Gln Leu Lys Ser Leu Ser Asp Thr Val Glu Lys Leu Lys
    1190                1195                1200
Asp Glu Val Leu Lys Glu Thr Val Ser Gln Arg Pro Gly Ala Thr
    1205                1210                1215
Val Pro Thr Asp Phe Ala Thr Phe Pro Ser Ser Ala Phe Leu Arg
    1220                1225                1230
Glu Asp Pro Lys Trp Glu Phe Pro Arg Lys Asn Leu Val Leu Gly
    1235                1240                1245
Lys Thr Leu Gly Glu Gly Glu Phe Gly Lys Val Val Lys Ala Thr
    1250                1255                1260
Ala Phe His Leu Lys Gly Arg Ala Gly Tyr Thr Thr Val Ala Val
    1265                1270                1275
Lys Met Leu Lys Glu Asn Ala Ser Pro Ser Glu Leu Arg Asp Leu
    1280                1285                1290
Leu Ser Glu Phe Asn Val Leu Lys Gln Val Asn His Pro His Val
    1295                1300                1305
Ile Lys Leu Tyr Gly Ala Cys Ser Gln Asp Gly Pro Leu Leu Leu
    1310                1315                1320
Ile Val Glu Tyr Ala Lys Tyr Gly Ser Leu Arg Gly Phe Leu Arg
    1325                1330                1335
Glu Ser Arg Lys Val Gly Pro Gly Tyr Leu Gly Ser Gly Gly Ser
    1340                1345                1350
Arg Asn Ser Ser Ser Leu Asp His Pro Asp Glu Arg Ala Leu Thr
    1355                1360                1365
Met Gly Asp Leu Ile Ser Phe Ala Trp Gln Ile Ser Gln Gly Met
    1370                1375                1380
Gln Tyr Leu Ala Glu Met Lys Leu Val His Arg Asp Leu Ala Ala
    1385                1390                1395
Arg Asn Ile Leu Val Ala Glu Gly Arg Lys Met Lys Ile Ser Asp
    1400                1405                1410
Phe Gly Leu Ser Arg Asp Val Tyr Glu Glu Asp Ser Tyr Val Lys
    1415                1420                1425
Arg Ser Gln Gly Arg Ile Pro Val Lys Trp Met Ala Ile Glu Ser
    1430                1435                1440
Leu Phe Asp His Ile Tyr Thr Thr Gln Ser Asp Val Trp Ser Phe
    1445                1450                1455
Gly Val Leu Leu Trp Glu Ile Val Thr Leu Gly Gly Asn Pro Tyr
    1460                1465                1470
Pro Gly Ile Pro Pro Glu Arg Leu Phe Asn Leu Leu Lys Thr Gly
    1475                1480                1485
His Arg Met Glu Arg Pro Asp Asn Cys Ser Glu Glu Met Tyr Arg
    1490                1495                1500
Leu Met Leu Gln Cys Trp Lys Gln Glu Pro Asp Lys Arg Pro Val
    1505                1510                1515
Phe Ala Asp Ile Ser Lys Asp Leu Glu Lys Met Met Val Lys Arg
    1520                1525                1530
Arg Asp Tyr Leu Asp Leu Ala Ala Ser Thr Pro Ser Asp Ser Leu
    1535                1540                1545
```

```
Ile Tyr Asp Asp Gly Leu Ser Glu Glu Glu Thr Pro Leu Val Asp
    1550                1555                1560

Cys Asn Asn Ala Pro Leu Pro Arg Ala Leu Pro Ser Thr Trp Ile
1565                1570                1575

Glu Asn Lys Leu Tyr Gly Arg Ile Ser His Ala Phe Thr Arg Phe
1580                1585                1590

<210> SEQ ID NO 5
<211> LENGTH: 4506
<212> TYPE: DNA
<213> ORGANISM: Artificial Sequence
<220> FEATURE:
<223> OTHER INFORMATION: coding sequence of fusion peptide

<400> SEQUENCE: 5
atgatgagac aggcaccgac agcccgaaag accacaactc ggcgacccaa gcccacgcgc      60
ccagccagta ctggggtggc tggggccagt agctccctgg cccctctgg ctcagcgtca     120 gcaggtgagc tgagcagcag tgagcccagc accccggctc agactccgct ggcagcaccc    180
atcatcccca cgccggtcct cacctctcct ggagcagtcc cccgcttcc ttccccatcc     240 aaggaggagg agggactaag ggctcaggtg cgggacctgg aggagaaact agagaccctg    300
agactgaaac gggcagaaga caaagcaaag ctaaagagc tggagaaaca caaaatccag     360
ctggagcagg tgcaggaatg gaagagcaaa atgcaggagc agcaggccga cctgcagcgg    420
cgcctcaagg aggcgagaaa ggaagccaag gaggcgctgg aggcaaagga acgctatatg    480
gaggagatgc ctgatactgc tgatgccatt gagatggcca ctttggacaa ggagatggct    540
gaagagcggg ctgagtccct gcagcaggag gtggaggcac tgaaggagcg ggtggacgag    600
ctcactactg acttagagat cctcaaggct gagattgaag agaagggctc agatggcgct    660
gcatccagtt atcagctcaa gcagcttgag gagcagaatg cccgcctgaa ggatgccctg    720
gtgaggatgc gggatctttc ttcctcagag aagcaggagc atgtgaagct ccagaagctc    780
atggaaaaga gaaccaaga gctggaagtt gtgaggcaac agcgggagcg tctgcaggag    840
gagctaagcc aggcagagag caccattgat gagctcaagg agcaggtgga tgctgctctg    900
ggtgctgagg agatggtgga gatgctgaca gatcggaacc tgaatctgga agagaaagtg    960
cgcgagttga gggagactgt gggagacttg aagcgatga atgagatgaa cgatgagctg    1020
caggagaatg cacgtgagac agaactggag ctgcgggagc agctggacat ggcaggcgcg   1080
cgggttcgtg aggcccagaa gcgtgtggag gcagcccagg agacggttgc agactaccag   1140
cagaccatca gaagtaccg ccagctgacc gcccatctac aggatgtgaa tcgggaactg   1200
acaaaccagc aggaagcatc tgtggagagg aacagcagc acctccaga gacctttgac    1260 ttcaaaatca gtttgctga actaaggcc catgccaagg caattgagat ggaattgagg    1320
cagatggagt ggcccaggc caatcgacac atgtccctgc tgacagcctt catgcctgac   1380
agcttccttc ggccaggtgg ggaccatgac tgcgttctgg tgctgttgct catgcctcgt   1440
ctcatttgca aggcagagct gatccggaag caggcccagg agaagtttga actaagtgag   1500
aactgttcag agcggcctgg gctgcgagga gctgctgggg agcaactcag ctttgctgct   1560
ggactggtgt actcgctgag cctgctgcag gccacgctac accgctatga gcatgccctc   1620
tctcagtgca gtgtggatgt gtataagaaa gtgggcagcc tgtaccctga tgagtgcc    1680 catgagcgct ccttggattt cctcattgaa ctgctgcaca ggatcagct ggatgagact   1740 gtcaatgtgg agcctctcac caaggccatc aagtactatc agcatctgta cagcatccac   1800
```

| | |
|---|---|
| cttgccgaac agcctgagga ctgtactatg cagctggctg accacattaa gttcacgcag | 1860 |
| agtgctctgg actgcatgag tgtggaggta ggacggctgc gtgccttctt gcagggtggg | 1920 |
| caggaggcta cagatattgc cctcctgctc cgggatctgg aaacttcatg cagtgacatc | 1980 |
| cgccagttct gcaagaagat ccgaaggcga atgccaggga cagatgctcc tgggatccca | 2040 |
| gctgcactgg cctttggacc acaggtatct gacacgctcc tagactgcag gaaacacttg | 2100 |
| acgtgggtcg tggctgtgct gcaggaggtg gcagctgctg ctgcccagct cattgcccca | 2160 |
| ctggcagaga atgaggggct acttgtggct gctctggagg aactggcttt caaagcaagc | 2220 |
| gagcagatct atgggacccc ctccagcagc ccctatgagt gtctgcgcca gtcatgcaac | 2280 |
| atcctcatca gtaccatgaa caagctggcc acagccatgc aggaggggga gtatgatgca | 2340 |
| gagcggcccc ccagcaagcc tccaccggtt gaactgcggg ctgctgccct tcgtgcagag | 2400 |
| atcacagatg ctgaaggcct gggtttgaag ctcgaagatc gagagacagt tattaaggag | 2460 |
| ttgaagaagt cactcaagat taagggagag gagctaagtg aggccaatgt gcggctgagc | 2520 |
| ctcctggaga agaagttgga cagtgctgcc aaggatgcag atgagcgcat cgagaaagtc | 2580 |
| cagactcggc tggaggagac ccaggcactg ctgcgaaaga aggagaaaga gtttgaggag | 2640 |
| acaatggatg cactccaggc tgacatcgac cagctggagg cagagaaggc agaactaaag | 2700 |
| cagcgtctga acagccagtc caaacgcacg attgagggac tccggggccc tcctccttca | 2760 |
| ggcattgcta ctctggtctc tggcattgct ggtgaagaac agcagcgagg agccatccct | 2820 |
| gggcaggctc cagggtctgt gccaggccca gggctggtga aggactcacc actgctgctt | 2880 |
| cagcagatct ctgccatgag gctgcacatc tcccagctcc agcatgagaa cagcatcctc | 2940 |
| aagggagccc agatgaaggc atccttggca tccctgcccc ctctgcatgt tgcaaagcta | 3000 |
| tcccatgagg gccctggcag tgagttacca gctggagcgc tgtatcgtaa gaccagccag | 3060 |
| ctgctggaga cattgaatca attgagcaca cacacgcacg tagtagacat cactcgcacc | 3120 |
| agccctgctg ccaagagccc gtcggcccaa cttatggagc aagtggctca gcttaagtcc | 3180 |
| ctgagtgaca ccgtcgagaa gctcaaggat gaggtcctca aggagacagt atctcagcgc | 3240 |
| cctggagcca cagtacccac tgactttgcc accttcccct catcagcctt cctcagggag | 3300 |
| gatccaaagt gggaattccc tcggaagaac ttggttcttg gaaaaactct aggagaaggc | 3360 |
| gaatttggaa aagtggtcaa ggcaacggcc ttccatctga aggcagagc agggtacacc | 3420 |
| acggtggccg tgaagatgct gaaagagaac gcctccccga gtgagcttcg agacctgctg | 3480 |
| tcagagttca acgtcctgaa gcaggtcaac cacccacatg tcatcaaatt gtatgggcc | 3540 |
| tgcagccagg atggcccgct cctcctcatc gtggagtacg ccaaatacgg ctccctgcgg | 3600 |
| ggcttcctcc gcgagagccg caaagtgggg cctggctacc tgggcagtgg aggcagccgc | 3660 |
| aactccagct ccctggacca cccggatgag cgggccctca ccatgggcga cctcatctca | 3720 |
| tttgcctggc agatctcaca ggggatgcag tatctggccg agatgaagct cgttcatcgg | 3780 |
| gacttggcag ccagaaacat cctggtagct gaggggcgga agatgaagat ttcggatttc | 3840 |
| ggcttgtccc gagatgttta tgaagaggat tcctacgtga agaggagcca gggtcggatt | 3900 |
| ccagttaaat ggatggcaat tgaatccctt tttgatcata tctacaccac gcaaagtgat | 3960 |
| gtatggtctt ttggtgtcct gctgtgggag atcgtgaccc tagggggaaa cccctatcct | 4020 |
| gggattcctc ctgagcggct cttcaacctt ctgaagaccg gccaccggat ggagaggcca | 4080 |
| gacaactgca gcgaggagat gtaccgcctg atgctgcaat gctggaagca ggagccggac | 4140 |

-continued

```
aaaaggccgg tgtttgcgga catcagcaaa gacctggaga agatgatggt taagaggaga    4200
gactacttgg accttgcggc gtccactcca tctgactccc tgatttatga cgacggcctc    4260
tcagaggagg agacaccgct ggtggactgt aataatgccc cctccctcg agccctccct     4320 tccacatgga ttgaaaacaa actctatggc atgtcagacc cgaactggcc tggagagagt    4380
cctgtaccac tcacgagagc tgatggcact aacactgggt ttccaagata tccaaatgat    4440
agtgtatatg ctaactggat gctttcaccc tcagcggcaa aattaatgga cacgtttgat    4500
agttaa                                                                4506
```

<210> SEQ ID NO 6
<211> LENGTH: 1501
<212> TYPE: PRT
<213> ORGANISM: Artificial Sequence
<220> FEATURE:
<223> OTHER INFORMATION: fusion peptide

<400> SEQUENCE: 6

```
Met Met Arg Gln Ala Pro Thr Ala Arg Lys Thr Thr Thr Arg Arg Pro
1               5                   10                  15

Lys Pro Thr Arg Pro Ala Ser Thr Gly Val Ala Gly Ala Ser Ser Ser
            20                  25                  30

Leu Gly Pro Ser Gly Ser Ala Ser Ala Gly Glu Leu Ser Ser Ser Glu
        35                  40                  45

Pro Ser Thr Pro Ala Gln Thr Pro Leu Ala Ala Pro Ile Ile Pro Thr
    50                  55                  60

Pro Val Leu Thr Ser Pro Gly Ala Val Pro Pro Leu Pro Ser Pro Ser
65                  70                  75                  80

Lys Glu Glu Glu Gly Leu Arg Ala Gln Val Arg Asp Leu Glu Glu Lys
                85                  90                  95

Leu Glu Thr Leu Arg Leu Lys Arg Ala Glu Asp Lys Ala Lys Leu Lys
            100                 105                 110

Glu Leu Glu Lys His Lys Ile Gln Leu Glu Gln Val Gln Glu Trp Lys
        115                 120                 125

Ser Lys Met Gln Glu Gln Gln Ala Asp Leu Gln Arg Arg Leu Lys Glu
    130                 135                 140

Ala Arg Lys Glu Ala Lys Glu Ala Leu Glu Ala Lys Glu Arg Tyr Met
145                 150                 155                 160

Glu Glu Met Ala Asp Thr Ala Asp Ala Ile Glu Met Ala Thr Leu Asp
                165                 170                 175

Lys Glu Met Ala Glu Glu Arg Ala Glu Ser Leu Gln Gln Glu Val Glu
            180                 185                 190

Ala Leu Lys Glu Arg Val Asp Glu Leu Thr Thr Asp Leu Glu Ile Leu
        195                 200                 205

Lys Ala Glu Ile Glu Glu Lys Gly Ser Asp Gly Ala Ala Ser Ser Tyr
    210                 215                 220

Gln Leu Lys Gln Leu Glu Glu Gln Asn Ala Arg Leu Lys Asp Ala Leu
225                 230                 235                 240

Val Arg Met Arg Asp Leu Ser Ser Ser Glu Lys Gln Glu His Val Lys
                245                 250                 255

Leu Gln Lys Leu Met Glu Lys Lys Asn Gln Glu Leu Glu Val Val Arg
            260                 265                 270

Gln Gln Arg Glu Arg Leu Gln Glu Glu Leu Ser Gln Ala Glu Ser Thr
        275                 280                 285

Ile Asp Glu Leu Lys Glu Gln Val Asp Ala Ala Leu Gly Ala Glu Glu
```

```
            290                 295                 300
Met Val Glu Met Leu Thr Asp Arg Asn Leu Asn Leu Glu Glu Lys Val
305                 310                 315                 320

Arg Glu Leu Arg Glu Thr Val Gly Asp Leu Glu Ala Met Asn Glu Met
                325                 330                 335

Asn Asp Glu Leu Gln Glu Asn Ala Arg Glu Thr Glu Leu Glu Leu Arg
                340                 345                 350

Glu Gln Leu Asp Met Ala Gly Ala Arg Val Arg Glu Ala Gln Lys Arg
                355                 360                 365

Val Glu Ala Ala Gln Glu Thr Val Ala Asp Tyr Gln Gln Thr Ile Lys
370                 375                 380

Lys Tyr Arg Gln Leu Thr Ala His Leu Gln Asp Val Asn Arg Glu Leu
385                 390                 395                 400

Thr Asn Gln Gln Glu Ala Ser Val Glu Arg Gln Gln Pro Pro Pro
                405                 410                 415

Glu Thr Phe Asp Phe Lys Ile Lys Phe Ala Glu Thr Lys Ala His Ala
                420                 425                 430

Lys Ala Ile Glu Met Glu Leu Arg Gln Met Glu Val Ala Gln Ala Asn
                435                 440                 445

Arg His Met Ser Leu Leu Thr Ala Phe Met Pro Asp Ser Phe Leu Arg
                450                 455                 460

Pro Gly Gly Asp His Asp Cys Val Leu Val Leu Leu Met Pro Arg
465                 470                 475                 480

Leu Ile Cys Lys Ala Glu Leu Ile Arg Lys Gln Ala Gln Glu Lys Phe
                485                 490                 495

Glu Leu Ser Glu Asn Cys Ser Glu Arg Pro Gly Leu Arg Gly Ala Ala
                500                 505                 510

Gly Glu Gln Leu Ser Phe Ala Ala Gly Leu Val Tyr Ser Leu Ser Leu
                515                 520                 525

Leu Gln Ala Thr Leu His Arg Tyr Glu His Ala Leu Ser Gln Cys Ser
                530                 535                 540

Val Asp Val Tyr Lys Lys Val Gly Ser Leu Tyr Pro Glu Met Ser Ala
545                 550                 555                 560

His Glu Arg Ser Leu Asp Phe Leu Ile Glu Leu Leu His Lys Asp Gln
                565                 570                 575

Leu Asp Glu Thr Val Asn Val Glu Pro Leu Thr Lys Ala Ile Lys Tyr
                580                 585                 590

Tyr Gln His Leu Tyr Ser Ile His Leu Ala Glu Gln Pro Glu Asp Cys
                595                 600                 605

Thr Met Gln Leu Ala Asp His Ile Lys Phe Thr Gln Ser Ala Leu Asp
610                 615                 620

Cys Met Ser Val Glu Val Gly Arg Leu Arg Ala Phe Leu Gln Gly Gly
625                 630                 635                 640

Gln Glu Ala Thr Asp Ile Ala Leu Leu Leu Arg Asp Leu Glu Thr Ser
                645                 650                 655

Cys Ser Asp Ile Arg Gln Phe Cys Lys Lys Ile Arg Arg Met Pro
                660                 665                 670

Gly Thr Asp Ala Pro Gly Ile Pro Ala Ala Leu Ala Phe Gly Pro Gln
                675                 680                 685

Val Ser Asp Thr Leu Leu Asp Cys Arg Lys His Leu Thr Trp Val Val
                690                 695                 700

Ala Val Leu Gln Glu Val Ala Ala Ala Ala Gln Leu Ile Ala Pro
705                 710                 715                 720
```

```
Leu Ala Glu Asn Glu Gly Leu Val Ala Leu Glu Glu Leu Ala
            725                 730                 735

Phe Lys Ala Ser Glu Gln Ile Tyr Gly Thr Pro Ser Ser Pro Tyr
            740                 745                 750

Glu Cys Leu Arg Gln Ser Cys Asn Ile Leu Ile Ser Thr Met Asn Lys
            755                 760                 765

Leu Ala Thr Ala Met Gln Glu Gly Tyr Asp Ala Glu Arg Pro
770                 775                 780

Ser Lys Pro Pro Pro Val Glu Leu Arg Ala Ala Ala Leu Arg Ala Glu
785                 790                 795                 800

Ile Thr Asp Ala Glu Gly Leu Gly Leu Lys Leu Glu Asp Arg Glu Thr
                    805                 810                 815

Val Ile Lys Glu Leu Lys Lys Ser Leu Lys Ile Lys Gly Glu Glu Leu
                    820                 825                 830

Ser Glu Ala Asn Val Arg Leu Ser Leu Leu Glu Lys Lys Leu Asp Ser
                    835                 840                 845

Ala Ala Lys Asp Ala Asp Glu Arg Ile Glu Lys Val Gln Thr Arg Leu
                    850                 855                 860

Glu Glu Thr Gln Ala Leu Leu Arg Lys Lys Glu Lys Glu Phe Glu Glu
865                 870                 875                 880

Thr Met Asp Ala Leu Gln Ala Asp Ile Asp Gln Leu Glu Ala Glu Lys
                    885                 890                 895

Ala Glu Leu Lys Gln Arg Leu Asn Ser Gln Ser Lys Arg Thr Ile Glu
                    900                 905                 910

Gly Leu Arg Gly Pro Pro Ser Gly Ile Ala Thr Leu Val Ser Gly
                    915                 920                 925

Ile Ala Gly Glu Glu Gln Gln Arg Gly Ala Ile Pro Gly Gln Ala Pro
        930                 935                 940

Gly Ser Val Pro Gly Pro Gly Leu Val Lys Asp Ser Pro Leu Leu Leu
945                 950                 955                 960

Gln Gln Ile Ser Ala Met Arg Leu His Ile Ser Gln Leu Gln His Glu
                    965                 970                 975

Asn Ser Ile Leu Lys Gly Ala Gln Met Lys Ala Ser Leu Ala Ser Leu
                    980                 985                 990

Pro Pro Leu His Val Ala Lys Leu  Ser His Glu Gly Pro  Gly Ser Glu
                    995                 1000                1005

Leu Pro  Ala Gly Ala Leu Tyr  Arg Lys Thr Ser Gln  Leu Leu Glu
        1010                1015                1020

Thr Leu  Asn Gln Leu Ser Thr  His Thr His Val Val  Asp Ile Thr
        1025                1030                1035

Arg Thr  Ser Pro Ala Ala Lys  Ser Pro Ser Ala Gln  Leu Met Glu
        1040                1045                1050

Gln Val  Ala Gln Leu Lys Ser  Leu Ser Asp Thr Val  Glu Lys Leu
        1055                1060                1065

Lys Asp  Glu Val Leu Lys Glu  Thr Val Ser Gln Arg  Pro Gly Ala
        1070                1075                1080

Thr Val  Pro Thr Asp Phe Ala  Thr Phe Pro Ser Ser  Ala Phe Leu
        1085                1090                1095

Arg Glu  Asp Pro Lys Trp Glu  Phe Pro Arg Lys Asn  Leu Val Leu
        1100                1105                1110

Gly Lys  Thr Leu Gly Glu Gly  Glu Phe Gly Lys Val  Val Lys Ala
        1115                1120                1125
```

```
Thr Ala Phe His Leu Lys Gly Arg Ala Gly Tyr Thr Val Ala
1130                1135                1140

Val Lys Met Leu Lys Glu Asn Ala Ser Pro Ser Glu Leu Arg Asp
1145                1150                1155

Leu Leu Ser Glu Phe Asn Val Leu Lys Gln Val Asn His Pro His
1160                1165                1170

Val Ile Lys Leu Tyr Gly Ala Cys Ser Gln Asp Gly Pro Leu Leu
1175                1180                1185

Leu Ile Val Glu Tyr Ala Lys Tyr Gly Ser Leu Arg Gly Phe Leu
1190                1195                1200

Arg Glu Ser Arg Lys Val Gly Pro Gly Tyr Leu Gly Ser Gly Gly
1205                1210                1215

Ser Arg Asn Ser Ser Leu Asp His Pro Asp Glu Arg Ala Leu
1220                1225                1230

Thr Met Gly Asp Leu Ile Ser Phe Ala Trp Gln Ile Ser Gln Gly
1235                1240                1245

Met Gln Tyr Leu Ala Glu Met Lys Leu Val His Arg Asp Leu Ala
1250                1255                1260

Ala Arg Asn Ile Leu Val Ala Glu Gly Arg Lys Met Lys Ile Ser
1265                1270                1275

Asp Phe Gly Leu Ser Arg Asp Val Tyr Glu Glu Asp Ser Tyr Val
1280                1285                1290

Lys Arg Ser Gln Gly Arg Ile Pro Val Lys Trp Met Ala Ile Glu
1295                1300                1305

Ser Leu Phe Asp His Ile Tyr Thr Thr Gln Ser Asp Val Trp Ser
1310                1315                1320

Phe Gly Val Leu Leu Trp Glu Ile Val Thr Leu Gly Gly Asn Pro
1325                1330                1335

Tyr Pro Gly Ile Pro Pro Glu Arg Leu Phe Asn Leu Leu Lys Thr
1340                1345                1350

Gly His Arg Met Glu Arg Pro Asp Asn Cys Ser Glu Glu Met Tyr
1355                1360                1365

Arg Leu Met Leu Gln Cys Trp Lys Gln Glu Pro Asp Lys Arg Pro
1370                1375                1380

Val Phe Ala Asp Ile Ser Lys Asp Leu Glu Lys Met Met Val Lys
1385                1390                1395

Arg Arg Asp Tyr Leu Asp Leu Ala Ala Ser Thr Pro Ser Asp Ser
1400                1405                1410

Leu Ile Tyr Asp Asp Gly Leu Ser Glu Glu Glu Thr Pro Leu Val
1415                1420                1425

Asp Cys Asn Asn Ala Pro Leu Pro Arg Ala Leu Pro Ser Thr Trp
1430                1435                1440

Ile Glu Asn Lys Leu Tyr Gly Met Ser Asp Pro Asn Trp Pro Gly
1445                1450                1455

Glu Ser Pro Val Pro Leu Thr Arg Ala Asp Gly Thr Asn Thr Gly
1460                1465                1470

Phe Pro Arg Tyr Pro Asn Asp Ser Val Tyr Ala Asn Trp Met Leu
1475                1480                1485

Ser Pro Ser Ala Ala Lys Leu Met Asp Thr Phe Asp Ser
1490                1495                1500

<210> SEQ ID NO 7
<211> LENGTH: 4380
<212> TYPE: DNA
```

<213> ORGANISM: Artificial Sequence
<220> FEATURE:
<223> OTHER INFORMATION: coding sequence of fusion peptide

<400> SEQUENCE: 7

```
atgatgagac aggcaccgac agcccgaaag accacaactc ggcgacccaa gcccacgcgc      60
ccagccagta ctggggtggc tggggccagt agctccctgg gccctctgg ctcagcgtca      120
gcaggtgagc tgagcagcag tgagcccagc accccggctc agactccgct ggcagcaccc     180
atcatcccca cgccggtcct cacctctcct ggagcagtcc ccccgcttcc ttccccatcc     240
aaggaggagg agggactaag ggctcaggtg cgggacctgg aggagaaact agagaccctg     300
agactgaaac gggcagaaga caaagcaaag ctaaaagagc tggagaaaca caaaatccag     360
ctggagcagg tgcaggaatg gaagagcaaa atgcaggagc agcaggccga cctgcagcgg     420
cgcctcaagg aggcgagaaa ggaagccaag gaggcgctgg aggcaaagga acgctatatg     480
gaggagatgg ctgatactgc tgatgccatt gagatggcca ctttggacaa ggagatggct     540
gaagagcggg ctgagtccct gcagcaggag gtggaggcac tgaaggagcg ggtggacgag     600
ctcactactg acttagagat cctcaaggct gagattgaag agaagggctc agatggcgct     660
gcatccagtt atcagctcaa gcagcttgag gagcagaatg cccgcctgaa ggatgccctg     720
gtgaggatgc gggatctttc ttcctcagag aagcaggagc atgtgaagct ccagaagctc     780
atggaaaaga gaaccaaga gctggaagtt gtgaggcaac agcgggagcg tctgcaggag     840
gagctaagcc aggcagagag caccattgat gagctcaagg agcaggtgga tgctgctctg     900
ggtgctgagg agatggtgga gatgctgaca gatcggaacc tgaatctgga agagaaagtg     960
cgcgagttga gggagactgt gggagacttg aagcgatga atgagatgaa cgatgagctg    1020
caggagaatg cacgtgagac agaactggag ctgcgggagc agctggacat ggcaggcgcg    1080
cgggttcgtg aggcccagaa gcgtgtggag gcagcccagg agacggttgc agactaccag    1140
cagaccatca gaagtaccg ccagctgacc gcccatctac aggatgtgaa tcgggaactg    1200
acaaaccagc aggaagcatc tgtggagagg caacagcagc cacctccaga gacctttgac    1260
ttcaaaatca gtttgctga gactaaggcc catgccaagg caattgagat ggaattgagg    1320
cagatggagg tggcccaggc caatcgacac atgtccctgc tgacagcctt catgcctgac    1380
agcttccttc ggccaggtgg ggaccatgac tgcgttctgg tgctgttgct catgcctcgt    1440
ctcatttgca aggcagagct gatccggaag caggcccagg agaagtttga actaagtgag    1500
aactgttcag agcggcctgg gctgcgagga gctgctgggg agcaactcag ctttgctgct    1560
ggactggtgt actcgctgag cctgctgcag gccacgctac accgctatga gcatgccctc    1620
tctcagtgca gtgtggatgt gtataagaaa gtgggcagcc tgtaccctga tgagtgcc    1680
catgagcgct ccttggattt cctcattgaa ctgctgcaca aggatcagct ggatgagact    1740
gtcaatgtgg agcctctcac caaggccatc aagtactatc agcatctgta cagcatccac    1800
cttgccgaac agcctgagga ctgtactatg cagctggctg accacattaa gttcacgcag    1860
agtgctctgg actgcatgag tgtggaggta ggacggctgc gtgccttctt gcagggtggg    1920
caggaggcta cagatattgc cctcctgctc cgggatctgg aaacttcatg cagtgacatc    1980
cgccagttct gcaagaagat ccgaaggcga atgccaggga cagatgctcc tgggatccca    2040
gctgcactgg cctttggacc acaggtatct gacacgctcc tagactgcag gaaacacttg    2100
acgtgggtcg tggctgtgct gcaggaggtg gcagctgctg ctgcccagct cattgcccca    2160
ctggcagaga atgagggggct acttgtggct gctctggagg aactggctt caaagcaagc    2220
```

```
gagcagatct atgggacccc ctccagcagc ccctatgagt gtctgcgcca gtcatgcaac    2280
atcctcatca gtaccatgaa caagctggcc acagccatgc aggaggggga gtatgatgca    2340
gagcggcccc ccagcaagcc tccaccggtt gaactgcggg ctgctgccct tcgtgcagag    2400
atcacagatg ctgaaggcct gggtttgaag ctcgaagatc gagagacagt tattaaggag    2460
ttgaagaagt cactcaagat taagggagag gagctaagtg aggccaatgt gcggctgagc    2520
ctcctggaga agaagttgga cagtgctgcc aaggatgcag atgagcgcat cgagaaagtc    2580
cagactcggc tggaggagac ccaggcactg ctgcgaaaga aggagaaaga gtttgaggag    2640
acaatggatg cactccaggc tgacatcgac cagctggagg cagagaaggc agaactaaag    2700
cagcgtctga acagccagtc caaacgcacg attgagggac tccggggccc tcctccttca    2760
ggcattgcta ctctggtctc tggcattgct ggtgaagaac agcagcgagg agccatccct    2820
gggcaggctc cagggtctgt gccaggccca gggctggtga aggactcacc actgctgctt    2880
cagcagatct ctgccatgag gctgcacatc tcccagctcc agcatgagaa cagcatcctc    2940
aagggagccc agatgaaggc atccttggca tccctgcccc ctctgcatgt tgcaaagcta    3000
tcccatgagg gccctggcag tgagttacca gctggagcgc tgtatcgtaa gaccagccag    3060
ctgctggaga cattgaatca attgagcaca cacacgcacg tagtagacat cactcgcacc    3120
agccctgctg ccaagagccc gtcggcccaa cttatggagc aagtggctca gcttaagtcc    3180
ctgagtgaca ccgtcgagaa gctcaaggat gaggtcctca aggagacagt atctcagcgc    3240
cctggagcca cagtacccac tgactttgcc accttccctt catcagcctt cctcagggag    3300
gatccaaagt gggaattccc tcggaagaac ttggttcttg gaaaaactct aggagaaggc    3360
gaatttggaa aagtggtcaa ggcaacggcc ttccatctga aggcagagc agggtacacc    3420 acggtggccg tgaagatgct gaaagagaac gcctccccga gtgagcttcg agacctgctg    3480
tcagagttca acgtcctgaa gcaggtcaac cacccacatg tcatcaaatt gtatggggcc    3540
tgcagccagg atgcccgct cctcctcatc gtggagtacg ccaaatacgg ctccctgcgg    3600
ggcttcctcc gcgagagccg caaagtgggg cctggctacc tggcagtgg aggcagccgc    3660 aactccagct ccctggacca cccggatgag cgggccctca ccatgggcga cctcatctca    3720
tttgcctggc agatctcaca ggggatgcag tatctggccg agatgaagct cgttcatcgg    3780
gacttggcag ccagaaacat cctggtagct gaggggcgga agatgaagat ttcggatttc    3840
ggcttgtccc gagatgttta tgaagaggat tcctacgtga agaggagcca gggtcggatt    3900
ccagttaaat ggatggcaat tgaatccctt tttgatcata tctacaccac gcaaagtgat    3960
gtatggtctt ttggtgtcct gctgtgggag atcgtgaccc taggggaaa cccctatcct    4020 gggattcctc ctgagcggct cttcaacctt ctgaagaccg gcaccggat ggagaggcca    4080 gacaactgca gcgaggagat gtaccgcctg atgctgcaat gctggaagca ggagccggac    4140
aaaaggccgg tgtttgcgga catcagcaaa gacctggaga agatgatggt taagaggaga    4200
gactacttgg accttgcggc gtccactcca tctgactccc tgatttatga cgacggcctc    4260
tcagaggagg agacaccgct ggtggactgt aataatgccc ccctccctcg agccctccct    4320
tccacatgga ttgaaaacaa actctatggt agaatttccc atgcatttac tagattctag    4380
```

<210> SEQ ID NO 8
<211> LENGTH: 1459
<212> TYPE: PRT
<213> ORGANISM: Artificial Sequence
<220> FEATURE:

<223> OTHER INFORMATION: fusion peptide

<400> SEQUENCE: 8

```
Met Met Arg Gln Ala Pro Thr Ala Arg Lys Thr Thr Thr Arg Arg Pro
1               5                   10                  15
Lys Pro Thr Arg Pro Ala Ser Thr Gly Val Ala Gly Ser Ser Ser Ser
            20                  25                  30
Leu Gly Pro Ser Gly Ser Ala Ser Ala Gly Glu Leu Ser Ser Ser Glu
        35                  40                  45
Pro Ser Thr Pro Ala Gln Thr Pro Leu Ala Ala Pro Ile Ile Pro Thr
    50                  55                  60
Pro Val Leu Thr Ser Pro Gly Ala Val Pro Leu Pro Ser Pro Ser
65                  70                  75                  80
Lys Glu Glu Glu Gly Leu Arg Ala Gln Val Arg Asp Leu Glu Lys
                85                  90                  95
Leu Glu Thr Leu Arg Leu Lys Arg Ala Glu Asp Lys Ala Lys Leu Lys
            100                 105                 110
Glu Leu Glu Lys His Lys Ile Gln Leu Glu Gln Val Gln Glu Trp Lys
        115                 120                 125
Ser Lys Met Gln Glu Gln Gln Ala Asp Leu Gln Arg Arg Leu Lys Glu
130                 135                 140
Ala Arg Lys Glu Ala Lys Glu Ala Leu Glu Ala Lys Glu Arg Tyr Met
145                 150                 155                 160
Glu Glu Met Ala Asp Thr Ala Asp Ala Ile Glu Met Ala Thr Leu Asp
                165                 170                 175
Lys Glu Met Ala Glu Glu Arg Ala Glu Ser Leu Gln Gln Glu Val Glu
            180                 185                 190
Ala Leu Lys Glu Arg Val Asp Glu Leu Thr Thr Asp Leu Glu Ile Leu
        195                 200                 205
Lys Ala Glu Ile Glu Glu Lys Gly Ser Asp Gly Ala Ala Ser Ser Tyr
    210                 215                 220
Gln Leu Lys Gln Leu Glu Glu Gln Asn Ala Arg Leu Lys Asp Ala Leu
225                 230                 235                 240
Val Arg Met Arg Asp Leu Ser Ser Ser Glu Lys Gln Glu His Val Lys
                245                 250                 255
Leu Gln Lys Leu Met Glu Lys Lys Asn Gln Glu Leu Glu Val Val Arg
            260                 265                 270
Gln Gln Arg Glu Arg Leu Gln Glu Glu Leu Ser Gln Ala Glu Ser Thr
        275                 280                 285
Ile Asp Glu Leu Lys Glu Gln Val Asp Ala Ala Leu Gly Ala Glu Glu
    290                 295                 300
Met Val Glu Met Leu Thr Asp Arg Asn Leu Asn Leu Glu Glu Lys Val
305                 310                 315                 320
Arg Glu Leu Arg Glu Thr Val Gly Asp Leu Glu Ala Met Asn Glu Met
                325                 330                 335
Asn Asp Glu Leu Gln Glu Asn Ala Arg Glu Thr Glu Leu Glu Leu Arg
            340                 345                 350
Glu Gln Leu Asp Met Ala Gly Ala Arg Val Arg Glu Ala Gln Lys Arg
        355                 360                 365
Val Glu Ala Ala Gln Glu Thr Val Ala Asp Tyr Gln Gln Thr Ile Lys
    370                 375                 380
Lys Tyr Arg Gln Leu Thr Ala His Leu Gln Asp Val Asn Arg Glu Leu
385                 390                 395                 400
```

-continued

```
Thr Asn Gln Gln Glu Ala Ser Val Glu Arg Gln Gln Pro Pro Pro
                405                 410                 415

Glu Thr Phe Asp Phe Lys Ile Lys Phe Ala Glu Thr Lys Ala His Ala
            420                 425                 430

Lys Ala Ile Glu Met Glu Leu Arg Gln Met Glu Val Ala Gln Ala Asn
                435                 440                 445

Arg His Met Ser Leu Leu Thr Ala Phe Met Pro Asp Ser Phe Leu Arg
            450                 455                 460

Pro Gly Gly Asp His Asp Cys Val Leu Val Leu Leu Met Pro Arg
465                 470                 475                 480

Leu Ile Cys Lys Ala Glu Leu Ile Arg Lys Gln Ala Gln Glu Lys Phe
                485                 490                 495

Glu Leu Ser Glu Asn Cys Ser Glu Arg Pro Gly Leu Arg Gly Ala Ala
            500                 505                 510

Gly Glu Gln Leu Ser Phe Ala Ala Gly Leu Val Tyr Ser Leu Ser Leu
            515                 520                 525

Leu Gln Ala Thr Leu His Arg Tyr Glu His Ala Leu Ser Gln Cys Ser
            530                 535                 540

Val Asp Val Tyr Lys Lys Val Gly Ser Leu Tyr Pro Glu Met Ser Ala
545                 550                 555                 560

His Glu Arg Ser Leu Asp Phe Leu Ile Glu Leu Leu His Lys Asp Gln
                565                 570                 575

Leu Asp Glu Thr Val Asn Val Glu Pro Leu Thr Lys Ala Ile Lys Tyr
            580                 585                 590

Tyr Gln His Leu Tyr Ser Ile His Leu Ala Glu Gln Pro Glu Asp Cys
            595                 600                 605

Thr Met Gln Leu Ala Asp His Ile Lys Phe Thr Gln Ser Ala Leu Asp
            610                 615                 620

Cys Met Ser Val Glu Val Gly Arg Leu Arg Ala Phe Leu Gln Gly Gly
625                 630                 635                 640

Gln Glu Ala Thr Asp Ile Ala Leu Leu Leu Arg Asp Leu Glu Thr Ser
                645                 650                 655

Cys Ser Asp Ile Arg Gln Phe Cys Lys Lys Ile Arg Arg Met Pro
            660                 665                 670

Gly Thr Asp Ala Pro Gly Ile Pro Ala Ala Leu Ala Phe Gly Pro Gln
            675                 680                 685

Val Ser Asp Thr Leu Leu Asp Cys Arg Lys His Leu Thr Trp Val Val
            690                 695                 700

Ala Val Leu Gln Glu Val Ala Ala Ala Ala Gln Leu Ile Ala Pro
705                 710                 715                 720

Leu Ala Glu Asn Glu Gly Leu Leu Val Ala Leu Glu Glu Leu Ala
                725                 730                 735

Phe Lys Ala Ser Glu Gln Ile Tyr Gly Thr Pro Ser Ser Pro Tyr
            740                 745                 750

Glu Cys Leu Arg Gln Ser Cys Asn Ile Leu Ile Ser Thr Met Asn Lys
            755                 760                 765

Leu Ala Thr Ala Met Gln Glu Gly Glu Tyr Asp Ala Glu Arg Pro Pro
            770                 775                 780

Ser Lys Pro Pro Pro Val Glu Leu Arg Ala Ala Leu Arg Ala Glu
785                 790                 795                 800

Ile Thr Asp Ala Glu Gly Leu Gly Leu Lys Leu Glu Asp Arg Glu Thr
                805                 810                 815

Val Ile Lys Glu Leu Lys Lys Ser Leu Lys Ile Lys Gly Glu Glu Leu
```

```
                820                 825                 830
Ser Glu Ala Asn Val Arg Leu Ser Leu Leu Glu Lys Lys Leu Asp Ser
                835                 840                 845
Ala Ala Lys Asp Ala Asp Glu Arg Ile Glu Lys Val Gln Thr Arg Leu
850                 855                 860
Glu Glu Thr Gln Ala Leu Leu Arg Lys Lys Glu Lys Glu Phe Glu Glu
865                 870                 875                 880
Thr Met Asp Ala Leu Gln Ala Asp Ile Asp Gln Leu Glu Ala Glu Lys
                885                 890                 895
Ala Glu Leu Lys Gln Arg Leu Asn Ser Gln Ser Lys Arg Thr Ile Glu
                900                 905                 910
Gly Leu Arg Gly Pro Pro Ser Gly Ile Ala Thr Leu Val Ser Gly
                915                 920                 925
Ile Ala Gly Glu Glu Gln Gln Arg Gly Ala Ile Pro Gly Gln Ala Pro
                930                 935                 940
Gly Ser Val Pro Gly Pro Gly Leu Val Lys Asp Ser Pro Leu Leu Leu
945                 950                 955                 960
Gln Gln Ile Ser Ala Met Arg Leu His Ile Ser Gln Leu Gln His Glu
                965                 970                 975
Asn Ser Ile Leu Lys Gly Ala Gln Met Lys Ala Ser Leu Ala Ser Leu
                980                 985                 990
Pro Pro Leu His Val Ala Lys Leu  Ser His Glu Gly Pro  Gly Ser Glu
                995                 1000                1005
Leu Pro  Ala Gly Ala Leu Tyr  Arg Lys Thr Ser Gln  Leu Leu Glu
                 1010                1015                1020
Thr Leu  Asn Gln Leu Ser Thr  His Thr His Val Val  Asp Ile Thr
                 1025                1030                1035
Arg Thr  Ser Pro Ala Ala Lys  Ser Pro Ser Ala Gln  Leu Met Glu
                 1040                1045                1050
Gln Val  Ala Gln Leu Lys Ser  Leu Ser Asp Thr Val  Glu Lys Leu
                 1055                1060                1065
Lys Asp  Glu Val Leu Lys Glu  Thr Val Ser Gln Arg  Pro Gly Ala
                 1070                1075                1080
Thr Val  Pro Thr Asp Phe Ala  Thr Phe Pro Ser Ser  Ala Phe Leu
                 1085                1090                1095
Arg Glu  Asp Pro Lys Trp Glu  Phe Pro Arg Lys Asn  Leu Val Leu
                 1100                1105                1110
Gly Lys  Thr Leu Gly Glu Gly  Glu Phe Gly Lys Val  Val Lys Ala
                 1115                1120                1125
Thr Ala  Phe His Leu Lys Gly  Arg Ala Gly Tyr Thr  Thr Val Ala
                 1130                1135                1140
Val Lys  Met Leu Lys Glu Asn  Ala Ser Pro Ser Glu  Leu Arg Asp
                 1145                1150                1155
Leu Leu  Ser Glu Phe Asn Val  Leu Lys Gln Val Asn  His Pro His
                 1160                1165                1170
Val Ile  Lys Leu Tyr Gly Ala  Cys Ser Gln Asp Gly  Pro Leu Leu
                 1175                1180                1185
Leu Ile  Val Glu Tyr Ala Lys  Tyr Gly Ser Leu Arg  Gly Phe Leu
                 1190                1195                1200
Arg Glu  Ser Arg Lys Val Gly  Pro Gly Tyr Leu Gly  Ser Gly Gly
                 1205                1210                1215
Ser Arg  Asn Ser Ser Ser Leu  Asp His Pro Asp Glu  Arg Ala Leu
                 1220                1225                1230
```

```
Thr Met Gly Asp Leu Ile Ser Phe Ala Trp Gln Ile Ser Gln Gly
    1235            1240                1245

Met Gln Tyr Leu Ala Glu Met Lys Leu Val His Arg Asp Leu Ala
    1250            1255                1260

Ala Arg Asn Ile Leu Val Ala Glu Gly Arg Lys Met Lys Ile Ser
    1265            1270                1275

Asp Phe Gly Leu Ser Arg Asp Val Tyr Glu Glu Asp Ser Tyr Val
    1280            1285                1290

Lys Arg Ser Gln Gly Arg Ile Pro Val Lys Trp Met Ala Ile Glu
    1295            1300                1305

Ser Leu Phe Asp His Ile Tyr Thr Thr Gln Ser Asp Val Trp Ser
    1310            1315                1320

Phe Gly Val Leu Leu Trp Glu Ile Val Thr Leu Gly Gly Asn Pro
    1325            1330                1335

Tyr Pro Gly Ile Pro Pro Glu Arg Leu Phe Asn Leu Leu Lys Thr
    1340            1345                1350

Gly His Arg Met Glu Arg Pro Asp Asn Cys Ser Glu Glu Met Tyr
    1355            1360                1365

Arg Leu Met Leu Gln Cys Trp Lys Gln Glu Pro Asp Lys Arg Pro
    1370            1375                1380

Val Phe Ala Asp Ile Ser Lys Asp Leu Glu Lys Met Met Val Lys
    1385            1390                1395

Arg Arg Asp Tyr Leu Asp Leu Ala Ala Ser Thr Pro Ser Asp Ser
    1400            1405                1410

Leu Ile Tyr Asp Asp Gly Leu Ser Glu Glu Glu Thr Pro Leu Val
    1415            1420                1425

Asp Cys Asn Asn Ala Pro Leu Pro Arg Ala Leu Pro Ser Thr Trp
    1430            1435                1440

Ile Glu Asn Lys Leu Tyr Gly Arg Ile Ser His Ala Phe Thr Arg
    1445            1450                1455

Phe

<210> SEQ ID NO 9
<211> LENGTH: 4833
<212> TYPE: DNA
<213> ORGANISM: Artificial Sequence
<220> FEATURE:
<223> OTHER INFORMATION: coding sequence of fusion peptide

<400> SEQUENCE: 9
atggcacaga gcaagaggca cgtgtacagc cggacgccca gcggcagcag gatgagtgcg      60
gaggcaagcg cccggcctct gcgggtgggc tcccgtgtag aggtgattgg aaaaggccac    120
cgaggcactg tggcctatgt tggagccaca ctgtttgcca ctggcaaatg ggtaggcgtg    180
attctggatg aagcaaaggg caaaaatgat ggaactgttc aaggcaggaa gtacttcact    240
tgtgatgaag ggcatggcat ctttgtgcgc cagtcccaga tccaggtatt tgaagatgga    300
gcagatacta cttccccaga cacctgat tcttctgctt caaaagtcct caaaagagag      360
ggaactgata caactgcaaa gactagcaaa ctgcccacgc gcccagccag tactggggtg    420
gctggggcca gtagctccct gggccccctct ggctcagcgt cagcaggtga gctgagcagc    480
agtgagccca gcaccccggc tcagactccg ctggcagcac ccatcatccc cacgccggtc    540
ctcacctctc ctggagcagt cccccgctt ccttccccat ccaaggagga ggagggacta     600
agggctcagg tgcgggacct ggaggagaaa ctagagaccc tgagactgaa acgggcagaa    660
```

```
gacaaagcaa agctaaaaga gctggagaaa cacaaaatcc agctggagca ggtgcaggaa    720
tggaagagca aaatgcagga gcagcaggcc gacctgcagc ggcgcctcaa ggaggcgaga    780
aaggaagcca aggaggcgct ggaggcaaag gaacgctata tggaggagat ggctgatact    840
gctgatgcca ttgagatggc cactttggac aaggagatgg ctgaagagcg ggctgagtcc    900
ctgcagcagg aggtggaggc actgaaggag cgggtggacg agctcactac tgacttagag    960
atcctcaagg ctgagattga agagaagggc tcagatggcg ctgcatccag ttatcagctc   1020
aagcagcttg aggagcagaa tgcccgcctg aaggatgccc tggtgaggat gcgggatctt   1080
tcttcctcag agaagcagga gcatgtgaag ctccagaagc tcatggaaaa gaagaaccaa   1140
gagctggaag ttgtgaggca acagcgggag cgtctgcagg aggagctaag ccaggcagag   1200
agcaccattg atgagctcaa ggagcaggtg gatgctgctc tgggtgctga ggagatggtg   1260
gagatgctga cagatcggaa cctgaatctg aagagaaag tgcgcgagtt gagggagact   1320
gtgggagact tggaagcgat gaatgagatg aacgatgagc tgcaggagaa tgcacgtgag   1380
acagaactgg agctgcggga gcagctggac atggcaggcg cgcgggttcg tgaggcccag   1440
aagcgtgtgg aggcagccca ggagacggtt gcagactacc agcagaccat caagaagtac   1500
cgccagctga ccgcccatct acaggatgtg aatcgggaac tgacaaacca gcaggaagca   1560
tctgtggaga ggcaacagca gccacctcca gagacctttg acttcaaaat caagtttgct   1620
gagactaagg cccatgccaa ggcaattgag atggaattga ggcagatgga ggtggcccag   1680
gccaatcgac acatgtccct gctgacagcc ttcatgcctg acagcttcct tcggccaggt   1740
ggggaccatg actgcgttct ggtgctgttg ctcatgcctc gtctcatttg caaggcagag   1800
ctgatccgga agcaggccca ggagaagttt gaactaagtg agaactgttc agagcggcct   1860
gggctgcgag gagctgctgg ggagcaactc agctttgctg ctggactggt gtactcgctg   1920
agcctgctgc aggccacgct acaccgctat gagcatgccc tctctcagtg cagtgtggat   1980
gtgtataaga aagtgggcag cctgtaccct gagatgagtg cccatgagcg ctccttggat   2040
ttcctcattg aactgctgca aaggatcag ctggatgaga ctgtcaatgt ggagcctctc   2100
accaaggcca tcaagtacta tcagcatctg tacagcatcc accttgccga acagcctgag   2160
gactgtacta gcagctggc tgaccacatt aagttcacgc agagtgctct ggactgcatg   2220
agtgtggagg taggacggct gcgtgccttc ttgcagggtg ggcaggaggc tacagatatt   2280
gccctcctgc tccgggatct ggaaacttca tgcagtgaca tccgccagtt ctgcaagaag   2340
atccgaaggc gaatgccagg gacagatgct cctgggatcc cagctgcact ggcctttgga   2400
ccacaggtat ctgacacgct cctagactgc aggaaacact tgacgtgggt cgtggctgtg   2460
ctgcaggagg tggcagctgc tgctgcccag ctcattgccc cactggcaga gaatgagggg   2520
ctacttgtgg ctgctctgga ggaactggct ttcaaagcaa gcgagcagat ctatgggacc   2580
ccctccagca gccctatga gtgtctgcgc cagtcatgca acatcctcat cagtaccatg   2640
aacaagctgg ccacagccat gcaggagggg gagtatgatg cagagcggcc ccccagcaag   2700
cctccaccgg ttgaactgcg ggctgctgcc cttcgtgcag gatcacaga tgctgaaggc   2760 ctgggtttga agctcgaaga tcgagagaca gttattaagg agttgaagaa gtcactcaag   2820
attaagggag aggagctaag tgaggccaat gtgcggctga gcctcctgga gaagaagttg   2880
gacagtgctg ccaaggatgc agatgagcgc atcgagaaag tccagactcg gctgaggag   2940 acccaggcac tgctgcgaaa gaaggagaaa gagtttgagg agacaatgga tgcactccag   3000
```

-continued

| | |
|---|---|
| gctgacatcg accagctgga ggcagagaag gcagaactaa agcagcgtct gaacagccag | 3060 |
| tccaaacgca cgattgaggg actccggggc cctcctcctt caggcattgc tactctggtc | 3120 |
| tctggcattg ctggtggagc catccctggg caggctccag ggtctgtgcc aggcccaggg | 3180 |
| ctggtgaagg actccaccact gctgcttcag cagatctctg ccatgaggct gcacatctcc | 3240 |
| cagctccagc atgagaacag catcctcaag ggagcccaga tgaaggcatc cttggcatcc | 3300 |
| ctgcccctc tgcatgttgc aaagctatcc catgagggcc ctggcagtga gttaccagct | 3360 |
| ggagcgctgt atcgtaagac cagccagctg ctggagacat tgaatcaatt gagcacacac | 3420 |
| acgcacgtag tagacatcac tcgcaccagc cctgctgcca agagcccgtc ggcccaactt | 3480 |
| atggagcaag tggctcagct taagtccctg agtgacaccg tcgagaagct caaggatgag | 3540 |
| gtcctcaagg agacagtatc tcagcgccct ggagccacag tacccactga ctttgccacc | 3600 |
| ttcccttcat cagccttcct cagggaggat ccaaagtggg aattccctcg gaagaacttg | 3660 |
| gttcttggaa aaactctagg agaaggcgaa tttggaaaag tggtcaaggc aacggccttc | 3720 |
| catctgaaag gcagagcagg gtacaccacg gtggccgtga agatgctgaa agagaacgcc | 3780 |
| tccccgagtg agcttcgaga cctgctgtca gagttcaacg tcctgaagca ggtcaaccac | 3840 |
| ccacatgtca tcaaattgta tggggcctgc agccaggatg gccgctcct cctcatcgtg | 3900 |
| gagtacgcca aatacggctc cctgcggggc ttcctccgcg agagccgcaa agtggggcct | 3960 |
| ggctacctgg gcagtggagg cagccgcaac tccagctccc tggaccaccc ggatgagcgg | 4020 |
| gccctcacca tgggcgacct catctcattt gcctggcaga tctcacaggg gatgcagtat | 4080 |
| ctggccgaga tgaagctcgt tcatcgggac ttggcagcca gaaacatcct ggtagctgag | 4140 |
| gggcggaaga tgaagatttc ggatttcggc ttgtcccgag atgtttatga gaggattcc | 4200 |
| tacgtgaaga ggagccaggg tcggattcca gttaaatgga tggcaattga atccttttt | 4260 |
| gatcatatct acaccacgca aagtgatgta tggtcttttg gtgtcctgct gtgggagatc | 4320 |
| gtgaccctag ggggaaaccc ctatcctggg attcctcctg agcggctctt caaccttctg | 4380 |
| aagaccggcc accggatgga gaggccagac aactgcagcg aggagatgta ccgcctgatg | 4440 |
| ctgcaatgct ggaagcagga gccggacaaa aggccggtgt tgcggacat cagcaaagac | 4500 |
| ctggagaaga tgatggttaa gaggagagac tacttggacc ttgcggcgtc cactccatct | 4560 |
| gactccctga tttatgacga cggcctctca gaggaggaga caccgctggt ggactgtaat | 4620 |
| aatgcccccc tccctcgagc cctcccttcc acatggattg aaaacaaact ctatggcatg | 4680 |
| tcagacccga actggcctgg agagagtcct gtaccactca cgagagctga tggcactaac | 4740 |
| actgggtttc aagatatcc aaatgatagt gtatatgcta actggatgct ttcaccctca | 4800 |
| gcggcaaaat taatggacac gtttgatagt taa | 4833 |

```
<210> SEQ ID NO 10
<211> LENGTH: 1610
<212> TYPE: PRT
<213> ORGANISM: Artificial Sequence
<220> FEATURE:
<223> OTHER INFORMATION: fusion peptide

<400> SEQUENCE: 10

Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
```

```
            35                  40                  45
Ala Thr Leu Phe Ala Thr Gly Lys Trp Val Gly Val Ile Leu Asp Glu
 50                  55                  60
Ala Lys Gly Lys Asn Asp Gly Thr Val Gln Gly Arg Lys Tyr Phe Thr
 65                  70                  75                  80
Cys Asp Glu Gly His Gly Ile Phe Val Arg Gln Ser Gln Ile Gln Val
                     85                  90                  95
Phe Glu Asp Gly Ala Asp Thr Thr Ser Pro Glu Thr Pro Asp Ser Ser
                    100                 105                 110
Ala Ser Lys Val Leu Lys Arg Glu Gly Thr Asp Thr Ala Lys Thr
                    115                 120                 125
Ser Lys Leu Pro Thr Arg Pro Ala Ser Thr Gly Val Ala Gly Ala Ser
                    130                 135                 140
Ser Ser Leu Gly Pro Ser Gly Ser Ala Ser Ala Gly Glu Leu Ser Ser
145                 150                 155                 160
Ser Glu Pro Ser Thr Pro Ala Gln Thr Pro Leu Ala Ala Pro Ile Ile
                    165                 170                 175
Pro Thr Pro Val Leu Thr Ser Pro Gly Ala Val Pro Pro Leu Pro Ser
                    180                 185                 190
Pro Ser Lys Glu Glu Gly Leu Arg Ala Gln Val Arg Asp Leu Glu
                    195                 200                 205
Glu Lys Leu Glu Thr Leu Arg Leu Lys Arg Ala Glu Asp Lys Ala Lys
210                 215                 220
Leu Lys Glu Leu Glu Lys His Lys Ile Gln Leu Glu Gln Val Gln Glu
225                 230                 235                 240
Trp Lys Ser Lys Met Gln Glu Gln Gln Ala Asp Leu Gln Arg Arg Leu
                    245                 250                 255
Lys Glu Ala Arg Lys Glu Ala Lys Glu Ala Leu Glu Ala Lys Glu Arg
                    260                 265                 270
Tyr Met Glu Glu Met Ala Asp Thr Ala Asp Ala Ile Glu Met Ala Thr
                    275                 280                 285
Leu Asp Lys Glu Met Ala Glu Glu Arg Ala Glu Ser Leu Gln Gln Glu
                    290                 295                 300
Val Glu Ala Leu Lys Glu Arg Val Asp Glu Leu Thr Thr Asp Leu Glu
305                 310                 315                 320
Ile Leu Lys Ala Glu Ile Glu Glu Lys Gly Ser Asp Gly Ala Ala Ser
                    325                 330                 335
Ser Tyr Gln Leu Lys Gln Leu Glu Glu Gln Asn Ala Arg Leu Lys Asp
                    340                 345                 350
Ala Leu Val Arg Met Arg Asp Leu Ser Ser Ser Glu Lys Gln Glu His
                    355                 360                 365
Val Lys Leu Gln Lys Leu Met Glu Lys Lys Asn Gln Glu Leu Glu Val
                    370                 375                 380
Val Arg Gln Gln Arg Glu Arg Leu Gln Glu Glu Leu Ser Gln Ala Glu
385                 390                 395                 400
Ser Thr Ile Asp Glu Leu Lys Glu Gln Val Asp Ala Ala Leu Gly Ala
                    405                 410                 415
Glu Glu Met Val Glu Met Leu Thr Asp Arg Asn Leu Asn Leu Glu Glu
                    420                 425                 430
Lys Val Arg Glu Leu Arg Glu Thr Val Gly Asp Leu Glu Ala Met Asn
                    435                 440                 445
Glu Met Asn Asp Glu Leu Gln Glu Asn Ala Arg Glu Thr Glu Leu Glu
                    450                 455                 460
```

```
Leu Arg Glu Gln Leu Asp Met Ala Gly Ala Arg Val Arg Glu Ala Gln
465                 470                 475                 480

Lys Arg Val Glu Ala Gln Glu Thr Val Ala Asp Tyr Gln Gln Thr
                485                 490                 495

Ile Lys Lys Tyr Arg Gln Leu Thr Ala His Leu Gln Asp Val Asn Arg
                500                 505                 510

Glu Leu Thr Asn Gln Gln Ala Ser Val Glu Arg Gln Gln Gln Pro
            515                 520                 525

Pro Pro Glu Thr Phe Asp Phe Lys Ile Lys Phe Ala Glu Thr Lys Ala
            530                 535                 540

His Ala Lys Ala Ile Glu Met Glu Leu Arg Gln Met Glu Val Ala Gln
545                 550                 555                 560

Ala Asn Arg His Met Ser Leu Leu Thr Ala Phe Met Pro Asp Ser Phe
                565                 570                 575

Leu Arg Pro Gly Gly Asp His Asp Cys Val Leu Val Leu Leu Leu Met
                580                 585                 590

Pro Arg Leu Ile Cys Lys Ala Glu Leu Ile Arg Lys Gln Ala Gln Glu
            595                 600                 605

Lys Phe Glu Leu Ser Glu Asn Cys Ser Glu Arg Pro Gly Leu Arg Gly
            610                 615                 620

Ala Ala Gly Glu Gln Leu Ser Phe Ala Ala Gly Leu Val Tyr Ser Leu
625                 630                 635                 640

Ser Leu Leu Gln Ala Thr Leu His Arg Tyr Glu His Ala Leu Ser Gln
                645                 650                 655

Cys Ser Val Asp Val Tyr Lys Lys Val Gly Ser Leu Tyr Pro Glu Met
                660                 665                 670

Ser Ala His Glu Arg Ser Leu Asp Phe Leu Ile Glu Leu Leu His Lys
            675                 680                 685

Asp Gln Leu Asp Glu Thr Val Asn Val Glu Pro Leu Thr Lys Ala Ile
            690                 695                 700

Lys Tyr Tyr Gln His Leu Tyr Ser Ile His Leu Ala Glu Gln Pro Glu
705                 710                 715                 720

Asp Cys Thr Met Gln Leu Ala Asp His Ile Lys Phe Thr Gln Ser Ala
                725                 730                 735

Leu Asp Cys Met Ser Val Glu Val Gly Arg Leu Arg Ala Phe Leu Gln
                740                 745                 750

Gly Gly Gln Glu Ala Thr Asp Ile Ala Leu Leu Leu Arg Asp Leu Glu
            755                 760                 765

Thr Ser Cys Ser Asp Ile Arg Gln Phe Cys Lys Lys Ile Arg Arg Arg
            770                 775                 780

Met Pro Gly Thr Asp Ala Pro Gly Ile Pro Ala Ala Leu Ala Phe Gly
785                 790                 795                 800

Pro Gln Val Ser Asp Thr Leu Asp Cys Arg Lys His Leu Thr Trp
                805                 810                 815

Val Val Ala Val Leu Gln Glu Val Ala Ala Ala Ala Gln Leu Ile
                820                 825                 830

Ala Pro Leu Ala Glu Asn Glu Gly Leu Leu Val Ala Ala Leu Glu Glu
            835                 840                 845

Leu Ala Phe Lys Ala Ser Glu Gln Ile Tyr Gly Thr Pro Ser Ser Ser
            850                 855                 860

Pro Tyr Glu Cys Leu Arg Gln Ser Cys Asn Ile Leu Ile Ser Thr Met
865                 870                 875                 880
```

```
Asn Lys Leu Ala Thr Ala Met Gln Glu Gly Glu Tyr Asp Ala Glu Arg
                885                 890                 895

Pro Pro Ser Lys Pro Pro Val Glu Leu Arg Ala Ala Leu Arg
        900                 905                 910

Ala Glu Ile Thr Asp Ala Glu Gly Leu Gly Leu Lys Leu Glu Asp Arg
        915                 920                 925

Glu Thr Val Ile Lys Glu Leu Lys Lys Ser Leu Lys Ile Lys Gly Glu
    930                 935                 940

Glu Leu Ser Glu Ala Asn Val Arg Leu Ser Leu Leu Glu Lys Lys Leu
945                 950                 955                 960

Asp Ser Ala Ala Lys Asp Ala Asp Glu Arg Ile Glu Lys Val Gln Thr
            965                 970                 975

Arg Leu Glu Glu Thr Gln Ala Leu Leu Arg Lys Lys Glu Lys Glu Phe
        980                 985                 990

Glu Glu Thr Met Asp Ala Leu Gln Ala Asp Ile Asp Gln Leu Glu Ala
    995                 1000                1005

Glu Lys Ala Glu Leu Lys Gln Arg Leu Asn Ser Gln Ser Lys Arg
    1010                1015                1020

Thr Ile Glu Gly Leu Arg Gly Pro Pro Ser Gly Ile Ala Thr
    1025                1030                1035

Leu Val Ser Gly Ile Ala Gly Gly Ala Ile Pro Gly Gln Ala Pro
    1040                1045                1050

Gly Ser Val Pro Gly Pro Gly Leu Val Lys Asp Ser Pro Leu Leu
    1055                1060                1065

Leu Gln Gln Ile Ser Ala Met Arg Leu His Ile Ser Gln Leu Gln
    1070                1075                1080

His Glu Asn Ser Ile Leu Lys Gly Ala Gln Met Lys Ala Ser Leu
    1085                1090                1095

Ala Ser Leu Pro Pro Leu His Val Ala Lys Leu Ser His Glu Gly
    1100                1105                1110

Pro Gly Ser Glu Leu Pro Ala Gly Ala Leu Tyr Arg Lys Thr Ser
    1115                1120                1125

Gln Leu Leu Glu Thr Leu Asn Gln Leu Ser Thr His Thr His Val
    1130                1135                1140

Val Asp Ile Thr Arg Thr Ser Pro Ala Ala Lys Ser Pro Ser Ala
    1145                1150                1155

Gln Leu Met Glu Gln Val Ala Gln Leu Lys Ser Leu Ser Asp Thr
    1160                1165                1170

Val Glu Lys Leu Lys Asp Glu Val Leu Lys Glu Thr Val Ser Gln
    1175                1180                1185

Arg Pro Gly Ala Thr Val Pro Thr Asp Phe Ala Thr Phe Pro Ser
    1190                1195                1200

Ser Ala Phe Leu Arg Glu Asp Pro Lys Trp Glu Phe Pro Arg Lys
    1205                1210                1215

Asn Leu Val Leu Gly Lys Thr Leu Gly Glu Gly Glu Phe Gly Lys
    1220                1225                1230

Val Val Lys Ala Thr Ala Phe His Leu Lys Gly Arg Ala Gly Tyr
    1235                1240                1245

Thr Thr Val Ala Val Lys Met Leu Lys Glu Asn Ala Ser Pro Ser
    1250                1255                1260

Glu Leu Arg Asp Leu Leu Ser Glu Phe Asn Val Leu Lys Gln Val
    1265                1270                1275

Asn His Pro His Val Ile Lys Leu Tyr Gly Ala Cys Ser Gln Asp
```

```
                   1280                1285                1290

Gly Pro Leu Leu Leu Ile Val Glu Tyr Ala Lys Tyr Gly Ser Leu
    1295                1300                1305

Arg Gly Phe Leu Arg Glu Ser Arg Lys Val Gly Pro Gly Tyr Leu
    1310                1315                1320

Gly Ser Gly Gly Ser Arg Asn Ser Ser Ser Leu Asp His Pro Asp
    1325                1330                1335

Glu Arg Ala Leu Thr Met Gly Asp Leu Ile Ser Phe Ala Trp Gln
    1340                1345                1350

Ile Ser Gln Gly Met Gln Tyr Leu Ala Glu Met Lys Leu Val His
    1355                1360                1365

Arg Asp Leu Ala Ala Arg Asn Ile Leu Val Ala Glu Gly Arg Lys
    1370                1375                1380

Met Lys Ile Ser Asp Phe Gly Leu Ser Arg Asp Val Tyr Glu Glu
    1385                1390                1395

Asp Ser Tyr Val Lys Arg Ser Gln Gly Arg Ile Pro Val Lys Trp
    1400                1405                1410

Met Ala Ile Glu Ser Leu Phe Asp His Ile Tyr Thr Thr Gln Ser
    1415                1420                1425

Asp Val Trp Ser Phe Gly Val Leu Leu Trp Glu Ile Val Thr Leu
    1430                1435                1440

Gly Gly Asn Pro Tyr Pro Gly Ile Pro Pro Glu Arg Leu Phe Asn
    1445                1450                1455

Leu Leu Lys Thr Gly His Arg Met Glu Arg Pro Asp Asn Cys Ser
    1460                1465                1470

Glu Glu Met Tyr Arg Leu Met Leu Gln Cys Trp Lys Gln Glu Pro
    1475                1480                1485

Asp Lys Arg Pro Val Phe Ala Asp Ile Ser Lys Asp Leu Glu Lys
    1490                1495                1500

Met Met Val Lys Arg Arg Asp Tyr Leu Asp Leu Ala Ala Ser Thr
    1505                1510                1515

Pro Ser Asp Ser Leu Ile Tyr Asp Asp Gly Leu Ser Glu Glu Glu
    1520                1525                1530

Thr Pro Leu Val Asp Cys Asn Asn Ala Pro Leu Pro Arg Ala Leu
    1535                1540                1545

Pro Ser Thr Trp Ile Glu Asn Lys Leu Tyr Gly Met Ser Asp Pro
    1550                1555                1560

Asn Trp Pro Gly Glu Ser Pro Val Pro Leu Thr Arg Ala Asp Gly
    1565                1570                1575

Thr Asn Thr Gly Phe Pro Arg Tyr Pro Asn Asp Ser Val Tyr Ala
    1580                1585                1590

Asn Trp Met Leu Ser Pro Ser Ala Ala Lys Leu Met Asp Thr Phe
    1595                1600                1605

Asp Ser
    1610

<210> SEQ ID NO 11
<211> LENGTH: 4707
<212> TYPE: DNA
<213> ORGANISM: Artificial Sequence
<220> FEATURE:
<223> OTHER INFORMATION: coding sequence of fusion peptide

<400> SEQUENCE: 11
atggcacaga gcaagaggca cgtgtacagc cggacgccca gcggcagcag gatgagtgcg      60
```

```
gaggcaagcg cccggcctct gcgggtgggc tcccgtgtag aggtgattgg aaaaggccac      120
cgaggcactg tggcctatgt tggagccaca ctgtttgcca ctggcaaatg gtaggcgtg       180 attctggatg aagcaaaggg caaaaatgat ggaactgttc aaggcaggaa gtacttcact      240
tgtgatgaag gcatggcat ctttgtgcgc cagtcccaga tccaggtatt tgaagatgga       300
gcagatacta cttccccaga gacacctgat tcttctgctt caaaagtcct caaagagag       360 ggaactgata caactgcaaa gactagcaaa ctgcccacgc gcccagccag tactggggtg      420
gctggggcca gtagctccct ggcccctct ggctcagcgt cagcaggtga gctgagcagc       480
agtgagccca gcaccccggc tcagactccg ctggcagcac ccatcatccc cacgccggtc      540
ctcacctctc ctggagcagt ccccccgctt ccttccccat ccaaggagga ggagggacta     600
agggctcagg tgcggacct ggaggagaaa ctagagaccc tgagactgaa acgggcagaa      660
gacaaagcaa agctaaaaga gctggagaaa cacaaaatcc agctggagca ggtgcaggaa     720
tggaagagca aaatgcagga gcagcaggcc gacctgcagc ggcgcctcaa ggaggcgaga     780
aaggaagcca aggaggcgct ggaggcaaag gaacgctata tggaggagat ggctgatact     840
gctgatgcca ttgagatggc cactttggac aaggagatgg ctgaagagcg ggctgagtcc     900
ctgcagcagg aggtggaggc actgaaggag cgggtggacg agctcactac tgacttagag     960
atcctcaagg ctgagattga agagaagggc tcagatggcg ctgcatccag ttatcagctc    1020
aagcagcttg aggagcagaa tgcccgcctg aaggatgccc tggtgaggat gcgggatctt    1080
tcttcctcag agaagcagga gcatgtgaag ctccagaagc tcatggaaaa gaagaaccaa    1140
gagctggaag ttgtgaggca acagcgggag cgtctgcagg aggagctaag ccaggcagag    1200
agcaccattg atgagctcaa ggagcaggtg gatgctgctc tgggtgctga ggagatggtg    1260
gagatgctga cagatcggaa cctgaatctg aagagaaag tgcgcgagtt gagggagact    1320
gtgggagact tggaagcgat gaatgagatg aacgatgagc tgcaggagaa tgcacgtgag    1380
acagaactgg agctgcggga gcagctggac atggcaggcg cgcgggttcg tgaggcccag    1440
aagcgtgtgg aggcagccca ggagacggtt gcagactacc agcagaccat caagaagtac    1500
cgccagctga ccgcccatct acaggatgtg aatcgggaac tgacaaacca gcaggaagca    1560
tctgtggaga ggcaacagca gccacctcca gagacctttg acttcaaaat caagtttgct    1620
gagactaagg cccatgccaa ggcaattgag atggaattga ggcagatgga ggtggcccag    1680
gccaatcgac acatgtccct gctgacagcc ttcatgcctg acagcttcct tcggccaggt    1740
ggggaccatg actgcgttct ggtgctgttg ctcatgcctc gtctcatttg caaggcagag    1800
ctgatccgga agcaggccca ggagaagttt gaactaagtg agaactgttc agagcggcct    1860
gggctgcgag gagctgctgg ggagcaactc agctttgctg ctggactggt gtactcgctg    1920
agcctgctgc aggccacgct acaccgctat gagcatgccc tctctcagtg cagtgtggat    1980
gtgtataaga aagtgggcag cctgtaccct gagatgagtg cccatgagcg ctccttggat    2040
ttcctcattg aactgctgca caaggatcag ctggatgaga ctgtcaatgt ggagcctctc    2100
accaaggcca tcaagtacta tcagcatctg tacagcatcc accttgccga acagcctgag    2160
gactgtacta tgcagctggc tgaccacatt aagttcacgc agagtgctct ggactgcatg    2220
agtgtggagg taggacggct gcgtgccttc ttgcagggtg ggcaggaggc tacagatatt    2280
gccctcctgc tcgggatct ggaaacttca tgcagtgaca tccgccagtt ctgcaagaag    2340
atccgaaggc gaatgccagg gacagatgct cctgggatcc cagctgcact ggcctttgga    2400
```

```
ccacaggtat ctgacacgct cctagactgc aggaaacact tgacgtgggt cgtggctgtg    2460
ctgcaggagg tggcagctgc tgctgcccag ctcattgccc cactggcaga gaatgagggg    2520
ctacttgtgg ctgctctgga ggaactggct ttcaaagcaa gcgagcagat ctatgggacc    2580
ccctccagca gccccctatga gtgtctgcgc cagtcatgca acatcctcat cagtaccatg    2640
aacaagctgg ccacagccat gcaggagggg gagtatgatg cagagcggcc ccccagcaag    2700
cctccaccgg ttgaactgcg ggctgctgcc cttcgtgcag atcacaga tgctgaaggc    2760
ctgggtttga agctcgaaga tcgagagaca gttattaagg agttgaagaa gtcactcaag    2820
attaagggag aggagctaag tgaggccaat gtgcggctga gcctcctgga agaagttg    2880
gacagtgctg ccaaggatgc agatgagcgc atcgagaaag tccagactcg gctggaggag    2940
acccaggcac tgctgcgaaa gaaggagaaa gagtttgagg agacaatgga tgcactccag    3000
gctgacatcg accagctgga ggcagagaag gcagaactaa agcagcgtct gaacagccag    3060
tccaaacgca cgattgaggg actccggggc cctcctcctt caggcattgc tactctggtc    3120
tctggcattg ctggtggagc catccctggg caggctccag ggtctgtgcc aggcccaggg    3180
ctggtgaagg actcaccact gctgcttcag cagatctctg ccatgaggct gcacatctcc    3240
cagctccagc atgagaacag catcctcaag ggagcccaga tgaaggcatc cttggcatcc    3300
ctgccccctc tgcatgttgc aaagctatcc catgagggcc ctggcagtga gttaccagct    3360
ggagcgctgt atcgtaagac cagccagctg ctggagacat tgaatcaatt gagcacacac    3420
acgcacgtag tagacatcac tcgcaccagc cctgctgcca agagcccgtc ggcccaactt    3480
atggagcaag tggctcagct taagtccctg agtgacaccg tcgagaagct caaggatgag    3540
gtcctcaagg agacagtatc tcagcgccct ggagccacag tacccactga ctttgccacc    3600
ttcccttcat cagccttcct cagggaggat ccaaagtggg aattccctcg gaagaacttg    3660
gttcttggaa aaactctagg agaaggcgaa tttggaaaag tggtcaaggc aacggccttc    3720
catctgaaag gcagagcagg gtacaccacg gtggccgtga gatgctgaaa agagaacgcc    3780
tcccgagtg agcttcgaga cctgctgtca gagttcaacg tcctgaagca ggtcaaccac    3840
ccacatgtca tcaaattgta tgggcctgc agccaggatg gcccgctcct cctcatcgtg    3900
gagtacgcca aatacggctc cctgcggggc ttcctccgcg agagccgcaa agtggggcct    3960
ggctacctgg gcagtggagg cagccgcaac tccagctccc tggaccaccc ggatgagcgg    4020
gccctcacca tgggcgacct catctcattt gcctggcaga tctcacaggg gatgcagtat    4080
ctggccgaga tgaagctcgt tcatcgggac ttggcagcca gaaacatcct ggtagctgag    4140
gggcggaaga tgaagatttc ggatttcggc ttgtcccgag atgtttatga agaggattcc    4200
tacgtgaaga ggagccaggg tcggattcca gttaaatgga tggcaattga atcccttttt    4260
gatcatatct acaccacgca aagtgatgta tggtcttttg gtgtcctgct gtgggagatc    4320
gtgaccctag ggggaaaccc ctatcctggg attcctcctg agcggctctt caaccttctg    4380
aagaccggcc accggatgga gaggccagac aactgcagcg aggagatgta ccgcctgatg    4440
ctgcaatgct ggaagcagga gccggacaaa aggccggtgt ttgcggacat cagcaaagac    4500
ctggagaaga tgatggttaa gaggagagac tacttggacc ttgcggcgtc cactccatct    4560
gactccctga tttatgacga cggcctctca gaggaggaga caccgctggt ggactgtaat    4620
aatgcccccc tccctcgagc cctcccttcc acatggattg aaaacaaact ctatggtaga    4680
atttcccatg catttactag attctag                                      4707
```

```
<210> SEQ ID NO 12
<211> LENGTH: 1568
<212> TYPE: PRT
<213> ORGANISM: Artificial Sequence
<220> FEATURE:
<223> OTHER INFORMATION: fusion peptide

<400> SEQUENCE: 12
```

| | | | | | | | | | | | | | | | |
|---|---|---|---|---|---|---|---|---|---|---|---|---|---|---|---|
| Met | Ala | Gln | Ser | Lys | Arg | His | Val | Tyr | Ser | Arg | Thr | Pro | Ser | Gly | Ser |
| 1 | | | | 5 | | | | | 10 | | | | | 15 | |
| Arg | Met | Ser | Ala | Glu | Ala | Ser | Ala | Arg | Pro | Leu | Arg | Val | Gly | Ser | Arg |
| | | | 20 | | | | | 25 | | | | | 30 | | |
| Val | Glu | Val | Ile | Gly | Lys | Gly | His | Arg | Gly | Thr | Val | Ala | Tyr | Val | Gly |
| | | | 35 | | | | | 40 | | | | | 45 | | |
| Ala | Thr | Leu | Phe | Ala | Thr | Gly | Lys | Trp | Val | Gly | Val | Ile | Leu | Asp | Glu |
| | 50 | | | | | 55 | | | | | 60 | | | | |
| Ala | Lys | Gly | Lys | Asn | Asp | Gly | Thr | Val | Gln | Gly | Arg | Lys | Tyr | Phe | Thr |
| 65 | | | | | 70 | | | | | 75 | | | | | 80 |
| Cys | Asp | Glu | Gly | His | Gly | Ile | Phe | Val | Arg | Gln | Ser | Gln | Ile | Gln | Val |
| | | | | 85 | | | | | 90 | | | | | 95 | |
| Phe | Glu | Asp | Gly | Ala | Asp | Thr | Thr | Ser | Pro | Glu | Thr | Pro | Asp | Ser | Ser |
| | | | 100 | | | | | 105 | | | | | 110 | | |
| Ala | Ser | Lys | Val | Leu | Lys | Arg | Glu | Gly | Thr | Asp | Thr | Ala | Lys | Thr |
| | 115 | | | | | 120 | | | | | 125 | | | | |
| Ser | Lys | Leu | Pro | Thr | Arg | Pro | Ala | Ser | Thr | Gly | Val | Ala | Gly | Ala | Ser |
| | 130 | | | | | 135 | | | | | 140 | | | | |
| Ser | Ser | Leu | Gly | Pro | Ser | Gly | Ser | Ala | Ser | Ala | Gly | Glu | Leu | Ser | Ser |
| 145 | | | | | 150 | | | | | 155 | | | | | 160 |
| Ser | Glu | Pro | Ser | Thr | Pro | Ala | Gln | Thr | Pro | Leu | Ala | Ala | Pro | Ile | Ile |
| | | | | 165 | | | | | 170 | | | | | 175 | |
| Pro | Thr | Pro | Val | Leu | Thr | Ser | Pro | Gly | Ala | Val | Pro | Pro | Leu | Pro | Ser |
| | | | 180 | | | | | 185 | | | | | 190 | | |
| Pro | Ser | Lys | Glu | Glu | Gly | Leu | Arg | Ala | Gln | Val | Arg | Asp | Leu | Glu |
| | 195 | | | | | 200 | | | | | 205 | | | | |
| Glu | Lys | Leu | Glu | Thr | Leu | Arg | Leu | Lys | Arg | Ala | Glu | Asp | Lys | Ala | Lys |
| | 210 | | | | | 215 | | | | | 220 | | | | |
| Leu | Lys | Glu | Leu | Glu | Lys | His | Lys | Ile | Gln | Leu | Glu | Gln | Val | Gln | Glu |
| 225 | | | | | 230 | | | | | 235 | | | | | 240 |
| Trp | Lys | Ser | Lys | Met | Gln | Glu | Gln | Gln | Ala | Asp | Leu | Gln | Arg | Arg | Leu |
| | | | | 245 | | | | | 250 | | | | | 255 | |
| Lys | Glu | Ala | Arg | Lys | Glu | Ala | Lys | Glu | Ala | Leu | Glu | Ala | Lys | Glu | Arg |
| | | | 260 | | | | | 265 | | | | | 270 | | |
| Tyr | Met | Glu | Glu | Met | Ala | Asp | Thr | Ala | Asp | Ala | Ile | Glu | Met | Ala | Thr |
| | | | | 275 | | | | | 280 | | | | | 285 | |
| Leu | Asp | Lys | Glu | Met | Ala | Glu | Glu | Arg | Ala | Glu | Ser | Leu | Gln | Gln | Glu |
| | 290 | | | | | 295 | | | | | 300 | | | | |
| Val | Glu | Ala | Leu | Lys | Glu | Arg | Val | Asp | Glu | Leu | Thr | Thr | Asp | Leu | Glu |
| 305 | | | | | 310 | | | | | 315 | | | | | 320 |
| Ile | Leu | Lys | Ala | Glu | Ile | Glu | Glu | Lys | Gly | Ser | Asp | Gly | Ala | Ala | Ser |
| | | | | 325 | | | | | 330 | | | | | 335 | |
| Ser | Tyr | Gln | Leu | Lys | Gln | Leu | Glu | Gln | Asn | Ala | Arg | Leu | Lys | Asp |
| | | | 340 | | | | | 345 | | | | | 350 | | |
| Ala | Leu | Val | Arg | Met | Arg | Asp | Leu | Ser | Ser | Ser | Glu | Lys | Gln | Glu | His |
| | | | | 355 | | | | | 360 | | | | | 365 | |
| Val | Lys | Leu | Gln | Lys | Leu | Met | Glu | Lys | Lys | Asn | Gln | Glu | Leu | Glu | Val |

```
                370                 375                 380
Val Arg Gln Gln Arg Glu Arg Leu Gln Glu Glu Leu Ser Gln Ala Glu
385                 390                 395                 400

Ser Thr Ile Asp Glu Leu Lys Glu Gln Val Asp Ala Ala Leu Gly Ala
                405                 410                 415

Glu Glu Met Val Glu Met Leu Thr Asp Arg Asn Leu Asn Leu Glu Glu
            420                 425                 430

Lys Val Arg Glu Leu Arg Glu Thr Val Gly Asp Leu Glu Ala Met Asn
                435                 440                 445

Glu Met Asn Asp Glu Leu Gln Glu Asn Ala Arg Glu Thr Glu Leu Glu
            450                 455                 460

Leu Arg Glu Gln Leu Asp Met Ala Gly Ala Arg Val Arg Glu Ala Gln
465                 470                 475                 480

Lys Arg Val Glu Ala Ala Gln Glu Thr Val Ala Asp Tyr Gln Gln Thr
                485                 490                 495

Ile Lys Lys Tyr Arg Gln Leu Thr Ala His Leu Gln Asp Val Asn Arg
            500                 505                 510

Glu Leu Thr Asn Gln Gln Glu Ala Ser Val Glu Arg Gln Gln Gln Pro
            515                 520                 525

Pro Pro Glu Thr Phe Asp Phe Lys Ile Lys Phe Ala Glu Thr Lys Ala
530                 535                 540

His Ala Lys Ala Ile Glu Met Glu Leu Arg Gln Met Glu Val Ala Gln
545                 550                 555                 560

Ala Asn Arg His Met Ser Leu Leu Thr Ala Phe Met Pro Asp Ser Phe
                565                 570                 575

Leu Arg Pro Gly Gly Asp His Asp Cys Val Leu Val Leu Leu Leu Met
            580                 585                 590

Pro Arg Leu Ile Cys Lys Ala Glu Leu Ile Arg Lys Gln Ala Gln Glu
            595                 600                 605

Lys Phe Glu Leu Ser Glu Asn Cys Ser Glu Arg Pro Gly Leu Arg Gly
            610                 615                 620

Ala Ala Gly Glu Gln Leu Ser Phe Ala Ala Gly Leu Val Tyr Ser Leu
625                 630                 635                 640

Ser Leu Leu Gln Ala Thr Leu His Arg Tyr Glu His Ala Leu Ser Gln
                645                 650                 655

Cys Ser Val Asp Val Tyr Lys Lys Val Gly Ser Leu Tyr Pro Glu Met
            660                 665                 670

Ser Ala His Glu Arg Ser Leu Asp Phe Leu Ile Glu Leu Leu His Lys
            675                 680                 685

Asp Gln Leu Asp Glu Thr Val Asn Val Glu Pro Leu Thr Lys Ala Ile
            690                 695                 700

Lys Tyr Tyr Gln His Leu Tyr Ser Ile His Leu Ala Glu Gln Pro Glu
705                 710                 715                 720

Asp Cys Thr Met Gln Leu Ala Asp His Ile Lys Phe Thr Gln Ser Ala
                725                 730                 735

Leu Asp Cys Met Ser Val Glu Val Gly Arg Leu Arg Ala Phe Leu Gln
            740                 745                 750

Gly Gly Gln Glu Ala Thr Asp Ile Ala Leu Leu Leu Arg Asp Leu Glu
            755                 760                 765

Thr Ser Cys Ser Asp Ile Arg Gln Phe Cys Lys Lys Ile Arg Arg Arg
            770                 775                 780

Met Pro Gly Thr Asp Ala Pro Gly Ile Pro Ala Ala Leu Ala Phe Gly
785                 790                 795                 800
```

```
Pro Gln Val Ser Asp Thr Leu Leu Asp Cys Arg Lys His Leu Thr Trp
            805                 810                 815

Val Val Ala Val Leu Gln Glu Val Ala Ala Ala Ala Gln Leu Ile
            820                 825                 830

Ala Pro Leu Ala Glu Asn Glu Gly Leu Leu Val Ala Leu Glu Glu
            835                 840                 845

Leu Ala Phe Lys Ala Ser Glu Gln Ile Tyr Gly Thr Pro Ser Ser Ser
850                 855                 860

Pro Tyr Glu Cys Leu Arg Gln Ser Cys Asn Ile Leu Ile Ser Thr Met
865                 870                 875                 880

Asn Lys Leu Ala Thr Ala Met Gln Glu Gly Tyr Asp Ala Glu Arg
            885                 890                 895

Pro Pro Ser Lys Pro Pro Val Glu Leu Arg Ala Ala Leu Arg
            900                 905                 910

Ala Glu Ile Thr Asp Ala Glu Gly Leu Gly Leu Lys Leu Glu Asp Arg
            915                 920                 925

Glu Thr Val Ile Lys Glu Leu Lys Lys Ser Leu Lys Ile Lys Gly Glu
            930                 935                 940

Glu Leu Ser Glu Ala Asn Val Arg Leu Ser Leu Leu Glu Lys Lys Leu
945                 950                 955                 960

Asp Ser Ala Ala Lys Asp Ala Asp Glu Arg Ile Glu Lys Val Gln Thr
                965                 970                 975

Arg Leu Glu Glu Thr Gln Ala Leu Leu Arg Lys Lys Glu Lys Glu Phe
            980                 985                 990

Glu Glu Thr Met Asp Ala Leu Gln Ala Asp Ile Asp Gln Leu Glu Ala
            995                 1000                1005

Glu Lys Ala Glu Leu Lys Gln Arg Leu Asn Ser Gln Ser Lys Arg
            1010                1015                1020

Thr Ile Glu Gly Leu Arg Gly Pro Pro Pro Ser Gly Ile Ala Thr
            1025                1030                1035

Leu Val Ser Gly Ile Ala Gly Gly Ala Ile Pro Gly Gln Ala Pro
            1040                1045                1050

Gly Ser Val Pro Gly Pro Gly Leu Val Lys Asp Ser Pro Leu Leu
            1055                1060                1065

Leu Gln Gln Ile Ser Ala Met Arg Leu His Ile Ser Gln Leu Gln
            1070                1075                1080

His Glu Asn Ser Ile Leu Lys Gly Ala Gln Met Lys Ala Ser Leu
            1085                1090                1095

Ala Ser Leu Pro Pro Leu His Val Ala Lys Leu Ser His Glu Gly
            1100                1105                1110

Pro Gly Ser Glu Leu Pro Ala Gly Ala Leu Tyr Arg Lys Thr Ser
            1115                1120                1125

Gln Leu Leu Glu Thr Leu Asn Gln Leu Ser Thr His Thr His Val
            1130                1135                1140

Val Asp Ile Thr Arg Thr Ser Pro Ala Ala Lys Ser Pro Ser Ala
            1145                1150                1155

Gln Leu Met Glu Gln Val Ala Gln Leu Lys Ser Leu Ser Asp Thr
            1160                1165                1170

Val Glu Lys Leu Lys Asp Glu Val Leu Lys Glu Thr Val Ser Gln
            1175                1180                1185

Arg Pro Gly Ala Thr Val Pro Thr Asp Phe Ala Thr Phe Pro Ser
            1190                1195                1200
```

```
Ser Ala Phe Leu Arg Glu Asp Pro Lys Trp Glu Phe Pro Arg Lys
1205                1210                1215

Asn Leu Val Leu Gly Lys Thr Leu Gly Glu Gly Glu Phe Gly Lys
1220                1225                1230

Val Val Lys Ala Thr Ala Phe His Leu Lys Gly Arg Ala Gly Tyr
1235                1240                1245

Thr Thr Val Ala Val Lys Met Leu Lys Glu Asn Ala Ser Pro Ser
1250                1255                1260

Glu Leu Arg Asp Leu Leu Ser Glu Phe Asn Val Leu Lys Gln Val
1265                1270                1275

Asn His Pro His Val Ile Lys Leu Tyr Gly Ala Cys Ser Gln Asp
1280                1285                1290

Gly Pro Leu Leu Leu Ile Val Glu Tyr Ala Lys Tyr Gly Ser Leu
1295                1300                1305

Arg Gly Phe Leu Arg Glu Ser Arg Lys Val Gly Pro Gly Tyr Leu
1310                1315                1320

Gly Ser Gly Gly Ser Arg Asn Ser Ser Ser Leu Asp His Pro Asp
1325                1330                1335

Glu Arg Ala Leu Thr Met Gly Asp Leu Ile Ser Phe Ala Trp Gln
1340                1345                1350

Ile Ser Gln Gly Met Gln Tyr Leu Ala Glu Met Lys Leu Val His
1355                1360                1365

Arg Asp Leu Ala Ala Arg Asn Ile Leu Val Ala Glu Gly Arg Lys
1370                1375                1380

Met Lys Ile Ser Asp Phe Gly Leu Ser Arg Asp Val Tyr Glu Glu
1385                1390                1395

Asp Ser Tyr Val Lys Arg Ser Gln Gly Arg Ile Pro Val Lys Trp
1400                1405                1410

Met Ala Ile Glu Ser Leu Phe Asp His Ile Tyr Thr Thr Gln Ser
1415                1420                1425

Asp Val Trp Ser Phe Gly Val Leu Leu Trp Glu Ile Val Thr Leu
1430                1435                1440

Gly Gly Asn Pro Tyr Pro Gly Ile Pro Pro Glu Arg Leu Phe Asn
1445                1450                1455

Leu Leu Lys Thr Gly His Arg Met Glu Arg Pro Asp Asn Cys Ser
1460                1465                1470

Glu Glu Met Tyr Arg Leu Met Leu Gln Cys Trp Lys Gln Glu Pro
1475                1480                1485

Asp Lys Arg Pro Val Phe Ala Asp Ile Ser Lys Asp Leu Glu Lys
1490                1495                1500

Met Met Val Lys Arg Arg Asp Tyr Leu Asp Leu Ala Ala Ser Thr
1505                1510                1515

Pro Ser Asp Ser Leu Ile Tyr Asp Asp Gly Leu Ser Glu Glu Glu
1520                1525                1530

Thr Pro Leu Val Asp Cys Asn Asn Ala Pro Leu Pro Arg Ala Leu
1535                1540                1545

Pro Ser Thr Trp Ile Glu Asn Lys Leu Tyr Gly Arg Ile Ser His
1550                1555                1560

Ala Phe Thr Arg Phe
1565

<210> SEQ ID NO 13
<211> LENGTH: 4491
<212> TYPE: DNA
```

<213> ORGANISM: Artificial Sequence
<220> FEATURE:
<223> OTHER INFORMATION: coding sequence of fusion peptide

<400> SEQUENCE: 13

```
atgatgagac aggcaccgac agcccgaaag accacaactc ggcgacccaa gcccacgcgc      60
ccagccagta ctggggtggc tggggccagt agctccctgg gcccctctgg ctcagcgtca     120
gcaggtgagc tgagcagcag tgagcccagc accccggctc agactccgct ggcagcaccc     180
atcatcccca cgccggtcct cacctctcct ggagcagtcc ccccgcttcc ttccccatcc     240
aaggaggagg agggactaag ggctcaggtg cgggacctgg aggagaaact agagaccctg     300
agactgaaac gggcagaaga caaagcaaag ctaaaagagc tggagaaaca caaaatccag     360
ctggagcagg tgcaggaatg gaagagcaaa atgcaggagc agcaggccga cctgcagcgg     420
cgcctcaagg aggcgagaaa ggaagccaag gaggcgctgg aggcaaagga acgctatatg     480
gaggagatgg ctgatactgc tgatgccatt gagatggcca ctttggacaa ggagatggct     540
gaagagcggg ctgagtccct gcagcaggag gtggaggcac tgaaggagcg ggtggacgag     600
ctcactactg acttagagat cctcaaggct gagattgaag agaagggctc agatggcgct     660
gcatccagtt atcagctcaa gcagcttgag gagcagaatg cccgcctgaa ggatgccctg     720
gtgaggatgc gggatctttc ttcctcagag aagcaggagc atgtgaagct ccagaagctc     780
atggaaaaga gaaccaaga gctggaagtt gtgaggcaac agcgggagcg tctgcaggag     840
gagctaagcc aggcagagag caccattgat gagctcaagg agcaggtgga tgctgctctg     900
ggtgctgagg agatggtgga gatgctgaca gatcggaacc tgaatctgga agagaaagtg     960
cgcgagttga gggagactgt gggagacttg gaagcgatga atgagatgaa cgatgagctg    1020
caggagaatg cacgtgagac agaactggag ctgcgggagc agctggacat ggcaggcgcg    1080
cgggttcgtg aggcccagaa gcgtgtggag gcagcccagg agacggttgc agactaccag    1140
cagaccatca gaagtaccg ccagctgacc gcccatctac aggatgtgaa tcgggaactg    1200
acaaaccagc aggaagcatc tgtggagagg caacagcagc cacctccaga gacctttgac    1260
ttcaaaatca gtttgctga gactaaggcc catgccaagg caattgagat ggaattgagg    1320
cagatggagg tggcccaggc caatcgacac atgtccctgc tgacagcctt catgcctgac    1380
agcttccttc ggccaggtgg ggaccatgac tgcgttctgg tgctgttgct catgcctcgt    1440
ctcatttgca aggcagagct gatccggaag caggcccagg agaagtttga actaagtgag    1500
aactgttcag agcggcctgg gctgcgagga gctgctgggg agcaactcag ctttgctgct    1560
ggactggtgt actcgctgag cctgctgcag gccacgctac accgctatga gcatgccctc    1620
tctcagtgca gtgtggatgt gtataagaaa gtgggcagcc tgtaccctga tgagtgcc    1680
catgagcgct ccttggattt cctcattgaa ctgctgcaca aggatcagct ggatgagact    1740
gtcaatgtgg agcctctcac caaggccatc aagtactatc agcatctgta cagcatccac    1800
cttgccgaac agcctgagga ctgtactatg cagctggctg accacattaa gttcacgcag    1860
agtgctctgg actgcatgag tgtggaggta ggacggctgc gtgccttctt gcagggtggg    1920
caggaggcta cagatattgc cctcctgctc cgggatctgg aaacttcatg cagtgacatc    1980
cgccagttct gcaagaagat ccgaaggcga atgccaggga cagatgctcc tgggatccca    2040
gctgcactgg cctttggacc acaggtatct gacacgctcc tagactgcag gaaacacttg    2100
acgtgggtcg tggctgtgct gcaggaggtg gcagctgctg ctgcccagct cattgcccca    2160
ctggcagaga atgagggggct acttgtggct gctctggagg aactggcttt caaagcaagc    2220
```

-continued

```
gagcagatct atgggacccc ctccagcagc ccctatgagt gtctgcgcca gtcatgcaac      2280
atcctcatca gtaccatgaa caagctggcc acagccatgc aggaggggga gtatgatgca      2340
gagcggcccc ccagcaagcc tccaccggtt gaactgcggg ctgctgccct tcgtgcagag      2400
atcacagatg ctgaaggcct gggtttgaag ctcgaagatc gagagacagt tattaaggag      2460
ttgaagaagt cactcaagat taagggagag gagctaagtg aggccaatgt gcggctgagc      2520
ctcctggaga agaagttgga cagtgctgcc aaggatgcag atgagcgcat cgagaaagtc      2580
cagactcggc tggaggagac ccaggcactg ctgcgaaaga aggagaaaga gtttgaggag      2640
acaatggatg cactccaggc tgacatcgac cagctggagg cagagaaggc agaactaaag      2700
cagcgtctga acagccagtc caaacgcacg attgagggac tccggggccc tcctccttca      2760
ggcattgcta ctctggtctc tggcattgct ggtggagcca tccctgggca ggctccaggg      2820
tctgtgccag gcccagggct ggtgaaggac tcaccactgc tgcttcagca gatctctgcc      2880
atgaggctgc acatctccca gctccagcat gagaacagca tcctcaaggg agcccagatg      2940
aaggcatcct tggcatccct gcccctctg catgttgcaa agctatccca tgagggccct      3000
ggcagtgagt taccagctgg agcgctgtat cgtaagacca gccagctgct ggagacattg      3060
aatcaattga gcacacacac gcacgtagta gacatcactc gcaccagccc tgctgccaag      3120
agcccgtcgg cccaacttat ggagcaagtg gctcagctta agtccctgag tgacaccgtc      3180
gagaagctca aggatgaggt cctcaaggag acagtatctc agcgccctgg agccacagta      3240
cccactgact ttgccaccct ccccttcatca gccttcctca gggaggatcc aaagtgggaa      3300
ttccctcgga agaacttggt tcttggaaaa actctaggag aaggcgaatt tggaaaagtg      3360
gtcaaggcaa cggccttcca tctgaaaggc agagcagggt acaccacggt ggccgtgaag      3420
atgctgaaag agaacgcctc cccgagtgag cttcgagacc tgctgtcaga gttcaacgtc      3480
ctgaagcagg tcaaccaccc acatgtcatc aaattgtatg gggcctgcag ccaggatggc      3540
ccgctcctcc tcatcgtgga gtacgccaaa tacggctccc tgcggggctt cctccgcgag      3600
agccgcaaag tggggcctgg ctacctgggc agtggaggca ccgcaactc cagctccctg      3660
gaccacccgg atgagcgggc cctcaccatg ggcgacctca tctcatttgc ctggcagatc      3720
tcacagggga tgcagtatct ggccgagatg aagctcgttc atcgggactt ggcagccaga      3780
aacatcctgg tagctgaggg gcggaagatg aagatttcgg atttcggctt gtcccgagat      3840
gtttatgaag aggattccta cgtgaagagg agccagggtc ggattccagt taaatggatg      3900
gcaattgaat cccttttga tcatatctac accacgcaaa gtgatgtatg gtcttttggt      3960
gtcctgctgt gggagatcgt gaccctaggg ggaaacccct atcctgggat tcctcctgag      4020
cggctcttca accttctgaa gaccggccac cggatggaga ggccagacaa ctgcagcgag      4080
gagatgtacc gcctgatgct gcaatgctgg aagcaggagc cggacaaaag gccggtgttt      4140
gcggacatca gcaaagacct ggagaagatg atggttaaga ggagagacta cttggacctt      4200
gcggcgtcca ctccatctga ctccctgatt tatgacgacg gcctctcaga ggaggagaca      4260
ccgctggtgg actgtaataa tgccccctc cctcgagccc tcccttccac atggattgaa      4320
aacaaactct atggcatgtc agacccgaac tggcctggag agagtcctgt accactcacg      4380
agagctgatg gcactaacac tgggtttcca agatatccaa atgatagtgt atatgctaac      4440
tggatgcttt caccctcagc ggcaaaatta atggacacgt ttgatagtta a              4491
```

<210> SEQ ID NO 14

<211> LENGTH: 1496
<212> TYPE: PRT
<213> ORGANISM: Artificial Sequence
<220> FEATURE:
<223> OTHER INFORMATION: fusion peptide

<400> SEQUENCE: 14

Met Met Arg Gln Ala Pro Thr Ala Arg Lys Thr Thr Thr Arg Arg Pro
1               5                   10                  15

Lys Pro Thr Arg Pro Ala Ser Thr Gly Val Ala Gly Ala Ser Ser Ser
            20                  25                  30

Leu Gly Pro Ser Gly Ser Ala Ser Ala Gly Glu Leu Ser Ser Ser Glu
        35                  40                  45

Pro Ser Thr Pro Ala Gln Thr Pro Leu Ala Ala Pro Ile Ile Pro Thr
    50                  55                  60

Pro Val Leu Thr Ser Pro Gly Ala Val Pro Pro Leu Pro Ser Pro Ser
65                  70                  75                  80

Lys Glu Glu Glu Gly Leu Arg Ala Gln Val Arg Asp Leu Glu Glu Lys
                85                  90                  95

Leu Glu Thr Leu Arg Leu Lys Arg Ala Glu Asp Lys Ala Lys Leu Lys
            100                 105                 110

Glu Leu Glu Lys His Lys Ile Gln Leu Glu Gln Val Gln Glu Trp Lys
        115                 120                 125

Ser Lys Met Gln Glu Gln Gln Ala Asp Leu Gln Arg Arg Leu Lys Glu
    130                 135                 140

Ala Arg Lys Glu Ala Lys Glu Ala Leu Glu Ala Lys Glu Arg Tyr Met
145                 150                 155                 160

Glu Glu Met Ala Asp Thr Ala Asp Ala Ile Glu Met Ala Thr Leu Asp
                165                 170                 175

Lys Glu Met Ala Glu Glu Arg Ala Glu Ser Leu Gln Gln Glu Val Glu
            180                 185                 190

Ala Leu Lys Glu Arg Val Asp Glu Leu Thr Thr Asp Leu Glu Ile Leu
        195                 200                 205

Lys Ala Glu Ile Glu Glu Lys Gly Ser Asp Gly Ala Ala Ser Ser Tyr
    210                 215                 220

Gln Leu Lys Gln Leu Glu Glu Gln Asn Ala Arg Leu Lys Asp Ala Leu
225                 230                 235                 240

Val Arg Met Arg Asp Leu Ser Ser Ser Glu Lys Gln Glu His Val Lys
                245                 250                 255

Leu Gln Lys Leu Met Glu Lys Lys Asn Gln Glu Leu Glu Val Val Arg
            260                 265                 270

Gln Gln Arg Glu Arg Leu Gln Glu Glu Leu Ser Gln Ala Glu Ser Thr
        275                 280                 285

Ile Asp Glu Leu Lys Glu Gln Val Asp Ala Ala Leu Gly Ala Glu Glu
    290                 295                 300

Met Val Glu Met Leu Thr Asp Arg Asn Leu Asn Leu Glu Glu Lys Val
305                 310                 315                 320

Arg Glu Leu Arg Glu Thr Val Gly Asp Leu Glu Ala Met Asn Glu Met
                325                 330                 335

Asn Asp Glu Leu Gln Glu Asn Ala Arg Glu Thr Glu Leu Glu Leu Arg
            340                 345                 350

Glu Gln Leu Asp Met Ala Gly Ala Arg Val Arg Glu Ala Gln Lys Arg
        355                 360                 365

Val Glu Ala Ala Gln Glu Thr Val Ala Asp Tyr Gln Gln Thr Ile Lys
    370                 375                 380

```
Lys Tyr Arg Gln Leu Thr Ala His Leu Gln Asp Val Asn Arg Glu Leu
385                 390                 395                 400

Thr Asn Gln Gln Glu Ala Ser Val Glu Arg Gln Gln Pro Pro Pro
            405                 410                 415

Glu Thr Phe Asp Phe Lys Ile Lys Phe Ala Glu Thr Lys Ala His Ala
        420                 425                 430

Lys Ala Ile Glu Met Glu Leu Arg Gln Met Glu Val Ala Gln Ala Asn
            435                 440                 445

Arg His Met Ser Leu Leu Thr Ala Phe Met Pro Asp Ser Phe Leu Arg
        450                 455                 460

Pro Gly Gly Asp His Asp Cys Val Leu Val Leu Leu Met Pro Arg
465                 470                 475                 480

Leu Ile Cys Lys Ala Glu Leu Ile Arg Lys Gln Ala Gln Glu Lys Phe
            485                 490                 495

Glu Leu Ser Glu Asn Cys Ser Glu Arg Pro Gly Leu Arg Gly Ala Ala
        500                 505                 510

Gly Glu Gln Leu Ser Phe Ala Ala Gly Leu Val Tyr Ser Leu Ser Leu
        515                 520                 525

Leu Gln Ala Thr Leu His Arg Tyr Glu His Ala Leu Ser Gln Cys Ser
530                 535                 540

Val Asp Val Tyr Lys Lys Val Gly Ser Leu Tyr Pro Glu Met Ser Ala
545                 550                 555                 560

His Glu Arg Ser Leu Asp Phe Leu Ile Glu Leu Leu His Lys Asp Gln
            565                 570                 575

Leu Asp Glu Thr Val Asn Val Glu Pro Leu Thr Lys Ala Ile Lys Tyr
        580                 585                 590

Tyr Gln His Leu Tyr Ser Ile His Leu Ala Glu Gln Pro Glu Asp Cys
        595                 600                 605

Thr Met Gln Leu Ala Asp His Ile Lys Phe Thr Gln Ser Ala Leu Asp
        610                 615                 620

Cys Met Ser Val Glu Val Gly Arg Leu Arg Ala Phe Leu Gln Gly Gly
625                 630                 635                 640

Gln Glu Ala Thr Asp Ile Ala Leu Leu Leu Arg Asp Leu Glu Thr Ser
            645                 650                 655

Cys Ser Asp Ile Arg Gln Phe Cys Lys Lys Ile Arg Arg Met Pro
            660                 665                 670

Gly Thr Asp Ala Pro Gly Ile Pro Ala Ala Leu Ala Phe Gly Pro Gln
        675                 680                 685

Val Ser Asp Thr Leu Leu Asp Cys Arg Lys His Leu Thr Trp Val Val
        690                 695                 700

Ala Val Leu Gln Glu Val Ala Ala Ala Ala Gln Leu Ile Ala Pro
705                 710                 715                 720

Leu Ala Glu Asn Glu Gly Leu Leu Val Ala Leu Glu Glu Leu Ala
            725                 730                 735

Phe Lys Ala Ser Glu Gln Ile Tyr Gly Thr Pro Ser Ser Pro Tyr
        740                 745                 750

Glu Cys Leu Arg Gln Ser Cys Asn Ile Leu Ile Ser Thr Met Asn Lys
        755                 760                 765

Leu Ala Thr Ala Met Gln Glu Gly Glu Tyr Asp Ala Glu Arg Pro Pro
        770                 775                 780

Ser Lys Pro Pro Val Glu Leu Arg Ala Ala Ala Leu Arg Ala Glu
785                 790                 795                 800
```

```
Ile Thr Asp Ala Glu Gly Leu Gly Leu Lys Leu Glu Asp Arg Glu Thr
            805                 810                 815

Val Ile Lys Glu Leu Lys Lys Ser Leu Lys Ile Lys Gly Glu Glu Leu
        820                 825                 830

Ser Glu Ala Asn Val Arg Leu Ser Leu Leu Glu Lys Lys Leu Asp Ser
            835                 840                 845

Ala Ala Lys Asp Ala Asp Glu Arg Ile Glu Lys Val Gln Thr Arg Leu
    850                 855                 860

Glu Glu Thr Gln Ala Leu Arg Lys Lys Glu Lys Glu Phe Glu Glu
865                 870                 875                 880

Thr Met Asp Ala Leu Gln Ala Asp Ile Asp Gln Leu Glu Ala Glu Lys
                885                 890                 895

Ala Glu Leu Lys Gln Arg Leu Asn Ser Gln Ser Lys Arg Thr Ile Glu
        900                 905                 910

Gly Leu Arg Gly Pro Pro Ser Gly Ile Ala Thr Leu Val Ser Gly
    915                 920                 925

Ile Ala Gly Gly Ala Ile Pro Gly Gln Ala Pro Gly Ser Val Pro Gly
    930                 935                 940

Pro Gly Leu Val Lys Asp Ser Pro Leu Leu Gln Gln Ile Ser Ala
945                 950                 955                 960

Met Arg Leu His Ile Ser Gln Leu Gln His Glu Asn Ser Ile Leu Lys
            965                 970                 975

Gly Ala Gln Met Lys Ala Ser Leu Ala Ser Leu Pro Pro Leu His Val
                980                 985                 990

Ala Lys Leu Ser His Glu Gly Pro  Gly Ser Glu Leu Pro  Ala Gly Ala
            995                 1000                1005

Leu Tyr  Arg Lys Thr Ser Gln  Leu Leu Glu Thr Leu   Asn Gln Leu
    1010                1015                1020

Ser Thr  His Thr  His Val Val  Asp Ile Thr Arg Thr   Ser Pro Ala
    1025                1030                1035

Ala Lys  Ser Pro Ser Ala Gln  Leu Met Glu Gln Val   Ala Gln Leu
    1040                1045                1050

Lys Ser  Leu Ser Asp Thr Val  Glu Lys Leu Lys Asp  Glu Val Leu
    1055                1060                1065

Lys Glu   Thr Val Ser Gln Arg  Pro Gly Ala Thr Val  Pro Thr Asp
    1070                1075                1080

Phe Ala  Thr Phe Pro Ser Ser  Ala Phe Leu Arg Glu  Asp Pro Lys
    1085                1090                1095

Trp Glu  Phe Pro Arg Lys Asn  Leu Val Leu Gly Lys   Thr Leu Gly
    1100                1105                1110

Glu Gly   Glu Phe Gly Lys Val  Val Lys Ala Thr Ala   Phe His Leu
    1115                1120                1125

Lys Gly  Arg Ala Gly Tyr Thr   Thr Val Ala Val Lys   Met Leu Lys
    1130                1135                1140

Glu Asn   Ala Ser Pro Ser Glu   Leu Arg Asp Leu Leu   Ser Glu Phe
    1145                1150                1155

Asn Val  Leu Lys Gln Val Asn   His Pro His Val Ile   Lys Leu Tyr
    1160                1165                1170

Gly Ala  Cys Ser Gln Asp Gly   Pro Leu Leu Leu Ile   Val Glu Tyr
    1175                1180                1185

Ala Lys  Tyr Gly Ser Leu Arg   Gly Phe Leu Arg Glu   Ser Arg Lys
    1190                1195                1200

Val Gly  Pro Gly Tyr Leu Gly   Ser Gly Gly Ser Arg   Asn Ser Ser
```

| | | | | | | | | | |
|---|---|---|---|---|---|---|---|---|---|
| | 1205 | | | 1210 | | | 1215 | | |
| Ser | Leu | Asp | His | Pro | Asp | Glu | Arg | Ala | Leu | Thr | Met | Gly | Asp | Leu |

Ser Leu Asp His Pro Asp Glu Arg Ala Leu Thr Met Gly Asp Leu
 1220                1225                1230

Ile Ser Phe Ala Trp Gln Ile Ser Gln Gly Met Gln Tyr Leu Ala
 1235                1240                1245

Glu Met Lys Leu Val His Arg Asp Leu Ala Ala Arg Asn Ile Leu
 1250                1255                1260

Val Ala Glu Gly Arg Lys Met Lys Ile Ser Asp Phe Gly Leu Ser
 1265                1270                1275

Arg Asp Val Tyr Glu Glu Asp Ser Tyr Val Lys Arg Ser Gln Gly
 1280                1285                1290

Arg Ile Pro Val Lys Trp Met Ala Ile Glu Ser Leu Phe Asp His
 1295                1300                1305

Ile Tyr Thr Thr Gln Ser Asp Val Trp Ser Phe Gly Val Leu Leu
 1310                1315                1320

Trp Glu Ile Val Thr Leu Gly Gly Asn Pro Tyr Pro Gly Ile Pro
 1325                1330                1335

Pro Glu Arg Leu Phe Asn Leu Leu Lys Thr Gly His Arg Met Glu
 1340                1345                1350

Arg Pro Asp Asn Cys Ser Glu Glu Met Tyr Arg Leu Met Leu Gln
 1355                1360                1365

Cys Trp Lys Gln Glu Pro Asp Lys Arg Pro Val Phe Ala Asp Ile
 1370                1375                1380

Ser Lys Asp Leu Glu Lys Met Met Val Lys Arg Arg Asp Tyr Leu
 1385                1390                1395

Asp Leu Ala Ala Ser Thr Pro Ser Asp Ser Leu Ile Tyr Asp Asp
 1400                1405                1410

Gly Leu Ser Glu Glu Glu Thr Pro Leu Val Asp Cys Asn Asn Ala
 1415                1420                1425

Pro Leu Pro Arg Ala Leu Pro Ser Thr Trp Ile Glu Asn Lys Leu
 1430                1435                1440

Tyr Gly Met Ser Asp Pro Asn Trp Pro Gly Glu Ser Pro Val Pro
 1445                1450                1455

Leu Thr Arg Ala Asp Gly Thr Asn Thr Gly Phe Pro Arg Tyr Pro
 1460                1465                1470

Asn Asp Ser Val Tyr Ala Asn Trp Met Leu Ser Pro Ser Ala Ala
 1475                1480                1485

Lys Leu Met Asp Thr Phe Asp Ser
 1490                1495

<210> SEQ ID NO 15
<211> LENGTH: 4365
<212> TYPE: DNA
<213> ORGANISM: Artificial Sequence
<220> FEATURE:
<223> OTHER INFORMATION: coding sequence of fusion peptide

<400> SEQUENCE: 15
atgatgagac aggcaccgac agcccgaaag accacaactc ggcgacccaa gcccacgcgc    60
ccagccagta ctggggtggc tggggccagt agctccctgg cccctctggg ctcagcgtca   120
gcaggtgagc tgagcagcag tgagcccagc accccggctc agactccgct ggcagcaccc   180
atcatcccca cgccggtcct cacctctcct ggagcagtcc cccgcttcc ttccccatcc   240 aaggaggagg agggactaag ggctcaggtg cgggacctgg aggagaaact agagaccctg   300

-continued

```
agactgaaac gggcagaaga caaagcaaag ctaaaagagc tggagaaaca caaaatccag    360
ctggagcagg tgcaggaatg gaagagcaaa atgcaggagc agcaggccga cctgcagcgg    420
cgcctcaagg aggcgagaaa ggaagccaag gaggcgctgg aggcaaagga acgctatatg    480
gaggagatgc tgatactgc tgatgccatt gagatggcca ctttggacaa ggagatggct    540
gaagagcggg ctgagtccct gcagcaggag gtggaggcac tgaaggagcg ggtggacgag    600
ctcactactg acttagagat cctcaaggct gagattgaag agaagggctc agatggcgct    660
gcatccagtt atcagctcaa gcagcttgag gagcagaatg cccgcctgaa ggatgccctg    720
gtgaggatgc gggatctttc ttcctcagag aagcaggagc atgtgaagct ccagaagctc    780
atggaaaaga gaaccaaga gctggaagtt gtgaggcaac agcgggagcg tctgcaggag    840
gagctaagcc aggcagagag caccattgat gagctcaagg agcaggtgga tgctgctctg    900
ggtgctgagg agatggtgga gatgctgaca gatcggaacc tgaatctgga agagaaagtg    960
cgcgagttga gggagactgt gggagacttg gaagcgatga atgagatgaa cgatgagctg   1020
caggagaatg cacgtgagac agaactggag ctgcgggagc agctggacat ggcaggcgcg   1080
cgggttcgtg aggcccagaa gcgtgtggag gcagcccagg agacggttgc agactaccag   1140
cagaccatca agaagtaccg ccagctgacc gcccatctac aggatgtgaa tcgggaactg   1200
acaaaccagc aggaagcatc tgtggagagg caacagcagc cacctccaga gacctttgac   1260
ttcaaaatca gtttgctga gactaaggcc catgccaagg caattgagat ggaattgagg   1320
cagatggagg tggcccaggc caatcgacac atgtccctgc tgacagcctt catgcctgac   1380
agcttccttc ggccaggtgg ggaccatgac tgcgttctgg tgctgttgct catgcctcgt   1440
ctcatttgca aggcagagct gatccggaag caggcccagg agaagtttga actaagtgag   1500
aactgttcag agcggcctgg gctgcgagga gctgctgggg agcaactcag ctttgctgct   1560
ggactggtgt actcgctgag cctgctgcag gccacgctac accgctatga gcatgccctc   1620
tctcagtgca gtgtggatgt gtataagaaa gtgggcagcc tgtaccctga tgagtgcc    1680 catgagcgct ccttggattt cctcattgaa ctgctgcaca aggatcagct ggatgagact   1740
gtcaatgtgg agcctctcac caaggccatc aagtactatc agcatctgta cagcatccac   1800
cttgccgaac agcctgagga ctgtactatg cagctggctg accacattaa gttcacgcag   1860
agtgctctgg actgcatgag tgtggaggta ggacggctgc gtgccttctt gcagggtggg   1920
caggaggcta cagatattgc cctcctgctc cgggatctgg aaacttcatg cagtgacatc   1980
cgccagttct gcaagaagat ccgaaggcga atgccaggga cagatgctcc tgggatccca   2040
gctgcactgg cctttggacc acaggtatct gacacgctcc tagactgcag gaaacacttg   2100
acgtgggtcg tggctgtgct gcaggaggtg gcagctgctg ctgcccagct cattgcccca   2160
ctggcagaga atgaggggct acttgtggct gctctggagg aactggcttt caaagcaagc   2220
gagcagatct atgggacccc ctccagcagc ccctatgagt gtctgcgcca gtcatgcaac   2280
atcctcatca gtaccatgaa caagctggcc acagccatgc aggagggga gtatgatgca   2340 gagcggcccc ccagcaagcc tccaccggtt gaactgcggg ctgctgccct tcgtgcagag   2400
atcacagatg ctgaaggcct gggtttgaag ctcgaagatc gagagacagt tattaaggag   2460
ttgaagaagt cactcaagat taaggagag gagctaagtg aggccaatgt gcggctgagc   2520
ctcctggaga agaagttgga cagtgctgcc aaggatgcag atgagcgcat cgagaaagtc   2580
cagactcggc tggaggagac ccaggcactg ctgcgaaaga aggagaaaga gtttgaggag   2640
acaatggatg cactccaggc tgacatcgac cagctggagg cagagaaggc agaactaaag   2700
```

```
cagcgtctga acagccagtc caaacgcacg attgagggac tccggggccc tcctccttca    2760
ggcattgcta ctctggtctc tggcattgct ggtggagcca tccctgggca ggctccaggg    2820
tctgtgccag gcccagggct ggtgaaggac tcaccactgc tgcttcagca gatctctgcc    2880
atgaggctgc acatctccca gctccagcat gagaacagca tcctcaaggg agcccagatg    2940
aaggcatcct tggcatccct gccccctctg catgttgcaa agctatccca tgagggccct    3000
ggcagtgagt taccagctgg agcgctgtat cgtaagacca ccagctgct ggagacattg     3060 aatcaattga gcacacacac gcacgtagta gacatcactc gcaccagccc tgctgccaag    3120
agcccgtcgg cccaacttat ggagcaagtg gctcagctta gtccctgag tgacaccgtc     3180 gagaagctca aggatgaggt cctcaaggag acagtatctc agcgccctgg agccacagta    3240
cccactgact ttgccaccct tccttcatca gccttcctca gggaggatcc aaagtgggaa    3300
ttccctcgga agaacttggt tcttggaaaa actctaggag aaggcgaatt tggaaaagtg    3360
gtcaaggcaa cggccttcca tctgaaaggc agagcagggt acaccacggt ggccgtgaag    3420
atgctgaaag agaacgcctc cccgagtgag cttcgagacc tgctgtcaga gttcaacgtc    3480
ctgaagcagg tcaaccaccc acatgtcatc aaattgtatg gggcctgcag ccaggatggc    3540
ccgctcctcc tcatcgtgga gtacgccaaa tacggctccc tgcggggctt cctccgcgag    3600
agccgcaaag tggggcctgg ctacctgggc agtggaggca gccgcaactc cagctccctg    3660
gaccacccgg atgagcgggc cctcaccatg gcgacctca tctcatttgc ctggcagatc     3720
tcacagggga tgcagtatct ggccgagatg aagctcgttc atcgggactt ggcagccaga    3780
aacatcctgg tagctgaggg gcggaagatg aagatttcgg atttcggctt gtcccgagat    3840
gtttatgaag aggattccta cgtgaagagg agccagggtc ggattccagt taaatggatg    3900
gcaattgaat ccctttttga tcatatctac accacgcaaa gtgatgtatg gtcttttggt    3960
gtcctgctgt gggagatcgt gaccctaggg ggaaacccct atcctgggat tcctcctgag    4020
cggctcttca accttctgaa gaccggccac cggatggaga ggccagacaa ctgcagcgag    4080
gagatgtacc gcctgatgct gcaatgctgg aagcaggagc cggacaaaag gccggtgttt    4140
gcggacatca gcaaagacct ggagaagatg atggttaaga ggagagacta cttggacctt    4200
gcggcgtcca ctccatctga ctccctgatt tatgacgacg gcctctcaga ggaggagaca    4260
ccgctggtgg actgtaataa tgcccccctc cctcgagccc tccttccac atggattgaa      4320 aacaaactct atggtagaat ttcccatgca tttactagat tctag                     4365
```

<210> SEQ ID NO 16
<211> LENGTH: 1454
<212> TYPE: PRT
<213> ORGANISM: Artificial Sequence
<220> FEATURE:
<223> OTHER INFORMATION: fusion peptide

<400> SEQUENCE: 16

```
Met Met Arg Gln Ala Pro Thr Ala Arg Lys Thr Thr Thr Arg Arg Pro
1               5                   10                  15

Lys Pro Thr Arg Pro Ala Ser Thr Gly Val Ala Gly Ala Ser Ser Ser
            20                  25                  30

Leu Gly Pro Ser Gly Ser Ala Ser Ala Gly Glu Leu Ser Ser Ser Glu
        35                  40                  45

Pro Ser Thr Pro Ala Gln Thr Pro Leu Ala Ala Pro Ile Ile Pro Thr
    50                  55                  60
```

-continued

```
Pro Val Leu Thr Ser Pro Gly Ala Val Pro Pro Leu Pro Ser Pro Ser
 65                  70                  75                  80

Lys Glu Glu Glu Gly Leu Arg Ala Gln Val Arg Asp Leu Glu Glu Lys
                 85                  90                  95

Leu Glu Thr Leu Arg Leu Lys Arg Ala Glu Asp Lys Ala Lys Leu Lys
            100                 105                 110

Glu Leu Glu Lys His Lys Ile Gln Leu Glu Gln Val Gln Glu Trp Lys
        115                 120                 125

Ser Lys Met Gln Glu Gln Ala Asp Leu Gln Arg Arg Leu Lys Glu
130                 135                 140

Ala Arg Lys Glu Ala Lys Glu Ala Leu Glu Ala Lys Glu Arg Tyr Met
145                 150                 155                 160

Glu Glu Met Ala Asp Thr Ala Asp Ala Ile Glu Met Ala Thr Leu Asp
                165                 170                 175

Lys Glu Met Ala Glu Glu Arg Ala Glu Ser Leu Gln Gln Glu Val Glu
            180                 185                 190

Ala Leu Lys Glu Arg Val Asp Glu Leu Thr Thr Asp Leu Glu Ile Leu
        195                 200                 205

Lys Ala Glu Ile Glu Glu Lys Gly Ser Asp Gly Ala Ala Ser Ser Tyr
210                 215                 220

Gln Leu Lys Gln Leu Glu Glu Gln Asn Ala Arg Leu Lys Asp Ala Leu
225                 230                 235                 240

Val Arg Met Arg Asp Leu Ser Ser Ser Glu Lys Gln Glu His Val Lys
                245                 250                 255

Leu Gln Lys Leu Met Glu Lys Lys Asn Gln Glu Leu Glu Val Val Arg
            260                 265                 270

Gln Gln Arg Glu Arg Leu Gln Glu Glu Leu Ser Gln Ala Glu Ser Thr
        275                 280                 285

Ile Asp Glu Leu Lys Glu Gln Val Asp Ala Ala Leu Gly Ala Glu Glu
290                 295                 300

Met Val Glu Met Leu Thr Asp Arg Asn Leu Asn Leu Glu Glu Lys Val
305                 310                 315                 320

Arg Glu Leu Arg Glu Thr Val Gly Asp Leu Glu Ala Met Asn Glu Met
                325                 330                 335

Asn Asp Glu Leu Gln Glu Asn Ala Arg Glu Thr Glu Leu Glu Leu Arg
            340                 345                 350

Glu Gln Leu Asp Met Ala Gly Ala Arg Val Arg Glu Ala Gln Lys Arg
        355                 360                 365

Val Glu Ala Ala Gln Glu Thr Val Ala Asp Tyr Gln Gln Thr Ile Lys
370                 375                 380

Lys Tyr Arg Gln Leu Thr Ala His Leu Gln Asp Val Asn Arg Glu Leu
385                 390                 395                 400

Thr Asn Gln Gln Glu Ala Ser Val Glu Arg Gln Gln Pro Pro Pro
                405                 410                 415

Glu Thr Phe Asp Phe Lys Ile Lys Phe Ala Glu Thr Lys Ala His Ala
            420                 425                 430

Lys Ala Ile Glu Met Glu Leu Arg Gln Met Glu Val Ala Gln Ala Asn
        435                 440                 445

Arg His Met Ser Leu Leu Thr Ala Phe Met Pro Asp Ser Phe Leu Arg
450                 455                 460

Pro Gly Gly Asp His Asp Cys Val Leu Val Leu Leu Met Pro Arg
465                 470                 475                 480

Leu Ile Cys Lys Ala Glu Leu Ile Arg Lys Gln Ala Gln Glu Lys Phe
```

-continued

```
                485                 490                 495
Glu Leu Ser Glu Asn Cys Ser Glu Arg Pro Gly Leu Arg Gly Ala Ala
            500                 505                 510
Gly Glu Gln Leu Ser Phe Ala Ala Gly Leu Val Tyr Ser Leu Ser Leu
            515                 520                 525
Leu Gln Ala Thr Leu His Arg Tyr Glu His Ala Leu Ser Gln Cys Ser
            530                 535                 540
Val Asp Val Tyr Lys Lys Val Gly Ser Leu Tyr Pro Glu Met Ser Ala
545                 550                 555                 560
His Glu Arg Ser Leu Asp Phe Leu Ile Glu Leu Leu His Lys Asp Gln
                565                 570                 575
Leu Asp Glu Thr Val Asn Val Glu Pro Leu Thr Lys Ala Ile Lys Tyr
                580                 585                 590
Tyr Gln His Leu Tyr Ser Ile His Leu Ala Glu Gln Pro Glu Asp Cys
                595                 600                 605
Thr Met Gln Leu Ala Asp His Ile Lys Phe Thr Gln Ser Ala Leu Asp
                610                 615                 620
Cys Met Ser Val Glu Val Gly Arg Leu Arg Ala Phe Leu Gln Gly Gly
625                 630                 635                 640
Gln Glu Ala Thr Asp Ile Ala Leu Leu Leu Arg Asp Leu Glu Thr Ser
                645                 650                 655
Cys Ser Asp Ile Arg Gln Phe Cys Lys Lys Ile Arg Arg Arg Met Pro
                660                 665                 670
Gly Thr Asp Ala Pro Gly Ile Pro Ala Ala Leu Ala Phe Gly Pro Gln
                675                 680                 685
Val Ser Asp Thr Leu Leu Asp Cys Arg Lys His Leu Thr Trp Val Val
690                 695                 700
Ala Val Leu Gln Glu Val Ala Ala Ala Ala Gln Leu Ile Ala Pro
705                 710                 715                 720
Leu Ala Glu Asn Glu Gly Leu Leu Val Ala Ala Leu Glu Glu Leu Ala
                725                 730                 735
Phe Lys Ala Ser Glu Gln Ile Tyr Gly Thr Pro Ser Ser Ser Pro Tyr
                740                 745                 750
Glu Cys Leu Arg Gln Ser Cys Asn Ile Leu Ile Ser Thr Met Asn Lys
                755                 760                 765
Leu Ala Thr Ala Met Gln Glu Gly Glu Tyr Asp Ala Glu Arg Pro Pro
                770                 775                 780
Ser Lys Pro Pro Pro Val Glu Leu Arg Ala Ala Ala Leu Arg Ala Glu
785                 790                 795                 800
Ile Thr Asp Ala Glu Gly Leu Gly Leu Lys Leu Glu Asp Arg Glu Thr
                805                 810                 815
Val Ile Lys Glu Leu Lys Lys Ser Leu Lys Ile Lys Gly Glu Glu Leu
                820                 825                 830
Ser Glu Ala Asn Val Arg Leu Ser Leu Glu Lys Lys Leu Asp Ser
                835                 840                 845
Ala Ala Lys Asp Ala Asp Glu Arg Ile Glu Lys Val Gln Thr Arg Leu
                850                 855                 860
Glu Glu Thr Gln Ala Leu Leu Arg Lys Lys Glu Lys Glu Phe Glu Glu
865                 870                 875                 880
Thr Met Asp Ala Leu Gln Ala Asp Ile Asp Gln Leu Glu Ala Glu Lys
                885                 890                 895
Ala Glu Leu Lys Gln Arg Leu Asn Ser Gln Ser Lys Arg Thr Ile Glu
                900                 905                 910
```

```
Gly Leu Arg Gly Pro Pro Ser Gly Ile Ala Thr Leu Val Ser Gly
            915                 920                 925

Ile Ala Gly Gly Ala Ile Pro Gly Gln Ala Pro Gly Ser Val Pro Gly
        930                 935                 940

Pro Gly Leu Val Lys Asp Ser Pro Leu Leu Gln Gln Ile Ser Ala
945                 950                 955                 960

Met Arg Leu His Ile Ser Gln Leu Gln His Glu Asn Ser Ile Leu Lys
                965                 970                 975

Gly Ala Gln Met Lys Ala Ser Leu Ala Ser Leu Pro Pro Leu His Val
                980                 985                 990

Ala Lys Leu Ser His Glu Gly Pro Gly Ser Glu Leu Pro Ala Gly Ala
            995                 1000                1005

Leu Tyr Arg Lys Thr Ser Gln Leu Leu Glu Thr Leu Asn Gln Leu
    1010                1015                1020

Ser Thr His Thr His Val Val Asp Ile Thr Arg Thr Ser Pro Ala
    1025                1030                1035

Ala Lys Ser Pro Ser Ala Gln Leu Met Glu Gln Val Ala Gln Leu
    1040                1045                1050

Lys Ser Leu Ser Asp Thr Val Glu Lys Leu Lys Asp Glu Val Leu
    1055                1060                1065

Lys Glu Thr Val Ser Gln Arg Pro Gly Ala Thr Val Pro Thr Asp
    1070                1075                1080

Phe Ala Thr Phe Pro Ser Ser Ala Phe Leu Arg Glu Asp Pro Lys
    1085                1090                1095

Trp Glu Phe Pro Arg Lys Asn Leu Val Leu Gly Lys Thr Leu Gly
    1100                1105                1110

Glu Gly Glu Phe Gly Lys Val Val Lys Ala Thr Ala Phe His Leu
    1115                1120                1125

Lys Gly Arg Ala Gly Tyr Thr Thr Val Ala Val Lys Met Leu Lys
    1130                1135                1140

Glu Asn Ala Ser Pro Ser Glu Leu Arg Asp Leu Leu Ser Glu Phe
    1145                1150                1155

Asn Val Leu Lys Gln Val Asn His Pro His Val Ile Lys Leu Tyr
    1160                1165                1170

Gly Ala Cys Ser Gln Asp Gly Pro Leu Leu Leu Ile Val Glu Tyr
    1175                1180                1185

Ala Lys Tyr Gly Ser Leu Arg Gly Phe Leu Arg Glu Ser Arg Lys
    1190                1195                1200

Val Gly Pro Gly Tyr Leu Gly Ser Gly Gly Ser Arg Asn Ser Ser
    1205                1210                1215

Ser Leu Asp His Pro Asp Glu Arg Ala Leu Thr Met Gly Asp Leu
    1220                1225                1230

Ile Ser Phe Ala Trp Gln Ile Ser Gln Gly Met Gln Tyr Leu Ala
    1235                1240                1245

Glu Met Lys Leu Val His Arg Asp Leu Ala Ala Arg Asn Ile Leu
    1250                1255                1260

Val Ala Glu Gly Arg Lys Met Lys Ile Ser Asp Phe Gly Leu Ser
    1265                1270                1275

Arg Asp Val Tyr Glu Glu Asp Ser Tyr Val Lys Arg Ser Gln Gly
    1280                1285                1290

Arg Ile Pro Val Lys Trp Met Ala Ile Glu Ser Leu Phe Asp His
    1295                1300                1305
```

Ile Tyr Thr Thr Gln Ser Asp Val Trp Ser Phe Gly Val Leu Leu
1310                1315                1320

Trp Glu Ile Val Thr Leu Gly Gly Asn Pro Tyr Pro Gly Ile Pro
1325                1330                1335

Pro Glu Arg Leu Phe Asn Leu Leu Lys Thr Gly His Arg Met Glu
1340                1345                1350

Arg Pro Asp Asn Cys Ser Glu Glu Met Tyr Arg Leu Met Leu Gln
1355                1360                1365

Cys Trp Lys Gln Glu Pro Asp Lys Arg Pro Val Phe Ala Asp Ile
1370                1375                1380

Ser Lys Asp Leu Glu Lys Met Met Val Lys Arg Arg Asp Tyr Leu
1385                1390                1395

Asp Leu Ala Ala Ser Thr Pro Ser Asp Ser Leu Ile Tyr Asp Asp
1400                1405                1410

Gly Leu Ser Glu Glu Glu Thr Pro Leu Val Asp Cys Asn Asn Ala
1415                1420                1425

Pro Leu Pro Arg Ala Leu Pro Ser Thr Trp Ile Glu Asn Lys Leu
1430                1435                1440

Tyr Gly Arg Ile Ser His Ala Phe Thr Arg Phe
1445                1450

<210> SEQ ID NO 17
<211> LENGTH: 4782
<212> TYPE: DNA
<213> ORGANISM: Artificial Sequence
<220> FEATURE:
<223> OTHER INFORMATION: coding sequence of fusion peptide

<400> SEQUENCE: 17

| | | | | | |
|---|---|---|---|---|---|
| atgagtgcgg | aggcaagcgc | ccggcctctg | cgggtgggct | cccgtgtaga | ggtgattgga | 60 |
| aaaggccacc | gaggcactgt | ggcctatgtt | ggagccacac | tgtttgccac | tggcaaatgg | 120 |
| gtaggcgtga | ttctggatga | agcaaagggc | aaaaatgatg | aactgttca | aggcaggaag | 180 |
| tacttcactt | gtgatgaagg | gcatggcatc | tttgtgcgcc | agtcccagat | ccaggtattt | 240 |
| gaagatggag | cagatactac | ttccccagag | acacctgatt | cttctgcttc | aaaagtcctc | 300 |
| aaaagagagg | gaactgatac | aactgcaaag | actagcaaac | tgcccacgcg | cccagccagt | 360 |
| actggggtgg | ctggggccag | tagctccctg | ggccctctg | gctcagcgtc | agcaggtgag | 420 |
| ctgagcagca | gtgagcccag | caccccggct | cagactccgc | tggcagcacc | catcatcccc | 480 |
| acgccggtcc | tcacctctcc | tggagcagtc | ccccgcttc | cttccccatc | caaggaggag | 540 |
| gagggactaa | gggctcaggt | gcgggacctg | gaggagaaac | tagagaccct | gagactgaaa | 600 |
| cgggcagaag | acaaagcaaa | gctaaaagag | ctggagaaac | acaaaatcca | gctggagcag | 660 |
| gtgcaggaat | ggaagagcaa | aatgcaggag | cagcaggccg | acctgcagcg | gcgcctcaag | 720 |
| gaggcgagaa | aggaagccaa | ggaggcgctg | gaggcaaagg | aacgctatat | ggaggagatg | 780 |
| gctgatactg | ctgatgccat | tgagatggcc | actttggaca | aggagatggc | tgaagagcgg | 840 |
| gctgagtccc | tgcagcagga | ggtggaggca | ctgaaggagc | gggtggacga | gctcactact | 900 |
| gacttagaga | tcctcaaggc | tgagattgaa | gagaagggct | cagatggcgc | tgcatccagt | 960 |
| tatcagctca | agcagcttga | ggagcagaat | gcccgcctga | aggatgccct | ggtgaggatg | 1020 |
| cgggatcttt | cttcctcaga | gaagcaggag | catgtgaagc | tccagaagct | catggaaaag | 1080 |
| aagaaccaag | agctgaagt | tgtgaggcaa | cagcggggag | gtctgcagga | ggagctaagc | 1140 |
| caggcagaga | gcaccattga | tgagctcaag | gagcaggtgg | atgctgctct | gggtgctgag | 1200 |

```
gagatggtgg agatgctgac agatcggaac ctgaatctgg aagagaaagt gcgcgagttg    1260
agggagactg tgggagactt ggaagcgatg aatgagatga acgatgagct gcaggagaat    1320
gcacgtgaga cagaactgga gctgcgggag cagctggaca tggcaggcgc gcgggttcgt    1380
gaggcccaga agcgtgtgga ggcagcccag agacgcgttg cagactacca gcagaccatc    1440
aagaagtacc gccagctgac cgcccatcta caggatgtga atcgggaact gacaaaccag    1500
caggaagcat ctgtggagag gcaacagcag ccacctccag agacctttga cttcaaaatc    1560
aagtttgctg agactaaggc ccatgccaag gcaattgaga tggaattgag gcagatggag    1620
gtggcccagg ccaatcgaca catgtccctg ctgacagcct tcatgcctga cagcttcctt    1680
cggccaggtg ggaccatga ctgcgttctg gtgctgttgc tcatgcctcg tctcatttgc    1740
aaggcagagc tgatccggaa gcaggcccag agaagtttg aactaagtga gaactgttca    1800
gagcggcctg ggctgcgagg agctgctggg gagcaactca gctttgctgc tggactggtg    1860
tactcgctga gcctgctgca ggccacgcta caccgctatg agcatgccct ctctcagtgc    1920
agtgtggatg tgtataagaa agtgggcagc ctgtaccctg agatgagtgc ccatgagcgc    1980
tccttggatt tcctcattga actgctgcac aaggatcagc tggatgagac tgtcaatgtg    2040
gagcctctca ccaaggccat caagtactat cagcatctgt acagcatcca ccttgccgaa    2100
cagcctgagg actgtactat gcagctggct gaccacatta agttcacgca gagtgctctg    2160
gactgcatga gtgtggaggt aggacggctg cgtgccttct gcagggtgg gcaggaggct    2220 acagatattg ccctcctgct ccgggatctg gaaacttcat gcagtgacat ccgccagttc    2280
tgcaagaaga tccgaaggcg aatgccaggg acagatgctc ctgggatccc agctgcactg    2340
gcctttggac cacaggtatc tgacacgctc ctagactgca ggaaacactt gacgtgggtc    2400
gtggctgtgc tgcaggaggt ggcagctgct gctgcccagc tcattgcccc actggcagag    2460
aatgaggggc tacttgtggc tgctctggag gaactggctt tcaaagcaag cgagcagatc    2520
tatgggaccc cctccagcag cccctatgag tgtctgcgcc agtcatgcaa catcctcatc    2580
agtaccatga acaagctggc cacagccatg caggaggggg agtatgatgc agagcggccc    2640
cccagcaagc ctccaccggt tgaactgcgg gctgctgccc ttcgtgcaga gatcacagat    2700
gctgaaggcc tgggttttgaa gctcgaagat cgagagacag ttattaagga gttgaagaag    2760
tcactcaaga ttaagggaga ggagctaagt gaggccaatg tgcggctgag cctcctggag    2820
aagaagttgg acagtgctgc caaggatgca gatgagcgca tcgagaaagt ccagactcgg    2880
ctggaggaga cccaggcact gctgcgaaag aaggagaaag agtttgagga gacaatggat    2940
gcactccagg ctgacatcga ccagctggag gcagagaagg cagaactaaa gcagcgtctg    3000
aacagccagt ccaaacgcac gattgaggga ctccggggcc ctcctccttc aggcattgct    3060
actctggtct ctggcattgc tggtggagcc atccctgggc aggctccagg gtctgtgcca    3120 ggccagggc tggtgaagga ctcaccactg ctgcttcagc agatctctgc catgaggctg    3180
cacatctccc agctccagca tgagaacagc atcctcaagg gagcccagat gaaggcatcc    3240
ttggcatccc tgcccctct gcatgttgca aagctatccc atgagggccc tggcagtgag    3300
ttaccagctg gagcgctgta tcgtaagacc agccagctgc tggagacatt gaatcaattg    3360
agcacacaca cgcacgtagt agacatcact cgcaccagcc ctgctgccaa gagcccgtcg    3420
gcccaactta tggagcaagt ggctcagctt aagtccctga gtgacaccgt cgagaagctc    3480
aaggatgagg tcctcaagga gacagtatct cagcgccctg gagccacagt acccactgac    3540
```

```
tttgccacct tcccttcatc agccttcctc agggaggatc caaagtggga attccctcgg   3600
aagaacttgg ttcttggaaa aactctagga gaaggcgaat ttggaaaagt ggtcaaggca   3660
acggccttcc atctgaaagg cagagcaggg tacaccacgg tggccgtgaa gatgctgaaa   3720
gagaacgcct ccccgagtga gcttcgagac ctgctgtcag agttcaacgt cctgaagcag   3780
gtcaaccacc cacatgtcat caaattgtat ggggcctgca gccaggatgg cccgctcctc   3840
ctcatcgtgg agtacgccaa atacggctcc ctgcggggct cctccgcga gagccgcaaa   3900 gtggggcctg gctacctggg cagtggaggc agccgcaact ccagctccct ggaccacccg   3960
gatgagcggg ccctcaccat gggcgacctc atctcatttg cctggcagat ctcacagggg   4020
atgcagtatc tggccgagat gaagctcgtt catcgggact tggcagccag aaacatcctg   4080
gtagctgagg ggcggaagat gaagatttcg gatttcggct tgtcccgaga tgtttatgaa   4140
gaggattcct acgtgaagag gagccagggt cggattccag ttaaatggat ggcaattgaa   4200 tcccttttg atcatatcta caccacgcaa agtgatgtat ggtcttttgg tgtcctgctg   4260
tgggagatcg tgaccctagg gggaaacccc tatcctggga ttcctcctga gcggctcttc   4320
aaccttctga agaccggcca ccggatggag aggccagaca actgcagcga ggagatgtac   4380
cgcctgatgc tgcaatgctg gaagcaggag ccggacaaaa ggccggtgtt tgcggacatc   4440
agcaaagacc tggagaagat gatggttaag aggagagact acttggacct tgcggcgtcc   4500
actccatctg actccctgat ttatgacgac ggcctctcag aggaggagac accgctggtg   4560
gactgtaata atgccccccct ccctcgagcc ctcccttcca catggattga aaacaaactc   4620
tatggcatgt cagacccgaa ctggcctgga gagagtcctg taccactcac gagagctgat   4680
ggcactaaca ctgggtttcc aagatatcca aatgatagtg tatatgctaa ctggatgctt   4740
tcaccctcag cggcaaaatt aatggacacg tttgatagtt aa                     4782
```

<210> SEQ ID NO 18
<211> LENGTH: 1593
<212> TYPE: PRT
<213> ORGANISM: Artificial Sequence
<220> FEATURE:
<223> OTHER INFORMATION: fusion peptide

<400> SEQUENCE: 18

```
Met Ser Ala Glu Ala Ser Ala Arg Pro Leu Arg Val Gly Ser Arg Val
1               5                   10                  15

Glu Val Ile Gly Lys Gly His Arg Gly Thr Val Ala Tyr Val Gly Ala
            20                  25                  30

Thr Leu Phe Ala Thr Gly Lys Trp Val Gly Val Ile Leu Asp Glu Ala
        35                  40                  45

Lys Gly Lys Asn Asp Gly Thr Val Gln Gly Arg Lys Tyr Phe Thr Cys
    50                  55                  60

Asp Glu Gly His Gly Ile Phe Val Arg Gln Ser Gln Ile Gln Val Phe
65                  70                  75                  80

Glu Asp Gly Ala Asp Thr Thr Ser Pro Glu Thr Pro Asp Ser Ser Ala
                85                  90                  95

Ser Lys Val Leu Lys Arg Glu Gly Thr Asp Thr Thr Ala Lys Thr Ser
            100                 105                 110

Lys Leu Pro Thr Arg Pro Ala Ser Thr Gly Val Ala Gly Ala Ser Ser
        115                 120                 125

Ser Leu Gly Pro Ser Gly Ser Ala Ser Ala Gly Glu Leu Ser Ser Ser
    130                 135                 140
```

-continued

```
Glu Pro Ser Thr Pro Ala Gln Thr Pro Leu Ala Pro Ile Ile Pro
145                 150                 155                 160

Thr Pro Val Leu Thr Ser Pro Gly Ala Val Pro Pro Leu Pro Ser Pro
                165                 170                 175

Ser Lys Glu Glu Glu Gly Leu Arg Ala Gln Val Arg Asp Leu Glu Glu
            180                 185                 190

Lys Leu Glu Thr Leu Arg Leu Lys Arg Ala Glu Asp Lys Ala Lys Leu
            195                 200                 205

Lys Glu Leu Glu Lys His Lys Ile Gln Leu Glu Gln Val Gln Glu Trp
            210                 215                 220

Lys Ser Lys Met Gln Glu Gln Ala Asp Leu Gln Arg Arg Leu Lys
225                 230                 235                 240

Glu Ala Arg Lys Glu Ala Lys Glu Ala Leu Glu Ala Lys Glu Arg Tyr
                245                 250                 255

Met Glu Glu Met Ala Asp Thr Ala Asp Ala Ile Glu Met Ala Thr Leu
                260                 265                 270

Asp Lys Glu Met Ala Glu Arg Ala Glu Ser Leu Gln Gln Glu Val
                275                 280                 285

Glu Ala Leu Lys Glu Arg Val Asp Glu Leu Thr Thr Asp Leu Glu Ile
290                 295                 300

Leu Lys Ala Glu Ile Glu Glu Lys Gly Ser Asp Gly Ala Ala Ser Ser
305                 310                 315                 320

Tyr Gln Leu Lys Gln Leu Glu Glu Asn Ala Arg Leu Lys Asp Ala
                325                 330                 335

Leu Val Arg Met Arg Asp Leu Ser Ser Ser Glu Lys Gln Glu His Val
                340                 345                 350

Lys Leu Gln Lys Leu Met Glu Lys Lys Asn Gln Glu Leu Glu Val Val
                355                 360                 365

Arg Gln Gln Arg Glu Arg Leu Gln Glu Glu Leu Ser Gln Ala Glu Ser
            370                 375                 380

Thr Ile Asp Glu Leu Lys Glu Gln Val Asp Ala Ala Leu Gly Ala Glu
385                 390                 395                 400

Glu Met Val Glu Met Leu Thr Asp Arg Asn Leu Asn Leu Glu Glu Lys
                405                 410                 415

Val Arg Glu Leu Arg Glu Thr Val Gly Asp Leu Glu Ala Met Asn Glu
                420                 425                 430

Met Asn Asp Glu Leu Gln Glu Asn Ala Arg Glu Thr Glu Leu Glu Leu
            435                 440                 445

Arg Glu Gln Leu Asp Met Ala Gly Ala Arg Val Arg Glu Ala Gln Lys
            450                 455                 460

Arg Val Glu Ala Ala Gln Glu Thr Val Ala Asp Tyr Gln Gln Thr Ile
465                 470                 475                 480

Lys Lys Tyr Arg Gln Leu Thr Ala His Leu Gln Asp Val Asn Arg Glu
                485                 490                 495

Leu Thr Asn Gln Gln Glu Ala Ser Val Glu Arg Gln Gln Gln Pro Pro
            500                 505                 510

Pro Glu Thr Phe Asp Phe Lys Ile Lys Phe Ala Glu Thr Lys Ala His
            515                 520                 525

Ala Lys Ala Ile Glu Met Glu Leu Arg Gln Met Glu Val Ala Gln Ala
            530                 535                 540

Asn Arg His Met Ser Leu Leu Thr Ala Phe Met Pro Asp Ser Phe Leu
545                 550                 555                 560

Arg Pro Gly Gly Asp His Asp Cys Val Leu Val Leu Leu Leu Met Pro
```

```
                565                 570                 575
Arg Leu Ile Cys Lys Ala Glu Leu Ile Arg Lys Gln Ala Gln Glu Lys
                580                 585                 590

Phe Glu Leu Ser Glu Asn Cys Ser Glu Arg Pro Gly Leu Arg Gly Ala
                595                 600                 605

Ala Gly Glu Gln Leu Ser Phe Ala Ala Gly Leu Val Tyr Ser Leu Ser
            610                 615                 620

Leu Leu Gln Ala Thr Leu His Arg Tyr Glu His Ala Leu Ser Gln Cys
625                 630                 635                 640

Ser Val Asp Val Tyr Lys Lys Val Gly Ser Leu Tyr Pro Glu Met Ser
                645                 650                 655

Ala His Glu Arg Ser Leu Asp Phe Leu Ile Glu Leu Leu His Lys Asp
                660                 665                 670

Gln Leu Asp Glu Thr Val Asn Val Glu Pro Leu Thr Lys Ala Ile Lys
                675                 680                 685

Tyr Tyr Gln His Leu Tyr Ser Ile His Leu Ala Glu Gln Pro Glu Asp
            690                 695                 700

Cys Thr Met Gln Leu Ala Asp His Ile Lys Phe Thr Gln Ser Ala Leu
705                 710                 715                 720

Asp Cys Met Ser Val Glu Val Gly Arg Leu Arg Ala Phe Leu Gln Gly
                725                 730                 735

Gly Gln Glu Ala Thr Asp Ile Ala Leu Leu Leu Arg Asp Leu Glu Thr
            740                 745                 750

Ser Cys Ser Asp Ile Arg Gln Phe Cys Lys Lys Ile Arg Arg Arg Met
            755                 760                 765

Pro Gly Thr Asp Ala Pro Gly Ile Pro Ala Ala Leu Ala Phe Gly Pro
            770                 775                 780

Gln Val Ser Asp Thr Leu Leu Asp Cys Arg Lys His Leu Thr Trp Val
785                 790                 795                 800

Val Ala Val Leu Gln Glu Val Ala Ala Ala Ala Gln Leu Ile Ala
                805                 810                 815

Pro Leu Ala Glu Asn Glu Gly Leu Leu Val Ala Ala Leu Glu Glu Leu
            820                 825                 830

Ala Phe Lys Ala Ser Glu Gln Ile Tyr Gly Thr Pro Ser Ser Ser Pro
            835                 840                 845

Tyr Glu Cys Leu Arg Gln Ser Cys Asn Ile Leu Ile Ser Thr Met Asn
            850                 855                 860

Lys Leu Ala Thr Ala Met Gln Glu Gly Glu Tyr Asp Ala Glu Arg Pro
865                 870                 875                 880

Pro Ser Lys Pro Pro Pro Val Glu Leu Arg Ala Ala Ala Leu Arg Ala
                885                 890                 895

Glu Ile Thr Asp Ala Glu Gly Leu Gly Leu Lys Leu Glu Asp Arg Glu
                900                 905                 910

Thr Val Ile Lys Glu Leu Lys Lys Ser Leu Lys Ile Lys Gly Glu Glu
                915                 920                 925

Leu Ser Glu Ala Asn Val Arg Leu Ser Leu Leu Glu Lys Lys Leu Asp
            930                 935                 940

Ser Ala Ala Lys Asp Ala Asp Glu Arg Ile Glu Lys Val Gln Thr Arg
945                 950                 955                 960

Leu Glu Glu Thr Gln Ala Leu Leu Arg Lys Lys Glu Lys Glu Phe Glu
                965                 970                 975

Glu Thr Met Asp Ala Leu Gln Ala Asp Ile Asp Gln Leu Glu Ala Glu
                980                 985                 990
```

```
Lys Ala Glu Leu Lys Gln Arg Leu  Asn Ser Gln Ser Lys  Arg Thr Ile
        995              1000                1005

Glu Gly  Leu Arg Gly Pro  Pro Ser Gly Ile Ala  Thr Leu Val
    1010             1015                 1020

Ser Gly  Ile Ala Gly Gly Ala  Ile Pro Gly Gln Ala  Pro Gly Ser
    1025                1030                 1035

Val Pro  Gly Pro Gly Leu Val  Lys Asp Ser Pro Leu  Leu Leu Gln
    1040                1045                 1050

Gln Ile  Ser Ala Met Arg Leu  His Ile Ser Gln Leu  Gln His Glu
    1055                1060                 1065

Asn Ser  Ile Leu Lys Gly Ala  Gln Met Lys Ala Ser  Leu Ala Ser
    1070                1075                 1080

Leu Pro  Pro Leu His Val Ala  Lys Leu Ser His Glu  Gly Pro Gly
    1085                1090                 1095

Ser Glu  Leu Pro Ala Gly Ala  Leu Tyr Arg Lys Thr  Ser Gln Leu
    1100                1105                 1110

Leu Glu  Thr Leu Asn Gln Leu  Ser Thr His Thr His  Val Val Asp
    1115                1120                 1125

Ile Thr  Arg Thr Ser Pro Ala  Ala Lys Ser Pro Ser  Ala Gln Leu
    1130                1135                 1140

Met Glu  Gln Val Ala Gln Leu  Lys Ser Leu Ser Asp  Thr Val Glu
    1145                1150                 1155

Lys Leu  Lys Asp Glu Val Leu  Lys Glu Thr Val Ser  Gln Arg Pro
    1160                1165                 1170

Gly Ala  Thr Val Pro Thr Asp  Phe Ala Thr Phe Pro  Ser Ser Ala
    1175                1180                 1185

Phe Leu  Arg Glu Asp Pro Lys  Trp Glu Phe Pro Arg  Lys Asn Leu
    1190                1195                 1200

Val Leu  Gly Lys Thr Leu Gly  Glu Gly Glu Phe Gly  Lys Val Val
    1205                1210                 1215

Lys Ala  Thr Ala Phe His Leu  Lys Gly Arg Ala Gly  Tyr Thr Thr
    1220                1225                 1230

Val Ala  Val Lys Met Leu Lys  Glu Asn Ala Ser Pro  Ser Glu Leu
    1235                1240                 1245

Arg Asp  Leu Leu Ser Glu Phe  Asn Val Leu Lys Gln  Val Asn His
    1250                1255                 1260

Pro His  Val Ile Lys Leu Tyr  Gly Ala Cys Ser Gln  Asp Gly Pro
    1265                1270                 1275

Leu Leu  Leu Ile Val Glu Tyr  Ala Lys Tyr Gly Ser  Leu Arg Gly
    1280                1285                 1290

Phe Leu  Arg Glu Ser Arg Lys  Val Gly Pro Gly Tyr  Leu Gly Ser
    1295                1300                 1305

Gly Gly  Ser Arg Asn Ser Ser  Ser Leu Asp His Pro  Asp Glu Arg
    1310                1315                 1320

Ala Leu  Thr Met Gly Asp Leu  Ile Ser Phe Ala Trp  Gln Ile Ser
    1325                1330                 1335

Gln Gly  Met Gln Tyr Leu Ala  Glu Met Lys Leu Val  His Arg Asp
    1340                1345                 1350

Leu Ala  Ala Arg Asn Ile Leu  Val Ala Glu Gly Arg  Lys Met Lys
    1355                1360                 1365

Ile Ser  Asp Phe Gly Leu Ser  Arg Asp Val Tyr Glu  Glu Asp Ser
    1370                1375                 1380
```

| | | | | | | | | | | |
|---|---|---|---|---|---|---|---|---|---|---|
|Tyr|Val|Lys|Arg|Ser|Gln|Gly|Arg|Ile|Pro|Val|Lys|Trp|Met|Ala|
| |1385| | | |1390| | | |1395| |

Tyr Val Lys Arg Ser Gln Gly Arg Ile Pro Val Lys Trp Met Ala
    1385                1390                1395

Ile Glu Ser Leu Phe Asp His Ile Tyr Thr Thr Gln Ser Asp Val
    1400                1405                1410

Trp Ser Phe Gly Val Leu Leu Trp Glu Ile Val Thr Leu Gly Gly
    1415                1420                1425

Asn Pro Tyr Pro Gly Ile Pro Pro Glu Arg Leu Phe Asn Leu Leu
    1430                1435                1440

Lys Thr Gly His Arg Met Glu Arg Pro Asp Asn Cys Ser Glu Glu
    1445                1450                1455

Met Tyr Arg Leu Met Leu Gln Cys Trp Lys Gln Glu Pro Asp Lys
    1460                1465                1470

Arg Pro Val Phe Ala Asp Ile Ser Lys Asp Leu Glu Lys Met Met
    1475                1480                1485

Val Lys Arg Arg Asp Tyr Leu Asp Leu Ala Ala Ser Thr Pro Ser
    1490                1495                1500

Asp Ser Leu Ile Tyr Asp Asp Gly Leu Ser Glu Glu Glu Thr Pro
    1505                1510                1515

Leu Val Asp Cys Asn Asn Ala Pro Leu Pro Arg Ala Leu Pro Ser
    1520                1525                1530

Thr Trp Ile Glu Asn Lys Leu Tyr Gly Met Ser Asp Pro Asn Trp
    1535                1540                1545

Pro Gly Glu Ser Pro Val Pro Leu Thr Arg Ala Asp Gly Thr Asn
    1550                1555                1560

Thr Gly Phe Pro Arg Tyr Pro Asn Asp Ser Val Tyr Ala Asn Trp
    1565                1570                1575

Met Leu Ser Pro Ser Ala Ala Lys Leu Met Asp Thr Phe Asp Ser
    1580                1585                1590

<210> SEQ ID NO 19
<211> LENGTH: 4656
<212> TYPE: DNA
<213> ORGANISM: Artificial Sequence
<220> FEATURE:
<223> OTHER INFORMATION: coding sequence of fusion peptide

<400> SEQUENCE: 19

```
atgagtgcgg aggcaagcgc ccggcctctg cgggtgggct cccgtgtaga ggtgattgga      60
aaaggccacc gaggcactgt ggcctatgtt ggagccacac tgtttgccac tggcaaatgg     120
gtaggcgtga ttctggatga agcaaagggc aaaaatgatg aactgttcca aggcaggaag     180
tacttcactt gtgatgaagg gcatggcatc tttgtgcgcc agtcccagat ccaggtattt     240
gaagatggag cagatactac ttccccagag acacctgatt cttctgcttc aaaagtcctc     300
aaaagagagg gaactgatac aactgcaaag actagcaaac tgcccacgcg cccagccagt     360
actgggtgg ctggggccag tagctccctg ggccctctg gctcagcgtc agcaggtgag     420
ctgagcagca gtgagcccag caccccggct cagactccgc tggcagcacc catcatcccc     480
acgccggtcc tcacctctcc tggagcagtc ccccgcttc cttccccatc caaggaggag     540
gagggactaa gggctcaggt gcgggacctg gaggagaaac tagagaccct gagactgaaa     600
cgggcagaag acaaagcaaa gctaaaagag ctggagaaac acaaaatcca gctggagcag     660
gtgcaggaat ggaagagcaa aatgcaggag cagcaggccg acctgcagcg gcgcctcaag     720
gaggcgagaa aggaagccaa ggaggcgctg gaggcaaagg aacgctatat ggaggagatg     780
gctgatactg ctgatgccat tgagatggcc actttggaca aggagatggc tgaagagcgg     840
```

-continued

```
gctgagtccc tgcagcagga ggtggaggca ctgaaggagc gggtggacga gctcactact      900
gacttagaga tcctcaaggc tgagattgaa gagaagggct cagatggcgc tgcatccagt      960
tatcagctca agcagcttga ggagcagaat gcccgcctga aggatgccct ggtgaggatg     1020
cgggatcttt cttcctcaga gaagcaggag catgtgaagc tccagaagct catggaaaag     1080
aagaaccaag agctggaagt tgtgaggcaa cagcgggagc gtctgcagga ggagctaagc     1140
caggcagaga gcaccattga tgagctcaag gagcaggtgg atgctgctct gggtgctgag     1200
gagatggtgg agatgctgac agatcggaac ctgaatctgg aagagaaagt gcgcgagttg     1260
agggagactg tgggagactt ggaagcgatg aatgagatga cgatgagct gcaggagaat     1320 gcacgtgaga cagaactgga gctgcgggag cagctggaca tggcaggcgc gcgggttcgt     1380
gaggcccaga agcgtgtgga ggcagcccag gagacggttg cagactacca gcagaccatc     1440
aagaagtacc gccagctgac cgcccatcta caggatgtga atcgggaact gacaaaccag     1500
caggaagcat ctgtggagag gcaacagcag ccacctccag agacctttga cttcaaaatc     1560
aagtttgctg agactaaggc ccatgccaag gcaattgaga tggaattgag gcagatggag     1620
gtggcccagg ccaatcgaca catgtccctg ctgacagcct tcatgcctga cagcttcctt     1680
cggccaggtg ggaccatga ctgcgttctg gtgctgttgc tcatgcctcg tctcatttgc     1740
aaggcagagc tgatccggaa gcaggcccag gagaagtttg aactaagtga gaactgttca     1800
gagcggcctg gctgcgagg agctgctggg gagcaactca gctttgctgc tggactggtg     1860
tactcgctga gcctgctgca ggccacgcta caccgctatg agcatgccct ctctcagtgc     1920
agtgtggatg tgtataagaa agtgggcagc ctgtaccctg atgagtgc ccatgagcgc     1980 tccttggatt tcctcattga actgctgcac aaggatcagc tggatgagac tgtcaatgtg     2040
gagcctctca ccaaggccat caagtactat cagcatctgt acagcatcca ccttgccgaa     2100
cagcctgagg actgtactat gcagctggct gaccacatta agttcacgca gagtgctctg     2160
gactgcatga gtgtggaggt aggacggctg cgtgccttct gcagggtgg gcaggaggct     2220 acagatattg ccctcctgct ccgggatctg gaaacttcat gcagtgacat ccgccagttc     2280
tgcaagaaga tccgaaggcg aatgccaggg acagatgctc ctgggatccc agctgcactg     2340
gcctttggac cacaggtatc tgacacgctc ctagactgca ggaaacactt gacgtgggtc     2400
gtggctgtgc tgcaggaggt ggcagctgct gctgcccagc tcattgcccc actggcagag     2460 aatgagggc tacttgtggc tgctctggag gaactggctt tcaaagcaag cgagcagatc     2520
tatgggaccc cctccagcag ccctatgag tgtctgcgcc agtcatgcaa catcctcatc     2580
agtaccatga caagctggc cacagccatg caggaggggg agtatgatgc agagcggccc     2640
cccagcaagc ctccaccggt tgaactgcgg gctgctgccc ttcgtgcaga gatcacagat     2700
gctgaaggcc tgggtttgaa gctcgaagat cgagagacag ttattaagga gttgaagaag     2760
tcactcaaga ttaagggaga ggagctaagt gaggccaatg tgcggctgag cctcctggag     2820
aagaagttgg acagtgctgc caaggatgca gatgagcgca tcgagaaagt ccagactcgg     2880
ctggaggaga cccaggcact gctgcgaaag aaggagaaag agtttgagga gacaatggat     2940
gcactccagg ctgacatcga ccagctggag gcagagaagg cagaactaaa gcagcgtctg     3000
aacagccagt ccaaacgcac gattgaggga ctccggggcc ctcctccttc aggcattgct     3060
actctggtct ctggcattgc tggtggagcc atccctgggc aggctccagg gtctgtgcca     3120
ggcccagggc tggtgaagga ctcaccactg ctgcttcagc agatctctgc catgaggctg     3180
```

```
cacatctccc agctccagca tgagaacagc atcctcaagg gagcccagat gaaggcatcc    3240
ttggcatccc tgcccctct gcatgttgca aagctatccc atgagggccc tggcagtgag     3300
ttaccagctg gagcgctgta tcgtaagacc agccagctgc tggagacatt gaatcaattg    3360
agcacacaca cgcacgtagt agacatcact cgcaccagcc ctgctgccaa gagcccgtcg    3420
gcccaactta tggagcaagt ggctcagctt aagtccctga gtgacaccgt cgagaagctc    3480
aaggatgagg tcctcaagga gacagtatct cagcgccctg gagccacagt acccactgac    3540
tttgccacct tcccttcatc agccttcctc agggaggatc caaagtggga attccctcgg    3600
aagaacttgg ttcttggaaa aactctagga gaaggcgaat ttggaaaagt ggtcaaggca    3660
acggccttcc atctgaaagg cagagcaggg tacaccacgg tggccgtgaa gatgctgaaa    3720
gagaacgcct ccccgagtga gcttcgagac ctgctgtcag agttcaacgt cctgaagcag    3780
gtcaaccacc cacatgtcat caaattgtat ggggcctgca gccaggatgg cccgctcctc    3840
ctcatcgtgg agtacgccaa atacggctcc ctgcggggct cctccgcga gagccgcaaa    3900 gtggggcctg gctacctggg cagtggaggc agccgcaact ccagctccct ggaccacccg    3960
gatgagcggg ccctcaccat gggcgacctc atctcatttg cctggcagat ctcacagggg    4020
atgcagtatc tggccgagat gaagctcgtt catcgggact tggcagccag aaacatcctg    4080
gtagctgagg ggcggaagat gaagatttcg gatttcggct tgtcccgaga tgtttatgaa    4140
gaggattcct acgtgaagag gagccagggt cggattccag ttaaatggat ggcaattgaa    4200 tcccttttg atcatatcta caccacgcaa agtgatgtat ggtcttttgg tgtcctgctg    4260
tgggagatcg tgaccctagg gggaaacccc tatcctggga ttcctcctga gcggctcttc    4320
aaccttctga agaccggcca ccggatggag aggccagaca actgcagcga ggagatgtac    4380
cgcctgatgc tgcaatgctg gaagcaggag ccggacaaaa ggccggtgtt tgcggacatc    4440
agcaaagacc tggagaagat gatggttaag aggagagact acttggacct tgcggcgtcc    4500
actccatctg actccctgat ttatgacgac ggcctctcag aggaggagac accgctggtg    4560
gactgtaata atgccccccct ccctcgagcc ctccctttcca catggattga aaacaaactc    4620
tatggtagaa tttcccatgc atttactaga ttctag                              4656
```

<210> SEQ ID NO 20
<211> LENGTH: 1551
<212> TYPE: PRT
<213> ORGANISM: Artificial Sequence
<220> FEATURE:
<223> OTHER INFORMATION: fusion peptide

<400> SEQUENCE: 20

```
Met Ser Ala Glu Ala Ser Ala Arg Pro Leu Arg Val Gly Ser Arg Val
1               5                   10                  15

Glu Val Ile Gly Lys Gly His Arg Gly Thr Val Ala Tyr Val Gly Ala
            20                  25                  30

Thr Leu Phe Ala Thr Gly Lys Trp Val Gly Val Ile Leu Asp Glu Ala
        35                  40                  45

Lys Gly Lys Asn Asp Gly Thr Val Gln Gly Arg Lys Tyr Phe Thr Cys
    50                  55                  60

Asp Glu Gly His Gly Ile Phe Val Arg Gln Ser Gln Ile Gln Val Phe
65                  70                  75                  80

Glu Asp Gly Ala Asp Thr Thr Ser Pro Glu Thr Pro Asp Ser Ser Ala
                85                  90                  95

Ser Lys Val Leu Lys Arg Glu Gly Thr Asp Thr Thr Ala Lys Thr Ser
```

```
                100             105             110
Lys Leu Pro Thr Arg Pro Ala Ser Thr Gly Val Ala Gly Ala Ser Ser
            115             120             125

Ser Leu Gly Pro Ser Gly Ser Ala Ser Ala Gly Glu Leu Ser Ser Ser
        130             135             140

Glu Pro Ser Thr Pro Ala Gln Thr Pro Leu Ala Ala Pro Ile Ile Pro
145             150             155             160

Thr Pro Val Leu Thr Ser Pro Gly Ala Val Pro Pro Leu Pro Ser Pro
                165             170             175

Ser Lys Glu Glu Glu Gly Leu Arg Ala Gln Val Arg Asp Leu Glu Glu
            180             185             190

Lys Leu Glu Thr Leu Arg Leu Lys Arg Ala Glu Asp Lys Ala Lys Leu
            195             200             205

Lys Glu Leu Glu Lys His Lys Ile Gln Leu Glu Gln Val Gln Glu Trp
        210             215             220

Lys Ser Lys Met Gln Glu Gln Ala Asp Leu Gln Arg Arg Leu Lys
225             230             235             240

Glu Ala Arg Lys Glu Ala Lys Glu Ala Leu Glu Ala Lys Glu Arg Tyr
            245             250             255

Met Glu Glu Met Ala Asp Thr Ala Asp Ala Ile Glu Met Ala Thr Leu
            260             265             270

Asp Lys Glu Met Ala Glu Glu Arg Ala Glu Ser Leu Gln Gln Glu Val
            275             280             285

Glu Ala Leu Lys Glu Arg Val Asp Glu Leu Thr Thr Asp Leu Glu Ile
            290             295             300

Leu Lys Ala Glu Ile Glu Glu Lys Gly Ser Asp Gly Ala Ala Ser Ser
305             310             315             320

Tyr Gln Leu Lys Gln Leu Glu Glu Gln Asn Ala Arg Leu Lys Asp Ala
                325             330             335

Leu Val Arg Met Arg Asp Leu Ser Ser Ser Glu Lys Gln Glu His Val
            340             345             350

Lys Leu Gln Lys Leu Met Glu Lys Lys Asn Gln Glu Leu Glu Val Val
            355             360             365

Arg Gln Gln Arg Glu Arg Leu Gln Glu Glu Leu Ser Gln Ala Glu Ser
            370             375             380

Thr Ile Asp Glu Leu Lys Glu Gln Val Asp Ala Ala Leu Gly Ala Glu
385             390             395             400

Glu Met Val Glu Met Leu Thr Asp Arg Asn Leu Asn Leu Glu Glu Lys
                405             410             415

Val Arg Glu Leu Arg Glu Thr Val Gly Asp Leu Glu Ala Met Asn Glu
            420             425             430

Met Asn Asp Glu Leu Gln Glu Asn Ala Arg Glu Thr Glu Leu Glu Leu
            435             440             445

Arg Glu Gln Leu Asp Met Ala Gly Ala Arg Val Arg Glu Ala Gln Lys
            450             455             460

Arg Val Glu Ala Ala Gln Glu Thr Val Ala Asp Tyr Gln Gln Thr Ile
465             470             475             480

Lys Lys Tyr Arg Gln Leu Thr Ala His Leu Gln Asp Val Asn Arg Glu
                485             490             495

Leu Thr Asn Gln Gln Glu Ala Ser Val Glu Arg Gln Gln Gln Pro Pro
            500             505             510

Pro Glu Thr Phe Asp Phe Lys Ile Lys Phe Ala Glu Thr Lys Ala His
            515             520             525
```

```
Ala Lys Ala Ile Glu Met Glu Leu Arg Gln Met Glu Val Ala Gln Ala
        530                 535                 540

Asn Arg His Met Ser Leu Leu Thr Ala Phe Met Pro Asp Ser Phe Leu
545                 550                 555                 560

Arg Pro Gly Gly Asp His Asp Cys Val Leu Val Leu Leu Leu Met Pro
                565                 570                 575

Arg Leu Ile Cys Lys Ala Glu Leu Ile Arg Lys Gln Ala Gln Glu Lys
            580                 585                 590

Phe Glu Leu Ser Glu Asn Cys Ser Glu Arg Pro Gly Leu Arg Gly Ala
        595                 600                 605

Ala Gly Glu Gln Leu Ser Phe Ala Ala Gly Leu Val Tyr Ser Leu Ser
    610                 615                 620

Leu Leu Gln Ala Thr Leu His Arg Tyr Glu His Ala Leu Ser Gln Cys
625                 630                 635                 640

Ser Val Asp Val Tyr Lys Lys Val Gly Ser Leu Tyr Pro Glu Met Ser
                645                 650                 655

Ala His Glu Arg Ser Leu Asp Phe Leu Ile Glu Leu His Lys Asp
            660                 665                 670

Gln Leu Asp Glu Thr Val Asn Val Glu Pro Leu Thr Lys Ala Ile Lys
        675                 680                 685

Tyr Tyr Gln His Leu Tyr Ser Ile His Leu Ala Glu Gln Pro Glu Asp
    690                 695                 700

Cys Thr Met Gln Leu Ala Asp His Ile Lys Phe Thr Gln Ser Ala Leu
705                 710                 715                 720

Asp Cys Met Ser Val Glu Val Gly Arg Leu Arg Ala Phe Leu Gln Gly
                725                 730                 735

Gly Gln Glu Ala Thr Asp Ile Ala Leu Leu Leu Arg Asp Leu Glu Thr
            740                 745                 750

Ser Cys Ser Asp Ile Arg Gln Phe Cys Lys Lys Ile Arg Arg Arg Met
        755                 760                 765

Pro Gly Thr Asp Ala Pro Gly Ile Pro Ala Ala Leu Ala Phe Gly Pro
    770                 775                 780

Gln Val Ser Asp Thr Leu Leu Asp Cys Arg Lys His Leu Thr Trp Val
785                 790                 795                 800

Val Ala Val Leu Gln Glu Val Ala Ala Ala Ala Gln Leu Ile Ala
                805                 810                 815

Pro Leu Ala Glu Asn Glu Gly Leu Leu Val Ala Ala Leu Glu Glu Leu
        820                 825                 830

Ala Phe Lys Ala Ser Glu Gln Ile Tyr Gly Thr Pro Ser Ser Ser Pro
    835                 840                 845

Tyr Glu Cys Leu Arg Gln Ser Cys Asn Ile Leu Ile Ser Thr Met Asn
850                 855                 860

Lys Leu Ala Thr Ala Met Gln Glu Gly Glu Tyr Asp Ala Glu Arg Pro
865                 870                 875                 880

Pro Ser Lys Pro Pro Val Glu Leu Arg Ala Ala Leu Arg Ala
            885                 890                 895

Glu Ile Thr Asp Ala Glu Gly Leu Gly Leu Lys Leu Glu Asp Arg Glu
                900                 905                 910

Thr Val Ile Lys Glu Leu Lys Lys Ser Leu Lys Ile Lys Gly Glu Glu
            915                 920                 925

Leu Ser Glu Ala Asn Val Arg Leu Ser Leu Leu Glu Lys Lys Leu Asp
        930                 935                 940
```

-continued

```
Ser Ala Ala Lys Asp Ala Asp Glu Arg Ile Glu Lys Val Gln Thr Arg
945                 950                 955                 960
Leu Glu Glu Thr Gln Ala Leu Leu Arg Lys Lys Glu Lys Glu Phe Glu
                965                 970                 975
Glu Thr Met Asp Ala Leu Gln Ala Asp Ile Asp Gln Leu Glu Ala Glu
                980                 985                 990
Lys Ala Glu Leu Lys Gln Arg Leu Asn Ser Gln Ser Lys Arg Thr Ile
        995                 1000                1005
Glu Gly Leu Arg Gly Pro Pro Ser Gly Ile Ala Thr Leu Val
    1010                1015                1020
Ser Gly Ile Ala Gly Gly Ala Ile Pro Gly Gln Ala Pro Gly Ser
    1025                1030                1035
Val Pro Gly Pro Gly Leu Val Lys Asp Ser Pro Leu Leu Leu Gln
    1040                1045                1050
Gln Ile Ser Ala Met Arg Leu His Ile Ser Gln Leu Gln His Glu
    1055                1060                1065
Asn Ser Ile Leu Lys Gly Ala Gln Met Lys Ala Ser Leu Ala Ser
    1070                1075                1080
Leu Pro Pro Leu His Val Ala Lys Leu Ser His Glu Gly Pro Gly
    1085                1090                1095
Ser Glu Leu Pro Ala Gly Ala Leu Tyr Arg Lys Thr Ser Gln Leu
    1100                1105                1110
Leu Glu Thr Leu Asn Gln Leu Ser Thr His Thr His Val Val Asp
    1115                1120                1125
Ile Thr Arg Thr Ser Pro Ala Ala Lys Ser Pro Ser Ala Gln Leu
    1130                1135                1140
Met Glu Gln Val Ala Gln Leu Lys Ser Leu Ser Asp Thr Val Glu
    1145                1150                1155
Lys Leu Lys Asp Glu Val Leu Lys Glu Thr Val Ser Gln Arg Pro
    1160                1165                1170
Gly Ala Thr Val Pro Thr Asp Phe Ala Thr Phe Pro Ser Ser Ala
    1175                1180                1185
Phe Leu Arg Glu Asp Pro Lys Trp Glu Phe Pro Arg Lys Asn Leu
    1190                1195                1200
Val Leu Gly Lys Thr Leu Gly Glu Gly Glu Phe Gly Lys Val Val
    1205                1210                1215
Lys Ala Thr Ala Phe His Leu Lys Gly Arg Ala Gly Tyr Thr Thr
    1220                1225                1230
Val Ala Val Lys Met Leu Lys Glu Asn Ala Ser Pro Ser Glu Leu
    1235                1240                1245
Arg Asp Leu Leu Ser Glu Phe Asn Val Leu Lys Gln Val Asn His
    1250                1255                1260
Pro His Val Ile Lys Leu Tyr Gly Ala Cys Ser Gln Asp Gly Pro
    1265                1270                1275
Leu Leu Leu Ile Val Glu Tyr Ala Lys Tyr Gly Ser Leu Arg Gly
    1280                1285                1290
Phe Leu Arg Glu Ser Arg Lys Val Gly Pro Gly Tyr Leu Gly Ser
    1295                1300                1305
Gly Gly Ser Arg Asn Ser Ser Leu Asp His Pro Asp Glu Arg
    1310                1315                1320
Ala Leu Thr Met Gly Asp Leu Ile Ser Phe Ala Trp Gln Ile Ser
    1325                1330                1335
Gln Gly Met Gln Tyr Leu Ala Glu Met Lys Leu Val His Arg Asp
```

| | | | | | | | | | | |
|---|---|---|---|---|---|---|---|---|---|---|
| | | 1340 | | | 1345 | | | 1350 | | |
| Leu | Ala | Ala | Arg | Asn | Ile | Leu | Val | Ala | Glu | Gly | Arg | Lys | Met | Lys |
| | 1355 | | | | 1360 | | | | 1365 | |
| Ile | Ser | Asp | Phe | Gly | Leu | Ser | Arg | Asp | Val | Tyr | Glu | Glu | Asp | Ser |
| 1370 | | | | | 1375 | | | | 1380 | |
| Tyr | Val | Lys | Arg | Ser | Gln | Gly | Arg | Ile | Pro | Val | Lys | Trp | Met | Ala |
| 1385 | | | | | 1390 | | | | 1395 | |
| Ile | Glu | Ser | Leu | Phe | Asp | His | Ile | Tyr | Thr | Thr | Gln | Ser | Asp | Val |
| 1400 | | | | | 1405 | | | | 1410 | |
| Trp | Ser | Phe | Gly | Val | Leu | Leu | Trp | Glu | Ile | Val | Thr | Leu | Gly | Gly |
| 1415 | | | | | 1420 | | | | 1425 | |
| Asn | Pro | Tyr | Pro | Gly | Ile | Pro | Pro | Glu | Arg | Leu | Phe | Asn | Leu | Leu |
| 1430 | | | | | 1435 | | | | 1440 | |
| Lys | Thr | Gly | His | Arg | Met | Glu | Arg | Pro | Asp | Asn | Cys | Ser | Glu | Glu |
| 1445 | | | | | 1450 | | | | 1455 | |
| Met | Tyr | Arg | Leu | Met | Leu | Gln | Cys | Trp | Lys | Gln | Glu | Pro | Asp | Lys |
| 1460 | | | | | 1465 | | | | 1470 | |
| Arg | Pro | Val | Phe | Ala | Asp | Ile | Ser | Lys | Asp | Leu | Glu | Lys | Met | Met |
| 1475 | | | | | 1480 | | | | 1485 | |
| Val | Lys | Arg | Arg | Asp | Tyr | Leu | Asp | Leu | Ala | Ala | Ser | Thr | Pro | Ser |
| 1490 | | | | | 1495 | | | | 1500 | |
| Asp | Ser | Leu | Ile | Tyr | Asp | Asp | Gly | Leu | Ser | Glu | Glu | Glu | Thr | Pro |
| 1505 | | | | | 1510 | | | | 1515 | |
| Leu | Val | Asp | Cys | Asn | Asn | Ala | Pro | Leu | Pro | Arg | Ala | Leu | Pro | Ser |
| 1520 | | | | | 1525 | | | | 1530 | |
| Thr | Trp | Ile | Glu | Asn | Lys | Leu | Tyr | Gly | Arg | Ile | Ser | His | Ala | Phe |
| 1535 | | | | | 1540 | | | | 1545 | |
| Thr | Arg | Phe |
| 1550 |

<210> SEQ ID NO 21
<211> LENGTH: 4887
<212> TYPE: DNA
<213> ORGANISM: Artificial Sequence
<220> FEATURE:
<223> OTHER INFORMATION: coding sequence of fusion peptide

<400> SEQUENCE: 21

```
atggcacaga gcaagaggca cgtgtacagc cggacgccca gcggcagcag gatgagtgcg    60
gaggcaagcg cccggcctct gcgggtgggc tcccgtgtag aggtgattgg aaaaggccac   120
cgaggcactg tggcctatgt tggagccaca ctgtttgcca ctggcaaatg ggtaggcgtg   180
attctggatg aagcaaaggg caaaaatgat ggaactgttc aaggcaggaa gtacttcact   240
tgtgatgaag gcatggcat ctttgtgcgc cagtcccaga tccaggtatt tgaagatgga   300
gcagatacta cttccccaga gacacctgat tcttctgctt caaagtcct caaaagagag   360
ggaactgata caactgcaaa gactagcaaa ctggcaccga cagcccgaaa gaccacaact   420
cggcgaccca gcccacgcg cccagccagt actggggtgg ctggggccag tagctccctg   480
ggcccctctg ctcagcgtc agcaggtgag ctgagcagca gtgagcccag caccccggct   540
cagactccgc tggcagcacc catcatcccc acgccggtcc tcacctctcc tggagcagtc   600
cccccgcttc cttccccatc caaggaggag gagggactaa gggctcaggt gcgggacctg   660
gaggagaaac tagagaccct gagactgaaa cgggcagaag acaaagcaaa gctaaaagag   720
ctggagaaac acaaaatcca gctggagcag gtgcaggaat ggaagagcaa aatgcaggag   780
```

```
cagcaggccg acctgcagcg gcgcctcaag gaggcgagaa aggaagccaa ggaggcgctg    840
gaggcaaagg aacgctatat ggaggagatg gctgatactg ctgatgccat tgagatggcc    900
actttggaca aggagatggc tgaagagcgg gctgagtccc tgcagcagga ggtggaggca    960
ctgaaggagc gggtggacga gctcactact gacttagaga tcctcaaggc tgagattgaa   1020
gagaagggct cagatggcgc tgcatccagt tatcagctca agcagcttga ggagcagaat   1080
gcccgcctga aggatgccct ggtgaggatg cgggatcttt cttcctcaga gaagcaggag   1140
catgtgaagc tccagaagct catggaaaag aagaaccaag agctggaagt tgtgaggcaa   1200
cagcgggagc gtctgcagga ggagctaagc caggcagaga gcaccattga tgagctcaag   1260
gagcaggtgg atgctgctct gggtgctgag agatggtgg agatgctgac agatcggaac    1320
ctgaatctgg aagagaaagt gcgcgagttg agggagactg tgggagactt ggaagcgatg   1380
aatgagatga acgatgagct gcaggagaat gcacgtgaga cagaactgga gctgcgggag   1440
cagctggaca tggcaggcgc gcgggttcgt gaggcccaga agcgtgtgga ggcagcccag   1500
gagacggttg cagactacca gcagaccatc aagaagtacc gccagctgac cgcccatcta   1560
caggatgtga atcgggaact gacaaaccag caggaagcat ctgtggagag caacagcag   1620
ccacctccag agacctttga cttcaaaatc aagtttgctg agactaaggc ccatgccaag   1680
gcaattgaga tggaattgag gcagatggag gtggcccagg ccaatcgaca catgtccctg   1740
ctgacagcct tcatgcctga cagcttcctt cggccaggtg gggaccatga ctgcgttctg   1800
gtgctgttgc tcatgcctcg tctcatttgc aaggcagagc tgatccggaa gcaggcccag   1860
gagaagtttg aactaagtga gaactgttca gagcggcctg ggctgcgagg agctgctggg   1920
gagcaactca gctttgctgc tggactggtg tactcgctga gctgctgca ggccacgcta    1980
caccgctatg agcatgccct ctctcagtgc agtgtggatg tgtataagaa agtgggcagc   2040
ctgtaccctg agatgagtgc ccatgagcgc tccttggatt tcctcattga actgctgcac   2100
aaggatcagc tggatgagac tgtcaatgtg gagcctctca ccaaggccat caagtactat   2160
cagcatctgt acagcatcca ccttgccgaa cagcctgagg actgtactat gcagctggct   2220
gaccacatta agttcacgca gagtgctctg gactgcatga gtgtggaggt aggacggctg   2280
cgtgccttct tgcagggtgg gcaggaggct acagatattg ccctcctgct ccgggatctg   2340
gaaacttcat gcagtgacat ccgccagttc tgcaagaaga tccgaaggcg aatgccaggg   2400
acagatgctc ctgggatccc agctgcactg gcctttggac cacaggtatc tgacacgctc   2460
ctagactgca ggaaacactt gacgtgggtc gtggctgtgc tgcaggaggt ggcagctgct   2520
gctgcccagc tcattgcccc actggcagag aatgaggggc tacttgtggc tgctctggag   2580
gaactggctt tcaaagcaag cgagcagatc tatgggaccc cctccagcag ccctatgag    2640
tgtctgcgcc agtcatgcaa catcctcatc agtaccatga caagctggc cacagccatg    2700
caggaggggg agtatgatgc agagcggccc cccagcaagc ctccaccggt tgaactgcgg   2760
gctgctgccc ttcgtgcaga gatcacagat gctgaaggcc tgggtttgaa gctcgaagat   2820
cgagagacag ttattaagga gttgaagaag tcactcaaga ttaagggaga ggagctaagt   2880
gaggccaatg tgcggctgag cctcctggag aagaagttgg acagtgctgc caaggatgca   2940
gatgagcgca tcgagaaagt ccagactcgg ctggaggaga cccaggcact gctgcgaaag   3000
aaggagaaag agtttgagga gacaatggat gcactccagg ctgacatcga ccagctggag   3060
gcagagaagg cagaactaaa gcagcgtctg aacagccagt ccaaacgcac gattgaggga   3120
```

```
ctccggggcc ctcctccttc aggcattgct actctggtct ctggcattgc tggtgaagaa    3180
cagcagcgag gagccatccc tgggcaggct ccagggtctg tgccaggccc agggctggtg    3240
aaggactcac cactgctgct tcagcagatc tctgccatga ggctgcacat ctcccagctc    3300
cagcatgaga acagcatcct caagggagcc cagatgaagg catccttggc atccctgccc    3360
cctctgcatg ttgcaaagct atcccatgag ggccctggca gtgagttacc agctggagcg    3420
ctgtatcgta agaccagcca gctgctggag acattgaatc aattgagcac acacacgcac    3480
gtagtagaca tcactcgcac cagccctgct gccaagagcc cgtcggccca acttatggag    3540
caagtggctc agcttaagtc cctgagtgac accgtcgaga agctcaagga tgaggtcctc    3600
aaggagacag tatctcagcg ccctggagcc acagtaccca ctgactttgc caccttccct    3660
tcatcagcct cctcaggga ggatccaaag tgggaattcc ctcggaagaa cttggttctt    3720
ggaaaaactc taggagaagg cgaatttgga aaagtggtca aggcaacggc cttccatctg    3780
aaaggcagag cagggtacac cacggtggcc gtgaagatgc tgaaagagaa cgcctccccg    3840
agtgagcttc gagacctgct gtcagagttc aacgtcctga gcaggtcaa ccacccacat    3900 gtcatcaaat tgtatgggc ctgcagccag gatggcccgc tcctcctcat cgtggagtac    3960
gccaaatacg gctccctgcg gggcttcctc cgcgagagcc gcaaagtggg gcctggctac    4020
ctgggcagtg gaggcagccg caactccagc tccctggacc acccggatga gcgggccctc    4080
accatgggcg acctcatctc atttgcctgg cagatctcac aggggatgca gtatctggcc    4140
gagatgaagc tcgttcatcg ggacttggca gccagaaaca tcctggtagc tgaggggcgg    4200
aagatgaaga tttcggattt cggcttgtcc cgagatgttt atgaagagga ttcctacgtg    4260
aagaggagcc agggtcggat tccagttaaa tggatggcaa ttgaatccct ttttgatcat    4320
atctacacca cgcaaagtga tgtatggtct tttggtgtcc tgctgtggga gatcgtgacc    4380 ctaggggaa accctatcc tgggattcct cctgagcggc tcttcaacct tctgaagacc    4440
ggccaccgga tggagaggcc agacaactgc agcgaggaga tgtaccgcct gatgctgcaa    4500
tgctggaagc aggagccgga caaaaggccg gtgtttgcgg acatcagcaa agacctggag    4560
aagatgatga ttaagaggag agactacttg gaccttgcgg cgtccactcc atctgactcc    4620
ctgatttatg acgacggcct ctcagaggag gagacaccgc tggtggactg taataatgcc    4680
cccctccctc gagccctccc ttccacatgg attgaaaaca aactctatgg catgtcagac    4740
ccgaactggc ctggagagag tcctgtacca ctcacgagag ctgatggcac taacactggg    4800
tttccaagat atccaaatga tagtgtatat gctaactgga tgcttttcacc ctcagcggca    4860 aaattaatgg acacgtttga tagttaa                                        4887
```

<210> SEQ ID NO 22
<211> LENGTH: 1628
<212> TYPE: PRT
<213> ORGANISM: Artificial Sequence
<220> FEATURE:
<223> OTHER INFORMATION: fusion peptide

<400> SEQUENCE: 22

```
Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45
```

```
Ala Thr Leu Phe Ala Thr Gly Lys Trp Val Gly Val Ile Leu Asp Glu
 50                  55                  60

Ala Lys Gly Lys Asn Asp Gly Thr Val Gln Gly Arg Lys Tyr Phe Thr
 65                  70                  75                  80

Cys Asp Glu Gly His Gly Ile Phe Val Arg Gln Ser Gln Ile Gln Val
                     85                  90                  95

Phe Glu Asp Gly Ala Asp Thr Thr Ser Pro Glu Thr Pro Asp Ser Ser
                    100                 105                 110

Ala Ser Lys Val Leu Lys Arg Glu Gly Thr Asp Thr Thr Ala Lys Thr
                115                 120                 125

Ser Lys Leu Ala Pro Thr Ala Arg Lys Thr Thr Thr Arg Arg Pro Lys
130                 135                 140

Pro Thr Arg Pro Ala Ser Thr Gly Val Ala Gly Ala Ser Ser Ser Leu
145                 150                 155                 160

Gly Pro Ser Gly Ser Ala Ser Ala Gly Glu Leu Ser Ser Ser Glu Pro
                165                 170                 175

Ser Thr Pro Ala Gln Thr Pro Leu Ala Ala Pro Ile Ile Pro Thr Pro
                180                 185                 190

Val Leu Thr Ser Pro Gly Ala Val Pro Pro Leu Pro Ser Pro Ser Lys
                195                 200                 205

Glu Glu Glu Gly Leu Arg Ala Gln Val Arg Asp Leu Glu Glu Lys Leu
210                 215                 220

Glu Thr Leu Arg Leu Lys Arg Ala Glu Asp Lys Ala Lys Leu Lys Glu
225                 230                 235                 240

Leu Glu Lys His Lys Ile Gln Leu Glu Gln Val Gln Glu Trp Lys Ser
                245                 250                 255

Lys Met Gln Glu Gln Gln Ala Asp Leu Gln Arg Arg Leu Lys Glu Ala
            260                 265                 270

Arg Lys Glu Ala Lys Glu Ala Leu Glu Ala Lys Glu Arg Tyr Met Glu
            275                 280                 285

Glu Met Ala Asp Thr Ala Asp Ala Ile Glu Met Ala Thr Leu Asp Lys
            290                 295                 300

Glu Met Ala Glu Glu Arg Ala Glu Ser Leu Gln Gln Glu Val Glu Ala
305                 310                 315                 320

Leu Lys Glu Arg Val Asp Glu Leu Thr Thr Asp Leu Glu Ile Leu Lys
                325                 330                 335

Ala Glu Ile Glu Glu Lys Gly Ser Asp Gly Ala Ala Ser Ser Tyr Gln
                340                 345                 350

Leu Lys Gln Leu Glu Glu Gln Asn Ala Arg Leu Lys Asp Ala Leu Val
            355                 360                 365

Arg Met Arg Asp Leu Ser Ser Ser Glu Lys Gln Glu His Val Lys Leu
            370                 375                 380

Gln Lys Leu Met Glu Lys Lys Asn Gln Glu Leu Glu Val Val Arg Gln
385                 390                 395                 400

Gln Arg Glu Arg Leu Gln Glu Glu Leu Ser Gln Ala Glu Ser Thr Ile
                405                 410                 415

Asp Glu Leu Lys Glu Gln Val Asp Ala Ala Leu Gly Ala Glu Glu Met
                420                 425                 430

Val Glu Met Leu Thr Asp Arg Asn Leu Asn Leu Glu Glu Lys Val Arg
            435                 440                 445

Glu Leu Arg Glu Thr Val Gly Asp Leu Glu Ala Met Asn Glu Met Asn
450                 455                 460

Asp Glu Leu Gln Glu Asn Ala Arg Glu Thr Glu Leu Glu Leu Arg Glu
```

```
              465                 470                 475                 480
        Gln Leu Asp Met Ala Gly Ala Arg Val Arg Glu Ala Gln Lys Arg Val
                        485                 490                 495
        Glu Ala Ala Gln Glu Thr Val Ala Asp Tyr Gln Gln Thr Ile Lys Lys
                        500                 505                 510
        Tyr Arg Gln Leu Thr Ala His Leu Gln Asp Val Asn Arg Glu Leu Thr
                        515                 520                 525
        Asn Gln Gln Glu Ala Ser Val Glu Arg Gln Gln Pro Pro Glu
                        530                 535                 540
        Thr Phe Asp Phe Lys Ile Lys Phe Ala Glu Thr Lys Ala His Ala Lys
        545                 550                 555                 560
        Ala Ile Glu Met Glu Leu Arg Gln Met Glu Val Ala Gln Ala Asn Arg
                        565                 570                 575
        His Met Ser Leu Leu Thr Ala Phe Met Pro Asp Ser Phe Leu Arg Pro
                        580                 585                 590
        Gly Gly Asp His Asp Cys Val Leu Val Leu Leu Met Pro Arg Leu
                        595                 600                 605
        Ile Cys Lys Ala Glu Leu Ile Arg Lys Gln Ala Gln Glu Lys Phe Glu
                        610                 615                 620
        Leu Ser Glu Asn Cys Ser Glu Arg Pro Gly Leu Arg Gly Ala Ala Gly
        625                 630                 635                 640
        Glu Gln Leu Ser Phe Ala Ala Gly Leu Val Tyr Ser Leu Ser Leu Leu
                        645                 650                 655
        Gln Ala Thr Leu His Arg Tyr Glu His Ala Leu Ser Gln Cys Ser Val
                        660                 665                 670
        Asp Val Tyr Lys Lys Val Gly Ser Leu Tyr Pro Glu Met Ser Ala His
                        675                 680                 685
        Glu Arg Ser Leu Asp Phe Leu Ile Glu Leu Leu His Lys Asp Gln Leu
                        690                 695                 700
        Asp Glu Thr Val Asn Val Glu Pro Leu Thr Lys Ala Ile Lys Tyr Tyr
        705                 710                 715                 720
        Gln His Leu Tyr Ser Ile His Leu Ala Glu Gln Pro Glu Asp Cys Thr
                        725                 730                 735
        Met Gln Leu Ala Asp His Ile Lys Phe Thr Gln Ser Ala Leu Asp Cys
                        740                 745                 750
        Met Ser Val Glu Val Gly Arg Leu Arg Ala Phe Leu Gln Gly Gly Gln
                        755                 760                 765
        Glu Ala Thr Asp Ile Ala Leu Leu Leu Arg Asp Leu Glu Thr Ser Cys
                        770                 775                 780
        Ser Asp Ile Arg Gln Phe Cys Lys Lys Ile Arg Arg Arg Met Pro Gly
        785                 790                 795                 800
        Thr Asp Ala Pro Gly Ile Pro Ala Ala Leu Ala Phe Gly Pro Gln Val
                        805                 810                 815
        Ser Asp Thr Leu Leu Asp Cys Arg Lys His Leu Thr Trp Val Val Ala
                        820                 825                 830
        Val Leu Gln Glu Val Ala Ala Ala Ala Gln Leu Ile Ala Pro Leu
                        835                 840                 845
        Ala Glu Asn Glu Gly Leu Leu Val Ala Ala Leu Glu Glu Leu Ala Phe
                        850                 855                 860
        Lys Ala Ser Glu Gln Ile Tyr Gly Thr Pro Ser Ser Pro Tyr Glu
        865                 870                 875                 880
        Cys Leu Arg Gln Ser Cys Asn Ile Leu Ile Ser Thr Met Asn Lys Leu
                        885                 890                 895
```

-continued

```
Ala Thr Ala Met Gln Glu Gly Glu Tyr Asp Ala Glu Arg Pro Pro Ser
            900                 905                 910

Lys Pro Pro Val Glu Leu Arg Ala Ala Leu Arg Ala Glu Ile
        915                 920                 925

Thr Asp Ala Glu Gly Leu Gly Leu Lys Leu Glu Asp Arg Glu Thr Val
        930                 935                 940

Ile Lys Glu Leu Lys Lys Ser Leu Lys Ile Lys Gly Glu Glu Leu Ser
945                 950                 955                 960

Glu Ala Asn Val Arg Leu Ser Leu Leu Glu Lys Lys Leu Asp Ser Ala
                965                 970                 975

Ala Lys Asp Ala Asp Glu Arg Ile Glu Lys Val Gln Thr Arg Leu Glu
        980                 985                 990

Glu Thr Gln Ala Leu Leu Arg Lys Lys Glu Lys Glu Phe Glu Glu Thr
        995                 1000                1005

Met Asp Ala Leu Gln Ala Asp Ile Asp Gln Leu Glu Ala Glu Lys
    1010                1015                1020

Ala Glu Leu Lys Gln Arg Leu Asn Ser Gln Ser Lys Arg Thr Ile
    1025                1030                1035

Glu Gly Leu Arg Gly Pro Pro Ser Gly Ile Ala Thr Leu Val
    1040                1045                1050

Ser Gly Ile Ala Gly Glu Gln Gln Arg Gly Ala Ile Pro Gly
    1055                1060                1065

Gln Ala Pro Gly Ser Val Pro Gly Pro Gly Leu Val Lys Asp Ser
    1070                1075                1080

Pro Leu Leu Gln Gln Ile Ser Ala Met Arg Leu His Ile Ser
    1085                1090                1095

Gln Leu Gln His Glu Asn Ser Ile Leu Lys Gly Ala Gln Met Lys
    1100                1105                1110

Ala Ser Leu Ala Ser Leu Pro Pro Leu His Val Ala Lys Leu Ser
    1115                1120                1125

His Glu Gly Pro Gly Ser Glu Leu Pro Ala Gly Ala Leu Tyr Arg
    1130                1135                1140

Lys Thr Ser Gln Leu Leu Glu Thr Leu Asn Gln Leu Ser Thr His
    1145                1150                1155

Thr His Val Val Asp Ile Thr Arg Thr Ser Pro Ala Ala Lys Ser
    1160                1165                1170

Pro Ser Ala Gln Leu Met Glu Gln Val Ala Gln Leu Lys Ser Leu
    1175                1180                1185

Ser Asp Thr Val Glu Lys Leu Lys Asp Glu Val Leu Lys Glu Thr
    1190                1195                1200

Val Ser Gln Arg Pro Gly Ala Thr Val Pro Thr Asp Phe Ala Thr
    1205                1210                1215

Phe Pro Ser Ser Ala Phe Leu Arg Glu Asp Pro Lys Trp Glu Phe
    1220                1225                1230

Pro Arg Lys Asn Leu Val Leu Gly Lys Thr Leu Gly Glu Gly Glu
    1235                1240                1245

Phe Gly Lys Val Val Lys Ala Thr Ala Phe His Leu Lys Gly Arg
    1250                1255                1260

Ala Gly Tyr Thr Thr Val Ala Val Lys Met Leu Lys Glu Asn Ala
    1265                1270                1275

Ser Pro Ser Glu Leu Arg Asp Leu Leu Ser Glu Phe Asn Val Leu
    1280                1285                1290
```

```
Lys Gln Val Asn His Pro His Val Ile Lys Leu Tyr Gly Ala Cys
1295                1300                1305

Ser Gln Asp Gly Pro Leu Leu Leu Ile Val Glu Tyr Ala Lys Tyr
1310                1315                1320

Gly Ser Leu Arg Gly Phe Leu Arg Glu Ser Arg Lys Val Gly Pro
1325                1330                1335

Gly Tyr Leu Gly Ser Gly Gly Ser Arg Asn Ser Ser Ser Leu Asp
1340                1345                1350

His Pro Asp Glu Arg Ala Leu Thr Met Gly Asp Leu Ile Ser Phe
1355                1360                1365

Ala Trp Gln Ile Ser Gln Gly Met Gln Tyr Leu Ala Glu Met Lys
1370                1375                1380

Leu Val His Arg Asp Leu Ala Ala Arg Asn Ile Leu Val Ala Glu
1385                1390                1395

Gly Arg Lys Met Lys Ile Ser Asp Phe Gly Leu Ser Arg Asp Val
1400                1405                1410

Tyr Glu Glu Asp Ser Tyr Val Lys Arg Ser Gln Gly Arg Ile Pro
1415                1420                1425

Val Lys Trp Met Ala Ile Glu Ser Leu Phe Asp His Ile Tyr Thr
1430                1435                1440

Thr Gln Ser Asp Val Trp Ser Phe Gly Val Leu Leu Trp Glu Ile
1445                1450                1455

Val Thr Leu Gly Gly Asn Pro Tyr Pro Gly Ile Pro Pro Glu Arg
1460                1465                1470

Leu Phe Asn Leu Leu Lys Thr Gly His Arg Met Glu Arg Pro Asp
1475                1480                1485

Asn Cys Ser Glu Glu Met Tyr Arg Leu Met Leu Gln Cys Trp Lys
1490                1495                1500

Gln Glu Pro Asp Lys Arg Pro Val Phe Ala Asp Ile Ser Lys Asp
1505                1510                1515

Leu Glu Lys Met Met Val Lys Arg Arg Asp Tyr Leu Asp Leu Ala
1520                1525                1530

Ala Ser Thr Pro Ser Asp Ser Leu Ile Tyr Asp Asp Gly Leu Ser
1535                1540                1545

Glu Glu Glu Thr Pro Leu Val Asp Cys Asn Asn Ala Pro Leu Pro
1550                1555                1560

Arg Ala Leu Pro Ser Thr Trp Ile Glu Asn Lys Leu Tyr Gly Met
1565                1570                1575

Ser Asp Pro Asn Trp Pro Gly Glu Ser Pro Val Pro Leu Thr Arg
1580                1585                1590

Ala Asp Gly Thr Asn Thr Gly Phe Pro Arg Tyr Pro Asn Asp Ser
1595                1600                1605

Val Tyr Ala Asn Trp Met Leu Ser Pro Ser Ala Ala Lys Leu Met
1610                1615                1620

Asp Thr Phe Asp Ser
    1625

<210> SEQ ID NO 23
<211> LENGTH: 4761
<212> TYPE: DNA
<213> ORGANISM: Artificial Sequence
<220> FEATURE:
<223> OTHER INFORMATION: coding sequence of fusion peptide

<400> SEQUENCE: 23
```

-continued

| | | | | | |
|---|---|---|---|---|---|
| atggcacaga | gcaagaggca | cgtgtacagc | cggacgccca | gcggcagcag | gatgagtgcg | 60 |
| gaggcaagcg | cccggcctct | gcgggtgggc | tcccgtgtag | aggtgattgg | aaaaggccac | 120 |
| cgaggcactg | tggcctatgt | tggagccaca | ctgtttgcca | ctggcaaatg | ggtaggcgtg | 180 |
| attctggatg | aagcaaaggg | caaaaatgat | ggaactgttc | aaggcaggaa | gtacttcact | 240 |
| tgtgatgaag | ggcatggcat | ctttgtgcgc | cagtcccaga | tccaggtatt | tgaagatgga | 300 |
| gcagatacta | cttccccaga | gacacctgat | tcttctgctt | caaaagtcct | caaaagagag | 360 |
| ggaactgata | caactgcaaa | gactagcaaa | ctggcaccga | cagcccgaaa | gaccacaact | 420 |
| cggcgaccca | agcccacgcg | cccagccagt | actggggtgg | ctggggccag | tagctccctg | 480 |
| ggcccctctg | gctcagcgtc | agcaggtgag | ctgagcagca | gtgagcccag | caccccggct | 540 |
| cagactccgc | tggcagcacc | catcatcccc | acgccggtcc | tcacctctcc | tggagcagtc | 600 |
| cccccgcttc | cttccccatc | caaggaggag | gagggactaa | gggctcaggt | gcgggacctg | 660 |
| gaggagaaac | tagagaccct | gagactgaaa | cgggcagaag | acaaagcaaa | gctaaaagag | 720 |
| ctggagaaac | acaaaatcca | gctggagcag | gtgcaggaat | ggaagagcaa | aatgcaggag | 780 |
| cagcaggccg | acctgcagcg | gcgcctcaag | gaggcgagaa | aggaagccaa | ggaggcgctg | 840 |
| gaggcaaagg | aacgctatat | ggaggagatg | gctgatactg | ctgatgccat | tgagatggcc | 900 |
| actttggaca | aggagatggc | tgaagagcgg | gctgagtccc | tgcagcagga | ggtggaggca | 960 |
| ctgaaggagc | gggtggacga | gctcactact | gacttagaga | tcctcaaggc | tgagattgaa | 1020 |
| gagaagggct | cagatggcgc | tgcatccagt | tatcagctca | agcagcttga | ggagcagaat | 1080 |
| gcccgcctga | aggatgccct | ggtgaggatg | cgggatcttt | cttcctcaga | gaagcaggag | 1140 |
| catgtgaagc | tccagaagct | catggaaaag | aagaaccaag | agctggaagt | tgtgaggcaa | 1200 |
| cagcggggagc | gtctgcagga | ggagctaagc | caggcagaga | gcaccattga | tgagctcaag | 1260 |
| gagcaggtgg | atgctgctct | gggtgctgag | gagatggtgg | agatgctgac | agatcggaac | 1320 |
| ctgaatctgg | aagagaaagt | gcgcgagttg | agggagactg | tgggagactt | ggaagcgatg | 1380 |
| aatgagatga | acgatgagct | gcaggagaat | gcacgtgaga | cagaactgga | gctgcgggag | 1440 |
| cagctggaca | tggcaggcgc | gcgggttcgt | gaggcccaga | agcgtgtgga | ggcagcccag | 1500 |
| gagacggttg | cagactacca | gcagaccatc | aagaagtacc | gccagctgac | cgcccatcta | 1560 |
| caggatgtga | atcgggaact | gacaaaccag | caggaagcat | ctgtggagag | gcaacagcag | 1620 |
| ccacctccag | agacctttga | cttcaaaatc | aagtttgctg | agactaaggc | ccatgccaag | 1680 |
| gcaattgaga | tggaattgag | gcagatggag | gtggcccagg | ccaatcgaca | catgtccctg | 1740 |
| ctgacagcct | tcatgcctga | cagcttcctt | cggccaggtg | gggaccatga | ctgcgttctg | 1800 |
| gtgctgttgc | tcatgcctcg | tctcatttgc | aaggcagagc | tgatccggaa | gcaggccag | 1860 |
| gagaagtttg | aactaagtga | gaactgttca | gagcggcctg | ggctgcgagg | agctgctggg | 1920 |
| gagcaactca | gctttgctgc | tggactggtg | tactcgctga | gcctgctgca | ggccacgcta | 1980 |
| caccgctatg | agcatgccct | ctctcagtgc | agtgtggatg | tgtataagaa | agtgggcagc | 2040 |
| ctgtaccctg | agatgagtgc | ccatgagcgc | tccttggatt | tcctcattga | actgctgcac | 2100 |
| aaggatcagc | tggatgagac | tgtcaatgtg | gagcctctca | ccaaggccat | caagtactat | 2160 |
| cagcatctgt | acagcatcca | ccttgccgaa | cagcctgagg | actgtactat | gcagctggct | 2220 |
| gaccacatta | agttcacgca | gagtgctctg | gactgcatga | gtgtggaggt | aggacggctg | 2280 |
| cgtgccttct | gcagggtgg | gcaggaggct | acagatattg | ccctcctgct | ccgggatctg | 2340 |
| gaaacttcat | gcagtgacat | ccgccagttc | tgcaagaaga | tccgaaggcg | aatgccaggg | 2400 |

```
acagatgctc ctgggatccc agctgcactg gcctttggac cacaggtatc tgacacgctc   2460
ctagactgca ggaaacactt gacgtgggtc gtggctgtgc tgcaggaggt ggcagctgct   2520
gctgcccagc tcattgcccc actggcagag aatgaggggc tacttgtggc tgctctggag   2580
gaactggctt tcaaagcaag cgagcagatc tatgggaccc cctccagcag ccccctatgag   2640 tgtctgcgcc agtcatgcaa catcctcatc agtaccatga acaagctggc cacagccatg   2700
caggaggggg agtatgatgc agagcggccc cccagcaagc ctccaccggt tgaactgcgg   2760
gctgctgccc ttcgtgcaga gatcacagat gctgaaggcc tgggtttgaa gctcgaagat   2820
cgagagacag ttattaagga gttgaagaag tcactcaaga ttaagggaga ggagctaagt   2880
gaggccaatg tgcggctgag cctcctggag aagaagttgg acagtgctgc caaggatgca   2940
gatgagcgca tcgagaaagt ccagactcgg ctggaggaga cccaggcact gctgcgaaag   3000
aaggagaaag agtttgagga gacaatggat gcactccagg ctgacatcga ccagctggag   3060
gcagagaagg cagaactaaa gcagcgtctg aacagccagt ccaaacgcac gattgaggga   3120
ctccggggcc ctcctccttc aggcattgct actctggtct ctggcattgc tggtgaagaa   3180
cagcagcgag gagccatccc tgggcaggct ccagggtctg tgccaggccc agggctggtg   3240
aaggactcac cactgctgct tcagcagatc tctgccatga ggctgcacat ctcccagctc   3300
cagcatgaga acagcatcct caagggagcc cagatgaagg catccttggc atccctgccc   3360
cctctgcatg ttgcaaagct atcccatgag ggccctggca gtgagttacc agctggagcg   3420
ctgtatcgta agaccagcca gctgctggag acattgaatc aattgagcac acacacgcac   3480
gtagtagaca tcactcgcac cagccctgct gccaagagcc cgtcggccca acttatggag   3540
caagtggctc agcttaagtc cctgagtgac accgtcgaga agctcaagga tgaggtcctc   3600
aaggagacag tatctcagcg ccctggagcc acagtaccca ctgactttgc caccttccct   3660
tcatcagcct tcctcaggga ggatccaaag tgggaattcc ctcggaagaa cttggttctt   3720
ggaaaaactc taggagaagg cgaatttgga aaagtggtca aggcaacggc cttccatctg   3780
aaaggcagag cagggtacac cacggtggcc gtgaagatgc tgaaagagaa cgcctccccg   3840
agtgagcttc gagacctgct gtcagagttc aacgtcctga agcaggtcaa ccacccacat   3900
gtcatcaaat tgtatgggc ctgcagccag gatggcccgc tcctcctcat cgtggagtac   3960
gccaaatacg gctccctgcg gggcttcctc cgcgagagcc gcaaagtggg gcctggctac   4020
ctgggcagtg gaggcagccg caactccagc tccctggacc acccggatga gcgggccctc   4080
accatgggcg acctcatctc atttgcctgg cagatctcac aggggatgca gtatctggcc   4140
gagatgaagc tcgttcatcg ggacttggca gccagaaaca tcctggtagc tgagggcggg   4200
aagatgaaga tttcggattt cggcttgtcc cgagatgttt atgaagagga ttcctacgtg   4260
aagaggagcc agggtcggat tccagttaaa tggatggcaa ttgaatccct tttttgatcat   4320 atctacacca cgcaaagtga tgtatggtct tttggtgtcc tgctgtggga gatcgtgacc   4380 ctaggggaa acccctatcc tgggattcct cctgagcggc tcttcaacct tctgaagacc   4440
ggccaccgga tggagaggcc agacaactgc agcgaggaga tgtaccgcct gatgctgcaa   4500
tgctggaagc aggagccgga caaaaggccg gtgtttgcgg acatcagcaa agacctggag   4560
aagatgatgg ttaagaggag agactacttg gaccttgcgg cgtccactcc atctgactcc   4620
ctgatttatg acgacggcct ctcagaggag gagacaccgc tggtggactg taataatgcc   4680
cccctcccct gagccctccc ttccacatgg attgaaaaca aactctatgg tagaatttcc   4740
```
catgcattta ctagattcta g                                              4761

<210> SEQ ID NO 24
<211> LENGTH: 1586
<212> TYPE: PRT
<213> ORGANISM: Artificial Sequence
<220> FEATURE:
<223> OTHER INFORMATION: fusion peptide

<400> SEQUENCE: 24

```
Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Thr Ala Lys Thr
        115                 120                 125

Ser Lys Leu Ala Pro Thr Ala Arg Lys Thr Thr Thr Arg Arg Pro Lys
    130                 135                 140

Pro Thr Arg Pro Ala Ser Thr Gly Val Ala Gly Ala Ser Ser Ser Leu
145                 150                 155                 160

Gly Pro Ser Gly Ser Ala Ser Ala Gly Glu Leu Ser Ser Ser Glu Pro
                165                 170                 175

Ser Thr Pro Ala Gln Thr Pro Leu Ala Ala Pro Ile Ile Pro Thr Pro
            180                 185                 190

Val Leu Thr Ser Pro Gly Ala Val Pro Pro Leu Pro Ser Pro Ser Lys
        195                 200                 205

Glu Glu Glu Gly Leu Arg Ala Gln Val Arg Asp Leu Glu Glu Lys Leu
    210                 215                 220

Glu Thr Leu Arg Leu Lys Arg Ala Glu Asp Lys Ala Lys Leu Lys Glu
225                 230                 235                 240

Leu Glu Lys His Lys Ile Gln Leu Glu Gln Val Gln Glu Trp Lys Ser
                245                 250                 255

Lys Met Gln Glu Gln Gln Ala Asp Leu Gln Arg Arg Leu Lys Glu Ala
            260                 265                 270

Arg Lys Glu Ala Lys Glu Ala Leu Glu Ala Lys Glu Arg Tyr Met Glu
        275                 280                 285

Glu Met Ala Asp Thr Ala Asp Ala Ile Glu Met Ala Thr Leu Asp Lys
    290                 295                 300

Glu Met Ala Glu Glu Arg Ala Glu Ser Leu Gln Gln Glu Val Glu Ala
305                 310                 315                 320

Leu Lys Glu Arg Val Asp Glu Leu Thr Thr Asp Leu Glu Ile Leu Lys
                325                 330                 335

Ala Glu Ile Glu Glu Lys Gly Ser Asp Gly Ala Ala Ser Ser Tyr Gln
            340                 345                 350

Leu Lys Gln Leu Glu Glu Gln Asn Ala Arg Leu Lys Asp Ala Leu Val
```

```
            355                 360                 365
Arg Met Arg Asp Leu Ser Ser Ser Glu Lys Gln Glu His Val Lys Leu
        370                 375                 380
Gln Lys Leu Met Glu Lys Asn Gln Glu Leu Glu Val Val Arg Gln
385                 390                 395                 400
Gln Arg Glu Arg Leu Gln Glu Glu Leu Ser Gln Ala Glu Ser Thr Ile
                405                 410                 415
Asp Glu Leu Lys Glu Gln Val Asp Ala Ala Leu Gly Ala Glu Met
                420                 425                 430
Val Glu Met Leu Thr Asp Arg Asn Leu Asn Leu Glu Glu Lys Val Arg
        435                 440                 445
Glu Leu Arg Glu Thr Val Gly Asp Leu Glu Ala Met Asn Glu Met Asn
    450                 455                 460
Asp Glu Leu Gln Glu Asn Ala Arg Glu Thr Glu Leu Glu Leu Arg Glu
465                 470                 475                 480
Gln Leu Asp Met Ala Gly Ala Arg Val Arg Glu Ala Gln Lys Arg Val
                485                 490                 495
Glu Ala Ala Gln Glu Thr Val Ala Asp Tyr Gln Gln Thr Ile Lys Lys
                500                 505                 510
Tyr Arg Gln Leu Thr Ala His Leu Gln Asp Val Asn Arg Glu Leu Thr
        515                 520                 525
Asn Gln Gln Glu Ala Ser Val Glu Arg Gln Gln Pro Pro Pro Glu
    530                 535                 540
Thr Phe Asp Phe Lys Ile Lys Phe Ala Glu Thr Lys Ala His Ala Lys
545                 550                 555                 560
Ala Ile Glu Met Glu Leu Arg Gln Met Glu Val Ala Gln Ala Asn Arg
                565                 570                 575
His Met Ser Leu Leu Thr Ala Phe Met Pro Asp Ser Phe Leu Arg Pro
            580                 585                 590
Gly Gly Asp His Asp Cys Val Leu Val Leu Leu Leu Met Pro Arg Leu
            595                 600                 605
Ile Cys Lys Ala Glu Leu Ile Arg Lys Gln Ala Gln Glu Lys Phe Glu
        610                 615                 620
Leu Ser Glu Asn Cys Ser Glu Arg Pro Gly Leu Arg Gly Ala Ala Gly
625                 630                 635                 640
Glu Gln Leu Ser Phe Ala Ala Gly Leu Val Tyr Ser Leu Ser Leu Leu
                645                 650                 655
Gln Ala Thr Leu His Arg Tyr Glu His Ala Leu Ser Gln Cys Ser Val
                660                 665                 670
Asp Val Tyr Lys Lys Val Gly Ser Leu Tyr Pro Glu Met Ser Ala His
        675                 680                 685
Glu Arg Ser Leu Asp Phe Leu Ile Glu Leu Leu His Lys Asp Gln Leu
        690                 695                 700
Asp Glu Thr Val Asn Val Glu Pro Leu Thr Lys Ala Ile Lys Tyr Tyr
705                 710                 715                 720
Gln His Leu Tyr Ser Ile His Leu Ala Glu Gln Pro Glu Asp Cys Thr
                725                 730                 735
Met Gln Leu Ala Asp His Ile Lys Phe Thr Gln Ser Ala Leu Asp Cys
                740                 745                 750
Met Ser Val Glu Val Gly Arg Leu Arg Ala Phe Leu Gln Gly Gly Gln
            755                 760                 765
Glu Ala Thr Asp Ile Ala Leu Leu Leu Arg Asp Leu Glu Thr Ser Cys
        770                 775                 780
```

```
Ser Asp Ile Arg Gln Phe Cys Lys Lys Ile Arg Arg Met Pro Gly
785                 790                 795                 800

Thr Asp Ala Pro Gly Ile Pro Ala Ala Leu Ala Phe Gly Pro Gln Val
            805                 810                 815

Ser Asp Thr Leu Leu Asp Cys Arg Lys His Leu Thr Trp Val Val Ala
            820                 825                 830

Val Leu Gln Glu Val Ala Ala Ala Ala Gln Leu Ile Ala Pro Leu
            835                 840                 845

Ala Glu Asn Glu Gly Leu Leu Val Ala Ala Leu Glu Leu Ala Phe
850                 855                 860

Lys Ala Ser Glu Gln Ile Tyr Gly Thr Pro Ser Ser Pro Tyr Glu
865                 870                 875                 880

Cys Leu Arg Gln Ser Cys Asn Ile Leu Ile Ser Thr Met Asn Lys Leu
            885                 890                 895

Ala Thr Ala Met Gln Glu Gly Glu Tyr Asp Ala Glu Arg Pro Pro Ser
                900                 905                 910

Lys Pro Pro Pro Val Glu Leu Arg Ala Ala Ala Leu Arg Ala Glu Ile
            915                 920                 925

Thr Asp Ala Glu Gly Leu Gly Leu Lys Leu Glu Asp Arg Glu Thr Val
            930                 935                 940

Ile Lys Glu Leu Lys Lys Ser Leu Lys Ile Lys Gly Glu Leu Ser
945                 950                 955                 960

Glu Ala Asn Val Arg Leu Ser Leu Leu Glu Lys Lys Leu Asp Ser Ala
                965                 970                 975

Ala Lys Asp Ala Asp Glu Arg Ile Glu Lys Val Gln Thr Arg Leu Glu
            980                 985                 990

Glu Thr Gln Ala Leu Leu Arg Lys Lys Glu Lys Glu Phe Glu Glu Thr
            995                 1000                1005

Met Asp Ala Leu Gln Ala Asp Ile Asp Gln Leu Glu Ala Glu Lys
    1010                1015                1020

Ala Glu Leu Lys Gln Arg Leu Asn Ser Gln Ser Lys Arg Thr Ile
    1025                1030                1035

Glu Gly Leu Arg Gly Pro Pro Ser Gly Ile Ala Thr Leu Val
    1040                1045                1050

Ser Gly Ile Ala Gly Glu Gln Gln Arg Gly Ala Ile Pro Gly
    1055                1060                1065

Gln Ala Pro Gly Ser Val Pro Gly Pro Gly Leu Val Lys Asp Ser
    1070                1075                1080

Pro Leu Leu Gln Gln Ile Ser Ala Met Arg Leu His Ile Ser
    1085                1090                1095

Gln Leu Gln His Glu Asn Ser Ile Leu Lys Gly Ala Gln Met Lys
    1100                1105                1110

Ala Ser Leu Ala Ser Leu Pro Pro Leu His Val Ala Lys Leu Ser
    1115                1120                1125

His Glu Gly Pro Gly Ser Glu Leu Pro Ala Gly Ala Leu Tyr Arg
    1130                1135                1140

Lys Thr Ser Gln Leu Leu Glu Thr Leu Asn Gln Leu Ser Thr His
    1145                1150                1155

Thr His Val Val Asp Ile Thr Arg Thr Ser Pro Ala Ala Lys Ser
    1160                1165                1170

Pro Ser Ala Gln Leu Met Glu Gln Val Ala Gln Leu Lys Ser Leu
    1175                1180                1185
```

```
Ser Asp Thr Val Glu Lys Leu Lys Asp Glu Val Leu Lys Glu Thr
1190                1195                1200

Val Ser Gln Arg Pro Gly Ala Thr Val Pro Thr Asp Phe Ala Thr
1205                1210                1215

Phe Pro Ser Ser Ala Phe Leu Arg Glu Asp Pro Lys Trp Glu Phe
1220                1225                1230

Pro Arg Lys Asn Leu Val Leu Gly Lys Thr Leu Gly Glu Gly Glu
1235                1240                1245

Phe Gly Lys Val Val Lys Ala Thr Ala Phe His Leu Lys Gly Arg
1250                1255                1260

Ala Gly Tyr Thr Thr Val Ala Val Lys Met Leu Lys Glu Asn Ala
1265                1270                1275

Ser Pro Ser Glu Leu Arg Asp Leu Leu Ser Glu Phe Asn Val Leu
1280                1285                1290

Lys Gln Val Asn His Pro His Val Ile Lys Leu Tyr Gly Ala Cys
1295                1300                1305

Ser Gln Asp Gly Pro Leu Leu Leu Ile Val Glu Tyr Ala Lys Tyr
1310                1315                1320

Gly Ser Leu Arg Gly Phe Leu Arg Glu Ser Arg Lys Val Gly Pro
1325                1330                1335

Gly Tyr Leu Gly Ser Gly Gly Ser Arg Asn Ser Ser Ser Leu Asp
1340                1345                1350

His Pro Asp Glu Arg Ala Leu Thr Met Gly Asp Leu Ile Ser Phe
1355                1360                1365

Ala Trp Gln Ile Ser Gln Gly Met Gln Tyr Leu Ala Glu Met Lys
1370                1375                1380

Leu Val His Arg Asp Leu Ala Ala Arg Asn Ile Leu Val Ala Glu
1385                1390                1395

Gly Arg Lys Met Lys Ile Ser Asp Phe Gly Leu Ser Arg Asp Val
1400                1405                1410

Tyr Glu Glu Asp Ser Tyr Val Lys Arg Ser Gln Gly Arg Ile Pro
1415                1420                1425

Val Lys Trp Met Ala Ile Glu Ser Leu Phe Asp His Ile Tyr Thr
1430                1435                1440

Thr Gln Ser Asp Val Trp Ser Phe Gly Val Leu Leu Trp Glu Ile
1445                1450                1455

Val Thr Leu Gly Gly Asn Pro Tyr Pro Gly Ile Pro Pro Glu Arg
1460                1465                1470

Leu Phe Asn Leu Leu Lys Thr Gly His Arg Met Glu Arg Pro Asp
1475                1480                1485

Asn Cys Ser Glu Glu Met Tyr Arg Leu Met Leu Gln Cys Trp Lys
1490                1495                1500

Gln Glu Pro Asp Lys Arg Pro Val Phe Ala Asp Ile Ser Lys Asp
1505                1510                1515

Leu Glu Lys Met Met Val Lys Arg Arg Asp Tyr Leu Asp Leu Ala
1520                1525                1530

Ala Ser Thr Pro Ser Asp Ser Leu Ile Tyr Asp Asp Gly Leu Ser
1535                1540                1545

Glu Glu Glu Thr Pro Leu Val Asp Cys Asn Asn Ala Pro Leu Pro
1550                1555                1560

Arg Ala Leu Pro Ser Thr Trp Ile Glu Asn Lys Leu Tyr Gly Arg
1565                1570                1575

Ile Ser His Ala Phe Thr Arg Phe
```

-continued

```
        1580            1585

<210> SEQ ID NO 25
<211> LENGTH: 1278
<212> TYPE: PRT
<213> ORGANISM: Homo sapiens

<400> SEQUENCE: 25

Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Thr Ala Lys Thr
        115                 120                 125

Ser Lys Leu Arg Gly Leu Lys Pro Lys Ala Pro Thr Ala Arg Lys
    130                 135                 140

Thr Thr Thr Arg Arg Pro Lys Pro Thr Arg Pro Ala Ser Thr Gly Val
145                 150                 155                 160

Ala Gly Ala Ser Ser Ser Leu Gly Pro Ser Gly Ser Ala Ser Ala Gly
                165                 170                 175

Glu Leu Ser Ser Ser Glu Pro Ser Thr Pro Ala Gln Thr Pro Leu Ala
            180                 185                 190

Ala Pro Ile Ile Pro Thr Pro Val Leu Thr Ser Pro Gly Ala Val Pro
        195                 200                 205

Pro Leu Pro Ser Pro Ser Lys Glu Glu Glu Gly Leu Arg Ala Gln Val
    210                 215                 220

Arg Asp Leu Glu Glu Lys Leu Glu Thr Leu Arg Leu Lys Arg Ala Glu
225                 230                 235                 240

Asp Lys Ala Lys Leu Lys Glu Leu Glu Lys His Lys Ile Gln Leu Glu
                245                 250                 255

Gln Val Gln Glu Trp Lys Ser Lys Met Gln Glu Gln Gln Ala Asp Leu
            260                 265                 270

Gln Arg Arg Leu Lys Glu Ala Arg Lys Glu Ala Lys Glu Ala Leu Glu
        275                 280                 285

Ala Lys Glu Arg Tyr Met Glu Glu Met Ala Asp Thr Ala Asp Ala Ile
    290                 295                 300

Glu Met Ala Thr Leu Asp Lys Glu Met Ala Glu Arg Ala Glu Ser
305                 310                 315                 320

Leu Gln Gln Glu Val Glu Ala Leu Lys Glu Arg Val Asp Glu Leu Thr
                325                 330                 335

Thr Asp Leu Glu Ile Leu Lys Ala Glu Ile Glu Glu Lys Gly Ser Asp
            340                 345                 350

Gly Ala Ala Ser Ser Tyr Gln Leu Lys Gln Leu Glu Glu Gln Asn Ala
        355                 360                 365
```

-continued

```
Arg Leu Lys Asp Ala Leu Val Arg Met Arg Asp Leu Ser Ser Ser Glu
    370                 375                 380
Lys Gln Glu His Val Lys Leu Gln Lys Leu Met Glu Lys Lys Asn Gln
385                 390                 395                 400
Glu Leu Glu Val Val Arg Gln Gln Arg Glu Arg Leu Gln Glu Glu Leu
                405                 410                 415
Ser Gln Ala Glu Ser Thr Ile Asp Glu Leu Lys Glu Gln Val Asp Ala
            420                 425                 430
Ala Leu Gly Ala Glu Glu Met Val Glu Met Leu Thr Asp Arg Asn Leu
        435                 440                 445
Asn Leu Glu Glu Lys Val Arg Glu Leu Arg Glu Thr Val Gly Asp Leu
450                 455                 460
Glu Ala Met Asn Glu Met Asn Asp Glu Leu Gln Glu Asn Ala Arg Glu
465                 470                 475                 480
Thr Glu Leu Glu Leu Arg Glu Gln Leu Asp Met Ala Gly Ala Arg Val
                485                 490                 495
Arg Glu Ala Gln Lys Arg Val Glu Ala Ala Gln Glu Thr Val Ala Asp
            500                 505                 510
Tyr Gln Gln Thr Ile Lys Lys Tyr Arg Gln Leu Thr Ala His Leu Gln
        515                 520                 525
Asp Val Asn Arg Glu Leu Thr Asn Gln Gln Glu Ala Ser Val Glu Arg
530                 535                 540
Gln Gln Gln Pro Pro Glu Thr Phe Asp Phe Lys Ile Lys Phe Ala
545                 550                 555                 560
Glu Thr Lys Ala His Ala Lys Ala Ile Glu Met Glu Leu Arg Gln Met
                565                 570                 575
Glu Val Ala Gln Ala Asn Arg His Met Ser Leu Leu Thr Ala Phe Met
            580                 585                 590
Pro Asp Ser Phe Leu Arg Pro Gly Gly Asp His Asp Cys Val Leu Val
        595                 600                 605
Leu Leu Leu Met Pro Arg Leu Ile Cys Lys Ala Glu Leu Ile Arg Lys
    610                 615                 620
Gln Ala Gln Glu Lys Phe Glu Leu Ser Glu Asn Cys Ser Glu Arg Pro
625                 630                 635                 640
Gly Leu Arg Gly Ala Ala Gly Glu Gln Leu Ser Phe Ala Ala Gly Leu
                645                 650                 655
Val Tyr Ser Leu Ser Leu Leu Gln Ala Thr Leu His Arg Tyr Glu His
            660                 665                 670
Ala Leu Ser Gln Cys Ser Val Asp Val Tyr Lys Lys Val Gly Ser Leu
        675                 680                 685
Tyr Pro Glu Met Ser Ala His Glu Arg Ser Leu Asp Phe Leu Ile Glu
    690                 695                 700
Leu Leu His Lys Asp Gln Leu Asp Glu Thr Val Asn Val Glu Pro Leu
705                 710                 715                 720
Thr Lys Ala Ile Lys Tyr Tyr Gln His Leu Tyr Ser Ile His Leu Ala
                725                 730                 735
Glu Gln Pro Glu Asp Cys Thr Met Gln Leu Ala Asp His Ile Lys Phe
            740                 745                 750
Thr Gln Ser Ala Leu Asp Cys Met Ser Val Glu Val Gly Arg Leu Arg
        755                 760                 765
Ala Phe Leu Gln Gly Gly Gln Glu Ala Thr Asp Ile Ala Leu Leu Leu
    770                 775                 780
Arg Asp Leu Glu Thr Ser Cys Ser Asp Ile Arg Gln Phe Cys Lys Lys
```

-continued

```
                785              790               795               800
        Ile Arg Arg Arg Met Pro Gly Thr Asp Ala Pro Gly Ile Pro Ala Ala
                        805              810              815

Leu Ala Phe Gly Pro Gln Val Ser Asp Thr Leu Leu Asp Cys Arg Lys
                        820              825              830

His Leu Thr Trp Val Ala Val Leu Gln Glu Val Ala Ala Ala
                        835              840              845

Ala Gln Leu Ile Ala Pro Leu Ala Glu Asn Glu Gly Leu Leu Val Ala
            850              855              860

Ala Leu Glu Glu Leu Ala Phe Lys Ala Ser Glu Gln Ile Tyr Gly Thr
        865              870              875              880

Pro Ser Ser Ser Pro Tyr Glu Cys Leu Arg Gln Ser Cys Asn Ile Leu
                        885              890              895

Ile Ser Thr Met Asn Lys Leu Ala Thr Ala Met Gln Glu Gly Glu Tyr
                        900              905              910

Asp Ala Glu Arg Pro Pro Ser Lys Pro Pro Val Glu Leu Arg Ala
                    915              920              925

Ala Ala Leu Arg Ala Glu Ile Thr Asp Ala Glu Gly Leu Gly Leu Lys
            930              935              940

Leu Glu Asp Arg Glu Thr Val Ile Lys Glu Leu Lys Lys Ser Leu Lys
        945              950              955              960

Ile Lys Gly Glu Glu Leu Ser Glu Ala Asn Val Arg Leu Ser Leu Leu
                    965              970              975

Glu Lys Lys Leu Asp Ser Ala Ala Lys Asp Ala Asp Glu Arg Ile Glu
                    980              985              990

Lys Val Gln Thr Arg Leu Glu Glu  Thr Gln Ala Leu Leu  Arg Lys Lys
                995              1000              1005

Glu Lys  Glu Phe Glu Glu  Thr Met Asp Ala Leu Gln  Ala Asp Ile
            1010              1015              1020

Asp Gln  Leu Glu Ala Glu  Lys Ala Glu Leu Lys Gln  Arg Leu Asn
            1025              1030              1035

Ser Gln  Ser Lys Arg Thr  Ile Glu Gly Leu Arg Gly  Pro Pro Pro
            1040              1045              1050

Ser Gly  Ile Ala Thr Leu Val  Ser Gly Ile Ala Gly  Glu Glu Gln
            1055              1060              1065

Gln Arg  Gly Ala Ile Pro Gly  Gln Ala Pro Gly Ser  Val Pro Gly
            1070              1075              1080

Pro Gly  Leu Val Lys Asp Ser  Pro Leu Leu Leu Gln  Gln Ile Ser
            1085              1090              1095

Ala Met  Arg Leu His Ile Ser  Gln Leu Gln His Glu  Asn Ser Ile
            1100              1105              1110

Leu Lys  Gly Ala Gln Met Lys  Ala Ser Leu Ala Ser  Leu Pro Pro
            1115              1120              1125

Leu His  Val Ala Lys Leu Ser  His Glu Gly Pro Gly  Ser Glu Leu
            1130              1135              1140

Pro Ala  Gly Ala Leu Tyr Arg  Lys Thr Ser Gln Leu  Leu Glu Thr
            1145              1150              1155

Leu Asn  Gln Leu Ser Thr His  Thr His Val Val Asp  Ile Thr Arg
            1160              1165              1170

Thr Ser  Pro Ala Ala Lys Ser  Pro Ser Ala Gln Leu  Met Glu Gln
            1175              1180              1185

Val Ala  Gln Leu Lys Ser Leu  Ser Asp Thr Val Glu  Lys Leu Lys
            1190              1195              1200
```

Asp Glu Val Leu Lys Glu Thr Val Ser Gln Arg Pro Gly Ala Thr
1205                1210                1215

Val Pro Thr Asp Phe Ala Thr Phe Pro Ser Ser Ala Phe Leu Arg
1220                1225                1230

Ala Lys Glu Glu Gln Gln Asp Asp Thr Val Tyr Met Gly Lys Val
1235                1240                1245

Thr Phe Ser Cys Ala Ala Gly Phe Gly Gln Arg His Arg Leu Val
1250                1255                1260

Leu Thr Gln Glu Gln Leu His Gln Leu His Ser Arg Leu Ile Ser
1265                1270                1275

<210> SEQ ID NO 26
<211> LENGTH: 1144
<212> TYPE: PRT
<213> ORGANISM: Homo sapiens

<400> SEQUENCE: 26

Met Met Arg Gln Ala Pro Thr Ala Arg Lys Thr Thr Thr Arg Arg Pro
1               5                   10                  15

Lys Pro Thr Arg Pro Ala Ser Thr Gly Val Ala Gly Ala Ser Ser Ser
                20                  25                  30

Leu Gly Pro Ser Gly Ser Ala Ser Ala Gly Glu Leu Ser Ser Ser Glu
            35                  40                  45

Pro Ser Thr Pro Ala Gln Thr Pro Leu Ala Ala Pro Ile Ile Pro Thr
        50                  55                  60

Pro Val Leu Thr Ser Pro Gly Ala Val Pro Pro Leu Pro Ser Pro Ser
65                  70                  75                  80

Lys Glu Glu Gly Leu Arg Ala Gln Val Arg Asp Leu Glu Glu Lys
                85                  90                  95

Leu Glu Thr Leu Arg Leu Lys Arg Ala Glu Asp Lys Ala Lys Leu Lys
            100                 105                 110

Glu Leu Glu Lys His Lys Ile Gln Leu Glu Gln Val Gln Glu Trp Lys
        115                 120                 125

Ser Lys Met Gln Glu Gln Gln Ala Asp Leu Gln Arg Arg Leu Lys Glu
    130                 135                 140

Ala Arg Lys Glu Ala Lys Glu Ala Leu Glu Ala Lys Glu Arg Tyr Met
145                 150                 155                 160

Glu Glu Met Ala Asp Thr Ala Asp Ala Ile Glu Met Ala Thr Leu Asp
                165                 170                 175

Lys Glu Met Ala Glu Glu Arg Ala Glu Ser Leu Gln Gln Glu Val Glu
            180                 185                 190

Ala Leu Lys Glu Arg Val Asp Glu Leu Thr Thr Asp Leu Glu Ile Leu
        195                 200                 205

Lys Ala Glu Ile Glu Glu Lys Gly Ser Asp Gly Ala Ala Ser Ser Tyr
    210                 215                 220

Gln Leu Lys Gln Leu Glu Glu Gln Asn Ala Arg Leu Lys Asp Ala Leu
225                 230                 235                 240

Val Arg Met Arg Asp Leu Ser Ser Ser Glu Lys Gln Glu His Val Lys
                245                 250                 255

Leu Gln Lys Leu Met Glu Lys Lys Asn Gln Glu Leu Glu Val Val Arg
            260                 265                 270

Gln Gln Arg Glu Arg Leu Gln Glu Glu Leu Ser Gln Ala Glu Ser Thr
        275                 280                 285

Ile Asp Glu Leu Lys Glu Gln Val Asp Ala Ala Leu Gly Ala Glu Glu

```
                    290                 295                 300
Met Val Glu Met Leu Thr Asp Arg Asn Leu Asn Leu Glu Glu Lys Val
305                 310                 315                 320

Arg Glu Leu Arg Glu Thr Val Gly Asp Leu Glu Ala Met Asn Glu Met
                    325                 330                 335

Asn Asp Glu Leu Gln Glu Asn Ala Arg Glu Thr Glu Leu Glu Leu Arg
                340                 345                 350

Glu Gln Leu Asp Met Ala Gly Ala Arg Val Arg Glu Ala Gln Lys Arg
            355                 360                 365

Val Glu Ala Ala Gln Glu Thr Val Ala Asp Tyr Gln Gln Thr Ile Lys
370                 375                 380

Lys Tyr Arg Gln Leu Thr Ala His Leu Gln Asp Val Asn Arg Glu Leu
385                 390                 395                 400

Thr Asn Gln Gln Glu Ala Ser Val Glu Arg Gln Gln Pro Pro Pro
                405                 410                 415

Glu Thr Phe Asp Phe Lys Ile Lys Phe Ala Glu Thr Lys Ala His Ala
                420                 425                 430

Lys Ala Ile Glu Met Glu Leu Arg Gln Met Glu Val Ala Gln Ala Asn
                435                 440                 445

Arg His Met Ser Leu Leu Thr Ala Phe Met Pro Asp Ser Phe Leu Arg
            450                 455                 460

Pro Gly Gly Asp His Asp Cys Val Leu Val Leu Leu Met Pro Arg
465                 470                 475                 480

Leu Ile Cys Lys Ala Glu Leu Ile Arg Lys Gln Ala Gln Glu Lys Phe
                485                 490                 495

Glu Leu Ser Glu Asn Cys Ser Glu Arg Pro Gly Leu Arg Gly Ala Ala
                500                 505                 510

Gly Glu Gln Leu Ser Phe Ala Ala Gly Leu Val Tyr Ser Leu Ser Leu
            515                 520                 525

Leu Gln Ala Thr Leu His Arg Tyr Glu His Ala Leu Ser Gln Cys Ser
    530                 535                 540

Val Asp Val Tyr Lys Lys Val Gly Ser Leu Tyr Pro Glu Met Ser Ala
545                 550                 555                 560

His Glu Arg Ser Leu Asp Phe Leu Ile Glu Leu Leu His Lys Asp Gln
                565                 570                 575

Leu Asp Glu Thr Val Asn Val Glu Pro Leu Thr Lys Ala Ile Lys Tyr
                580                 585                 590

Tyr Gln His Leu Tyr Ser Ile His Leu Ala Glu Gln Pro Glu Asp Cys
            595                 600                 605

Thr Met Gln Leu Ala Asp His Ile Lys Phe Thr Gln Ser Ala Leu Asp
610                 615                 620

Cys Met Ser Val Glu Val Gly Arg Leu Arg Ala Phe Leu Gln Gly Gly
625                 630                 635                 640

Gln Glu Ala Thr Asp Ile Ala Leu Leu Leu Arg Asp Leu Glu Thr Ser
                645                 650                 655

Cys Ser Asp Ile Arg Gln Phe Cys Lys Lys Ile Arg Arg Arg Met Pro
                660                 665                 670

Gly Thr Asp Ala Pro Gly Ile Pro Ala Ala Leu Ala Phe Gly Pro Gln
            675                 680                 685

Val Ser Asp Thr Leu Leu Asp Cys Arg Lys His Leu Thr Trp Val Val
        690                 695                 700

Ala Val Leu Gln Glu Val Ala Ala Ala Ala Gln Leu Ile Ala Pro
705                 710                 715                 720
```

```
Leu Ala Glu Asn Glu Gly Leu Val Ala Leu Glu Glu Leu Ala
            725                 730                 735

Phe Lys Ala Ser Glu Gln Ile Tyr Gly Thr Pro Ser Ser Pro Tyr
            740                 745                 750

Glu Cys Leu Arg Gln Ser Cys Asn Ile Leu Ile Ser Thr Met Asn Lys
            755                 760                 765

Leu Ala Thr Ala Met Gln Glu Gly Tyr Asp Ala Glu Arg Pro Pro
770             775                 780

Ser Lys Pro Pro Val Glu Leu Arg Ala Ala Leu Arg Ala Glu
785             790                 795                 800

Ile Thr Asp Ala Glu Gly Leu Gly Leu Lys Leu Glu Asp Arg Glu Thr
                805                 810                 815

Val Ile Lys Glu Leu Lys Lys Ser Leu Lys Ile Lys Gly Glu Glu Leu
                820                 825                 830

Ser Glu Ala Asn Val Arg Leu Ser Leu Leu Glu Lys Lys Leu Asp Ser
                835                 840                 845

Ala Ala Lys Asp Ala Asp Glu Arg Ile Glu Lys Val Gln Thr Arg Leu
                850                 855                 860

Glu Glu Thr Gln Ala Leu Leu Arg Lys Lys Glu Lys Glu Phe Glu Glu
865                 870                 875                 880

Thr Met Asp Ala Leu Gln Ala Asp Ile Asp Gln Leu Glu Ala Glu Lys
                885                 890                 895

Ala Glu Leu Lys Gln Arg Leu Asn Ser Gln Ser Lys Arg Thr Ile Glu
                900                 905                 910

Gly Leu Arg Gly Pro Pro Ser Gly Ile Ala Thr Leu Val Ser Gly
                915                 920                 925

Ile Ala Gly Glu Glu Gln Gln Arg Gly Ala Ile Pro Gly Gln Ala Pro
930                 935                 940

Gly Ser Val Pro Gly Pro Gly Leu Val Lys Asp Ser Pro Leu Leu Leu
945                 950                 955                 960

Gln Gln Ile Ser Ala Met Arg Leu His Ile Ser Gln Leu His Glu
                965                 970                 975

Asn Ser Ile Leu Lys Gly Ala Gln Met Lys Ala Ser Leu Ala Ser Leu
                980                 985                 990

Pro Pro Leu His Val Ala Lys Leu Ser His Glu Gly Pro Gly Ser Glu
                995                1000                1005

Leu Pro Ala Gly Ala Leu Tyr Arg Lys Thr Ser Gln Leu Leu Glu
    1010                1015                1020

Thr Leu Asn Gln Leu Ser Thr His Thr His Val Val Asp Ile Thr
    1025                1030                1035

Arg Thr Ser Pro Ala Ala Lys Ser Pro Ser Ala Gln Leu Met Glu
    1040                1045                1050

Gln Val Ala Gln Leu Lys Ser Leu Ser Asp Thr Val Glu Lys Leu
    1055                1060                1065

Lys Asp Glu Val Leu Lys Glu Thr Val Ser Gln Arg Pro Gly Ala
    1070                1075                1080

Thr Val Pro Thr Asp Phe Ala Thr Phe Pro Ser Ser Ala Phe Leu
    1085                1090                1095

Arg Ala Lys Glu Glu Gln Gln Asp Asp Thr Val Tyr Met Gly Lys
    1100                1105                1110

Val Thr Phe Ser Cys Ala Ala Gly Phe Gly Gln Arg His Arg Leu
    1115                1120                1125
```

```
Val Leu Thr Gln Glu Gln Leu His Gln Leu His Ser Arg Leu Ile
    1130                1135                1140

Ser

<210> SEQ ID NO 27
<211> LENGTH: 1253
<212> TYPE: PRT
<213> ORGANISM: Homo sapiens

<400> SEQUENCE: 27

Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65              70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Ala Lys Thr
        115                 120                 125

Ser Lys Leu Pro Thr Arg Pro Ala Ser Thr Gly Val Ala Gly Ala Ser
    130                 135                 140

Ser Ser Leu Gly Pro Ser Gly Ser Ala Ser Ala Gly Glu Leu Ser Ser
145                 150                 155                 160

Ser Glu Pro Ser Thr Pro Ala Gln Thr Pro Leu Ala Ala Pro Ile Ile
                165                 170                 175

Pro Thr Pro Val Leu Thr Ser Pro Gly Ala Val Pro Pro Leu Pro Ser
            180                 185                 190

Pro Ser Lys Glu Glu Gly Leu Arg Ala Gln Val Arg Asp Leu Glu
        195                 200                 205

Glu Lys Leu Glu Thr Leu Arg Leu Lys Arg Ala Glu Asp Lys Ala Lys
    210                 215                 220

Leu Lys Glu Leu Glu Lys His Lys Ile Gln Leu Glu Gln Val Gln Glu
225                 230                 235                 240

Trp Lys Ser Lys Met Gln Glu Gln Gln Ala Asp Leu Gln Arg Arg Leu
                245                 250                 255

Lys Glu Ala Arg Lys Glu Ala Lys Glu Ala Leu Glu Ala Lys Glu Arg
            260                 265                 270

Tyr Met Glu Glu Met Ala Asp Thr Ala Asp Ala Ile Glu Met Ala Thr
        275                 280                 285

Leu Asp Lys Glu Met Ala Glu Glu Arg Ala Glu Ser Leu Gln Gln Glu
    290                 295                 300

Val Glu Ala Leu Lys Glu Arg Val Asp Glu Leu Thr Thr Asp Leu Glu
305                 310                 315                 320

Ile Leu Lys Ala Glu Ile Glu Glu Lys Gly Ser Asp Gly Ala Ala Ser
                325                 330                 335

Ser Tyr Gln Leu Lys Gln Leu Glu Glu Gln Asn Ala Arg Leu Lys Asp
            340                 345                 350
```

```
Ala Leu Val Arg Met Arg Asp Leu Ser Ser Glu Lys Gln Glu His
            355                 360                 365

Val Lys Leu Gln Lys Leu Met Glu Lys Asn Gln Glu Leu Glu Val
    370                 375                 380

Val Arg Gln Gln Arg Glu Arg Leu Gln Glu Glu Leu Ser Gln Ala Glu
385                 390                 395                 400

Ser Thr Ile Asp Glu Leu Lys Glu Gln Val Asp Ala Ala Leu Gly Ala
                405                 410                 415

Glu Glu Met Val Glu Met Leu Thr Asp Arg Asn Leu Asn Leu Glu Glu
            420                 425                 430

Lys Val Arg Glu Leu Arg Glu Thr Val Gly Asp Leu Glu Ala Met Asn
    435                 440                 445

Glu Met Asn Asp Glu Leu Gln Glu Asn Ala Arg Glu Thr Glu Leu Glu
450                 455                 460

Leu Arg Glu Gln Leu Asp Met Ala Gly Ala Arg Val Arg Glu Ala Gln
465                 470                 475                 480

Lys Arg Val Glu Ala Ala Gln Glu Thr Val Ala Asp Tyr Gln Gln Thr
                485                 490                 495

Ile Lys Lys Tyr Arg Gln Leu Thr Ala His Leu Gln Asp Val Asn Arg
            500                 505                 510

Glu Leu Thr Asn Gln Gln Glu Ala Ser Val Glu Arg Gln Gln Gln Pro
    515                 520                 525

Pro Pro Glu Thr Phe Asp Phe Lys Ile Lys Phe Ala Glu Thr Lys Ala
        530                 535                 540

His Ala Lys Ala Ile Glu Met Glu Leu Arg Gln Met Glu Val Ala Gln
545                 550                 555                 560

Ala Asn Arg His Met Ser Leu Leu Thr Ala Phe Met Pro Asp Ser Phe
                565                 570                 575

Leu Arg Pro Gly Gly Asp His Asp Cys Val Leu Val Leu Leu Leu Met
            580                 585                 590

Pro Arg Leu Ile Cys Lys Ala Glu Leu Ile Arg Lys Gln Ala Gln Glu
    595                 600                 605

Lys Phe Glu Leu Ser Glu Asn Cys Ser Glu Arg Pro Gly Leu Arg Gly
610                 615                 620

Ala Ala Gly Glu Gln Leu Ser Phe Ala Ala Gly Leu Val Tyr Ser Leu
625                 630                 635                 640

Ser Leu Leu Gln Ala Thr Leu His Arg Tyr Glu His Ala Leu Ser Gln
                645                 650                 655

Cys Ser Val Asp Val Tyr Lys Lys Val Gly Ser Leu Tyr Pro Glu Met
            660                 665                 670

Ser Ala His Glu Arg Ser Leu Asp Phe Leu Ile Glu Leu Leu His Lys
    675                 680                 685

Asp Gln Leu Asp Glu Thr Val Asn Val Glu Pro Leu Thr Lys Ala Ile
690                 695                 700

Lys Tyr Tyr Gln His Leu Tyr Ser Ile His Leu Ala Glu Gln Pro Glu
705                 710                 715                 720

Asp Cys Thr Met Gln Leu Ala Asp His Ile Lys Phe Thr Gln Ser Ala
                725                 730                 735

Leu Asp Cys Met Ser Val Glu Val Gly Arg Leu Arg Ala Phe Leu Gln
            740                 745                 750

Gly Gly Gln Glu Ala Thr Asp Ile Ala Leu Leu Leu Arg Asp Leu Glu
    755                 760                 765

Thr Ser Cys Ser Asp Ile Arg Gln Phe Cys Lys Lys Ile Arg Arg Arg
```

-continued

```
            770             775             780
Met Pro Gly Thr Asp Ala Pro Gly Ile Pro Ala Ala Leu Ala Phe Gly
785                 790             795                 800

Pro Gln Val Ser Asp Thr Leu Leu Asp Cys Arg Lys His Leu Thr Trp
            805             810             815

Val Val Ala Val Leu Gln Glu Val Ala Ala Ala Ala Gln Leu Ile
                820             825             830

Ala Pro Leu Ala Glu Asn Glu Gly Leu Leu Val Ala Leu Glu Glu
            835             840             845

Leu Ala Phe Lys Ala Ser Glu Gln Ile Tyr Gly Thr Pro Ser Ser Ser
        850             855             860

Pro Tyr Glu Cys Leu Arg Gln Ser Cys Asn Ile Leu Ile Ser Thr Met
865             870             875             880

Asn Lys Leu Ala Thr Ala Met Gln Glu Gly Tyr Asp Ala Glu Arg
                885             890             895

Pro Pro Ser Lys Pro Pro Val Glu Leu Arg Ala Ala Ala Leu Arg
                900             905             910

Ala Glu Ile Thr Asp Ala Glu Gly Leu Gly Leu Lys Leu Glu Asp Arg
            915             920             925

Glu Thr Val Ile Lys Glu Leu Lys Lys Ser Leu Lys Ile Lys Gly Glu
930             935             940

Glu Leu Ser Glu Ala Asn Val Arg Leu Ser Leu Leu Glu Lys Lys Leu
945             950             955             960

Asp Ser Ala Ala Lys Asp Ala Asp Glu Arg Ile Glu Lys Val Gln Thr
                965             970             975

Arg Leu Glu Glu Thr Gln Ala Leu Leu Arg Lys Lys Glu Lys Glu Phe
            980             985             990

Glu Glu Thr Met Asp Ala Leu Gln Ala Asp Ile Asp Gln Leu Glu Ala
                995             1000            1005

Glu Lys Ala Glu Leu Lys Gln Arg Leu Asn Ser Gln Ser Lys Arg
        1010            1015            1020

Thr Ile Glu Gly Leu Arg Gly Pro Pro Ser Gly Ile Ala Thr
        1025            1030            1035

Leu Val Ser Gly Ile Ala Gly Gly Ala Ile Pro Gly Gln Ala Pro
        1040            1045            1050

Gly Ser Val Pro Gly Pro Gly Leu Val Lys Asp Ser Pro Leu Leu
        1055            1060            1065

Leu Gln Gln Ile Ser Ala Met Arg Leu His Ile Ser Gln Leu Gln
        1070            1075            1080

His Glu Asn Ser Ile Leu Lys Gly Ala Gln Met Lys Ala Ser Leu
        1085            1090            1095

Ala Ser Leu Pro Pro Leu His Val Ala Lys Leu Ser His Glu Gly
        1100            1105            1110

Pro Gly Ser Glu Leu Pro Ala Gly Ala Leu Tyr Arg Lys Thr Ser
        1115            1120            1125

Gln Leu Leu Glu Thr Leu Asn Gln Leu Ser Thr His Thr His Val
        1130            1135            1140

Val Asp Ile Thr Arg Thr Ser Pro Ala Ala Lys Ser Pro Ser Ala
        1145            1150            1155

Gln Leu Met Glu Gln Val Ala Gln Leu Lys Ser Leu Ser Asp Thr
        1160            1165            1170

Val Glu Lys Leu Lys Asp Glu Val Leu Lys Glu Thr Val Ser Gln
        1175            1180            1185
```

```
Arg Pro Gly Ala Thr Val Pro Thr Asp Phe Ala Thr Phe Pro Ser
    1190                1195                1200

Ser Ala Phe Leu Arg Ala Lys Glu Glu Gln Gln Asp Asp Thr Val
    1205                1210                1215

Tyr Met Gly Lys Val Thr Phe Ser Cys Ala Ala Gly Phe Gly Gln
    1220                1225                1230

Arg His Arg Leu Val Leu Thr Gln Glu Gln Leu His Gln Leu His
    1235                1240                1245

Ser Arg Leu Ile Ser
    1250

<210> SEQ ID NO 28
<211> LENGTH: 1139
<212> TYPE: PRT
<213> ORGANISM: Homo sapiens

<400> SEQUENCE: 28

Met Met Arg Gln Ala Pro Thr Ala Arg Lys Thr Thr Thr Arg Arg Pro
1               5                   10                  15

Lys Pro Thr Arg Pro Ala Ser Thr Gly Val Ala Gly Ala Ser Ser Ser
                20                  25                  30

Leu Gly Pro Ser Gly Ser Ala Ser Ala Gly Glu Leu Ser Ser Ser Glu
            35                  40                  45

Pro Ser Thr Pro Ala Gln Thr Pro Leu Ala Ala Pro Ile Ile Pro Thr
        50                  55                  60

Pro Val Leu Thr Ser Pro Gly Ala Val Pro Pro Leu Pro Ser Pro Ser
65                  70                  75                  80

Lys Glu Glu Gly Leu Arg Ala Gln Val Arg Asp Leu Glu Glu Lys
                85                  90                  95

Leu Glu Thr Leu Arg Leu Lys Arg Ala Glu Asp Lys Ala Lys Leu Lys
                100                 105                 110

Glu Leu Glu Lys His Lys Ile Gln Leu Glu Gln Val Gln Glu Trp Lys
            115                 120                 125

Ser Lys Met Gln Glu Gln Gln Ala Asp Leu Gln Arg Arg Leu Lys Glu
        130                 135                 140

Ala Arg Lys Glu Ala Lys Glu Ala Leu Glu Ala Lys Glu Arg Tyr Met
145                 150                 155                 160

Glu Glu Met Ala Asp Thr Ala Asp Ala Ile Glu Met Ala Thr Leu Asp
                165                 170                 175

Lys Glu Met Ala Glu Glu Arg Ala Glu Ser Leu Gln Gln Glu Val Glu
                180                 185                 190

Ala Leu Lys Glu Arg Val Asp Glu Leu Thr Thr Asp Leu Glu Ile Leu
            195                 200                 205

Lys Ala Glu Ile Glu Glu Lys Gly Ser Asp Gly Ala Ala Ser Ser Tyr
        210                 215                 220

Gln Leu Lys Gln Leu Glu Glu Gln Asn Ala Arg Leu Lys Asp Ala Leu
225                 230                 235                 240

Val Arg Met Arg Asp Leu Ser Ser Ser Glu Lys Gln Glu His Val Lys
                245                 250                 255

Leu Gln Lys Leu Met Glu Lys Lys Asn Gln Glu Leu Glu Val Val Arg
                260                 265                 270

Gln Gln Arg Glu Arg Leu Gln Glu Glu Leu Ser Gln Ala Glu Ser Thr
            275                 280                 285

Ile Asp Glu Leu Lys Glu Gln Val Asp Ala Ala Leu Gly Ala Glu Glu
```

-continued

```
            290                 295                 300
Met Val Glu Met Leu Thr Asp Arg Asn Leu Asn Leu Glu Glu Lys Val
305                 310                 315                 320

Arg Glu Leu Arg Glu Thr Val Gly Asp Leu Glu Ala Met Asn Glu Met
                325                 330                 335

Asn Asp Glu Leu Gln Glu Asn Ala Arg Glu Thr Glu Leu Glu Leu Arg
                340                 345                 350

Glu Gln Leu Asp Met Ala Gly Ala Arg Val Arg Glu Ala Gln Lys Arg
                355                 360                 365

Val Glu Ala Ala Gln Glu Thr Val Ala Asp Tyr Gln Gln Thr Ile Lys
370                 375                 380

Lys Tyr Arg Gln Leu Thr Ala His Leu Gln Asp Val Asn Arg Glu Leu
385                 390                 395                 400

Thr Asn Gln Gln Glu Ala Ser Val Glu Arg Gln Gln Pro Pro Pro
                405                 410                 415

Glu Thr Phe Asp Phe Lys Ile Lys Phe Ala Glu Thr Lys Ala His Ala
                420                 425                 430

Lys Ala Ile Glu Met Glu Leu Arg Gln Met Glu Val Ala Gln Ala Asn
                435                 440                 445

Arg His Met Ser Leu Leu Thr Ala Phe Met Pro Asp Ser Phe Leu Arg
450                 455                 460

Pro Gly Gly Asp His Asp Cys Val Leu Val Leu Leu Met Pro Arg
465                 470                 475                 480

Leu Ile Cys Lys Ala Glu Leu Ile Arg Lys Gln Ala Gln Glu Lys Phe
                485                 490                 495

Glu Leu Ser Glu Asn Cys Ser Glu Arg Pro Gly Leu Arg Gly Ala Ala
                500                 505                 510

Gly Glu Gln Leu Ser Phe Ala Ala Gly Leu Val Tyr Ser Leu Ser Leu
                515                 520                 525

Leu Gln Ala Thr Leu His Arg Tyr Glu His Ala Leu Ser Gln Cys Ser
                530                 535                 540

Val Asp Val Tyr Lys Lys Val Gly Ser Leu Tyr Pro Glu Met Ser Ala
545                 550                 555                 560

His Glu Arg Ser Leu Asp Phe Leu Ile Glu Leu Leu His Lys Asp Gln
                565                 570                 575

Leu Asp Glu Thr Val Asn Val Glu Pro Leu Thr Lys Ala Ile Lys Tyr
                580                 585                 590

Tyr Gln His Leu Tyr Ser Ile His Leu Ala Glu Gln Pro Glu Asp Cys
                595                 600                 605

Thr Met Gln Leu Ala Asp His Ile Lys Phe Thr Gln Ser Ala Leu Asp
610                 615                 620

Cys Met Ser Val Glu Val Gly Arg Leu Arg Ala Phe Leu Gln Gly Gly
625                 630                 635                 640

Gln Glu Ala Thr Asp Ile Ala Leu Leu Leu Arg Asp Leu Glu Thr Ser
                645                 650                 655

Cys Ser Asp Ile Arg Gln Phe Cys Lys Lys Ile Arg Arg Met Pro
                660                 665                 670

Gly Thr Asp Ala Pro Gly Ile Pro Ala Ala Leu Ala Phe Gly Pro Gln
                675                 680                 685

Val Ser Asp Thr Leu Leu Asp Cys Arg Lys His Leu Thr Trp Val Val
                690                 695                 700

Ala Val Leu Gln Glu Val Ala Ala Ala Ala Gln Leu Ile Ala Pro
705                 710                 715                 720
```

```
Leu Ala Glu Asn Glu Gly Leu Val Ala Leu Glu Glu Leu Ala
            725                 730                 735

Phe Lys Ala Ser Glu Gln Ile Tyr Gly Thr Pro Ser Ser Pro Tyr
            740                 745                 750

Glu Cys Leu Arg Gln Ser Cys Asn Ile Leu Ile Ser Thr Met Asn Lys
            755                 760                 765

Leu Ala Thr Ala Met Gln Glu Gly Tyr Asp Ala Glu Arg Pro Pro
770                 775                 780

Ser Lys Pro Pro Val Glu Leu Arg Ala Ala Leu Arg Ala Glu
785                 790                 795                 800

Ile Thr Asp Ala Glu Gly Leu Gly Leu Lys Leu Glu Asp Arg Glu Thr
                    805                 810                 815

Val Ile Lys Glu Leu Lys Lys Ser Leu Lys Ile Lys Gly Glu Glu Leu
                    820                 825                 830

Ser Glu Ala Asn Val Arg Leu Ser Leu Leu Glu Lys Lys Leu Asp Ser
                    835                 840                 845

Ala Ala Lys Asp Ala Asp Glu Arg Ile Glu Lys Val Gln Thr Arg Leu
                    850                 855                 860

Glu Glu Thr Gln Ala Leu Leu Arg Lys Lys Glu Lys Glu Phe Glu Glu
865                 870                 875                 880

Thr Met Asp Ala Leu Gln Ala Asp Ile Asp Gln Leu Glu Ala Glu Lys
                    885                 890                 895

Ala Glu Leu Lys Gln Arg Leu Asn Ser Gln Ser Lys Arg Thr Ile Glu
                    900                 905                 910

Gly Leu Arg Gly Pro Pro Pro Ser Gly Ile Ala Thr Leu Val Ser Gly
                    915                 920                 925

Ile Ala Gly Gly Ala Ile Pro Gly Gln Ala Pro Gly Ser Val Pro Gly
                    930                 935                 940

Pro Gly Leu Val Lys Asp Ser Pro Leu Leu Leu Gln Gln Ile Ser Ala
945                 950                 955                 960

Met Arg Leu His Ile Ser Gln Leu Gln His Glu Asn Ser Ile Leu Lys
                    965                 970                 975

Gly Ala Gln Met Lys Ala Ser Leu Ala Ser Leu Pro Pro Leu His Val
                    980                 985                 990

Ala Lys Leu Ser His Glu Gly Pro Gly Ser Glu Leu Pro Ala Gly Ala
                    995                 1000                1005

Leu Tyr Arg Lys Thr Ser Gln Leu Leu Glu Thr Leu Asn Gln Leu
        1010                1015                1020

Ser Thr His Thr His Val Val Asp Ile Thr Arg Thr Ser Pro Ala
        1025                1030                1035

Ala Lys Ser Pro Ser Ala Gln Leu Met Glu Gln Val Ala Gln Leu
        1040                1045                1050

Lys Ser Leu Ser Asp Thr Val Glu Lys Leu Lys Asp Glu Val Leu
        1055                1060                1065

Lys Glu Thr Val Ser Gln Arg Pro Gly Ala Thr Val Pro Thr Asp
        1070                1075                1080

Phe Ala Thr Phe Pro Ser Ser Ala Phe Leu Arg Ala Lys Glu Glu
        1085                1090                1095

Gln Gln Asp Asp Thr Val Tyr Met Gly Lys Val Thr Phe Ser Cys
        1100                1105                1110

Ala Ala Gly Phe Gly Gln Arg His Arg Leu Val Leu Thr Gln Glu
        1115                1120                1125
```

```
Gln Leu His Gln Leu His Ser Arg Leu Ile Ser
    1130                1135

<210> SEQ ID NO 29
<211> LENGTH: 1236
<212> TYPE: PRT
<213> ORGANISM: Homo sapiens

<400> SEQUENCE: 29

Met Ser Ala Glu Ala Ser Ala Arg Pro Leu Arg Val Gly Ser Arg Val
1               5                   10                  15

Glu Val Ile Gly Lys Gly His Arg Gly Thr Val Ala Tyr Val Gly Ala
            20                  25                  30

Thr Leu Phe Ala Thr Gly Lys Trp Val Gly Val Ile Leu Asp Glu Ala
            35                  40                  45

Lys Gly Lys Asn Asp Gly Thr Val Gln Gly Arg Lys Tyr Phe Thr Cys
50                  55                  60

Asp Glu Gly His Gly Ile Phe Val Arg Gln Ser Gln Ile Gln Val Phe
65                  70                  75                  80

Glu Asp Gly Ala Asp Thr Thr Ser Pro Glu Thr Pro Asp Ser Ser Ala
            85                  90                  95

Ser Lys Val Leu Lys Arg Glu Gly Thr Asp Thr Thr Ala Lys Thr Ser
            100                 105                 110

Lys Leu Pro Thr Arg Pro Ala Ser Thr Gly Val Ala Gly Ala Ser Ser
            115                 120                 125

Ser Leu Gly Pro Ser Gly Ser Ala Ser Ala Gly Glu Leu Ser Ser Ser
        130                 135                 140

Glu Pro Ser Thr Pro Ala Gln Thr Pro Leu Ala Ala Pro Ile Ile Pro
145                 150                 155                 160

Thr Pro Val Leu Thr Ser Pro Gly Ala Val Pro Pro Leu Pro Ser Pro
                165                 170                 175

Ser Lys Glu Glu Glu Gly Leu Arg Ala Gln Val Arg Asp Leu Glu Glu
                180                 185                 190

Lys Leu Glu Thr Leu Arg Leu Lys Arg Ala Glu Asp Lys Ala Lys Leu
            195                 200                 205

Lys Glu Leu Glu Lys His Lys Ile Gln Leu Glu Gln Val Gln Glu Trp
        210                 215                 220

Lys Ser Lys Met Gln Glu Gln Gln Ala Asp Leu Gln Arg Arg Leu Lys
225                 230                 235                 240

Glu Ala Arg Lys Glu Ala Lys Glu Ala Leu Glu Ala Lys Glu Arg Tyr
                245                 250                 255

Met Glu Glu Met Ala Asp Thr Ala Asp Ala Ile Glu Met Ala Thr Leu
                260                 265                 270

Asp Lys Glu Met Ala Glu Glu Arg Ala Glu Ser Leu Gln Gln Glu Val
            275                 280                 285

Glu Ala Leu Lys Glu Arg Val Asp Glu Leu Thr Thr Asp Leu Glu Ile
        290                 295                 300

Leu Lys Ala Glu Ile Glu Glu Lys Gly Ser Asp Gly Ala Ala Ser Ser
305                 310                 315                 320

Tyr Gln Leu Lys Gln Leu Glu Glu Gln Asn Ala Arg Leu Lys Asp Ala
                325                 330                 335

Leu Val Arg Met Arg Asp Leu Ser Ser Ser Glu Lys Gln Glu His Val
                340                 345                 350

Lys Leu Gln Lys Leu Met Glu Lys Lys Asn Gln Glu Leu Glu Val Val
            355                 360                 365
```

```
Arg Gln Gln Arg Glu Arg Leu Gln Glu Glu Leu Ser Gln Ala Glu Ser
    370                 375                 380

Thr Ile Asp Glu Leu Lys Glu Gln Val Asp Ala Ala Leu Gly Ala Glu
385                 390                 395                 400

Glu Met Val Glu Met Leu Thr Asp Arg Asn Leu Asn Leu Glu Glu Lys
                405                 410                 415

Val Arg Glu Leu Arg Glu Thr Val Gly Asp Leu Glu Ala Met Asn Glu
            420                 425                 430

Met Asn Asp Glu Leu Gln Glu Asn Ala Arg Glu Thr Glu Leu Glu Leu
        435                 440                 445

Arg Glu Gln Leu Asp Met Ala Gly Ala Arg Val Arg Glu Ala Gln Lys
    450                 455                 460

Arg Val Glu Ala Ala Gln Glu Thr Val Ala Asp Tyr Gln Gln Thr Ile
465                 470                 475                 480

Lys Lys Tyr Arg Gln Leu Thr Ala His Leu Gln Asp Val Asn Arg Glu
            485                 490                 495

Leu Thr Asn Gln Gln Glu Ala Ser Val Glu Arg Gln Gln Gln Pro Pro
        500                 505                 510

Pro Glu Thr Phe Asp Phe Lys Ile Lys Phe Ala Glu Thr Lys Ala His
    515                 520                 525

Ala Lys Ala Ile Glu Met Glu Leu Arg Gln Met Glu Val Ala Gln Ala
530                 535                 540

Asn Arg His Met Ser Leu Leu Thr Ala Phe Met Pro Asp Ser Phe Leu
545                 550                 555                 560

Arg Pro Gly Gly Asp His Asp Cys Val Leu Val Leu Leu Leu Met Pro
            565                 570                 575

Arg Leu Ile Cys Lys Ala Glu Leu Ile Arg Lys Gln Ala Gln Glu Lys
        580                 585                 590

Phe Glu Leu Ser Glu Asn Cys Ser Glu Arg Pro Gly Leu Arg Gly Ala
    595                 600                 605

Ala Gly Glu Gln Leu Ser Phe Ala Ala Gly Leu Val Tyr Ser Leu Ser
610                 615                 620

Leu Leu Gln Ala Thr Leu His Arg Tyr Glu His Ala Leu Ser Gln Cys
625                 630                 635                 640

Ser Val Asp Val Tyr Lys Lys Val Gly Ser Leu Tyr Pro Glu Met Ser
            645                 650                 655

Ala His Glu Arg Ser Leu Asp Phe Leu Ile Glu Leu Leu His Lys Asp
        660                 665                 670

Gln Leu Asp Glu Thr Val Asn Val Glu Pro Leu Thr Lys Ala Ile Lys
    675                 680                 685

Tyr Tyr Gln His Leu Tyr Ser Ile His Leu Ala Glu Gln Pro Glu Asp
690                 695                 700

Cys Thr Met Gln Leu Ala Asp His Ile Lys Phe Thr Gln Ser Ala Leu
705                 710                 715                 720

Asp Cys Met Ser Val Glu Val Gly Arg Leu Arg Ala Phe Leu Gln Gly
            725                 730                 735

Gly Gln Glu Ala Thr Asp Ile Ala Leu Leu Leu Arg Asp Leu Glu Thr
        740                 745                 750

Ser Cys Ser Asp Ile Arg Gln Phe Cys Lys Lys Ile Arg Arg Arg Met
    755                 760                 765

Pro Gly Thr Asp Ala Pro Gly Ile Pro Ala Ala Leu Ala Phe Gly Pro
770                 775                 780
```

```
Gln Val Ser Asp Thr Leu Leu Asp Cys Arg Lys His Leu Thr Trp Val
785                 790                 795                 800

Val Ala Val Leu Gln Glu Val Ala Ala Ala Ala Gln Leu Ile Ala
        805                 810                 815

Pro Leu Ala Glu Asn Glu Gly Leu Leu Val Ala Ala Leu Glu Leu
        820                 825                 830

Ala Phe Lys Ala Ser Glu Gln Ile Tyr Gly Thr Pro Ser Ser Pro
        835                 840                 845

Tyr Glu Cys Leu Arg Gln Ser Cys Asn Ile Leu Ile Ser Thr Met Asn
        850                 855                 860

Lys Leu Ala Thr Ala Met Gln Glu Gly Glu Tyr Asp Ala Glu Arg Pro
865                 870                 875                 880

Pro Ser Lys Pro Pro Val Glu Leu Arg Ala Ala Leu Arg Ala
        885                 890                 895

Glu Ile Thr Asp Ala Glu Gly Leu Gly Leu Lys Leu Glu Asp Arg Glu
        900                 905                 910

Thr Val Ile Lys Glu Leu Lys Lys Ser Leu Lys Ile Lys Gly Glu Glu
        915                 920                 925

Leu Ser Glu Ala Asn Val Arg Leu Ser Leu Leu Glu Lys Lys Leu Asp
        930                 935                 940

Ser Ala Ala Lys Asp Ala Asp Glu Arg Ile Glu Lys Val Gln Thr Arg
945                 950                 955                 960

Leu Glu Glu Thr Gln Ala Leu Leu Arg Lys Lys Glu Lys Glu Phe Glu
                965                 970                 975

Glu Thr Met Asp Ala Leu Gln Ala Asp Ile Asp Gln Leu Glu Ala Glu
                980                 985                 990

Lys Ala Glu Leu Lys Gln Arg Leu  Asn Ser Gln Ser Lys  Arg Thr Ile
        995                 1000                1005

Glu Gly Leu Arg Gly Pro Pro  Pro Ser Gly Ile Ala  Thr Leu Val
        1010                1015                1020

Ser Gly Ile Ala Gly Gly Ala  Ile Pro Gly Gln Ala  Pro Gly Ser
        1025                1030                1035

Val Pro Gly Pro Gly Leu Val  Lys Asp Ser Pro Leu  Leu Leu Gln
        1040                1045                1050

Gln Ile Ser Ala Met Arg Leu  His Ile Ser Gln Leu  Gln His Glu
        1055                1060                1065

Asn Ser Ile Leu Lys Gly Ala  Gln Met Lys Ala Ser  Leu Ala Ser
        1070                1075                1080

Leu Pro Pro Leu His Val Ala  Lys Leu Ser His Glu  Gly Pro Gly
        1085                1090                1095

Ser Glu Leu Pro Ala Gly Ala  Leu Tyr Arg Lys Thr  Ser Gln Leu
        1100                1105                1110

Leu Glu Thr Leu Asn Gln Leu  Ser Thr His Thr His  Val Val Asp
        1115                1120                1125

Ile Thr Arg Thr Ser Pro Ala  Ala Lys Ser Pro Ser  Ala Gln Leu
        1130                1135                1140

Met Glu Gln Val Ala Gln Leu  Lys Ser Leu Ser Asp  Thr Val Glu
        1145                1150                1155

Lys Leu Lys Asp Glu Val Leu  Lys Glu Thr Val Ser  Gln Arg Pro
        1160                1165                1170

Gly Ala Thr Val Pro Thr Asp  Phe Ala Thr Phe Pro  Ser Ser Ala
        1175                1180                1185

Phe Leu Arg Ala Lys Glu Glu  Gln Gln Asp Asp Thr  Val Tyr Met
```

```
                    1190               1195              1200

Gly Lys Val Thr Phe Ser Cys Ala Ala Gly Phe Gly Gln Arg His
    1205                1210                1215

Arg Leu Val Leu Thr Gln Glu Gln Leu His Gln Leu His Ser Arg
    1220                1225                1230

Leu Ile Ser
    1235

<210> SEQ ID NO 30
<211> LENGTH: 1271
<212> TYPE: PRT
<213> ORGANISM: Homo sapiens

<400> SEQUENCE: 30

Met Ala Gln Ser Lys Arg His Val Tyr Ser Arg Thr Pro Ser Gly Ser
1               5                   10                  15

Arg Met Ser Ala Glu Ala Ser Ala Arg Pro Leu Arg Val Gly Ser Arg
                20                  25                  30

Val Glu Val Ile Gly Lys Gly His Arg Gly Thr Val Ala Tyr Val Gly
            35                  40                  45

Ala Thr Leu Phe Ala Thr Gly Lys Trp Val Gly Val Ile Leu Asp Glu
        50                  55                  60

Ala Lys Gly Lys Asn Asp Gly Thr Val Gln Gly Arg Lys Tyr Phe Thr
65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Thr Asp Thr Thr Ala Lys Thr
        115                 120                 125

Ser Lys Leu Ala Pro Thr Ala Arg Lys Thr Thr Thr Arg Arg Pro Lys
    130                 135                 140

Pro Thr Arg Pro Ala Ser Thr Gly Val Ala Gly Ala Ser Ser Ser Leu
145                 150                 155                 160

Gly Pro Ser Gly Ser Ala Ser Ala Gly Glu Leu Ser Ser Ser Glu Pro
                165                 170                 175

Ser Thr Pro Ala Gln Thr Pro Leu Ala Ala Pro Ile Ile Pro Thr Pro
            180                 185                 190

Val Leu Thr Ser Pro Gly Ala Val Pro Pro Leu Pro Ser Pro Ser Lys
        195                 200                 205

Glu Glu Glu Gly Leu Arg Ala Gln Val Arg Asp Leu Glu Glu Lys Leu
    210                 215                 220

Glu Thr Leu Arg Leu Lys Arg Ala Glu Asp Lys Ala Lys Leu Lys Glu
225                 230                 235                 240

Leu Glu Lys His Lys Ile Gln Leu Glu Gln Val Gln Glu Trp Lys Ser
                245                 250                 255

Lys Met Gln Glu Gln Ala Asp Leu Gln Arg Arg Leu Lys Glu Ala
            260                 265                 270

Arg Lys Glu Ala Lys Glu Ala Leu Glu Ala Lys Glu Arg Tyr Met Glu
        275                 280                 285

Glu Met Ala Asp Thr Ala Asp Ala Ile Glu Met Ala Thr Leu Asp Lys
    290                 295                 300

Glu Met Ala Glu Glu Arg Ala Glu Ser Leu Gln Gln Glu Val Glu Ala
305                 310                 315                 320
```

-continued

```
Leu Lys Glu Arg Val Asp Glu Leu Thr Thr Asp Leu Glu Ile Leu Lys
            325                 330                 335

Ala Glu Ile Glu Glu Lys Gly Ser Asp Gly Ala Ala Ser Ser Tyr Gln
            340                 345                 350

Leu Lys Gln Leu Glu Glu Gln Asn Ala Arg Leu Lys Asp Ala Leu Val
            355                 360                 365

Arg Met Arg Asp Leu Ser Ser Ser Glu Lys Gln Glu His Val Lys Leu
        370                 375                 380

Gln Lys Leu Met Glu Lys Asn Gln Glu Leu Glu Val Val Arg Gln
385                 390                 395                 400

Gln Arg Glu Arg Leu Gln Glu Glu Leu Ser Gln Ala Glu Ser Thr Ile
                405                 410                 415

Asp Glu Leu Lys Glu Gln Val Asp Ala Ala Leu Gly Ala Glu Glu Met
            420                 425                 430

Val Glu Met Leu Thr Asp Arg Asn Leu Asn Leu Glu Glu Lys Val Arg
        435                 440                 445

Glu Leu Arg Glu Thr Val Gly Asp Leu Glu Ala Met Asn Glu Met Asn
    450                 455                 460

Asp Glu Leu Gln Glu Asn Ala Arg Glu Thr Glu Leu Glu Leu Arg Glu
465                 470                 475                 480

Gln Leu Asp Met Ala Gly Ala Arg Val Arg Glu Ala Gln Lys Arg Val
                485                 490                 495

Glu Ala Ala Gln Glu Thr Val Ala Asp Tyr Gln Gln Thr Ile Lys Lys
            500                 505                 510

Tyr Arg Gln Leu Thr Ala His Leu Gln Asp Val Asn Arg Glu Leu Thr
        515                 520                 525

Asn Gln Gln Glu Ala Ser Val Glu Arg Gln Gln Pro Pro Glu
    530                 535                 540

Thr Phe Asp Phe Lys Ile Lys Phe Ala Glu Thr Lys Ala His Ala Lys
545                 550                 555                 560

Ala Ile Glu Met Glu Leu Arg Gln Met Glu Val Ala Gln Ala Asn Arg
                565                 570                 575

His Met Ser Leu Leu Thr Ala Phe Met Pro Asp Ser Phe Leu Arg Pro
            580                 585                 590

Gly Gly Asp His Asp Cys Val Leu Val Leu Leu Met Pro Arg Leu
        595                 600                 605

Ile Cys Lys Ala Glu Leu Ile Arg Lys Gln Ala Gln Glu Lys Phe Glu
    610                 615                 620

Leu Ser Glu Asn Cys Ser Glu Arg Pro Gly Leu Arg Gly Ala Ala Gly
625                 630                 635                 640

Glu Gln Leu Ser Phe Ala Ala Gly Leu Val Tyr Ser Leu Ser Leu Leu
                645                 650                 655

Gln Ala Thr Leu His Arg Tyr Glu His Ala Leu Ser Gln Cys Ser Val
            660                 665                 670

Asp Val Tyr Lys Lys Val Gly Ser Leu Tyr Pro Glu Met Ser Ala His
        675                 680                 685

Glu Arg Ser Leu Asp Phe Leu Ile Glu Leu Leu His Lys Asp Gln Leu
    690                 695                 700

Asp Glu Thr Val Asn Val Glu Pro Leu Thr Lys Ala Ile Lys Tyr Tyr
705                 710                 715                 720

Gln His Leu Tyr Ser Ile His Leu Ala Glu Gln Pro Glu Asp Cys Thr
                725                 730                 735

Met Gln Leu Ala Asp His Ile Lys Phe Thr Gln Ser Ala Leu Asp Cys
```

-continued

```
            740                 745                 750
Met Ser Val Glu Val Gly Arg Leu Arg Ala Phe Leu Gln Gly Gly Gln
            755                 760                 765

Glu Ala Thr Asp Ile Ala Leu Leu Arg Asp Leu Glu Thr Ser Cys
    770                 775                 780

Ser Asp Ile Arg Gln Phe Cys Lys Lys Ile Arg Arg Met Pro Gly
785                 790                 795                 800

Thr Asp Ala Pro Gly Ile Pro Ala Ala Leu Ala Phe Gly Pro Gln Val
                    805                 810                 815

Ser Asp Thr Leu Leu Asp Cys Arg Lys His Leu Thr Trp Val Val Ala
                    820                 825                 830

Val Leu Gln Glu Val Ala Ala Ala Ala Gln Leu Ile Ala Pro Leu
            835                 840                 845

Ala Glu Asn Glu Gly Leu Leu Val Ala Ala Leu Glu Glu Leu Ala Phe
            850                 855                 860

Lys Ala Ser Glu Gln Ile Tyr Gly Thr Pro Ser Ser Pro Tyr Glu
865                 870                 875                 880

Cys Leu Arg Gln Ser Cys Asn Ile Leu Ile Ser Thr Met Asn Lys Leu
                    885                 890                 895

Ala Thr Ala Met Gln Glu Gly Glu Tyr Asp Ala Glu Arg Pro Pro Ser
                    900                 905                 910

Lys Pro Pro Pro Val Glu Leu Arg Ala Ala Leu Arg Ala Glu Ile
            915                 920                 925

Thr Asp Ala Glu Gly Leu Gly Leu Lys Leu Glu Asp Arg Glu Thr Val
            930                 935                 940

Ile Lys Glu Leu Lys Lys Ser Leu Lys Ile Lys Gly Glu Glu Leu Ser
945                 950                 955                 960

Glu Ala Asn Val Arg Leu Ser Leu Leu Glu Lys Lys Leu Asp Ser Ala
                    965                 970                 975

Ala Lys Asp Ala Asp Glu Arg Ile Glu Lys Val Gln Thr Arg Leu Glu
                    980                 985                 990

Glu Thr Gln Ala Leu Leu Arg Lys Lys Glu Lys Glu Phe Glu Glu Thr
            995                 1000                1005

Met Asp Ala Leu Gln Ala Asp Ile Asp Gln Leu Glu Ala Glu Lys
    1010                1015                1020

Ala Glu Leu Lys Gln Arg Leu Asn Ser Gln Ser Lys Arg Thr Ile
    1025                1030                1035

Glu Gly Leu Arg Gly Pro Pro Pro Ser Gly Ile Ala Thr Leu Val
    1040                1045                1050

Ser Gly Ile Ala Gly Glu Glu Gln Gln Arg Gly Ala Ile Pro Gly
    1055                1060                1065

Gln Ala Pro Gly Ser Val Pro Gly Pro Gly Leu Val Lys Asp Ser
    1070                1075                1080

Pro Leu Leu Leu Gln Gln Ile Ser Ala Met Arg Leu His Ile Ser
    1085                1090                1095

Gln Leu Gln His Glu Asn Ser Ile Leu Lys Gly Ala Gln Met Lys
    1100                1105                1110

Ala Ser Leu Ala Ser Leu Pro Pro Leu His Val Ala Lys Leu Ser
    1115                1120                1125

His Glu Gly Pro Gly Ser Glu Leu Pro Ala Gly Ala Leu Tyr Arg
    1130                1135                1140

Lys Thr Ser Gln Leu Leu Glu Thr Leu Asn Gln Leu Ser Thr His
    1145                1150                1155
```

Thr His Val Val Asp Ile Thr Arg Thr Ser Pro Ala Ala Lys Ser
    1160                1165               1170

Pro Ser Ala Gln Leu Met Glu Gln Val Ala Gln Leu Lys Ser Leu
    1175                1180               1185

Ser Asp Thr Val Glu Lys Leu Lys Asp Glu Val Leu Lys Glu Thr
    1190                1195               1200

Val Ser Gln Arg Pro Gly Ala Thr Val Pro Thr Asp Phe Ala Thr
    1205                1210               1215

Phe Pro Ser Ser Ala Phe Leu Arg Ala Lys Glu Glu Gln Gln Asp
    1220                1225               1230

Asp Thr Val Tyr Met Gly Lys Val Thr Phe Ser Cys Ala Ala Gly
    1235                1240               1245

Phe Gly Gln Arg His Arg Leu Val Leu Thr Gln Glu Gln Leu His
    1250                1255               1260

Gln Leu His Ser Arg Leu Ile Ser
    1265                1270

<210> SEQ ID NO 31
<211> LENGTH: 1114
<212> TYPE: PRT
<213> ORGANISM: Homo sapiens

<400> SEQUENCE: 31

Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
                35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val

-continued

```
                    245                 250                 255
Pro Phe Pro Val Thr Val Tyr Asp Glu Asp Ser Ala Pro Thr Phe
                260                 265                 270

Pro Ala Gly Val Asp Thr Ala Ser Ala Val Val Glu Phe Lys Arg Lys
                275                 280                 285

Glu Asp Thr Val Val Ala Thr Leu Arg Val Phe Asp Ala Asp Val Val
                290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
                355                 360                 365

Thr Met Gln Leu Ala Val Leu Val Asn Asp Ser Asp Phe Gln Gly Pro
                370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
                435                 440                 445

Cys Ser Thr Leu Gly Val Val Thr Ser Ala Glu Asp Thr Ser Gly Ile
                450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
                500                 505                 510

Ala Gly Cys Pro Leu Ser Cys Ala Val Ser Lys Arg Arg Leu Glu Cys
                515                 520                 525

Glu Glu Cys Gly Gly Leu Gly Ser Pro Thr Gly Arg Cys Glu Trp Arg
                530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
                580                 585                 590

Gly His Glu Pro Gly Glu Pro Arg Gly Ile Lys Ala Gly Tyr Gly Thr
                595                 600                 605

Cys Asn Cys Phe Pro Glu Glu Lys Cys Phe Cys Glu Pro Glu Asp
                610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
                660                 665                 670
```

```
Glu Met Thr Phe Arg Arg Pro Ala Gln Ala Phe Pro Val Ser Tyr Ser
            675                 680                 685

Ser Ser Gly Ala Arg Arg Pro Ser Leu Asp Ser Met Glu Asn Gln Val
        690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
            755                 760                 765

Leu Arg Asp Leu Leu Ser Glu Phe Asn Val Leu Lys Gln Val Asn His
        770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080
```

-continued

```
Asn Thr Gly Phe Pro Arg Tyr Pro Asn Asp Ser Val Tyr Ala Asn
        1085                1090                1095

Trp Met Leu Ser Pro Ser Ala Ala Lys Leu Met Asp Thr Phe Asp
    1100                1105                1110

Ser
```

<210> SEQ ID NO 32
<211> LENGTH: 1072
<212> TYPE: PRT
<213> ORGANISM: Homo sapiens

<400> SEQUENCE: 32

```
Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
        130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335
```

```
Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
            355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
            515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
            595                 600                 605

Cys Asn Cys Phe Pro Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
    675                 680                 685

Ser Ser Gly Ala Arg Arg Pro Ser Leu Asp Ser Met Glu Asn Gln Val
690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
```

```
                      755                 760                 765
Leu Arg Asp Leu Leu Ser Glu Phe Asn Val Leu Lys Gln Val Asn His
770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                    805                 810                 815

Arg Glu Ser Arg Lys Val Gly Pro Gly Tyr Leu Gly Ser Gly Gly Ser
                820                 825                 830

Arg Asn Ser Ser Ser Leu Asp His Pro Asp Glu Arg Ala Leu Thr Met
                835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                    885                 890                 895

Arg Asp Val Tyr Glu Glu Asp Ser Tyr Val Lys Arg Ser Gln Gly Arg
                900                 905                 910

Ile Pro Val Lys Trp Met Ala Ile Glu Ser Leu Phe Asp His Ile Tyr
            915                 920                 925

Thr Thr Gln Ser Asp Val Trp Ser Phe Gly Val Leu Leu Trp Glu Ile
930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                    965                 970                 975

Ser Glu Glu Met Tyr Arg Leu Met Leu Gln Cys Trp Lys Gln Glu Pro
                980                 985                 990

Asp Lys Arg Pro Val Phe Ala Asp Ile Ser Lys Asp Leu Glu Lys Met
                995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
    1040                1045                1050

Ser Thr Trp Ile Glu Asn Lys Leu Tyr Gly Arg Ile Ser His Ala
    1055                1060                1065

Phe Thr Arg Phe
    1070

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
tgtccagctt tgtgcctgat tgatgt                                          26

<210> SEQ ID NO 34
<211> LENGTH: 26
<212> TYPE: DNA
<213> ORGANISM: Artificial Sequence
```

```
<220> FEATURE:
<223> OTHER INFORMATION: primer

<400> SEQUENCE: 34
gctgggcact gaagagaaag gaatgc                                          26

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
agcaggatga gtgcggaggc aagc                                            24

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
ttaactatca aacgtgtcca ttaattttgc cgc                                  33

<210> SEQ ID NO 37
<211> LENGTH: 18
<212> TYPE: DNA
<213> ORGANISM: Artificial Sequence
<220> FEATURE:
<223> OTHER INFORMATION: primer

<400> SEQUENCE: 37
agtactgggg tggctggg                                                   18

<210> SEQ ID NO 38
<211> LENGTH: 19
<212> TYPE: DNA
<213> ORGANISM: Artificial Sequence
<220> FEATURE:
<223> OTHER INFORMATION: primer

<400> SEQUENCE: 38
cactttggac aaggagatg                                                  19

<210> SEQ ID NO 39
<211> LENGTH: 18
<212> TYPE: DNA
<213> ORGANISM: Artificial Sequence
<220> FEATURE:
<223> OTHER INFORMATION: primer

<400> SEQUENCE: 39
acagaactgg agctgcgg                                                   18

<210> SEQ ID NO 40
<211> LENGTH: 18
<212> TYPE: DNA
<213> ORGANISM: Artificial Sequence
<220> FEATURE:
<223> OTHER INFORMATION: primer

<400> SEQUENCE: 40
ggactggtgt actcgctg                                                   18
```

```
<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
tcctagactg caggaaacac                                                    20

<210> SEQ ID NO 42
<211> LENGTH: 18
<212> TYPE: DNA
<213> ORGANISM: Artificial Sequence
<220> FEATURE:
<223> OTHER INFORMATION: primer

<400> SEQUENCE: 42
catcgagaaa gtccagac                                                      18

<210> SEQ ID NO 43
<211> LENGTH: 18
<212> TYPE: DNA
<213> ORGANISM: Artificial Sequence
<220> FEATURE:
<223> OTHER INFORMATION: primer

<400> SEQUENCE: 43
gctgctggag acattgaa                                                      18

<210> SEQ ID NO 44
<211> LENGTH: 18
<212> TYPE: DNA
<213> ORGANISM: Artificial Sequence
<220> FEATURE:
<223> OTHER INFORMATION: primer

<400> SEQUENCE: 44
tcactgctgc tcagctca                                                      18

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gaggatccaa agtgggaatt                                                    20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
agtatctggc cgagatgaag                                                    20

<210> SEQ ID NO 47
<211> LENGTH: 20
<212> TYPE: DNA
<213> ORGANISM: Artificial Sequence
<220> FEATURE:
<223> OTHER INFORMATION: primer
```

<400> SEQUENCE: 47
gcaaagacct ggagaagatg                                          20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
aggacgttga actctgacag                                          20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
cctttgcttc atccagaatc                                          20

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
gattttgtgt ttctccagct ct                                       22

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cctgcttctc tgaggaagaa                                          20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
gggccttagt ctcagcaaac                                          20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
gagcactctg cgtgaactta                                          20

<210> SEQ ID NO 54

```
<211> LENGTH: 21
<212> TYPE: DNA
<213> ORGANISM: Artificial Sequence
<220> FEATURE:
<223> OTHER INFORMATION: primer

<400> SEQUENCE: 54
cagcttgttc atggtactga t                                              21

<210> SEQ ID NO 55
<211> LENGTH: 18
<212> TYPE: DNA
<213> ORGANISM: Artificial Sequence
<220> FEATURE:
<223> OTHER INFORMATION: primer

<400> SEQUENCE: 55
tggtgagtcc ttcaccag                                                  18

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
cctagagttt ttccaagaac ca                                             22

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
catttaactg gaatccgacc                                                20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gactctctcc aggccagttc                                                20

<210> SEQ ID NO 59
<211> LENGTH: 22
<212> TYPE: DNA
<213> ORGANISM: Artificial Sequence
<220> FEATURE:
<223> OTHER INFORMATION: primer

<400> SEQUENCE: 59
ggctatcaga agtaaaacca cc                                             22

<210> SEQ ID NO 60
<211> LENGTH: 18
<212> TYPE: DNA
<213> ORGANISM: Artificial Sequence
<220> FEATURE:
<223> OTHER INFORMATION: primer

<400> SEQUENCE: 60
```
cgagagctga tggcacta                                                  18

<210> SEQ ID NO 61
<211> LENGTH: 24
<212> TYPE: DNA
<213> ORGANISM: Artificial Sequence
<220> FEATURE:
<223> OTHER INFORMATION: primer

<400> SEQUENCE: 61
cttcatcaca agtgaagtac ttcc                                           24

<210> SEQ ID NO 62
<211> LENGTH: 19
<212> TYPE: DNA
<213> ORGANISM: Artificial Sequence
<220> FEATURE:
<223> OTHER INFORMATION: primer

<400> SEQUENCE: 62
cgtactccac gatgaggag                                                 19

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
gattctggat gaagcaaagg                                                20

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
ggaagtactt cacttgtgat gaag                                           24

<210> SEQ ID NO 65
<211> LENGTH: 18
<212> TYPE: DNA
<213> ORGANISM: Artificial Sequence
<220> FEATURE:
<223> OTHER INFORMATION: primer

<400> SEQUENCE: 65
cccagccacc ccagtact                                                  18

<210> SEQ ID NO 66
<211> LENGTH: 17
<212> TYPE: DNA
<213> ORGANISM: Artificial Sequence
<220> FEATURE:
<223> OTHER INFORMATION: primer

<400> SEQUENCE: 66
gtaaaacgac ggccagt                                                   17

<210> SEQ ID NO 67
<211> LENGTH: 17
<212> TYPE: DNA

```
<213> ORGANISM: Artificial Sequence
<220> FEATURE:
<223> OTHER INFORMATION: primer

<400> SEQUENCE: 67
gttttcccag tcacgac                                                  17

<210> SEQ ID NO 68
<211> LENGTH: 17
<212> TYPE: DNA
<213> ORGANISM: Artificial Sequence
<220> FEATURE:
<223> OTHER INFORMATION: primer

<400> SEQUENCE: 68
caggaaacag ctatgac                                                  17

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ctggagccac agtacccact                                               20

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
tccaaattcg ccttctccta                                               20

<210> SEQ ID NO 71
<211> LENGTH: 25
<212> TYPE: DNA
<213> ORGANISM: Artificial Sequence
<220> FEATURE:
<223> OTHER INFORMATION: primer

<400> SEQUENCE: 71
ttcatcagcc ttcctcaggg aggat                                         25

<210> SEQ ID NO 72
<211> LENGTH: 41
<212> TYPE: DNA
<213> ORGANISM: Artificial Sequence
<220> FEATURE:
<223> OTHER INFORMATION: Primer

<400> SEQUENCE: 72
ggggacaagt ttgtacaaaa aagcaggctt cgccaccagc a                       41

<210> SEQ ID NO 73
<211> LENGTH: 42
<212> TYPE: DNA
<213> ORGANISM: Artificial Sequence
<220> FEATURE:
<223> OTHER INFORMATION: primer

<400> SEQUENCE: 73
ggggaccact ttgtacaaga aagctgggtt ttaactatca aa                      42
```

```
<210> SEQ ID NO 74
<211> LENGTH: 21
<212> TYPE: RNA
<213> ORGANISM: Artificial Sequence
<220> FEATURE:
<223> OTHER INFORMATION: RET siRNA1
<220> FEATURE:
<221> NAME/KEY: misc_feature
<223> OTHER INFORMATION: n stand for thymine
<220> FEATURE:
<221> NAME/KEY: misc_feature
<222> LOCATION: (20)..(21)
<223> OTHER INFORMATION: n stand for thymine

<400> SEQUENCE: 74
cacaugucau caaauuguan n                                              21

<210> SEQ ID NO 75
<211> LENGTH: 21
<212> TYPE: RNA
<213> ORGANISM: Artificial Sequence
<220> FEATURE:
<223> OTHER INFORMATION: RET siRNA2
<220> FEATURE:
<221> NAME/KEY: misc_feature
<222> LOCATION: (20)..(21)
<223> OTHER INFORMATION: n stand for thymine

<400> SEQUENCE: 75
ggauugaaaa caaacucuan n                                              21

<210> SEQ ID NO 76
<211> LENGTH: 21
<212> TYPE: RNA
<213> ORGANISM: Artificial Sequence
<220> FEATURE:
<223> OTHER INFORMATION: RET siRNA
<220> FEATURE:
<221> NAME/KEY: misc_feature
<222> LOCATION: (20)..(21)
<223> OTHER INFORMATION: n stand for thymine

<400> SEQUENCE: 76
gcuugucccg agauguuuan n                                              21

<210> SEQ ID NO 77
<211> LENGTH: 21
<212> TYPE: RNA
<213> ORGANISM: Artificial Sequence
<220> FEATURE:
<223> OTHER INFORMATION: RET siRNA3
<220> FEATURE:
<221> NAME/KEY: misc_feature
<222> LOCATION: (20)..(21)
<223> OTHER INFORMATION: n stand for thymine

<400> SEQUENCE: 77
ccacugcuac cacaaguuun n                                              21
```

FUSION PROTEIN OF DCTN1 PROTEIN WITH RET PROTEIN

CROSS REFERENCE TO RELATED APPLICATION

This application is a 35 U.S.C. 371 National Phase Entry Application from PCT/JP2018/030688, filed Aug. 20, 2018, which claims the benefit of Japanese Patent Application No. 2017-158796 filed on Aug. 21, 2017, the disclosures of which are incorporated herein in their entirety by reference.

The instant application contains a Sequence Listing which has been submitted via EFS-Web and is hereby incorporated by reference in its entirety. Said Sequence Listing, created on Feb. 21, 2020, is named P17-158 Sequence Listing.txt. and is 321 kilobytes in size.

TECHNICAL FIELD

The present invention relates to a polypeptide that is a fusion protein of DCTN1 protein and RET protein; a polynucleotide that encodes the polypeptide; a method for detecting the polypeptide or the polynucleotide; a compound that targets the polypeptide or the polynucleotide; and a method of screening for the compound.

BACKGROUND ART

Cancer is the leading cause of death by disease in Japan, and its treatment must be improved. Although the number of individuals affected with thyroid cancer is increasing, appropriate treatment at the initial stage leads to a high survival rate because of the slow progress of the disease in most cases. The disease, however, has almost no subjective symptoms, and early diagnosis is essential for appropriate treatment.

Thyroid cancer is divided by histological types into papillary cancer, follicular cancer, medullary cancer, anaplastic cancer, and malignant lymphoma. Papillary cancer accounts for about 80% of thyroid cancer, and anaplastic cancer, which has a lower incidence though, is known to have a very poor prognosis (Non-patent Literature 1).

Papillary cancer is known to develop largely because of the activation of oncogenes, and mutually exclusive genetic abnormalities, such as BRAF mutation gene (50 to 60%), RAS mutation gene (10 to 20%), and RET fusion gene (5 to 10%), have been revealed to occur. Studies also report that in non-small-cell lung cancer as well, RET fusion gene is present at a frequency of 1 to 2% mutually exclusively with other driver mutation genes, such as EGFR mutation gene (Non-patent Literature 2 to 5).

Drug treatment is the dominant mode of advanced thyroid cancer treatment, and a variety of multikinase inhibitors have been approved. However, medicinal agents that exhibit an effect specific to driver mutation genes remain unapproved. A study reports that RET fusion gene-positive patients with lung cancer show benefit from inhibiting RET (Non-patent Literature 6); it is necessary in thyroid cancer, as well, to identify gene abnormalities, such as mutation genes or fusion genes, which can be an indicator of the effect of medicinal agents.

There has been a strong desire to identify mutation genes (mutation proteins), fusion genes (fusion proteins), etc., which can be drivers of cancer; this is because such identification will elucidate the nature of cancer, and significantly contribute to the development of novel cancer treatment drugs or testing methods that target these mutation genes or fusion genes. However, mutation genes, fusion genes, etc., which can be drivers of cancer development, have yet to be fully elucidated, and identifying gene abnormalities that may be associated with therapeutic effects of medicinal agents will be highly significant.

CITATION LIST

Non-Patent Literature

Non-patent Literature 1: Cancer, 115 (16), pp. 3801-7 (2009)
Non-patent Literature 2: Oncogene, 22 (29), pp. 4578-80 (2003)
Non-patent Literature 3: Cell, 159 (3), pp. 676-90 (2014)
Non-patent Literature 4: Cancer Discov., 3 (6), pp. 630-5 (2013)
Non-patent Literature 5: Nature, 511 (7511), pp. 543-50 (2014)
Non-patent Literature 6: Lancet Respir Med., 5 (1), pp. 42-50 (2017)

SUMMARY OF INVENTION

Technical Problem

An object of the present invention is to provide a novel polypeptide that is a fusion protein incorporating at least a portion of RET protein; a polynucleotide encoding the polypeptide; a method for detecting the polypeptide or the polynucleotide; a compound targeting the polypeptide or the polynucleotide; and a method of screening for the compound.

Solution to Problem

The present inventors conducted extensive research to achieve the object, and identified a novel polypeptide in which a portion of DCTN1 protein is fused to a portion of RET protein, and a polynucleotide encoding the polypeptide in the cells derived from thyroid cancer patients. The inventors also found a method for detecting the polynucleotide or polypeptide of the present invention in cancer cells, and a method of screening for a compound that inhibits the expression of the polynucleotide or the expression and/or activity of the polypeptide. It is a novel finding and cannot be predicted from the prior art that, among a wide range of proteins, a fusion protein containing a combination of the N-terminal portion of DCTN1 protein and the C-terminal portion of RET protein naturally occurs intracellularly; and that because the fusion gene of DCTN1 and RET functions as a cancer driver, the fusion protein is useful in cancer diagnosis. They further found a pharmaceutical composition that contains a compound that inhibits RET as an active ingredient and that is for use in the treatment of cancer patients who have the expression of the polypeptide and/or the polynucleotide, and completed the present invention.

Specifically, the present invention provides the following subject matter.

Item 1.
A polypeptide wherein an N-terminal portion of DCTN1 protein is fused to a C-terminal portion of RET protein.

Item 2.
The polypeptide according to Item 1, which is selected from the following (a) to (c):
(a) a polypeptide comprising the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24;
(b) a polypeptide comprising an amino acid sequence wherein one or several amino acids are substituted, deleted, or added in the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24; and
(c) a polypeptide comprising an amino acid sequence that has at least 90% identity with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.
Item 3.
A polynucleotide encoding the polypeptide according to Item 1 or 2.
Item 4.
The polynucleotide according to Item 3, which is selected from the following (d) to (f):
(d) a polynucleotide encoding a polypeptide comprising the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24;
(e) a polynucleotide encoding a polypeptide comprising an amino acid sequence wherein one or several amino acids are substituted, deleted, or added in the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24; and
(f) a polynucleotide encoding a polypeptide comprising an amino acid sequence that has at least 90% identity with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.
Item 5.
The polynucleotide according to Item 3, which is selected from the following (g) to (i):
(g) a polynucleotide comprising the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23;
(h) a polynucleotide hybridizing under stringent conditions with a polynucleotide comprising a base sequence complementary to the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23; and
(i) a polynucleotide having at least 90% identity with the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.
Item 6.
An expression vector comprising the polynucleotide according to any one of Items 3 to 5.
Item 7.
A cell transfected with the polynucleotide according to any one of Items 3 to 5.

Item 8.
An antibody that specifically binds to the polypeptide according to Item 1 or 2.
Item 9.
A method for detecting the presence of the polypeptide according to Item 1 or 2 in a sample.
Item 10.
A primer or probe for detecting the presence of the polynucleotide according to any one of Items 3 to 5 in a sample, the primer or probe being a polynucleotide selected from the following (j) to (1):
(j) a polynucleotide that is at least one probe selected from the group consisting of probes hybridizing with a polynucleotide encoding DCTN1 protein, and probes hybridizing with a polynucleotide encoding RET protein;
(k) a polynucleotide that is a probe that hybridizes to a point of fusion between a polynucleotide encoding DCTN1 protein and a polynucleotide encoding RET protein; and
(l) a polynucleotide that is a set of a sense primer and an antisense primer designed to sandwich a point of fusion between a polynucleotide encoding DCTN1 protein and a polynucleotide encoding RET protein.
Item 11.
A method for detecting the presence of the polynucleotide according to any one of Items 3 to 5 in a sample.
Item 12.
A method for diagnosing cancer in a patient when the presence of the polypeptide according to Item 1 or 2 or the polynucleotide according to any one of Items 3 to 5 is detected in a sample derived from the patient by the detection method according to Item 9 or 11.
Item 13.
A pharmaceutical composition for treating cancer that is positive for a fusion gene of DCTN1 gene and RET gene and/or positive for a fusion protein of DCTN1 protein and RET protein, the composition comprising a compound that inhibits RET as an active ingredient.
Item 14.
A method of screening for a compound that inhibits expression and/or activity of the polypeptide according to Item 1 or 2 or expression of the polynucleotide according to any one of Items 3 to 5, the method comprising the following steps (1) and (2):
(1) the step of bringing the polypeptide according to Item 1 or 2, a cell expressing the polypeptide according to Item 1 or 2 or the polynucleotide according to any one of Items 3 to 5, or the cell according to Item 7 into contact with a test compound; and
(2) the step of measuring whether expression and/or activity of the polypeptide according to Item 1 or 2 or expression of the polynucleotide according to any one of Items 3 to 5 is inhibited in step (1), or the step of measuring whether growth of the cell in step (1) is inhibited.
Item 15.
A method using the polypeptide according to Item 1 or 2 or the polynucleotide according to any one of Items 3 to 5 as an indicator for determining whether a chemotherapy using a compound that inhibits RET is effective,
the method comprising determining that the chemotherapy using the compound that inhibits RET is effective when the polypeptide according to Item 1 or 2 is detected in a sample by the detection method according to Item 9, and/or when the presence of the polynucleotide according to any one of Items 3 to 5 is detected in a sample by the detection method according to
Item 11.
Item 16.

A biomarker for detecting cancer, the biomarker comprising at least one member selected from the group consisting of polypeptides wherein an N-terminal portion of DCTN1 protein is fused to a C-terminal portion of RET protein, and polynucleotides encoding the polypeptides.

Item 17.

A method for treating cancer, the method comprising giving a chemotherapy using a compound that inhibits RET to a cancer patient who is positive for a fusion gene of DCTN1 gene and RET gene, and/or positive for a fusion protein of DCTN1 protein and RET protein.

Item 18.

A method for treating cancer, the method comprising
detecting the presence of the polypeptide according to Item 1 or 2, and/or the presence of the polynucleotide according to any one of Items 3 to 5 in a sample derived from a test subject, and
giving a chemotherapy using a compound that inhibits RET to the test subject when the presence of the polypeptide according to Item 1 or 2 has been detected, and/or the presence of the polynucleotide according to any one of Items 3 to 5 has been detected.

Item 19.

A compound that inhibits RET for use in the treatment of a cancer patient who is positive for a fusion gene of DCTN1 gene and RET gene, and/or positive for a fusion protein of DCTN1 protein and RET protein.

Item 20.

Use of a compound that inhibits RET in the production of a pharmaceutical composition for cancer treatment for treating a cancer patient who is positive for a fusion gene of DCTN1 gene and RET gene, and/or positive for a fusion protein of DCTN1 protein and RET protein.

Item 21.

A method for producing a reagent for determining whether a chemotherapy using a compound that inhibits RET is effective, using a means to detect the presence of the polypeptide according to Item 1 or 2 in a sample, and/or a means to detect the presence of the polynucleotide according to any one of Items 3 to 5 in a sample.

Item 22.

A combination of an anti-DCTN1 antibody and an anti-RET antibody for detecting the presence of the polynucleotide according to any one of Items 3 to 5.

Item 23.

Use of the antibody according to Item 8, the combination of the antibodies according to Item 22, or the primer or probe according to Item 10 in the production of a detection reagent for detecting the presence of the polypeptide according to Item 1 or 2, or the presence of the polynucleotide according to any one of Items 3 to 5.

Advantageous Effects of Invention

The present invention has demonstrated that the polynucleotide and/or polypeptide of the present invention is specifically expressed in a cancer cell. The polynucleotide, polypeptide, and cell expressing the polynucleotide and/or polypeptide of the present invention can be used in a method of screening for a compound that inhibits the expression of the polynucleotide, or the expression and/or activity of the polypeptide of the present invention. The use of the presence of the polynucleotide and/or polypeptide of the present invention as an indicator enables detection of a target positive for a fusion gene of DCTN1 gene and RET gene, and/or a target positive for a fusion protein of DCTN1 protein and RET protein. A compound that inhibits RET is useful as a pharmaceutical composition for treating cancer that is positive for a fusion gene of DCTN1 gene and RET gene, and/or positive for a fusion protein of DCTN1 protein and RET protein.

DESCRIPTION OF EMBODIMENTS

Figure 1:
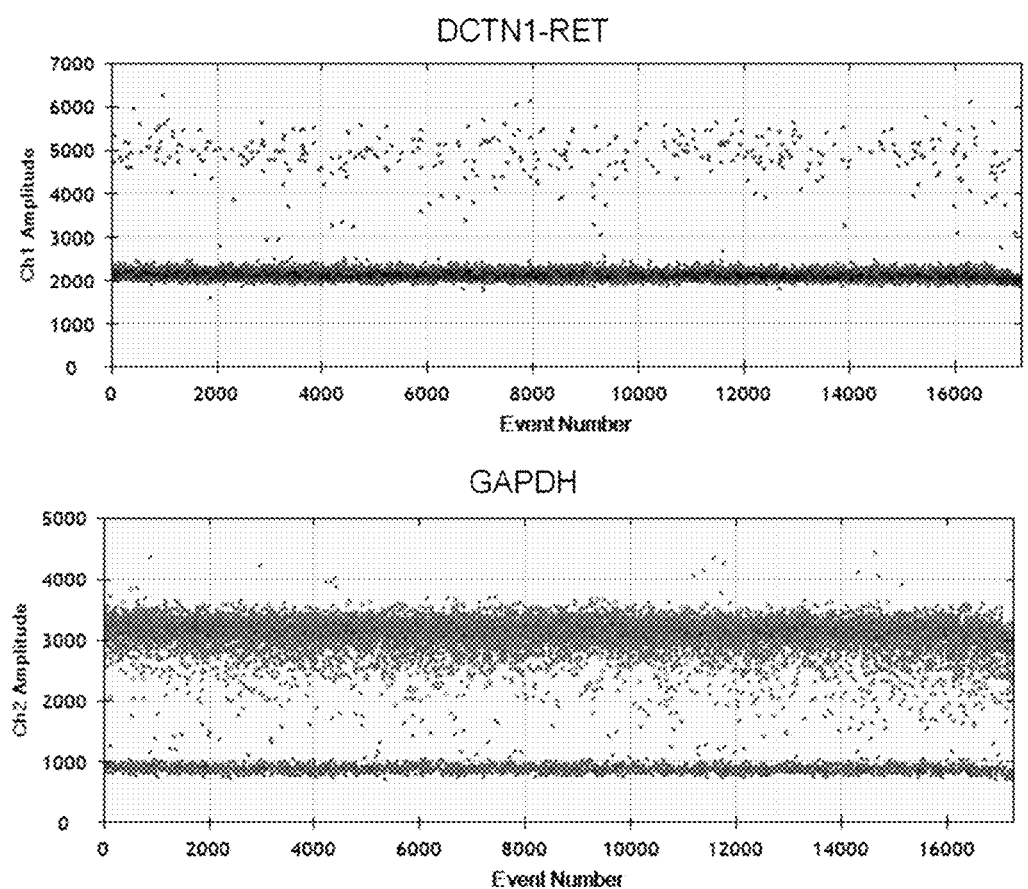
FIG. 1: Confirmation of the expression of DCTN1-RET fusion gene and GAPDH in thyroid cancer tissue using Droplet Digital PCR (ddPCR).

The present invention relates to a novel polynucleotide or polypeptide; a method for detecting the polynucleotide or polypeptide; a compound targeting the polynucleotide or polypeptide; and a method of screening for the compound.

The present invention provides a polypeptide in which the N-terminal portion of DCTN1 protein is fused to the C-terminal portion of RET protein (which may be hereinafter referred to as the "polypeptide of the present invention"). The present invention also provides a polynucleotide encoding the polypeptide (which may be hereinafter referred to as the "polynucleotide of the present invention").

"DCTN1 (Dynactin Subunit 1) protein" in the present invention is also called 150 kDa dynein-associated polypeptide protein or DAP-150 protein, and includes human or non-human mammal DCTN1 protein, with human DCTN1 protein being preferable. DCTN1 protein is encoded by a gene located on 2p13.1 in humans. In the present invention, "DCTN1 protein" includes isoforms (its splice variants), and examples of human-derived DCTN1 protein includes polypeptides comprising the amino acid sequence represented by GenPept accession number NP_004073, NP_075408, NP 001128512, NP 001128513, NP 001177765, or NP 001177766. More specifically, examples include polypeptides comprising the amino acid sequence represented by SEQ ID NO: 25, SEQ ID NO: 26, SEQ ID NO: 27, SEQ ID NO: 28, SEQ ID NO: 29, or SEQ ID NO: 30. Additionally, "N-terminal portion of DCTN1 protein" in the present invention refers to a polypeptide containing part of or the entire coiled-coil domain that is in the N-terminal side of DCTN1 protein, and preferably a polypeptide containing the entire coiled-coil domain that is in the N-terminal side of DCTN1 protein.

"RET protein" in the present invention is also called RET proto-oncogene protein, RET receptor tyrosine kinase protein, or protein rearranged during transfection; and includes human or non-human mammal RET protein, with human RET protein being preferable. RET protein is encoded by a gene located on 10q11.2 in humans. In the present invention, "RET protein" includes isoforms (its splice variants), and examples of human-derived RET protein includes polypeptides comprising the amino acid sequence represented by GenPept accession number NP 066124 or NP 065681. More specifically, examples include polypeptides comprising the amino acid sequence represented by SEQ ID NO: 31 or SEQ ID NO: 32. Additionally, "C-terminal portion of RET protein" in the present invention refers to a polypeptide containing a kinase domain that is in the C-terminal side of RET protein.

"A polypeptide in which the N-terminal portion of DCTN1 protein is fused to the C-terminal portion of RET protein" in the present invention is a polypeptide in which the polypeptide containing part of or the entire coiled-coil domain that is in the N-terminal side of DCTN1 protein is fused to the polypeptide containing a kinase domain that is in the C-terminal side of the RET protein, preferably a polypeptide in which the polypeptide containing the entire coiled-coil domain that is in the N-terminal side of DCTN1 protein is fused to the polypeptide containing a kinase domain that is in the C-terminal side of the RET protein, and more preferably a polypeptide selected from the following (a) to (c). These polypeptides preferably have kinase activity and/or a cell-proliferating effect.
(a) A polypeptide comprising the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.
(b) A polypeptide comprising an amino acid sequence wherein one or several amino acids are substituted, deleted, or added in the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.
(c) A polypeptide comprising an amino acid sequence that has at least 90% identity with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.

More preferably, the polypeptide is selected from the following (a) to (c). These polypeptides preferably have kinase activity or a cell-proliferating effect.
(a) A polypeptide comprising the amino acid sequence represented by SEQ ID NO: 18.
(b) A polypeptide comprising an amino acid sequence wherein one or several amino acids are substituted, deleted, or added in the amino acid sequence represented by SEQ ID NO: 18.
(c) A polypeptide comprising an amino acid sequence that has at least 90% identity with the amino acid sequence represented by SEQ ID NO: 18.

"A polypeptide in which the N-terminal portion of DCTN1 protein is fused to the C-terminal portion of RET protein" in the present invention includes polypeptides comprising an amino acid sequence wherein one or several amino acids are substituted, deleted, or added in the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24 (item (b) above). Examples of the polypeptides comprising such an amino acid sequence wherein the N-terminal portion of DCTN1 protein is fused to the C-terminal portion of RET protein include isoforms of polypeptides comprising the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24 wherein the N-terminal portion of DCTN1 protein is fused to the C-terminal portion of RET protein. These polypeptides preferably have kinase activity or a cell-proliferating effect. As used herein, "several amino acids that are substituted, deleted, or added" means, for example, preferably 1 to 10 amino acids, and more preferably 1 to 5 amino acids. The "addition" includes addition of one to several amino acids to the N-terminal or C-terminal, or addition of one to several amino acids to both terminals.

Examples of the polypeptide wherein one or several amino acids are substituted include polypeptides in which valine at position 804 (at position 1325 in SEQ ID NO: 2 and SEQ ID NO: 4, at position 1191 in SEQ ID NO: 6 and SEQ ID NO: 8, at position 1300 in SEQ ID NO: 10 and SEQ ID NO: 12, at position 1186 in SEQ ID NO: 14 and SEQ ID NO: 16, at position 1283 in SEQ ID NO: 18 and SEQ ID NO: 20, at position 1318 in SEQ ID NO: 22 and SEQ ID NO: 24), which is at the gatekeeper site of RET protein comprising the amino acid sequence represented by GenPept accession number: NP 066124 (SEQ ID NO: 31) or NP 065681 (SEQ ID NO: 32), is substituted with leucine, methionine, or glutamic acid; and polypeptides in which tyrosine at position 806 (at position 1327 in SEQ ID NO: 2 and SEQ ID NO: 4, at position 1193 in SEQ ID NO: 6 and SEQ ID NO: 8, at position 1302 in SEQ ID NO: 10 and SEQ ID NO: 12, at position 1188 in SEQ ID NO: 14 and SEQ ID NO: 16, at position 1285 in SEQ ID NO: 18 and SEQ ID NO: 20, at position 1320 in SEQ ID NO: 22 and SEQ ID NO: 24) is substituted with cysteine, glutamic acid, serine, histidine, or asparagine.

Examples also include amino acids located at a position other than the gatekeeper site, but are not limited to, polypeptides in which glutamic acid at position 768 (at position 1289 in SEQ ID NO: 2 and SEQ ID NO: 4, at position 1155 in SEQ ID NO: 6 and SEQ ID NO: 8, at position 1264 in SEQ ID NO: 10 and SEQ ID NO: 12, at position 1150 in SEQ ID NO: 14 and SEQ ID NO: 16, at position 1247 in SEQ ID NO: 18 and SEQ ID NO: 20, at position 1282 in SEQ ID NO: 22 and SEQ ID NO: 24) is substituted with aspartic acid; polypeptides in which alanine at position 883 (at position 1404 in SEQ ID NO: 2 and SEQ ID NO: 4, at position 1270 in SEQ ID NO: 6 and SEQ ID NO: 8, at position 1379 in SEQ ID NO: 10 and SEQ ID NO: 12, at position 1265 in SEQ ID NO: 14 and SEQ ID NO: 16, at position 1362 in SEQ ID NO: 18 and SEQ ID NO: 20, at position 1397 in SEQ ID NO: 22 and SEQ ID NO: 24) is substituted with phenylalanine or serine; polypeptides in which glutamic acid at position 884 (at position 1405 in SEQ ID NO: 2 and SEQ ID NO: 4, at position 1271 in SEQ ID NO: 6 and SEQ ID NO: 8, at position 1380 in SEQ ID NO:

10 and SEQ ID NO: 12, at position 1266 in SEQ ID NO: 14 and SEQ ID NO: 16, at position 1363 in SEQ ID NO: 18 and SEQ ID NO: 20, at position 1398 in SEQ ID NO: 22 and SEQ ID NO: 24) is substituted with valine; polypeptides in which serine at position 891 (at position 1412 in SEQ ID NO: 2 and SEQ ID NO: 4, at position 1278 in SEQ ID NO: 6 and SEQ ID NO: 8, at position 1387 in SEQ ID NO: 10 and SEQ ID NO: 12, at position 1273 in SEQ ID NO: 14 and SEQ ID NO: 16, at position 1370 in SEQ ID NO: 18 and SEQ ID NO: 20, at position 1405 in SEQ ID NO: 22 and SEQ ID NO: 24) is substituted with alanine or leucine; and polypeptides in which methionine at position 918 (at position 1439 in SEQ ID NO: 2 and SEQ ID NO: 4, at position 1305 in SEQ ID NO: 6 and SEQ ID NO: 8, at position 1414 in SEQ ID NO: 10 and SEQ ID NO: 12, at position 1300 in SEQ ID NO: 14 and SEQ ID NO: 16, at position 1397 in SEQ ID NO: 18 and SEQ ID NO: 20, at position 1432 in SEQ ID NO: 22 and SEQ ID NO: 24) is substituted with threonine.

The polypeptide in which the N-terminal portion of DCTN1 protein is fused to the C-terminal portion of RET protein of the present invention includes polypeptides comprising an amino acid sequence that has at least 90% identity with the amino acid sequence represented by any of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24, upon appropriate alignment thereof (item (c) above). These polypeptides preferably have kinase activity or a cell-proliferating effect.

The identity with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24 is preferably at least 90%, more preferably at least 95%, and still more preferably at least 98%. The identity of the amino acid sequence can be calculated by a commonly used method.

The polypeptide of the present invention may comprise amino acids constituting a protein tag in addition to the amino acid sequence constituting the polypeptide of the present invention. Examples of usable tags include those well known to a person skilled in the art; for example, usable tags include tags for improving expression efficiency and tags for improving purification efficiency, such as His tag, Myc tag, and FLAG tag.

The polynucleotide of the present invention encodes the polypeptide in which the N-terminal portion of DCTN1 protein is fused to the C-terminal portion of RET protein, and is preferably a polynucleotide selected from the following (d) to (i). These polynucleotides preferably encode polypeptides that have kinase activity or a cell-proliferating effect.

(d) A polynucleotide encoding a polypeptide comprising the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.

(e) A polynucleotide encoding a polypeptide comprising an amino acid sequence wherein one or several amino acids are substituted, deleted, or added in the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.

(f) A polynucleotide encoding a polypeptide comprising an amino acid sequence that has at least 90% identity with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.

(g) A polynucleotide comprising the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

(h) A polynucleotide hybridizing under stringent conditions with a polynucleotide comprising a base sequence complementary to the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

(i) A polynucleotide that has at least 90% identity with the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23.

More preferably, the polynucleotide of the present invention is selected from the following (d) to (i). These polynucleotides preferably encode polypeptides that have kinase activity or a cell-proliferating effect.

(d) A polynucleotide encoding a polypeptide comprising the amino acid sequence represented by SEQ ID NO: 18.

(e) A polynucleotide encoding a polypeptide comprising an amino acid sequence wherein one or several amino acids are substituted, deleted, or added in the amino acid sequence represented by SEQ ID NO: 18.

(f) A polynucleotide encoding a polypeptide comprising an amino acid sequence that has at least 90% identity with the amino acid sequence represented by SEQ ID NO: 18.

(g) A polynucleotide comprising the base sequence represented by SEQ ID NO: 17.

(h) A polynucleotide hybridizing under stringent conditions with a polynucleotide comprising a base sequence complementary to the base sequence represented by SEQ ID NO: 17.

(i) A polynucleotide that has at least 90% identity with the base sequence represented by SEQ ID NO: 17.

The polynucleotide of the present invention includes not only its double-stranded DNA but also various types of single-stranded DNA and RNA that constitute the double-stranded DNA, such as sense strands and antisense strands. The antisense strands can be used as probes and the like. DNA includes those obtained by cloning, chemical synthesis, or a combination thereof, such as cDNA and genomic DNA. Additionally, base sequences, such as untranslated region (UTR) sequences, may be added to the polynucleotide of the present invention, in addition to the base sequence to encode the polypeptide of the present invention.

Stringent conditions as used herein include, for example, conditions described in Molecular Cloning: A Laboratory Manual (Second Edition, J. Sambrook et al., 1989). Specifically, stringent conditions include conditions such that a solution containing 6×SSC (1×SSC composition: 0.15 M sodium chloride, 0.015 M sodium citrate, pH 7.0), 0.5% SDS, 5×Denhalt, and 100 mg/mL herring sperm DNA is subjected to isothermal treatment together with a probe at 65° C. for 8 to 16 hours to perform hybridization.

The identity with the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23 is preferably at least 90%, more preferably at least 95%, and still more preferably at least 98%. The identity of the base sequence can be calculated by a commonly used method.

In this specification, the phrase "have kinase activity" in "have kinase activity or a cell-proliferating effect" means having an enzymatic activity to phosphorylate tyrosine. Additionally, the phrase "have a cell-proliferating effect" in "have kinase activity or a cell-proliferating effect" means that transfection of the polynucleotide and/or polypeptide of the present invention into a cell improves the cellular proliferative ability, compared with a cell to which the polynucleotide and/or polypeptide is not transfected. This effect can be confirmed, for example, as follows: the polynucleotide and/or polypeptide is transfected into a cell line that cytokine-dependently proliferates, and if the cell line proliferates cytokine-independently, the polynucleotide and/or polypeptide has a cell-proliferating effect.

The polynucleotide of the present invention can be extracted, for example, using a cDNA library or genomic DNA library prepared from thyroid cancer etc. that retains a fusion gene of DCTN1 gene and RET gene, using a primer that specifically hybridizes with part of the base sequence of the polynucleotide of the present invention. For this primer, any primer of any sequence and any length can be used, as long as the primer specifically hybridizes with at least a portion of the polynucleotide of the present invention or its antisense strand. A method for artificially synthesizing a polynucleotide may also be used (Nat. Methods, 11: 499-507, 2014).

The expression vector of the present invention is not particularly limited as long as the expression vector comprises the polynucleotide of the present invention, and allows for the expression of the polypeptide of the present invention. Examples include expression vectors obtained by inserting the polynucleotide of the present invention into a known expression vector suitably selected according to the host for use.

The host is not particularly limited as long as the host is a living cell that can undergo transformation, and examples include bacteria, such as *E. coli* and *Bacillus subtilis*; true fungi, such as yeast and filamentous fungi; insect cells, such as Sf9 cells; insects, such as silkworm; animal cells; and plants or plant-derived cells.

The vector for inserting the polynucleotide of the present invention is not particularly limited as long as the vector is replicable in the host. The vector can be suitably selected in accordance with, for example, the type of introduced host, and the introduction method. Examples include plasmid DNA, phage DNA, and virus vectors. For vector DNA for use in construction of an expression vector, a widely prevalent and readily available vector DNA can be used. Examples include pUC19 (Takara Bio Inc.), pTV118N (Takara Bio Inc.), pMAMneo (Clontech Laboratories, Inc.), pGEX (GE Healthcare), pET160 (Invitrogen), pDEST (Invitrogen), pIEx (Merck Millipore), and pBacPAK (Clontech Laboratories, Inc.). Examples of virus vectors include DNA viruses and RNA viruses, such as baculovirus vectors, retroviral vectors, lentiviral vectors (e.g., human immunodeficiency virus or HIV), adenovirus vectors, adeno-associated virus vectors (AAV vector), herpes virus, vaccinia virus, poxvirus, poliovirus, Sindbis virus, Sendai virus, and simian virus-40 (SV-40).

Transformation of a host using the expression vector can be performed, for example, by the protoplast method, competent cell method, or electroporation method. The obtained transformant may be cultured under suitable conditions in a medium containing a carbon source, a nitrogen source, metal salts, vitamins, etc., that can be utilized by the host.

Examples of the cell transfected with the polynucleotide according to the present invention include cells transformed by the expression vector of the present invention, and cells to which the polynucleotide of the present invention has been introduced by genome editing. The cell for use includes the host cells listed above. Examples of the method for confirming whether the cell has been transformed by the expression vector include the method for detecting the presence of the polypeptide of the present invention, and the method for detecting the presence of the polynucleotide of the present invention.

"Cells to which the polynucleotide of the present invention has been introduced by genome editing" are preferably cells having a gene obtained by fusing independently present DCTN1 gene and RET gene by genome editing, and more preferably cells having a gene obtained by fusing exon 27 of DCTN1 and exon 12 of RET in respective independently present DCTN1 gene and RET gene by genome editing. These cells can be prepared by a commonly used method, and examples include a method described in Cell Rep., 9(4), pp. 1219-1227 (2014), Nat. Commun., 5, 3728 (2014). Examples of the method for confirming whether the cell is a cell to which the polynucleotide of the present invention has been introduced by genome editing include the method for detecting the presence of the polypeptide of the present invention, and the method for detecting the presence of the polynucleotide of the present invention.

The polypeptide of the present invention can be obtained by preparing a culture solution and/or cells by culturing cells transformed by the expression vector of the present invention in a medium suitable for cell culture under suitable conditions, and then collecting and purifying the protein from the culture solution and/or cells by a typical method. The polypeptide of the present invention can also be obtained by incorporating the expression vector containing the polynucleotide of the present invention, or template RNA or template DNA that encodes the polynucleotide of the present invention, into a cell-free protein synthesis system (e.g., human cell line-derived cell extract, rabbit reticulocyte extract, wheat germ extract, and *E. coli* extract); incubating the result under suitable conditions; and collecting and purifying the protein from the obtained reaction solution by a typical method.

In the present invention, the antibody that specifically binds to the polypeptide of the present invention includes an antibody that specifically binds to the point of fusion of the N-terminal portion of DCTN1 protein and the C-terminal portion of RET protein. The antibody refers to an antibody that specifically binds to the point of fusion of the N-terminal portion of DCTN1 protein and the C-terminal portion of RET protein, but that binds to none of wild-type DCTN1 and wild-type RET protein.

In the present invention, the phrase "the point of fusion" in "the point of fusion of the N-terminal portion of DCTN1 protein and the C-terminal portion of RET protein" refers to the point at which a polypeptide derived from the N-terminal portion of DCTN1 protein is fused to a polypeptide derived from the C-terminal portion of RET protein. The point of fusion in SEQ ID NO: 2 is the point at which a polypeptide having the amino acid sequence of positions 1-1233 of SEQ ID NO: 2, which is derived from the N-terminal portion of DCTN1, is fused to a polypeptide having the amino acid sequence of positions 1234-1635 of SEQ ID NO: 2, which is derived from the C-terminal portion of RET. The point of fusion in SEQ ID NO: 4 is the point at which a polypeptide having the amino acid sequence of positions 1-1233 of SEQ ID NO: 4, which is derived from the N-terminal portion of DCTN 1, is fused to a polypeptide having the amino acid sequence of positions 1234-1593 of SEQ ID NO: 4, which is derived from the C-terminal portion of RET. The point of fusion in SEQ ID NO: 6 is the point at which a polypeptide having the amino acid sequence of positions 1-1099 of SEQ ID NO: 6, which is derived from the N-terminal portion of DCTN1, is fused to a polypeptide having the amino acid sequence of positions 1100-1501 of SEQ ID NO: 6, which is derived from the C-terminal portion of RET. The point of fusion in SEQ ID NO: 8 is the point at which a polypeptide having the amino acid sequence of positions 1-1099 of SEQ ID NO: 8, which is derived from the N-terminal portion of DCTN1, is fused to a polypeptide having the amino acid sequence of positions 1100-1459 of SEQ ID NO: 8, which is derived from the C-terminal portion of RET. The point of fusion in SEQ ID NO: 10 is the point at which a polypeptide having the amino acid sequence of positions 1-1208 of SEQ ID NO: 10, which is derived from the N-terminal portion of DCTN1, is fused to a polypeptide having the amino acid sequence of positions 1209-1610 of SEQ ID NO: 10, which is derived from the C-terminal portion of RET. The point of fusion in SEQ ID NO: 12 is the point at which a polypeptide having the amino acid sequence of positions 1-1208 of SEQ ID NO: 12, which is derived from the N-terminal portion of DCTN1, is fused to a polypeptide having the amino acid sequence of positions 1209-1568 of SEQ ID NO: 12, which is derived from the C-terminal portion of RET. The point of fusion in SEQ ID NO: 14 is the point at which a polypeptide having the amino acid sequence of positions 1-1094 of SEQ ID NO: 14, which is derived from the N-terminal portion of DCTN1, is fused to a polypeptide having the amino acid sequence of positions 1095-1496 of SEQ ID NO: 14, which is derived from the C-terminal portion of RET. The point of fusion in SEQ ID NO: 16 is the point at which a polypeptide having the amino acid sequence of positions 1-1094 of SEQ ID NO: 16, which is derived from the N-terminal portion of DCTN1, is fused to a polypeptide having the amino acid sequence of positions 1095-1454 of SEQ ID NO: 16, which is derived from the C-terminal portion of RET. The point of fusion in SEQ ID NO: 18 is the point at which a polypeptide having the amino acid sequence of positions 1-1191 of SEQ ID NO: 18, which is derived from the N-terminal portion of DCTN1, is fused to a polypeptide having the amino acid sequence of positions 1192-1593 of SEQ ID NO: 18, which is derived from the C-terminal portion of RET. The point of fusion in SEQ ID NO: 20 is the point at which a polypeptide having the amino acid sequence of positions 1-1191 of SEQ ID NO: 20, which is derived from the N-terminal portion of DCTN1, is fused to a polypeptide having the amino acid sequence of positions 1192-1551 of SEQ ID NO: 20, which is derived from the C-terminal portion of RET. The point of fusion in SEQ ID NO: 22 is the point at which a polypeptide having the amino acid sequence of positions 1-1226 of SEQ ID NO: 22, which is derived from the N-terminal portion of DCTN1, is fused to a polypeptide having the amino acid sequence of positions 1227-1628 of SEQ ID NO: 22, which is derived from the C-terminal portion of RET. The point of fusion in SEQ ID NO: 24 is the point at which a polypeptide having the amino acid sequence of positions 1-1226 of SEQ ID NO: 24, which is derived from the N-terminal portion of DCTN1, is fused to a polypeptide having the amino acid sequence of positions 1227-1586 of SEQ ID NO: 24, which is derived from the C-terminal portion of RET.

Examples of the antibody include immunoglobulins (e.g., IgA, IgD, IgE, IgG, IgM, and IgY), Fab fragments, F(ab')$_2$ fragments, single-stranded antibody fragments (scFv), single-domain antibodies, and diabodies (Nat. Rev. Immunol., 6: 343-357, 2006). These include, but are not limited to, monoclonal antibodies and polyclonal antibodies of, for example, human antibodies, humanized antibodies, chimeric antibodies, mouse antibodies, llama antibodies, and chicken antibodies.

The antibody can be prepared by various known methods, and the preparation method is not particularly limited. The known methods include a method in which the polypeptide of the present invention, a polypeptide fragment containing the point of fusion of the N-terminal portion of DCTN1 protein and the C-terminal portion of RET protein, or the like is inoculated into an immunized animal to activate the immune system of the animal, and the serum of the animal is collected to obtain a polyclonal antibody; and a method for obtaining a monoclonal antibody, for example, by the hybridoma method and phage display method.

The method of screening for a compound that inhibits expression and/or activity of the polypeptide of the present invention or expression of the polynucleotide of the present invention can be performed by the method comprising the following steps (1) and (2).

Specifically, the screening method of the present invention is performed by the method comprising:
(1) the step of bringing the polypeptide of the present invention, or a cell expressing the polypeptide and/or the polynucleotide of the present invention into contact with a test compound; and
(2) the step of measuring whether expression and/or activity of the polypeptide of the present invention or expression of the polynucleotide of the present invention is inhibited in step (1), or the step of measuring whether growth of the cell in step (1) is inhibited.

More preferably, the screening method of the present invention is a method comprising the following steps (1) and (2).
(1) The step of bringing a cell expressing the polypeptide and/or polynucleotide of the present invention into contact with a test compound.
(2) The step of measuring whether growth of the cell in step (1) is inhibited.

The method of screening for a compound that inhibits expression and/or activity of the polypeptide of the present invention or expression of the polynucleotide of the present invention can be performed by the method comprising the following steps (1) to (3).

Specifically, the screening method of the present invention is performed by the method comprising:
(1) the step of bringing the polypeptide of the present invention or a cell expressing the polypeptide and/or the polynucleotide of the present invention into contact with a test compound;
(2) the step of measuring whether expression and/or activity of the polypeptide of the present invention, or expression of the polynucleotide of the present invention is inhibited in step (1), or the step of measuring whether growth of the cell in step (1) is inhibited; and
(3) the step of determining that the test compound inhibits expression and/or activity of the polypeptide of the present invention or expression of the polynucleotide of the present invention when expression and/or activity of the polypeptide of the present invention or expression of the polynucleotide of the present invention is inhibited in step (2), or when growth of the cell in step (1) is inhibited in step (2).

More preferably, the screening method of the present invention is a method comprising the following steps (1) to (3).
(1) The step of bringing a cell expressing the polypeptide and/or the polynucleotide of the present invention into contact with a test compound.
(2) The step of measuring whether growth of the cell in step (1) is inhibited.
(3) The step of determining that the test compound inhibits expression and/or activity of the polypeptide of the present invention, or expression of the polynucleotide of the present invention, when growth of the cell in step (1) is inhibited in step (2).

"A cell expressing the polypeptide and/or the polynucleotide of the present invention" includes cells transformed by the expression vector of the present invention, cells introducing the polynucleotide of the present invention by genome editing, primary culture cells expressing the polypeptide and/or polynucleotide of the present invention, cell lines expressing the polypeptide and/or polynucleotide of the present invention, and cancer patient-derived cells expressing the polypeptide and/or polynucleotide of the present invention. Examples of the method for confirming whether the cell is expressing the polypeptide and/or polynucleotide of the present invention include the method for detecting the presence of the polypeptide of the present invention, and the method for detecting the presence of the polynucleotide of the present invention.

In the present invention, "expression of the polypeptide of the present invention or expression of the polynucleotide of the present invention is inhibited" in the phrase "expression and/or activity of the polypeptide of the present invention or expression of the polynucleotide of the present invention is inhibited" means, for example, as follows. A cell expressing the polypeptide and/or polynucleotide of the present invention is brought into contact with a test compound, and the expression level of the polypeptide or polynucleotide of the present invention in the cell is evaluated using the method for detecting the presence of the polypeptide or polynucleotide of the present invention. When the cell brought into contact with the test compound exhibits a statistically significantly lowered expression level of the polypeptide or polynucleotide of the present invention than a cell that has not been brought into contact with the test compound, expression of the polypeptide or polynucleotide of the present invention is determined to be inhibited.

The phrase "activity of the polypeptide of the present invention is inhibited" in the phrase "expression and/or activity of the polypeptide of the present invention or expression of the polynucleotide of the present invention is inhibited" means, for example, as follows. When the polypeptide of the present invention or a cell expressing the polypeptide of the present invention that has been brought into contact with a test compound results in a statistically significantly lowered tyrosine phosphorylation percentage than a polypeptide or cell that has not been brought into contact with the test compound, activity of the polypeptide of the present invention is determined to be inhibited.

When a cell expressing the polypeptide of the present invention that has been brought into contact with a test compound exhibits statistically significantly inhibited cell growth compared with a cell that has not been brought into contact with the test compound, activity of the polypeptide of the present invention is determined to be inhibited.

In the present invention, "tyrosine phosphorylation" includes not only phosphorylation of tyrosine in RET protein (including RET protein fused to other protein), but also phosphorylation of tyrosine in a protein on signaling downstream of RET. Examples of proteins on downstream signaling of RET include STAT, AKT, and ERK. Tyrosine phosphorylation is preferably phosphorylation of tyrosine in RET protein (including RET protein fused to other protein).

"Tyrosine phosphorylation percentage" can be measured using, for example, a phosphorylated RET-specific antibody by Western blotting, immnunoprecipitation, imnunohistochemistry, ELISA, or flow cytometry.

In the present invention, "sample" includes not only biological samples (e.g., cells, tissues, organs, body fluids (e.g., blood and lymph), digestive juice, and urine), but also nucleic acid extracts (e.g., genomic DNA extracts, mRNA extracts, and cDNA preparations and cRNA preparations prepared from mRNA extracts) and protein extracts obtained from these biological samples. The sample may be those subjected to formalin fixation, alcohol fixation, freeze treatment, or paraffin embedding. The biological sample for use may be those collected from a living body, and is preferably a sample derived from a cancer patient, and more preferably a sample containing tumor cells. The method for collecting a biological sample can be suitably selected depending on the type of biological sample.

The present invention encompasses a method for detecting the presence of the polypeptide of the present invention in a sample.

In the present invention, the method for detecting the presence of the polypeptide of the present invention in a sample includes detection methods in accordance with commonly used methods, such as ELISA, Western blotting, or immunohistochemical staining, using an antibody that specifically binds to the polypeptide of the present invention; and FRET (fluorescence resonance energy transfer) using an antibody that specifically binds to DCTN1 protein, and an antibody that specifically binds to RET protein. The detection method is preferably ELISA, Western blotting, or immunohistochemical staining, using an antibody that specifically binds to the polypeptide of the present invention.

The antibody that specifically binds to DCTN1 protein and the antibody that specifically binds to RET protein are preferably an antibody that binds to an N-terminal portion from the point of fusion in DCTN1 protein, and an antibody that binds to a C-terminal portion from the point in fusion of RET protein. These antibodies may be commercially available products, or prepared by a typical known method.

In the present invention, the method for detecting the presence of the polypeptide of the present invention in a sample preferably comprises the step of detecting the polypeptide of the present invention using an antibody that specifically binds to the polypeptide of the present invention, or an antibody that specifically binds to DCTN1 protein and an antibody that specifically binds to RET protein; and more preferably comprises the step of detecting the polypeptide of the present invention using an antibody that specifically binds to the polypeptide of the present invention. The means to detect the presence of the polypeptide of the present invention is not particularly limited, and examples thereof include a combination of an antibody that specifically binds to DCTN1 protein and an antibody that specifically binds to RET protein; and an antibody that specifically binds to the polypeptide of the present invention.

The present invention encompasses a primer or probe for detecting the presence of the polynucleotide of the present invention in a sample. In the present invention, the means to detect the presence of the polypeptide of the present invention is not particularly limited, and examples thereof include a primer or probe for detecting the presence of the polynucleotide of the present invention.

The primer or probe includes polynucleotides selected from the following (j) to (l):

(j) a polynucleotide that is at least one probe selected from the group consisting of probes hybridizing with a polynucleotide encoding DCTN1 protein, and probes hybridizing with a polynucleotide encoding RET protein;

(k) a polynucleotide that is a probe that hybridizes to the point of fusion between a polynucleotide encoding DCTN1 protein and a polynucleotide encoding RET protein; and (l) a polynucleotide that is a set of a sense primer and an antisense primer designed to sandwich the point of fusion between a polynucleotide encoding DCTN1 protein and a polynucleotide encoding RET protein.

In the present invention, "the point of fusion" in the phrase "the point of fusion between a polynucleotide encoding DCTN1 protein and a polynucleotide encoding RET protein" refers to the point at which a polynucleotide encoding DCTN1 protein is fused to a polynucleotide encoding RET protein. The point of fusion in SEQ ID NO: 1 is the point at which a polynucleotide having the base sequence of positions 1-3699 of SEQ ID NO: 1, which is derived from the polynucleotide encoding DCTN1, is fused to a polynucleotide having the base sequence of positions 3700-4905 of SEQ ID NO: 1, which is derived from the polynucleotide encoding RET. The point of fusion in SEQ ID NO: 3 is the point at which a polynucleotide having the base sequence of positions 1-3699 of SEQ ID NO: 3, which is derived from the polynucleotide encoding DCTN1, is fused to a polynucleotide having the base sequence of positions 3700-4779 of SEQ ID NO: 3, which is derived from the polynucleotide encoding RET. The point of fusion in SEQ ID NO: 5 is the point at which a polynucleotide having the base sequence of positions 1-3297 of SEQ ID NO: 5, which is derived from the polynucleotide encoding DCTN1, is fused to a polynucleotide having the base sequence of positions 3298-4503 of SEQ ID NO: 5, which is derived from the polynucleotide encoding RET. The point of fusion in SEQ ID NO: 7 is the point at which a polynucleotide having the base sequence of positions 1-3297 of SEQ ID NO: 7, which is derived from the polynucleotide encoding DCTN1, is fused to a polynucleotide having the base sequence of positions 3298-4377 of SEQ ID NO: 7, which is derived from the polynucleotide encoding RET. The point of fusion in SEQ ID NO: 9 is the point at which a polynucleotide having the base sequence of positions 1-3624 of SEQ ID NO: 9, which is derived from the polynucleotide encoding DCTN1, is fused to a polynucleotide having the base sequence of positions 3625-4830 of SEQ ID NO: 9, which is derived from the polynucleotide encoding RET. The point of fusion in SEQ ID NO: 11 is the point at which a polynucleotide having the base sequence of positions 1-3624 of SEQ ID NO: 11, which is derived from the polynucleotide encoding DCTN1, is fused to a polynucleotide having the base sequence of positions 3625-4704 of SEQ ID NO: 11, which is derived from the polynucleotide encoding RET. The point of fusion in SEQ ID NO: 13 is the point at which a polynucleotide having the base sequence of positions 1-3282 of SEQ ID NO: 13, which is derived from the polynucleotide encoding DCTN1, is fused to a polynucleotide having the base sequence of positions 3283-4488 of SEQ ID NO: 13, which is derived from the polynucleotide encoding RET. The point of fusion in SEQ ID NO: 15 is the point at which a polynucleotide having the base sequence of positions 1-3282 of SEQ ID NO: 15, which is derived from the polynucleotide encoding DCTN1, is fused to a polynucleotide having the base sequence of positions 3283-4362 of SEQ ID NO: 15, which is derived from the polynucleotide encoding RET. The point of fusion in SEQ ID NO: 17 is the point at which a polynucleotide having the base sequence of positions 1-3573 of SEQ ID NO: 17, which is derived from the polynucleotide encoding DCTN1, is fused to a polynucleotide having the base sequence of positions 3574-4779 of SEQ ID NO: 17, which is derived from the polynucleotide encoding RET. The point of fusion in SEQ ID NO: 19 is the point at which a polynucleotide having the base sequence of positions 1-3573 of SEQ ID NO: 19, which is derived from the polynucleotide encoding DCTN1, is fused to a polynucleotide having the base sequence of positions 3574-4653 of SEQ ID NO: 19, which is derived from the polynucleotide encoding RET. The point of fusion in SEQ ID NO: 21 is the point at which a polynucleotide having the base sequence of positions 1-3678 of SEQ ID NO: 21, which is derived from the polynucleotide encoding DCTN1, is fused to a polynucleotide having the base sequence of positions 3679-4884 of SEQ ID NO: 21, which is derived from the polynucleotide encoding RET. The point of fusion in SEQ ID NO: 23 is the point at which a polynucleotide having the base sequence of positions 1-3678 of SEQ ID NO: 23, which is derived from the polynucleotide encoding DCTN1, is fused to a polynucleotide having the base sequence of positions 3679-4758 of SEQ ID NO: 23, which is derived from the polynucleotide encoding RET.

In the present invention, the primer or probe is prepared as a polynucleotide that specifically hybridizes with the polynucleotide of the present invention on the basis of the sequence information of the polynucleotide of the present invention, in accordance with a typical known method. The number of bases for the primer or probe is 10 to 50, preferably 15 to 50, and more preferably 18 to 35.

The primer or probe does not need to be completely complementary, as long as the primer or probe specifically hybridizes with the polynucleotide of the present invention. The primer or probe is a polynucleotide that has at least 70% identity, preferably at least 80% identity, more preferably at least 90% identity, more preferably at least 95% identity, and more preferably at least 98% identity with the corresponding base sequence.

The primer or probe of the present invention is preferably a polynucleotide represented by (i) SEQ ID NO: 69, (ii) SEQ ID NO: 70, or (iii) SEQ ID NO: 71, more preferably a polynucleotide that is a set of a sense primer and an antisense primer represented by (iv) SEQ ID NO: 69 and SEQ ID NO: 70, and more preferably a polynucleotide that is a set of a sense primer, an antisense primer, and a probe represented by (v) SEQ ID NO: 69, SEQ ID NO: 70, and SEQ ID NO: 71.

The present invention encompasses a method for detecting the presence of the polynucleotide of the present invention in a sample.

In the present invention, the method for detecting the presence of the polynucleotide of the present invention in a sample is a detection method in accordance with a commonly used detection method, such as Northern blotting, Southern blotting, RT-PCR, real-time PCR, digital PCR, DNA microarray, in situ hybridization, and sequence analysis.

In the present invention, the method for detecting the presence of the polynucleotide of the present invention in a sample also includes a method for detecting the presence of a polynucleotide of RET fusion gene including the polynucleotide of the present invention. The method includes a method in which a PCR product amplified by the 5' RACE technique using a primer that hybridizes with a polynucleotide encoding RET protein (e.g., a primer that hybridizes with a sequence of the 3' side from the RET kinase domain) is subjected to sequence analysis.

In the present invention, the method for detecting the presence of the polynucleotide of the present invention in a sample preferably comprises the step of detecting the polynucleotide of the present invention using the primer or probe of the present invention.

The present invention encompasses a pharmaceutical composition for treating cancer that is positive for a fusion gene of DCTN1 gene and RET gene and/or positive for a fusion protein of DCTN1 protein and RET protein, the composition comprising a compound that inhibits RET as an active ingredient.

More preferably, the present invention encompasses a pharmaceutical composition for treating cancer that is positive for a fusion gene of DCTN1 gene and RET gene and/or positive for a fusion protein of DCTN1 protein and RET protein, the composition comprising a compound that inhibits expression and/or activity of the polypeptide of the present invention or expression of the polynucleotide of the present invention as an active ingredient.

In the present invention, "cancer that is positive for a fusion gene of DCTN1 gene and RET gene" in the phrase "cancer that is positive for a fusion gene of DCTN1 gene and RET gene and/or positive for a fusion protein of DCTN1 protein and RET protein" refers to cancer that expresses the polynucleotide of the present invention, and preferably to cancer in which the polynucleotide of the present invention has been detected using the method for detecting the presence of the polynucleotide of the present invention.

In the present invention, "cancer that is positive for a fusion protein of DCTN1 protein and RET protein" in the phrase "cancer that is positive for a fusion gene of DCTN1 gene and RET gene and/or positive for a fusion protein of DCTN1 protein and RET protein" refers to cancer that expresses the polypeptide of the present invention, and preferably to cancer in which the polypeptide of the present invention has been detected using the method for detecting the presence of the polypeptide of the present invention.

The active ingredient of the pharmaceutical composition for cancer treatment according to the present invention is a compound that inhibits RET, and more preferably a compound that inhibits expression and/or activity of the polypeptide of the present invention, or expression of the polynucleotide of the present invention. A compound selected by the screening method of the present invention may also be used as an active ingredient. For example, a compound known to inhibit RET can be used as an active ingredient of the pharmaceutical composition of the present invention. The compound that inhibits RET may be a compound that inhibits expression and/or activity of other tyrosine kinases, as long as the compound can inhibit the expression and/or activity of RET, and more preferably a compound that can inhibit the activity of RET and expression and/or activity of other tyrosine kinases. Examples of such compounds include vandetanib, sorafenib, sunitinib, motesanib, cabozantinib, lenvatinib, and compounds described in the WO2016/127074 pamphlet, WO2017/043550 pamphlet, WO2017/011776 pamphlet, and WO2017/146116 pamphlet.

The active ingredient for a pharmaceutical composition for treating cancer positive for a fusion gene of DCTN1 gene and RET gene, and/or positive for a fusion protein of DCTN1 protein and RET protein is a compound that inhibits RET; more preferably vandetanib, cabozantinib, lenvatinib, the fused pyrimidine compound represented by formula (1) disclosed in the WO2017/043550 pamphlet, and the fused pyrimidine compound represented by formula (1) disclosed in the WO2017/146116 pamphlet; more preferably vandetanib, cabozantinib, lenvatinib, Example Compounds 1 to 90 disclosed in the WO2017/043550 pamphlet, and Example Compounds 1 to 207 disclosed in the WO2017/146116 pamphlet; still more preferably vandetanib, cabozantinib, lenvatinib, 4-amino-1-(tert-butyl)-N-(5-methyl-1H-pyrazol-3-yl)-1H-pyrazolo[3,4-d]pyrimidine-3-carboxamide, 4-amino-7-(tert-butyl)-N-(5-methyl-1H-pyrazol-3-yl)-7H-pyrrolo[2,3-d]pyrimidine-5-carboxamide, 4-amino-7-(1-fluoro-2-methylpropan-2-yl)-N-(5-methyl-1H-pyrazol-3-yl)-7H-pyrrolo[2,3-d]pyrimidine-5-carboxamide, 4-amino-N-(5-methyl-1H-pyrazol-3-yl)-7-(1-methylcyclopropyl)-7H-pyrrolo[2,3-d]pyrimidine-5-carboxamide, 4-amino-7-(2-cyclopropylpropan-2-yl)-N-(5-methyl-1H-pyrazol-3-yl)-7H-pyrrolo[2,3-d]pyrimidine-5-carboxamide, 4-amino-N-[4-(methoxymethyl)phenyl]-7-(1-methylcyclopropyl)-6-(3-morpholinopro-1-pyn-1-yl)-7H-pyrrolo[2,3-d]pyrimidine-5-carboxamide, 4-amino-N-[4-(methoxymethyl)phenyl]-7-(1-methylcyclopropyl)-6-((tetrahydro-2H-pyran-4-yl)ethynyl)-7H-pyrrolo[2,3-d]pyrimidine-5-carboxamide, (R)-4-amino-N-[4-(methoxymethyl)phenyl]-7-(1-methylcyclopropyl)-6-((tetrahydrofuran-2-yl)methoxy)-7H-pyrrolo[2,3-d]pyrimidine-5-carboxamide, and 4-amino-N-[4-(methoxymethyl)phenyl]-6-((1-methyl-1H-pyrazol-4-yl)ethynyl)-7-(1-methylcyclopropyl)-7H-pyrrolo[2,3-d]pyrimidine-5-carboxamide; and particularly preferably 4-amino-1-(tert-butyl)-N-(5-methyl-1H-pyrazol-3-yl)-1H-pyrazolo[3,4-d]pyrimidine-3-carboxamide, 4-amino-7-(tert-butyl)-N-(5-methyl-1H-pyrazol-3-yl)-7H-pyrrolo[2,3-d]pyrimidine-5-carboxamide, 4-amino-7-(1-fluoro-2-methylpropan-2-yl)-N-(5-methyl-1H-pyrazol-3-yl)-7H-pyrrolo[2,3-d]pyrimidine-5-carboxamide, 4-amino-N-(5-methyl-1H-pyrazol-3-yl)-7-(1-methylcyclopropyl)-7H-pyrrolo[2,3-d]pyrimidine-5-carboxamide, 4-amino-7-(2-cyclopropylpropan-2-yl)-N-(5-methyl-1H-pyrazol-3-yl)-7H-pyrrolo[2,3-d]pyrimidine-5-carboxamide, 4-amino-N-[4-(methoxymethyl)phenyl]-7-(1-methylcyclopropyl)-6-(3-morpholinopro-1-pyn-1-yl)-7H-pyrrolo[2,3-d]pyrimidine-5-carboxamide, 4-amino-N-[4-(methoxymethyl)phenyl]-7-(1-methylcyclopropyl)-6-((tetrahydro-2H-pyran-4-yl)ethynyl)-7H-pyrrolo[2,3-d]pyrimidine-5-carboxamide, (R)-4-amino-N-[4-(methoxymethyl)phenyl]-7-(1-methylcyclopropyl)-6-((tetrahydrofuran-2-yl)methoxy)-7H-pyrrolo[2,3-d]pyrimidine-5-carboxamide, and 4-amino-N-[4-(methoxymethyl)phenyl]-6-((1-methyl-1H-pyrazol-4-yl)ethynyl)-7-(1-methylcyclopropyl)-7H-pyrrolo[2,3-d]pyrimidine-5-carboxamide.

In the present invention, "can inhibit the expression of RET" in the phrase "the compound can inhibit the expression and/or activity of RET" means, for example, as follows. A cell expressing the polypeptide and/or polynucleotide of RET is brought into contact with a test compound, and the expression level of the polypeptide or polynucleotide of RET in the cell is detected. When the cell brought into contact with the test compound exhibits a lowered expression level of the polypeptide or polynucleotide of RET than a cell that has not been brought into contact with the test compound, the expression of RET is determined to be inhibited. Such compounds include compounds described above, siRNA, miRNA, and nucleic acid (DNA, RNA) aptamers. Examples of siRNA include CACAUGUCAU-CAAAUUGUAUU (SEQ ID NO: 74), GGAUUGAAAACAAACUCUAUU (SEQ ID NO: 75), and GCUUGUCCCGAGAUGUUUAUU (SEQ ID NO: 76); and siRNA is preferably CACAUGUCAUCAAAUUGUATT (SEQ ID NO: 74) or GGAUUGAAAACAAACUCUATT (SEQ ID NO: 75).

Whether a compound "can inhibit the activity of RET" in the phrase "the compound can inhibit the expression and/or activity of RET" can be determined using tyrosine phosphorylation as an indicator. Examples of the method for measuring tyrosine phosphorylation include a method described in Test Example 1 in WO2017/043550 pamphlet.

Additionally, a compound can be determined as being able to inhibit the activity of RET using a cell expressing the polypeptide and/or polynucleotide of RET, with the cell growth inhibitory effect being an indicator. Examples of a method for measuring the cell growth inhibitory effect include a method described in Test Example 3 and Test Example 4 of WO2017/043550 pamphlet.

The cancer targeted by the pharmaceutical composition of the present invention is not particularly limited, as long as the cancer expresses the polynucleotide and/or the polypeptide of the present invention, and examples include head and neck cancer, thyroid cancer, gastroenterological cancer (e.g., esophageal cancer, stomach cancer, duodenal cancer, liver cancer, biliary tract cancer (e.g., gallbladder cancer and bile duct cancer), pancreas cancer, small intestine cancer, bowel cancer (e.g., colorectal cancer, colon cancer, rectal cancer), and gastrointestinal stromal tumor), lung cancer (non-small-cell lung cancer, small-cell lung cancer), breast cancer, ovarian cancer, uterus cancer (e.g., cervical cancer, endometrial cancer), kidney cancer, bladder cancer, prostate cancer, and skin cancer. The cancer is preferably thyroid cancer or lung cancer (non-small-cell lung cancer, small-cell lung cancer). The cancer as used herein includes not only primary tumors, but also cancer that has spread to other organs (e.g., liver).

A preparation containing a compound that inhibits expression and/or activity of the polypeptide of the present invention or expression of the polynucleotide of the present invention as an active ingredient can be prepared in the form of a pharmaceutical composition containing a pharmaceutical carrier so as to suit a variety of dosage forms. Examples of dosage forms include oral agents, injections, suppositories, ointments, and patches. These dosage forms can be prepared by preparation methods known and common to a person skilled in the art.

The pharmaceutical carrier for use includes various organic or inorganic carrier substances commonly used as preparation materials, and these are added as excipients, binders, disintegrators, lubricants, coating agents, and the like for solid formulations; and solvents, solubilizing agents, suspending agents, tonicity agents, pH regulators and buffers, soothing agents, and the like for liquid formulations. Optionally usable are additives for formulations, such as preservatives, antioxidants, colorants, flavorings, and stabilizers.

In preparing an oral solid formulation, an excipient, optionally with an excipient, a binder, a disintegrator, a lubricant, a colorant, a flavoring, etc., is added to the compound of the present invention, and then tablets, coated tablets, granules, powders, capsules, and the like are produced in accordance with an ordinary method.

In preparing an oral liquid formulation, a pH regulator and a buffer, a stabilizer, a flavoring, and the like are added to the compound of the present invention, and an internal liquid medicine, a syrup medicine, an elixir, and the like are produced in accordance with an ordinary method.

In preparing an injections, a pH regulator and a buffer, a stabilizer, a tonicity agent, a local anesthetic, and the like are added to the compound of the present invention, and then a subcutaneously, intramuscularly, or intravenously injection is produced in accordance with an ordinary method.

The present invention encompasses a method for diagnosing cancer when the presence of the polypeptide of the present invention or the polynucleotide of the present invention is detected in a sample by the method for detecting the presence of the polypeptide of the present invention, or by the method for detecting the presence of the polynucleotide of the present invention. The cancer diagnosed in this invention includes those listed as targets of the pharmaceutical composition of the present invention. As described above, the use of the polypeptide or polynucleotide of the present invention enables diagnosis of cancer. Thus, the polypeptide and the polynucleotide of the present invention can be used as a biomarker for detecting cancer.

The present invention encompasses a method using the polypeptide of the present invention or the polynucleotide of the present invention as an indicator for determining whether a chemotherapy using a compound that inhibits RET is effective, the method determining that the chemotherapy using the compound that inhibits RET is effective when the polypeptide of the present invention is detected in a sample by the detection method of the present invention, and/or when the presence of the polynucleotide of the present invention is detected in a sample by the detection method of the present invention.

More preferably, the present invention encompasses a method using the polypeptide of the present invention or the polynucleotide of the present invention as an indicator for determining whether a chemotherapy using a compound that inhibits expression and/or activity of the polypeptide of the present invention, or expression of the polynucleotide of the present invention, is effective, the method determining that the chemotherapy using the compound that inhibits expression and/or activity of the polypeptide of the present invention, or expression of the polynucleotide of the present invention, is effective when the polypeptide of the present invention is detected in a sample by the detection method of the present invention, and/or when the presence of the polynucleotide of the present invention is detected in a sample by the detection method of the present invention.

More preferably, the present invention encompasses a method using the polypeptide of the present invention or the polynucleotide of the present invention as an indicator for determining whether a chemotherapy using a compound obtained in the screening method of the present invention is effective, the method determining that the chemotherapy using the compound obtained in the screening method of the present invention is effective when the polypeptide of the present invention is detected in a sample by the detection method of the present invention, and/or when the presence of the polynucleotide of the present invention is detected in a sample by the detection method of the present invention.

The following Examples describe the present invention in detail. However, the present invention is not limited to these Examples.

EXAMPLES

Example 1: Preparation of Fusion Gene of DCTN1 Gene and RET Gene (DCTN1-RET Fusion Gene)

1-1: Extraction of RNA Derived from Clinical Specimen

RNA was extracted from a human thyroid cancer tissue purchased from Asterand Bioscience using an RNeasy Mini Kit (Qiagen) in accordance with the following method. 600

µL of Buffer RLT was added to the thyroid cancer tissue, and applied to a QIAshredder spin column, followed by centrifugation (16,000 rpm, 2 minutes, room temperature), thereby collecting the filtrate. An equivalent amount of a 70% ethanol aqueous solution was added to the collected filtrate. After they were mixed, the mixture was applied to an RNeasy Mini column, and then centrifuged (10,000 rpm, 15 seconds, room temperature). 700 µL of Buffer RW1 was added to an RNeasy Mini column, and centrifuged (10,000 rpm, 15 seconds, room temperature). 500 µL of Buffer RPE was further added thereto, and centrifuged (10,000 rpm, 15 seconds, room temperature). In the same manner, 500 µL of Buffer RPE was added again, and centrifuged (10,000 rpm, 2 minutes, room temperature). The RNeasy Mini column was centrifuged again (16,000 rpm, 1 minute, room temperature), and the remaining buffer was removed. 40 µL of RNase-free water was applied to the RNeasy Mini column and centrifuged (10,000 rpm, 1 minute, room temperature), thereby collecting the filtrate as total RNA.

1-2: Preparation of cDNA Derived from Clinical Specimen cDNA was synthesized from the total RNA obtained in section 1-1 above using a SuperScript VILO cDNA Synthesis Kit (Invitrogen) in accordance with the following method. 500 ng of total RNA was adjusted with RNAse-free water to give an amount of 14 µL, and 4 µL of 5×VILO Reaction Mix and 2 µL of 10×SuperScript Enzyme Mix were added thereto and mixed. The mixture was kept warm at 25° C. for 10 minutes, and subsequently kept warm at 42° C. for 60 minutes. To stop the reaction, the mixture was finally incubated at 85° C. for 5 minutes, thereby obtaining cDNA.

1-3: Preparation and Purification of Cloning Vector

To amplify DCTN1-RET fusion gene, primers shown in Table 1 were designed: primer 1 (SEQ ID NO: 33) as a sense primer and primer 2 (SEQ ID NO: 34) as an antisense primer, as well as primer 3 (SEQ ID NO: 35) as a sense primer and primer 4 (SEQ ID NO: 36) as an antisense primer for use in nested PCR.

TABLE 1

| Primer 1 | 5'-TGTCCAGCTTTGTGCCTGATTG ATGT-3' | SEQ ID NO: 33 |
| --- | --- | --- |
| Primer 2 | 5'-GCTGGGCACTGAAGAGAAAGGA ATGC-3' | SEQ ID NO: 34 |
| Primer 3 | 5'-AGCAGGATGAGTGCGGAGGCAA GC-3' | SEQ ID NO: 35 |
| Primer 4 | 5'-TTAACTATCAAACGTGTCCATT AATTTTGCCGC-3' | SEQ ID NO: 36 |

DCTN1-RET fusion gene was amplified with cDNA synthesized in section 1-2 above as a template using these primers and using KOD-Plus-Neo (Toyobo) in accordance with the following method. 2 µL of cDNA, 5 µL of 10×PCR Buffer for KOD-Plus-Neo, 5 µL of 2 mM dNTPs, 3 µL of 25 mM MgSO$_4$, 1 µL of KOD-Plus-Neo, 1.5 µL of primer 1 (10 µM), 1.5 µL of primer 2 (10 µM), and 31 µL of double distilled water (DDW) were mixed; and PCR was performed. Subsequently, the obtained PCR product was diluted by a factor of 100, and 2 µL of the diluted PCR product, 5 µL of 10×PCR Buffer for KOD-Plus-Neo, 5 µL of 2 mM dNTPs, 3 µL of 25 mM MgSO$_4$, 1 µL of KOD-Plus-Neo, 1.5 µL of primer 3 (10 µM), 1.5 µL of primer 4 (10 µM), and 31 µL of DDW were mixed; and nested PCR was performed.

The nested PCR product was separated by electrophoresis using 1% agarose gel (Nacalai Tesque), and the PCR product was purified from the gel using a QIAquick Gel Extraction Kit (Qiagen).

pUC18 DNA (Takara Bio Inc.) cleaved by a restriction enzyme SmaI (NEB), the purified PCR product, T4 DNA ligase (NEB), and T4 DNA ligase reaction buffer (NEB) were mixed, and the mixture was incubated at 16° C. overnight. The ligation product was treated with SmaI (NEB), and transformation of competent cells was performed by the following method. The ligation product treated with SmaI was added to 50 µL of *E. coli* DH5a competent cells (Takara Bio Inc.), and allowed to stand on ice for 30 minutes. Thereafter, the cells were subjected to heat shock at 42° C. for 30 seconds, and allowed to stand on ice for 2 minutes. A SOC medium (Takara Bio Inc.) was added thereto, and the cells were cultured with shaking at 37° C. for 1 hour. The culture solution was then applied onto an ampicillin-containing LB agar medium plate (Unitech), and allowed to stand at 37° C. overnight. The *E. coli* colonies were suspended in an ampicillin-containing LB medium (InvivoGen), and cultured with shaking at 37° C. overnight. Plasmid DNA inserting DCTN1-RET fusion gene was purified from the proliferated *E. coli* using a QIAquick Spin Miniprep Kit (Qiagen) in accordance with the protocol provided with the kit.

1-4: Determination of Sequence

A sequence reaction was performed with the plasmid DNA obtained in section 1-3 above as a template, using primers 5 to 36 for sequencing shown in Table 2 and using a BigDye Terminator V3.1 Cycle Sequencing Kit; and sequence analysis was performed using an Applied Biosystems 3730xl DNA Analyzer. The results of the sequence analysis revealed that DCTN1-RET fusion gene was a gene (SEQ ID NO: 17) in which exons 12 to 20 of RET variant 2 (GenBank accession number: NM_020975) were fused downstream of the 3' side of exons 1 to 27 of DCTN1 variant 5 (GenBank accession number: NM_001190836).

TABLE 2

| Primer 5 | 5'-AGTACTGGGGTGGCTGGG-3' | SEQ ID NO: 37 |
| --- | --- | --- |
| Primer 6 | 5'-CACTTTGGACAAGGAGATG-3' | SEQ ID NO: 38 |
| Primer 7 | 5'-ACAGAACTGGAGCTGCGG-3' | SEQ ID NO: 39 |
| Primer 8 | 5'-GGACTGGTGTACTCGCTG-3' | SEQ ID NO: 40 |
| Primer 9 | 5'-TCCTAGACTGCAGGAAACAC-3' | SEQ ID NO: 41 |
| Primer 10 | 5'-CATCGAGAAAGTCCAGAC-3' | SEQ ID NO: 42 |
| Primer 11 | 5'-GCTGCTGGAGACATTGAA-3' | SEQ ID NO: 43 |
| Primer 12 | 5'-TCACTGCTGCTCAGCTCA-3' | SEQ ID NO: 44 |
| Primer 13 | 5'-GAGGATCCAAAGTGGGAATT-3' | SEQ ID NO: 45 |
| Primer 14 | 5'-AGTATCTGGCCGAGATGAAG-3' | SEQ ID NO: 46 |

TABLE 2-continued

| | | |
|---|---|---|
| Primer 15 | 5'-GCAAAGACCTGGAGAAGATG-3' | SEQ ID NO: 47 |
| Primer 16 | 5'-AGGACGTTGAACTCTGACAG-3' | SEQ ID NO: 48 |
| Primer 17 | 5'-CCTTTGCTTCATCCAGAATC-3' | SEQ ID NO: 49 |
| Primer 18 | 5'-GATTTTGTGTTTCTCCAGCTCT-3' | SEQ ID NO: 50 |
| Primer 19 | 5'-CCTGCTTCTCTGAGGAAGAA-3' | SEQ ID NO: 51 |
| Primer 20 | 5'-GGGCCTTAGTCTCAGCAAAC-3' | SEQ ID NO: 52 |
| Primer 21 | 5'-GAGCACTCTGCGTGAACTTA-3' | SEQ ID NO: 53 |
| Primer 22 | 5'-CAGCTTGTTCATGGTACTGAT-3' | SEQ ID NO: 54 |
| Primer 23 | 5'-TGGTGAGTCCTTCACCAG-3' | SEQ ID NO: 55 |
| Primer 24 | 5'-CCTAGAGTTTTTCCAAGAACCA-3' | SEQ ID NO: 56 |
| Primer 25 | 5'-CATTTAACTGGAATCCGACC-3' | SEQ ID NO: 57 |
| Primer 26 | 5'-GACTCTCTCCAGGCCAGTTC-3' | SEQ ID NO: 58 |
| Primer 27 | 5'-GGCTATCAGAAGTAAAACCACC-3' | SEQ ID NO: 59 |
| Primer 28 | 5'-CGAGAGCTGATGGCACTA-3' | SEQ ID NO: 60 |
| Primer 29 | 5'-CTTCATCACAAGTGAAGTACTTCC-3' | SEQ ID NO: 61 |
| Primer 30 | 5'-CGTACTCCACGATGAGGAG-3' | SEQ ID NO: 62 |
| Primer 31 | 5'-GATTCTGGATGAAGCAAAGG-3' | SEQ ID NO: 63 |
| Primer 32 | 5'-GGAAGTACTTCACTTGTGATGAAG-3' | SEQ ID NO: 64 |
| Primer 33 | 5'-CCCAGCCACCCCAGTACT-3' | SEQ ID NO: 65 |
| Primer 34 | 5'-GTAAAACGACGGCCAGT-3' | SEQ ID NO: 66 |
| Primer 35 | 5'-GTTTTCCCAGTCACGAC-3' | SEQ ID NO: 67 |
| Primer 36 | 5'-CAGGAAACAGCTATGAC-3' | SEQ ID NO: 68 |

Example 2: Detection of DCTN1-RET Fusion Gene cDNA was synthesized from normal human thyroid tissue-derived RNA purchased from Asterand Bioscience and human thyroid cancer tissue-derived RNA obtained in section 1-1 using a SuperScript VILO cDNA Synthesis Kit (Invitrogen) in accordance with the following method. 280 ng of total RNA was adjusted with RNAse-free water to give an amount of 14 µL, and 4 µL of 5×VILO Reaction Mix and 2 µL of 10×SuperScript Enzyme Mix were added respectively thereto and mixed. The mixture was kept warm at 25° C. for 10 minutes, and subsequently kept warm at 42° C. for 60 minutes. To end the reaction, the mixture was finally incubated at 85° C. for 5 minutes.

To detect DCTN1-RET fusion gene, primers and a probe shown in Table 3 were designed: primer 37 (SEQ ID NO: 69) as a sense primer for detecting DCTN1-RET fusion gene, primer 38 (SEQ ID NO: 70) as an antisense primer for detecting DCTN1-RET fusion gene, and primer 39 (SEQ ID NO: 71) as a probe for detecting DCTN1-RET fusion gene (probe: TaqMan MGB probe; fluorescent dye: FAM (Thermo Fisher Scientific)).

TABLE 3

| | | |
|---|---|---|
| Primer 37 | 5'-CTGGAGCCACAGTACCCACT-3' | SEQ ID NO: 69 |
| Primer 38 | 5'-TCCAAATTCGCCTTCTCCTA-3' | SEQ ID NO: 70 |
| Primer 39 | 5'-TTCATCAGCCTTCCTCAGGGAGGAT-3' | SEQ ID NO: 71 |

Figure 2:
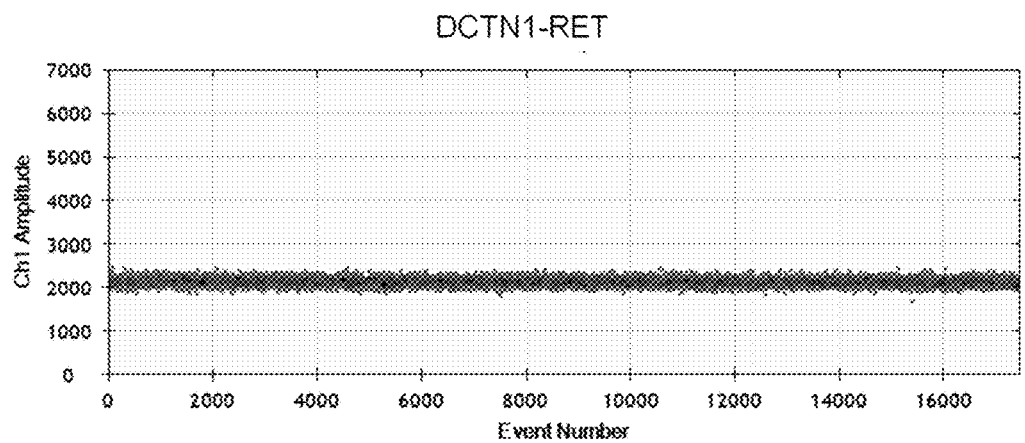
FIG. 2: Confirmation of the expression of DCTN1-RET fusion gene and GAPDH in a normal thyroid tissue using Droplet Digital PCR (ddPCR).
Figure 2:
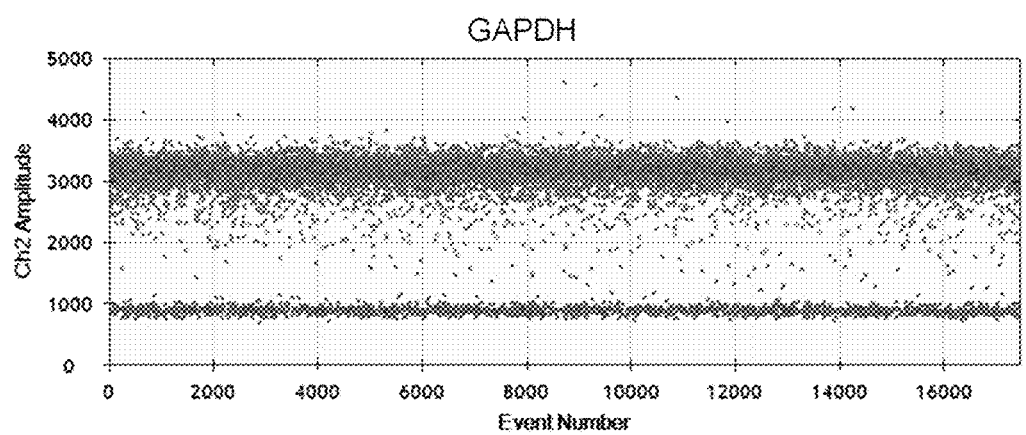

The obtained cDNA was diluted by a factor of 10, and 1.1 µL thereof was used as a template. 11 µL of ddPCR Supermix for probe (Bio-Rad), 2 µL of primer 37 (10 µM), 2 µL of primer 38 (10 µM), 0.6 µL of primer 39 (10 µM), and 1.1 µL of 20×HEX assay for detecting GAPDH (Prime PCR ddPCR Expression Probe Assay: GAPDH, Human, Bio-Rad) were mixed; and droplets were prepared using an automated droplet generator (Bio-Rad). PCR was performed on the prepared droplets, and droplets positive for DCTN1-RET and GAPDH were counted with a droplet reader (Bio-Rad). FIGS. 1 and 2 show the results.

Figure 3:
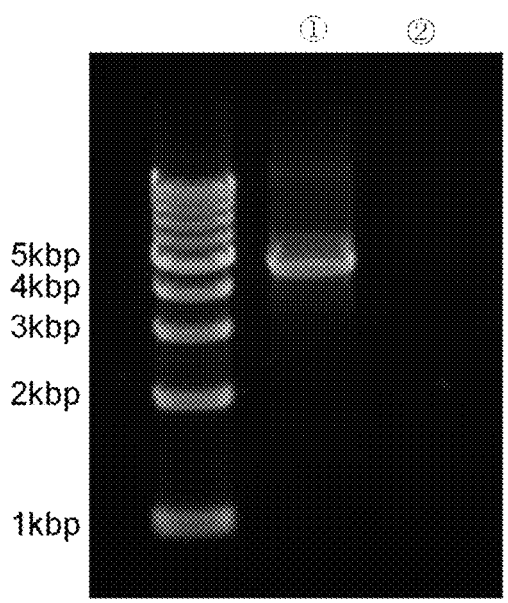
FIG. 3: Confirmation of the expression of a full-length DCTN1-RET fusion gene in a normal thyroid tissue and a thyroid cancer tissue.

DCTN1-RET fusion gene was amplified with the cDNA synthesized above as a template using KOD-Plus-Neo (Toyobo) in accordance with the following method. 2 µL of cDNA, 5 µL of 10×PCR buffer for KOD-Plus-Neo, 5 µL of 2 mM dNTPs, 3 µL of 25 mM MgSO$_4$, 1 µL of KOD-Plus-Neo, 1.5 µL of primer 1 (10 µM), 1.5 µL of primer 2 (10 µM), and 31 µL of DDW were mixed, and PCR was performed. Subsequently, the obtained PCR product was diluted by a factor of 100, and 2 µL of the diluted PCR product, 5 µL of 10×PCR Buffer for KOD-Plus-Neo, 5 µL of 2 mM dNTPs, 3 µL of 25 mM MgSO$_4$, 1 µL of KOD-Plus-Neo, 1.5 µL of primer 3 (10 µM), 1.5 µL of primer 4 (10 µM), and 31 µL of DDW were mixed; and nested PCR was performed. The nested PCR product was separated by electrophoresis using 1% agarose gel (Nacalai Tesque), and photographed. FIG. 3 shows the results.

As shown in FIG. 1, FIG. 2, and FIG. 3, while DCTN1-RET fusion gene was detected in cDNA synthesized from human thyroid cancer tissue-derived RNA, DCTN1-RET fusion gene was not detected in cDNA synthesized from normal human thyroid tissue-derived RNA. These results indicate that DCTN1-RET fusion gene is useful as a biomarker for cancer.

Example 3: Construction of Expression Vector for DCTN1-RET Fusion Gene

To construct an expression vector, Primer 40 (SEQ ID NO: 72) as a sense primer and Primer 41 (SEQ ID NO: 73) as an antisense primer were designed as shown in Table 4.

TABLE 4

| Primer 40 | 5'-GGGGACAAGTTTGTACAAAAAAGCAGG CTTCGCCACCAGCAGGATGAGTGCGGAGGC AAGCGCCCGG-3' | SEQ ID NO: 72 |
|---|---|---|
| Primer 41 | 5'-GGGGACCACTTTGTACAAGAAAGCTGG GTTTTAACTATCAAACGTGTCCATTAATTT TGC-3' | SEQ ID NO: 73 |

A DCTN1-RET fusion gene was amplified using these primers, cDNA synthesized in section 1-2 above as a template, and Prime STAR Max DNA Polymerase (TaKaRa) in accordance with the method described below. 1 µL of cDNA, 25 µL of 2×Prime STAR Max DNA Polymerase, 1 µL of Primer 40 (10 µM), 1 µL of Primer 41 (10 µM), and 22 µL of double-distilled water (DDW) were mixed to perform PCR. The obtained PCR product was separated by electrophoresis using 1% agarose gel (Nacalai Tesque), and the PCR product was purified from the gel using GFX PCR DNA and Gel Band Purification Kit (GE Healthcare). Subsequently, the purified PCR product was inserted into a Gateway pDONR221 Vector using a Gateway BP Clonase II Enzyme Mix (Thermo Fisher) in accordance with the method described below, thereby preparing an entry vector. Specifically, 5.0 µL of the purified PCR product, 3.5 µL of pDONR221 (85 ng/µL), 4.0 µL of BP Clonase II Enzyme Mix, and 7.5 µL of TE were mixed and incubated at 25° C. for 90 minutes. After incubation, 1 µL of Proteinase K (2 mg/mL) was added thereto, followed by incubation at 37° C. for 10 minutes, thereby preparing the entry vector.

The obtained entry vector was added to 50 µL of *E. coli* DH5a Competent Cells (Takara Bio Inc.), and allowed to stand on ice for 30 minutes. Thereafter, the cells were given heat shock at 37° C. for 20 seconds, and allowed to stand for 2 minutes on ice. A SOC medium (Takara Bio Inc.) was then added thereto, and the cells were subjected to shaking culture at 37° C. for 1 hour. The culture solution was then applied onto a Kanamycin-containing LB agar medium plate, and allowed to stand at 37° C. overnight. The *Escherichia coli* colonies were suspended in a Kanamycin-containing LB medium, and subjected to shaking culture at 370° C. overnight. From the grown *Escherichia coli*, a DCTN1-RET fusion gene inserted-plasmid DNA (entry vector clone) was purified with a GENE PREP STAR PI-480 automated DNA isolation system (Kurabo Industries Ltd.).

The DCTN1-RET fusion gene was inserted into a pJTI Fast DEST vector using the obtained plasmid and a Gateway LR Clonase II Enzyme Mix (Thermo Fisher) in accordance with the method described below, thereby preparing an expression vector. 150 ng of the entry vector clone, 1 µL of a pJTI Fast DEST vector (150 ng/µL), 2 µL of an LR Clonase II Enzyme Mix, and a TE buffer were mixed to give 10 µL in total, and the mixture was incubated at 25° C. for 90 minutes. After incubation, 1 µL of Proteinase K (2 mg/mL) was added thereto, followed by incubation at 37° C. for 10 minutes, thereby obtaining a DCTN1-RET fusion gene-inserted pJTI Fast DEST vector (DCTN1-RET fusion gene expression vector). The obtained DCTN1-RET fusion gene expression vector was added to 50 µL of *E. coli* DH5a Competent Cells (Takara Bio Inc.), and allowed to stand for 30 minutes on ice. Thereafter, the cells were then given heat shock at 37° C. for 20 seconds, and allowed to stand for 2 minutes on ice. A SOC medium (Takara Bio Inc.) was then added thereto, and the cells were subjected to shaking culture at 37° C. for 1 hour. The culture solution was applied onto an ampicillin-containing LB agar medium plate, and allowed to stand at 37° C. overnight. The *Escherichia coli* colonies were suspended in an ampicillin-containing LB medium, and subjected to shaking culture at 37° C. overnight. From the grown *Escherichia coli*, a DCTN1-RET fusion gene-inserted plasmid DNA (DCTN1-RET fusion gene expression vector) was purified using a Plasmid Plus Maxi Kit (QIAGEN).

Example 4: Establishment of DCTN1-RET Fusion Gene-Expressing Cell 4-1: Establishment of Cell For the host cell for establishing a DCTN1-RET fusion gene-expressing cell, mouse embryonic fibroblast NIH/3T3 cells (American Type Culture Collection) were chosen, and the cells were transfected with the DCTN1-RET fusion gene-inserted expression vector prepared above, thereby establishing a DCTN1-RET fusion gene-expressing cell. The details of the procedure are as follows. NIH/3T3 cells were prepared by culture in a medium for typical culture (2-dimensional cell culture) at 37° C. in 5% $CO_2$; and the medium for use in the 2-dimensional cell culture was prepared by adding newborn calf serum (NBCS) (Gibco) to D-MEM (high glucose) (containing L-glutamine, phenol red, sodium pyruvate, 1500 mg/L sodium hydrogen carbonate) (Wako) to give 10%. On the day before performing transfection, NIH/3T3 cells were seeded onto a 6-well plate (Iwaki) at $1.5 \times 10^5$ cells/2 mL, and incubated at 37° C. in 5% $CO_2$ overnight. A ViaFect transfection reagent was added to a mixture solution prepared by mixing 1.5 µg of the DCTN1-RET fusion gene expression vector and 1.5 µg of a pJTI phiC31 integrase vector such that the amount of the ViaFect transfection reagent was six times the amount of the mixture solution; and then Opti-MEM was added thereto to give a total amount of 300 µL, followed by incubation at room temperature for 5 minutes, thereby preparing a transfection solution. From the wells on which NIH/3T3 cells were seeded, 300 µL of the medium was removed, and 300 µL of the prepared transfection solution was added to the wells, followed by incubation at 37° C. in 5% $CO_2$ overnight. The next day, the medium was replaced to remove the transfection solution. When replacing the medium, hygromycin B (Nacalai Tesque) was added to a new medium to give 500 µg/mL. Hygromycin B removed cells that did not transfect the DCTN1-RET fusion gene-inserted expression vector. After transfection, while replacing the medium about twice a week, the cells were cultured until they proliferated. After 22 days from the transfection, the cells were collected with trypsin, and single-cell cloning was performed in accordance with the following method. The number of cells collected was measured, and a medium was added thereto to give 1 cell/200 µL. The cells were seeded onto a 96-well plate (Thermo Fisher) to give 200 µL per well. After seeding, the cells were observed daily, and cells grown from a single cell were taken; these cells were DCTN1-RET fusion gene-expressing cells (DCTN1-RET fusion gene-expressing NIH/3T3 cells).

4-2: Confirmation of Expression of Target Protein

Figure 4:
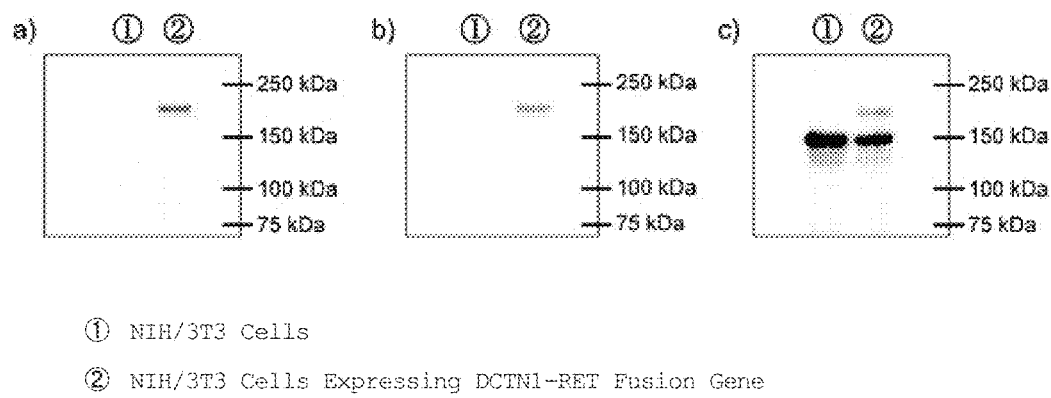
FIG. 4: Confirmation of the expression of DCTN1-RET fusion protein in DCTN1-RET fusion gene-expressing NIH/3T3 cells:
a) Detection of a DCTN1-RET fusion protein using an anti-phosphorylated RET antibody;
b) Detection of a DCTN1-RET fusion protein using an anti-RET antibody; and
c) Detection of a DCTN1-RET fusion protein using an anti-DCTN1 antibody.

The expression of DCTN1-RET fusion protein in the obtained DCTN1-RET fusion gene-expressing NIH/3T3 cells was confirmed by western blotting. Specifically, the medium was removed from the culture flask, followed by washing with PBS once. Sample Diluent Concentrate 2 (R&D Systems) containing a phosphatase inhibitor (Roche) and a protease inhibitor (Roche) was added to the culture flask, and the cell lysate was collected with a scraper. From the collected cell lysate, a protein sample was obtained by centrifugation. The protein sample was subjected to protein determination, and the protein concentration was adjusted to a prescribed concentration. A sample buffer solution with reducing reagent (6×) for SDS-PAGE (Nacalai Tesque) was added to the protein sample of a prescribed concentration; and the mixture was incubated at 95° C. for 5 minutes to denature the protein, thereby obtaining a sample for use in western blotting. For negative control, a sample for western blotting was obtained using NIH/3T3 cells (parental cell line) in accordance with the same procedure. The expression of the protein was confirmed using the samples in accordance with the method described below. The protein was separated using a 4-15% acrylamide gel (Bio-Rad) and 1× Tris/Glycine/SDS buffer by SDS-PAGE (for 30 minutes at 200 V). The protein was transferred onto a PVDF membrane using a Trans-Blot Turbo RTA Midi PVDF Transfer Kit (Bio-Rad) and a Trans-Blot Turbo transcription system (Bio-Rad), and the PVDF membrane was immersed in Blocking One-P for 1 hour. A solution was prepared by diluting Blocking One-P with TBS-T to give 10%, and a primary antibody (Phospho-RET (Tyr905) Antibody (CST), Ret (C31B4) Rabbit mAb (CST), and Anti-Dctn1 Antibody (Atlas Antibodies)) was diluted with the prepared solution to give a concentration of 1/1000. The PVDF membrane was immersed in the resulting solution, and incubated at 4° C. overnight. After being washed with TBS-T, the PVDF membrane was immersed in a secondary antibody dilution solution that was prepared by diluting an anti-rabbit IgG, HRP-linked antibody (CST) with TBS-T to give a concentration of 1/2000; and incubated at room temperature for 1 hour. After the membrane was washed with TBS-T, the protein was detected using a SuperSignal West Dura Extended Duration Substrate (Thermo Fisher) with an Amersham Imager 600 lumino image analyzer (GE Healthcare). The molecular weight of the detected protein was confirmed with Precision Plus Protein Kaleidoscope Prestained Protein Standards (Bio-Rad). As shown in FIG. 4a) and 4b), endogenous RET (150 and 175 kDa) was not detected when the anti-pRET antibody or the anti-RET antibody was used. However, a band that appeared to be of the DCTN1-RET fusion protein was confirmed at around 175 kDa only in the DCTN1-RET fusion gene-expressing NIH/3T3 cells. Additionally, as shown in FIG. 4c), endogenous DCTN1 was detected at around 150 kDa in the use of the anti-DCTN1 antibody. A band was also detected at around 175 kDa above the band of endogenous DCTN1 at around 150 kDa only in the DCTN1-RET fusion gene-expressing NIH/3T3 cells. Specifically, a band at around 175 kDa was detected both in the use of the antibody against RET and the antibody against DCTN1 only in the DCTN1-RET fusion gene-expressing NIH/3T3 cells; this clearly indicates that a fusion protein of DCTN1 and RET was expressed in the prepared DCTN1-RET fusion gene-expressing NIH/3T3 cells.

Figure 5:
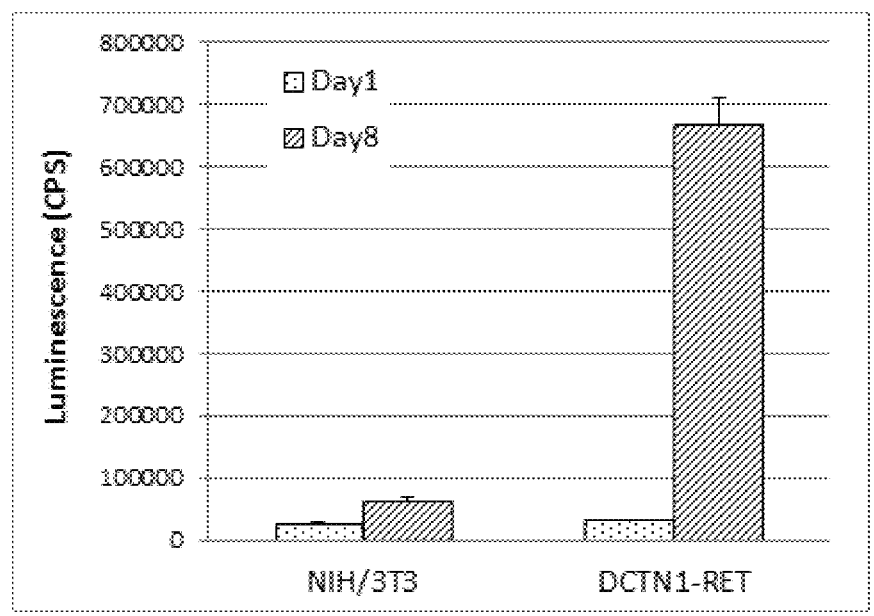
FIG. 5: Confirmation of the growth of NIH/3T3 cells expressing a DCTN1-RET fusion gene in a 3-dimensional culture. N=3, average+SD.

Example 5: Confirmation of Growth of DCTN1-RET Fusion Gene-Expressing NIH/3T3 Cells by 3-dimensional Cell Culture NIH/3T3 cells grow well under 2-dimensional cell culture conditions, but barely grow under 3-dimensional cell culture conditions. However, NIH/3T3 cells are also known to grow under 3-dimensional cell culture conditions when an oncogene is expressed in the cells. Thus, whether the DCTN1-RET fusion gene is an oncogene was confirmed using this character. DCTN1-RET fusion gene-expressing NIH/3T3 cells and NIH/3T3 cells were cultured at 37° C. in 5% $CO_2$ in a 2-dimensional cell culture; and collected with trypsin, followed by counting the number of cells. To perform a 3-dimensional cell culture, a medium for 3-dimensional cell culture was prepared using an FCeM-series Preparation Kit (Nissan Chemical Industries, Ltd.), D-MEM (high glucose) (containing L-glutamine, phenol red, sodium pyruvate, and 1500 mg/L sodium hydrogen carbonate) (Wako), and newborn calf serum (NBCS) (Gibco). The cells were suspended in the prepared medium for 3-dimensional cell culture to give 1000 cells/90 μL, and seeded onto a 96-well clear black round bottom, spheroid microplate (Corning), 90 μL per well, followed by incubation at 37° C. in 5%. $CO_2$. The day following seeding (day 1) and after 8 days from seeding (day 8), the luminescence level (counts per second: cps) was measured using a detection reagent for intracellular ATP luminescence (CellTiter-Glo 2.0 reagent, Promega) with a luminometer (EnSpire, PerkinElmer), and the result was determined to be the indicator for viable cell count. The cell growth rate was then calculated from the measurement result on day 1 and the measurement result on day 8 (N=3). As a result, as shown in FIG. 5, while the number of cells in the NIH/3T3 cells on day 8 was 2.4 times the number of cells on day 1, the number of cells in the DCTN1-RET fusion gene-expressing NIH/3T3 cells on day 8 was 20.9 times the number of cells on day 1. Additionally, while no cellular aggregates were formed in the NIH/3T3 cells by the 3-dimensional cell culture, cellular aggregates were confirmed to have formed in the DCTN1-RET fusion gene-expressing NIH/3T3 cells by the 3-dimensional cell culture. This clearly indicates that transfection of the DCTN1-RET fusion gene enhanced cell growth, suggesting that the DCTN1-RET fusion gene is an oncogene.

Example 6: Confirmation of Tumorigenicity in DCTN1-RET Fusion Gene-Expressing NIH/3T3 Cells in vivo To confirm tumorigenicity in DCTN1-RET fusion gene-expressing NIH/3T3 cells in vivo, a transplant experiment was performed with nude mice. The NIH/3T3 cell, which is a parental cell line, is commonly known to not grow subcutaneously in nude mice; and it can be confirmed whether the DCTN1-RET fusion gene contributes to tumorigenicity, or whether the DCTN1-RET fusion gene is an oncogene, by subcutaneously transplanting nude mice with the DCTN1-RET fusion gene-expressing NIH/3T3 cells. Nude mice, BALB/cAJcl-nu/nu (CLEA Japan, Inc.) were used for transplantation. The DCTN1-RET fusion gene-expressing NIH/3T3 cells were collected with trypsin, and suspended in PBS to finally give $1\times10^8$ cells/mL. An equivalent amount of a Matrigel Basement Membrane Matrix (Corning) was added thereto, and adjusted to give $5\times10^7$ cells/mL to prepare a cell suspension for transplantation. 0.1 mL of the cell suspension for transplantation was subcutaneously transplanted into the right-side chest of each nude mouse (N=10) using a 25G injection needle and a 1-mL syringe. On day 10, 13, and 17 after transplantation, the major axis and short axis of a tumor of each mouse was measured with a digital caliper (Mitutoyo Corporation), and the tumor volume was calculated based on the following equation.

The tumor volume $(mm^3)$=(major axis: mm)×(short axis: in)×(short axis: mm)/2

Figure 6:
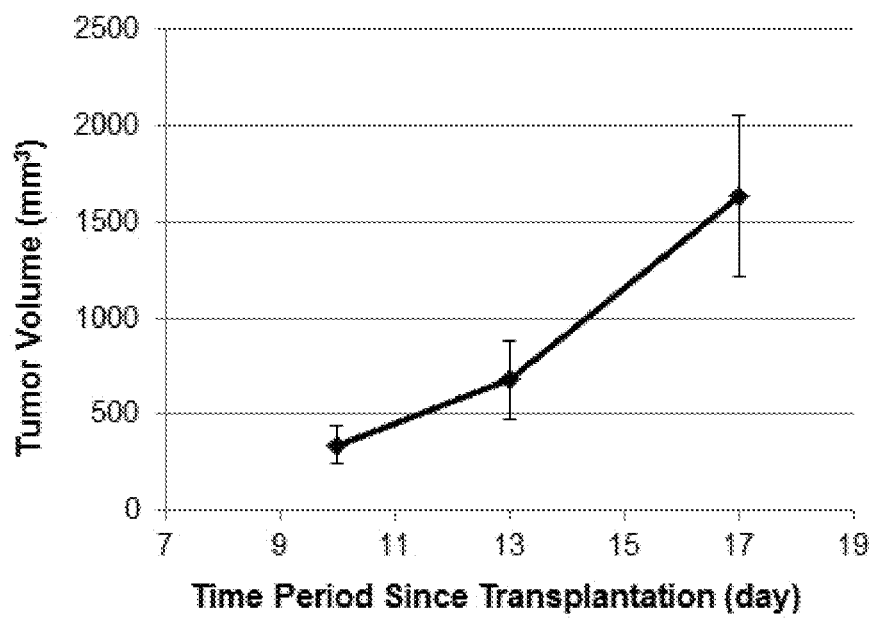
FIG. 6: Confirmation of tumorigenicity of NIH/3T3 cells expressing a DCTN1-RET fusion gene in vivo.

FIG. 6 shows the measurement results of tumor volume. The DCTN1-RET fusion gene-expressing NIH/3T3 cells subcutaneously transplanted in nude mice were confirmed to have tumorigenesis and to have grown well; thus, this in vivo experiment also suggests that the DCTN1-RET fusion gene is an oncogene.

Example 7: Confirmation of Inhibition of DCTN1-RET Fusion Protein and Cell Growth Inhibitory Effect by siRNA in DCTN1-RET Fusion Gene Expressing NIH/3T3 Cells The effect of siRNA treatment on the DCTN1-RET fusion gene-expressing NIH/3T3 cells was examined. The siRNA for use was as follows: three types of RET siRNA shown in Table 5 below, and Silencer Select Negative Control #1 siRNA (Ambion) as a negative control. The target of three types of RET siRNA is human RET; and RET siRNA1 and RET siRNA2 contain a sequence that binds to the RET portion of the DCTN1-RET fusion gene, while RET siRNA3 contains no sequence that binds to the DCTN1-RET fusion gene. In other words, RET siRNA1 and RET siRNA2 were assumed to inhibit the expression of the DCTN1-RET fusion gene, and RET siRNA3 would not. The following describes the method of the experiment using siRNA.

TABLE 5

| RET siRNA1 | CACAUGUCAUCAAAUUGUATT | SEQ ID NO: 74 |
| --- | --- | --- |
| RET siRNA2 | GGAUUGAAAACAAACUCUATT | SEQ ID NO: 75 |
| RET siRNA3 | CCACUGCUACCACAAGUUUTT | SEQ ID NO: 77 |

Figure 7:
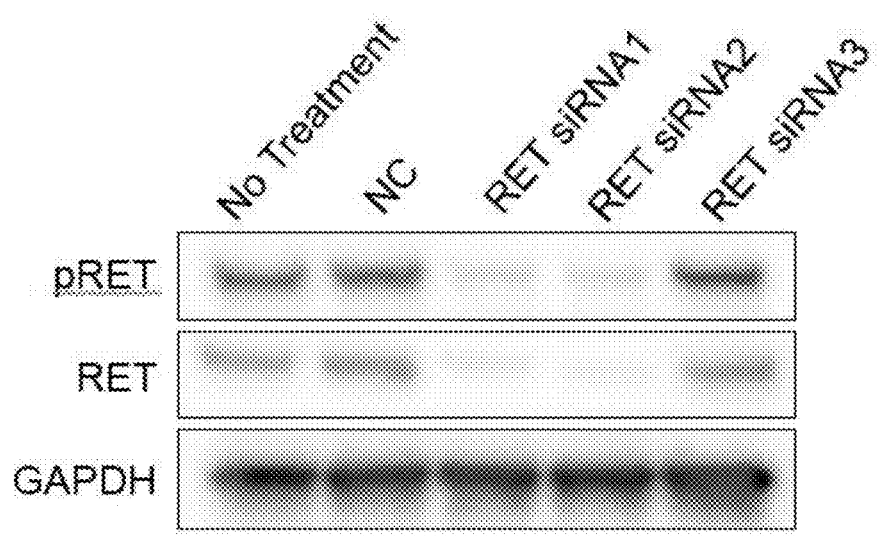
FIG. 7: Confirmation of the inhibition of expression of phosphorylated RET by RET siRNA in NIH/3T3 cells expressing a DCTN1-RET fusion gene.

DCTN1-RET fusion gene-expressing NIH/3T3 cells for use were prepared by culture in a medium for 2-dimensional cell culture at 37° C. in 5% $CO_2$. On the day before siRNA treatment, the cells were seeded onto a 6-well plate (Iwaki), $3 \times 10^5$ cells/2 mL, and incubated at 37° C. in 5% $CO_2$ overnight. 12 μL of each type of siRNA adjusted to 20 μM beforehand using water, 4 μL of a Lipofectamine RNAiMAX Transfection Reagent (Thermo Fisher), and 384 μL of Opti-MEM were mixed; and incubated at room temperature for 15 minutes, thereby preparing siRNA solutions. 400 μL of each siRNA solution was added to the wells in which the cells were seeded, and incubation was performed at 37° C. in 5% $CO_2$ overnight. The following day, a portion of the incubated cells was taken as a sample for use in protein expression analysis; and another portion was also taken and reseeded for use in confirmation of cell growth. The sampling for protein expression analysis and the protein expression analysis were performed in the same manner as in 4-2: Confirmation of Expression of Target Protein described above, except for the use of a Phospho-RET (Tyr905) antibody (CST), Ret (C31B4) Rabbit mAb (CST), and GAPDH (D16H11) XP Rabbit mAb (CST) as primary antibodies. The results indicate, as shown in FIG. 7, that the expression of the DCTN1-RET fusion protein was not inhibited in the cells treated with the negative control siRNA (NC), compared with cells without siRNA treatment (no treatment). When the cells were treated with RET siRNA1 or RET siRNA2, the expression of the DCTN1-RET fusion protein was confirmed to have been inhibited in the DCTN1-RET fusion gene-expressing NIH/3T3 cells, and not inhibited when RET siRNA3 was used.

Figure 8:
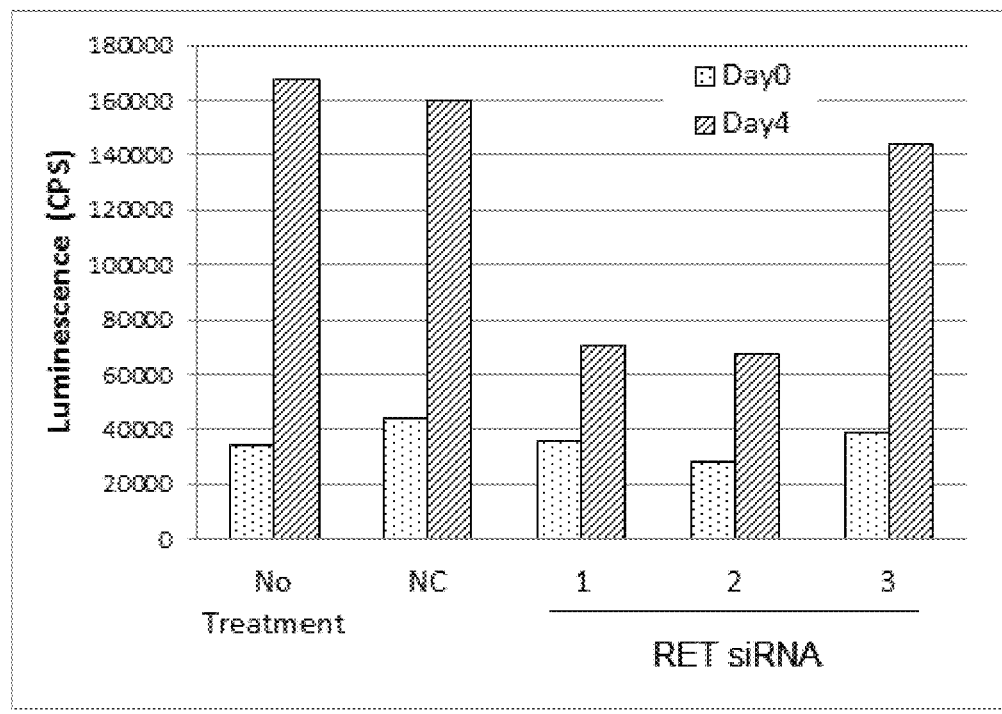
FIG. 8: Confirmation of the growth inhibitory effect on NIH/3T3 cells expressing a DCTN1-RET fusion gene by RET siRNA.

Subsequently, to confirm a cell growth inhibitory effect, cells were collected with trypsin from the wells without treatment and wells treated with siRNA, and the number of cells was counted. A 3-dimensional cell culture was then performed in the same manner as in Example 5, and on the day seeding was performed (day 0) and after 4 days from seeding (day 4), the number of viable cells was counted in the same manner as in Example 5. The growth rate of the cells was calculated from the measurement result on day 0 and the measurement result on day 4. The results indicate, as shown in FIG. 8, that cells that were without siRNA treatment (no treatment) and cells that were treated with the negative control siRNA (NC) respectively exhibited the number of cells on day 4 4.9 times and 3.6 times that on day 0; however, cells treated with RET siRNA1 and cells treated with RET siRNA2 merely exhibited growth of about 2.0 times and 2.4 times, respectively, which were both notably lower. The cells treated with RET siRNA3 exhibited growth of 3.7 times, which is substantially equal to the growth of the cells treated with negative control siRNA, rarely showing a decrease in growth. These results reveal that the growth of the DCTN1-RET fusion gene-expressing NIH/3T3 cells is also inhibited when the expression of RET is inhibited by siRNA.

Example 8: Cell Growth Inhibitory Effect in DCTN1-RET Fusion Gene-Expressing NIH/3T3 Cells An in vitro cell growth assay was performed on DCTN1-RET fusion gene-expressing NIH/3T3 cells. A 3-dimensional cell culture and seeding were performed in the same manner as in Example 5. After seeding, incubation was performed at 37° C. in 5' $CO_2$ overnight (day 0). Cabozantinib, vandetanib, alectinib, lenvatinib, and fused pyrimidine compounds (Compounds 1 to 9 shown in Table 6), which are reported as capable of inhibiting RET, were dissolved in dimethyl sulfoxide to give a concentration of 10 mmol/L; and further diluted with a medium for 3-dimensional cell culture such that these compounds have a final concentration of 1000, 333, 111, 37.0, 12.3, 4.12, 1.37, and 0.457 nmol/L. These diluted compounds were then individually added to each well (0.01 mL per well) of the plate in which the cells were seeded (day 1); and the cells were incubated at 37° C. in 5% $CO_2$ for 7 days. After culture (day 8), an intracellular ATP luminescence detection reagent (CellTiter-Glo 2.0 reagent, Promega) was added to each well, and the luminescence level (counts per second: cps) was measured with a luminometer (EnSpire, PerkinElmer). The growth rate from day 1 of cells treated with the compounds of different concentrations was calculated based on the following equation, according to the value of $T_{day8}$ and $C_{day1}$, and the concentration of each test compound at which cell growth is inhibited by 50% ($GI_{50}$ (nM)) was determined.

1) When $T_{day8} \geq C_{day1}$ $$\text{Growth Rate (\%)} = (T_{day8} - C_{day1})/(C_{day8} - C_{day1}) \times 100$$

T: cps of a well to which a test compound was added

C: cps of a well to which a test compound was not added

Day 1: the day on which a test compound was added

Day 8: the day on which evaluation was performed

2) When $T_{day8} < C_{day1}$ $$\text{Growth Rate (3)} = (T_{day8} - C_{day1})/(C_{day1}) \times 100$$

T: cps of a well to which a test compound was added

C: cps of a well to which a test compound was not added

Day 1: the day on which a test compound was added

Day 8: the day on which evaluation was performed

TABLE 6

| Compound No | Structural Formula | Chemical Name | International Publication No. and Example No. |
|---|---|---|---|
| Compound 1 | | 4-amino-1-(tert-butyl)-N-(5-methyl-1H-pyrazol-3-yl)-1H-pyrazolo[3,4-d]pyrimidine-3-carboxamide | WO2017/043550 Example Compound 34 |
| Compound 2 | | 4-amino-7-(tert-butyl)-N-(5-methyl-1H-pyrazol-3-yl)-7H-pyrrolo[2,3-d]pyrimidine-5-carboxamide | WO2017/043550 Example Compound 48 |
| Compound 3 | | 4-amino-7-(1-fluoro-2-methylpropan-2-yl)-N-(5-methyl-1H-pyrazol-3-yl)-7H-pyrrolo[2,3-d]pyrimidine-5-carboxamide | WO2017/043550 Example Compound 50 |
| Compound 4 | | 4-amino-N-(5-methyl-1H-pyrazol-3-yl)-7-(1-methylcyclopropyl)-7H-pyrrolo[2,3-d]pyrimidine-5-carboxamide | WO2017/043550 Example Compound 51 |

TABLE 6-continued

| Compound No | Structural Formula | Chemical Name | International Publication No. and Example No. |
|---|---|---|---|
| Compound 5 | | 4-amino-7-(2-cyclopropylpropan-2-yl)-N-(5-methyl-1H-pyrazol-3-yl)-7H-pyrrolo[2,3-d]pyrimidine-5-carboxamide | WO2017/043550 Example Compound 52 |
| Compound 6 | | 4-amino-N-[4-(methoxymethyl)phenyl]-7-(1-methylcyclopropyl)-6-(3-morpholinopro-1-pyn-1-yl)-7H-pyrrolo[2,3-d]pyrimidine-5-carboxamide | WO2017/146116 Example Compound 85 |
| Compound 7 | | 4-amino-N-[4-(methoxymethyl)phenyl]-7-(1-methylcyclopropyl)-6-((tetrahydro-2H-pyran-4-yl)ethynyl)-7H-pyrrolo[2,3-d]pyrimidine-5-carboxamide | WO2017/146116 Example Compound 87 |
| Compound 8 | | (R)-4-amino-N-[4-(methoxymethyl)phenyl]-7-(1-methylcyclopropyl)-6-((tetrahydrofuran-2-yl)methoxy)-7H-pyrrolo[2,3-d]pyrimidine-5-carboxamide | WO2017/146116 Example Compound 89 |

TABLE 6-continued

| Compound No | Structural Formula | Chemical Name | International Publication No. and Example No. |
|---|---|---|---|
| Compound 9 | | 4-amino-N-[4-(methoxymethyl)phenyl]-6-((1-methyl-1H-pyrazol-4-yl)ethynyl)-7-(1-methylcyclopropyl)-7H-pyrrolo[2,3-d]pyrimidine-5-carboxamide | WO2017/146116 Example Compound 90 |

The results indicate, as shown in Table 7, that cabozantinib, vandetanib, lenvatinib, and fused pyrimidine compounds (Compounds 1 to 9) inhibited the growth of DCTN1-RET fusion gene-expressing NIH/3T3 cells.

TABLE 7

| Compound | $GI_{50}$ ( nmol/L ) |
|---|---|
| Compound 1 | 8.50 |
| Compound 2 | 5.80 |
| Compound 3 | 5.40 |
| Compound 4 | 5.70 |
| Compound 5 | 4.20 |
| Compound 6 | 3.60 |
| Compound 7 | 11.40 |
| Compound 8 | 17.90 |
| Compound 9 | 4.80 |
| Cabozantinib | 91.10 |
| Vandetanib | 68.70 |
| Lenvatinib | 50.30 |
| Alectinib | >1000 |

The results above suggest the potential usefulness of these RET inhibitors as a therapeutic agent for cancer in which the DCTN1-RET fusion gene has been detected. The results also suggest that the use of the DCTN1-RET fusion gene-expressing NIH/3T3 cells enables screening for a compound that inhibits DCTN1-RET.

Figure 9:
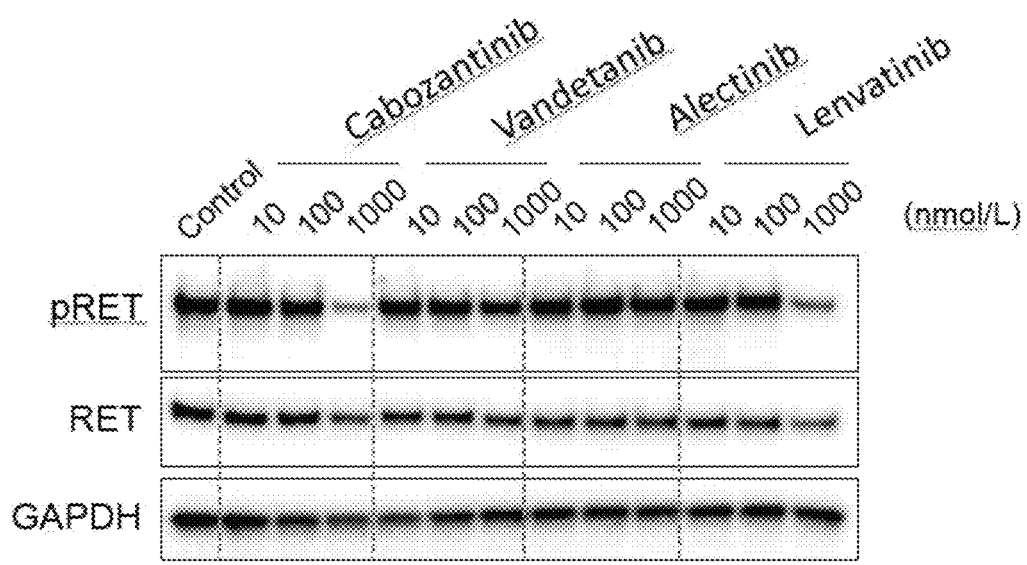
FIG. 9: Confirmation of the inhibition of expression of phosphorylated RET in NIH/3T3 cells expressing a DCTN1-RET fusion gene by compounds that inhibit RET.

Example 9: Inhibition of RET Phosphorylation in DCTN1-RET Fusion Gene-Expressing Cells The following examined whether RET phosphorylation in DCTN1-RET fusion gene-expressing cells is inhibited by existing medicinal agents that are reported as inhibiting RET in accordance with the method described below. The DCTN1-RET fusion gene-expressing NIH/3T3 cells for use were prepared by culture in a medium for 2-dimensional cell culture at 37° C. in 5% C02. On the day before treating the cells with a medicinal agent, the cells were seeded onto a 6-well plate (Iwaki), $3\times10^5$ cells/2 mL, and incubated at 37° C. in 5% $CO_2$ overnight. Cabozantinib, vandetanib, alectinib, and lenvatinib were dissolved in dimethyl sulfoxide to give a concentration of 10 mmol/L, and further diluted with PBS such that these compounds have a final concentration of 1000, 100, and 10 nmol/L. The diluted compounds were individually added to each well onto which the cells were previously seeded, 20 µL per well (day 1), and incubated at 37° C. in 5% $CO_2$ for 1 hour. After incubation, a sample of the cells for protein expression analysis was taken in the same manner as in Example 7, and protein expression was analyzed. The results indicate, as shown in FIG. 9, that phosphorylated RET levels in the DCTN1-RET fusion gene-expressing NIH/3T3 cells notably decreased by cabozantinib and lenvatinib. Additionally, the inhibition of RET phosphorylation by the fused pyrimidine compounds was also evaluated in the same manner as above, and RET phosphorylation was also confirmed to have notably decreased by the fused pyrimidine compounds. These results suggest that a medicinal agent capable of notably decreasing the phosphorylated RET levels would be a compound that can inhibit the growth of the DCTN1-RET fusion gene-expressing NIH/3T3 cells, and that the compound is potentially useful as a therapeutic agent for cancer in which the DCTN1-RET fusion gene has been detected. The results also suggest that the use of phosphorylated RET levels in DCTN1-RET fusion gene-expressing NIH/3T3 cells enables screening for a RET inhibitor.

Sequence List Free Text

SEQ ID NO: 1 shows the base sequence of the polynucleotide encoding a fusion peptide of DCTN1 variant 1 (v1) (a portion of SEQ ID NO: 25) and RET variant 2 (v2) (a portion of SEQ ID NO: 31).
SEQ ID NO: 2 shows the amino acid sequence of a fusion peptide of DCTN1 v1 and RET v2.
SEQ ID NO: 3 shows the base sequence of the polynucleotide encoding a fusion peptide of DCTN1 v1 and RET variant 4 (v4) (a portion of SEQ ID NO: 32).
SEQ ID NO: 4 shows the amino acid sequence of a fusion peptide of DCTN1 v1 and RET v4.
SEQ ID NO: 5 shows the base sequence of the polynucleotide encoding a fusion peptide of DCTN1 variant 2 (v2) (a portion of SEQ ID NO: 26) and RET v2.
SEQ ID NO: 6 shows the amino acid sequence of a fusion peptide of DCTN1 v2 and RET v2.
SEQ ID NO: 7 shows the base sequence of the polynucleotide encoding a fusion peptide of DCTN1 v2 and RET v4.
SEQ ID NO: 8 shows the amino acid sequence of a fusion peptide of DCTN1 v2 and RET v4.
SEQ ID NO: 9 shows the base sequence of the polynucleotide encoding a fusion peptide of DCTN1 variant 3 (v3) (a portion of SEQ ID NO: 27) and RET v2.
SEQ ID NO: 10 shows the amino acid sequence of a fusion peptide of DCTN1 v3 and RET v2.

SEQ ID NO: 11 shows the base sequence of the polynucleotide encoding a fusion peptide of DCTN1 v3 and RET v4.
SEQ ID NO: 12 shows the amino acid sequence of a fusion peptide of DCTN1 v3 and RET v4.
SEQ ID NO: 13 shows the base sequence of the polynucleotide encoding a fusion peptide of DCTN1 variant 4 (v4) (a portion of SEQ ID NO: 28) and RET v2.
SEQ ID NO: 14 shows the amino acid sequence of a fusion peptide of DCTN1 v4 and RET v2.
SEQ ID NO: 15 shows the base sequence of the polynucleotide encoding a fusion peptide of DCTN1 v4 and RET v4.
SEQ ID NO: 16 shows the amino acid sequence of a fusion peptide of DCTN1 v4 and RET v4.
SEQ ID NO: 17 shows the base sequence of the polynucleotide encoding a fusion peptide of DCTN1 variant 5 (v5) (a portion of SEQ ID NO: 29) and RET v2.
SEQ ID NO: 18 shows the amino acid sequence of a fusion peptide of DCTN1 v5 and RET v2.
SEQ ID NO: 19 shows the base sequence of the polynucleotide encoding a fusion peptide of DCTN1 v5 and RET v4.
SEQ ID NO: 20 shows the amino acid sequence of a fusion peptide of DCTN1 v5 and RET v4.
SEQ ID NO: 21 shows the base sequence of the polynucleotide encoding a fusion peptide of DCTN1 v6 and RET v2.
SEQ ID NO: 22 shows the amino acid sequence of a fusion peptide of DCTN1 v6 and RET v2.
SEQ ID NO: 23 shows the base sequence of the polynucleotide encoding a fusion peptide of DCTN1 v6 and RET v4.
SEQ ID NO: 24 shows the amino acid sequence of a fusion peptide of DCTN1 v6 and RET v4.
SEQ ID NO: 33 shows the base sequence of a primer.
SEQ ID NO: 34 shows the base sequence of a primer.
SEQ ID NO: 35 shows the base sequence of a primer.
SEQ ID NO: 36 shows the base sequence of a primer.
SEQ ID NO: 37 shows the base sequence of a primer.
SEQ ID NO: 38 shows the base sequence of a primer.
SEQ ID NO: 39 shows the base sequence of a primer.
SEQ ID NO: 40 shows the base sequence of a primer.
SEQ ID NO: 41 shows the base sequence of a primer.
SEQ ID NO: 42 shows the base sequence of a primer.
SEQ ID NO: 43 shows the base sequence of a primer.
SEQ ID NO: 44 shows the base sequence of a primer.
SEQ ID NO: 45 shows the base sequence of a primer.
SEQ ID NO: 46 shows the base sequence of a primer.
SEQ ID NO: 47 shows the base sequence of a primer.
SEQ ID NO: 48 shows the base sequence of a primer.
SEQ ID NO: 49 shows the base sequence of a primer.
SEQ ID NO: 50 shows the base sequence of a primer.
SEQ ID NO: 51 shows the base sequence of a primer.
SEQ ID NO: 52 shows the base sequence of a primer.
SEQ ID NO: 53 shows the base sequence of a primer.
SEQ ID NO: 54 shows the base sequence of a primer.
SEQ ID NO: 55 shows the base sequence of a primer.
SEQ ID NO: 56 shows the base sequence of a primer.
SEQ ID NO: 57 shows the base sequence of a primer.
SEQ ID NO: 58 shows the base sequence of a primer.
SEQ ID NO: 59 shows the base sequence of a primer.
SEQ ID NO: 60 shows the base sequence of a primer.
SEQ ID NO: 61 shows the base sequence of a primer.
SEQ ID NO: 62 shows the base sequence of a primer.
SEQ ID NO: 63 shows the base sequence of a primer.
SEQ ID NO: 64 shows the base sequence of a primer.
SEQ ID NO: 65 shows the base sequence of a primer.
SEQ ID NO: 66 shows the base sequence of a primer.
SEQ ID NO: 67 shows the base sequence of a primer.
SEQ ID NO: 68 shows the base sequence of a primer.
SEQ ID NO: 69 shows the base sequence of a primer.
SEQ ID NO: 70 shows the base sequence of a primer.
SEQ ID NO: 71 shows the base sequence of a primer.
SEQ ID NO: 72 shows the base sequence of a primer.
SEQ ID NO: 73 shows the base sequence of a primer.
SEQ ID NO: 74 shows the base sequence of RET siRNA.
SEQ ID NO: 75 shows the base sequence of RET siRNA.
SEQ ID NO: 76 shows the base sequence of RET siRNA.
SEQ ID NO: 77 shows the base sequence of RET siRNA.
Sequence Table
P17-158WOPCT_DCTN1_PROTEIN_20180820_115457_8.txt

The invention claimed is:

1. A fused polypeptide wherein a polypeptide containing part of or the entire coiled-coil domain that is in an N-terminal portion of Dynactin Subunit 1 (DCTN1) protein is fused to a polypeptide containing a kinase domain that is in a C-terminal portion of Ret Proto-Oncogene protein (RET), which is:

a polypeptide comprising an amino acid sequence wherein one to ten amino acids are substituted, deleted, or added in the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24, wherein the fused polypeptide comprises at least one protein tag selected from the group consisting of His tag, Myc tag, and FLAG tag.

* * * * *